United States Patent
Reya

(10) Patent No.: US 10,578,608 B1
(45) Date of Patent: Mar. 3, 2020

(54) TOOLS TO DETECT, TRACK AND TARGET CANCER CELLS IN VIVO

(71) Applicant: The Regents of the University of California, Oakland, CA (US)

(72) Inventor: Tannishtha Reya, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 92 days.

(21) Appl. No.: 15/294,492

(22) Filed: Oct. 14, 2016

Related U.S. Application Data

(60) Provisional application No. 62/242,190, filed on Oct. 15, 2015.

(51) Int. Cl.

| | |
|---|---|
| G01N 33/567 | (2006.01) |
| C12N 5/00 | (2006.01) |
| C12N 5/02 | (2006.01) |
| A01K 67/027 | (2006.01) |
| G01N 33/50 | (2006.01) |
| G01N 33/58 | (2006.01) |
| C12N 9/14 | (2006.01) |
| C07K 14/435 | (2006.01) |
| A61K 49/00 | (2006.01) |
| A01K 67/033 | (2006.01) |

(52) U.S. Cl.
CPC ...... *G01N 33/5011* (2013.01); *A01K 67/0271* (2013.01); *A61K 49/0008* (2013.01); *A61K 49/0047* (2013.01); *C07K 14/43595* (2013.01); *C12N 9/14* (2013.01); *C12Y 306/05002* (2013.01); *G01N 33/5073* (2013.01); *G01N 33/5088* (2013.01); *G01N 33/582* (2013.01); *A01K 2217/072* (2013.01); *A01K 2217/075* (2013.01); *A01K 2227/105* (2013.01); *A01K 2267/0331* (2013.01); *A01K 2267/0393* (2013.01)

(58) Field of Classification Search
CPC ........... G01N 33/5011; G01N 33/5073; G01N 33/5088; G01N 33/50; A01K 67/0271
See application file for complete search history.

(56) References Cited

U.S. PATENT DOCUMENTS

| | | | |
|---|---|---|---|
| 2002/0028510 A1* | 3/2002 | Sanberg | C12N 5/0618 435/368 |
| 2013/0011404 A1* | 1/2013 | MacNicol | C07K 16/18 424/139.1 |

OTHER PUBLICATIONS

Cambuli (2013, Stem Cells, 31:2273-2278).*
Kanai (2006, Gene Therapy, 13:106-116).*
Chang (2008, Oncogene, 27:6365-6375).*
Hingorani (2005, Cancer Cell, 7:469-483).*
Morton (2010, PNAS, 107:246-251).*
Hingorani (2003, Cancer Cell, 4:437-450).*
Szabat (2011, Cel Death and Disease, 2:e232, 1-12).*
Trobridge (2009, Gastroenterology, 136:1680-1688).*
Kharas (2010, Nat Med, 16:903-908).*
Almoguera, C. et al. Most human carcinomas of the exocrine pancreas contain mutant c-K-ras genes. Cell 53, 549-554 (1988).
Bardeesy, N. et al. Both p16Ink4a and the p19Arf-p53 pathway constrain progression of pancreatic adenocarcinomain the mouse. PNAS Apr., vol. No. 103, 5947-5952 (2006).
Benjamini et al., Controlling the false discovery rate: a practical and powerful approach to multiple testing. Journal of the Royal Statistical Society. Series B (Methodological) 289-300 (1995).
Carroll, J. B. et al., Potent and Selective Antisense Oligonucleotides Targeting Single-Nucleotide Polymorphisms in the Huntington Disease Gene / Allele-Specific Silencing of Mutant Huntingtin. Molecular Therapy 19, 2178-2185 (2009).
De Andres-Aguayo, L. et al., Musashi 2 is a regulator of the HSC compartment identified by a retroviral insertion screen and knockout mice. Blood 118, 554-564 (2011).
Delitto et al., c-Met signaling in the development of tumorigenesis and chemoresistance: potential applications in pancreatic cancer. World J. Gastroenterol. 20, 8458-8470 (2014).
Fan, L.-F. et al., Expression of putative stem cell genes Musashi-1 and β1-integrin in human colorectal adenomas and adenocarcinomas. Int J Colorectal Dis 25, 17-23 (2009).
Hahn, S. A. et al. DPC4, a candidate tumor suppressor gene at human chromosome 18q21.1. Science 271, 350-353 (1996).
Hermann, P. C. et al. Distinct Populations of Cancer Stem Cells Determine Tumor Growth and Metastatic Activity in Human Pancreatic Cancer. Cell Stem Cell 1, 313-323 (2007).
Hingorani, S. R. et al. Preinvasive and invasive ductal pancreatic cancer and its early detection in the mouse. Cancer Cell 4, 437-450 (2003).
Hope, K. J. et al., An RNAi screen identifies Msi2 and Prox1 as having opposite roles in the regulation of hematopoietic stem cell activity. Cell Stem Cell 7, 101-113 (2010).
Hung, G. et al., Characterization of Target mRNA Reduction Through in Situ RNA Hybridization in Multiple Organ Systems Following Systemic Antisense Treatment in Animals. Nucleic Acid Therapeutics 23, 369-378 (2013).
Ito, T. et al., Regulation of myeloid leukaemia by the cell-fate determinant Musashi. Nature 466, 765-768 (2010).
Jackson, E. L. et al. Analysis of lung tumor initiation and progression using conditional expression of oncogenic K-ras. Genes & Development 15, 3243-3248 (2001).

(Continued)

*Primary Examiner* — Valarie E Bertoglio
(74) *Attorney, Agent, or Firm* — Perkins Coie LLP

(57) ABSTRACT

Some embodiments include a genetically engineered cell comprising a nucleic acid encoding a detectable polypeptide operably linked to the Msi1 or Msi2 promoter and genetically engineered organisms comprising these genetically engineered cells.

15 Claims, 61 Drawing Sheets

Specification includes a Sequence Listing.

(56) References Cited

OTHER PUBLICATIONS

Jemal, A. et al. Global cancer statistics. CA: A Cancer Journal for Clinicians 61, 69-90 (2011).
Jones, S. et al. Core signaling pathways in human pancreatic cancers revealed by global genomic analyses. Science 321, 1801-1806 (2008).
Kadowaki, Y. et al., Reg protein is overexpressed in gastric cancer cells, where it activates a signal transduction pathway that converges on ERK1/2 to stimulate growth. FEBS Letters 530, 59-64 (2002).
Kaneko et al., Musashi1: An evolutionarily conserved marker for CNS progenitor cells including neural stem cells. Dev. Neurosci. 22, 139-153 (2000).
Kawaguchi, Y. et al., The role of the transcriptional regulator Ptf1a in converting intestinal to pancreatic progenitors. Nat Genet 32, 128-134 (2002).
Kharas, M. G. et al., Musashi-2 regulates normal hematopoiesis and promotes aggressive myeloid leukemia. Nat Med 16, 903-908 (2010).
Kim et al., ALDH Activity Selectively Defines an Enhanced Tumor-Initiating Cell Population Relative to CD133 Expression in Human Pancreatic Adenocarcinoma. PLoS One 6, e20636 (2011).
Kwon, H. Y. et al. Tetraspanin 3 Is Required for the Development and Propagation of Acute Myelogenous Leukemia. Stem Cell 17, 152-164 (2015).
Lee et al., Antisense technology: an emerging platform for cardiovascular disease therapeutics. J Cardiovasc Transl Res 6, 969-980 (2013).
Li, C. et al., c-Met is a marker of pancreatic cancer stem cells and therapeutic target. Gastroenterology 141, 2218-2227.e5 (2011.
Li et al., Mipomersen is a Promising Therapy in the Management of Hypercholesterolemia: A Meta-Analysis of Randomized Controlled Trials. Am J Cardiovasc Drugs 14, 367-376 (2014).
Macnicol et al., Function and regulation of the mammalian Musashi mRNA translational regulator. Biochem. Soc. Trans 36, 528 (2008).
Marcato et al., Aldehyde dehydrogenase: Its role as a cancer stem cell marker comes down to the specific isoform. cc 10, 1378-1384 (2011).
Marino et al., Induction of medulloblastomas in p53-null mutant mice by somatic inactivation of Rb in the external granular layer cells of the cerebellum. Genes & Development 14, 994-1004 (2000).
Nakamura et al., Musashi, a neural RNA-binding protein required for Drosophila adult external sensory organ development. Neuron 13, 67-81 (1994).
Nikpour et akl., The stem cell self-renewal gene, Musashi 1, is highly expressed in tumor and non-tumor samples of human bladder. Indian J Cancer 50, 214-218 (2013).
Okano et al., Musashi: A translational regulator of cell fate. J. Cell. Sci. 115, 1355-1359 (2002).
Okano, H. et al., Function of RNA-binding protein Musashi-1 in stem cells. Experimental Cell Research 306, 349-356 (2005).
Paulson et al., "Therapeutic advances in pancreatic cancer", Gastroenterology 144, 1316-1326 (2013).
Prakash, T. P. et al., Antisense Oligonucleotides Containing Conformationally Constrained 2',4'-(N-Methoxy) aminomethylene and 2',4'-Aminooxymethylene and 2'-O,4'-C-Aminomethylene Bridged Nucleoside Analogues Show Improved Potency in Animal Models . . . medicinal chemistry (2010).
Raal, F. J. et al. Mipomersen, an apolipoprotein B synthesis inhibitor, for lowering of LDL cholesterol concentrations in patients with homozygous familial hypercholesterolaemia: a randomised, double-blind, placebo-controlled trial. The Lancet 375, 998-1006 (2010).
Rasheed et al., Biological and clinical relevance of stem cells in pancreatic adenocarcinoma. Journal of Gastroenterology and Hepatology 27, 15-18 (2012).
Redston, M. S. et al,. p53 mutations in pancreatic carcinoma and evidence of common involvement of homocopolymer tracts in DNA microdeletions. Cancer Res. 54, 3025-3033 (1994).
Reya et al., Stem cells, cancer, and cancer stem cells. Nature 414(6859):105-11 (2001).
Rhim, A. D. et al, "EMT and dissemination precede pancreatic tumor formation", Cell 148, 349-361 (2012).
Rigo, F. et al. Pharmacology of a central nervous system delivered 2'-O-methoxyethyl-modified survival of motor neuron splicing oligonucleotide in mice and nonhuman primates. Journal of Pharmacology and Experimental Therapeutics 350, 46-55 (2014).
Rovira, M. et al. Isolation and characterization of centroacinar/terminal ductal progenitor cells in adult mouse pancreas. Proceedings of the National Academy of Sciences 107, 75-80 (2010).
Saad, F. et al., Randomized phase II trial of Custirsen (OGX-011) in combination with docetaxel or mitoxantrone as second-line therapy in patients with metastatic castrate-resistant prostate cancer progressing after first-line docetaxel: CUOG trial P-06c. Clin. Cancer Res. 17, 5765-5773 (2011).
Sakakibara et al., RNA-binding protein Musashi family: roles for CNS stem cells and a subpopulation of ependymal cells revealed by targeted disruption and antisense ablation. Proc. Natl. Acad. Sci. U.S.A. 99, 15194-15199 (2002).
Samuel, V. T. et al. Targeting foxo1 in mice using antisense oligonucleotide improves hepatic and peripheral insulin action. Diabetes 55, 2042-2050 (2006).
Sasik et al., Microarray truths and consequences. J. Mol. Endocrinol. 33, 1-9 (2004).
Sayer, R. A. et al. High insulin-like growth factor-2 (IGF-2) gene expression is an independent predictor of poor survival for patients with advanced stage serous epithelial ovarian cancer. Gynecologic Oncology 96, 355-361 (2005.
Schutte et al., "Abrogation of the Rb/p16 tumor-suppressive pathway in virtually all pancreatic carcinomas", Cancer Res. 57, 3126-3130 (1997).
Seth, P. P. et al., Short Antisense Oligonucleotides with Novel 2'-4' Conformationaly Restricted Nucleoside Analogues Show Improved Potency without Increased Toxicity in Animals. J. Med. Chem. 52, 10-13 (2009).
Shu et al., Expression of the Musashi1 gene encoding the RNA-binding protein in human hepatoma cell lines. Biochem. Biophys. Res. Commun. 293, 150-154 (2002).
Sutherland et al., The Musashi family of RNA binding proteins: master regulators of multiple stem cell populations. Adv. Exp. Med. Biol. 786, 233-245 (2013).
Tusher et al., Significance analysis of microarrays applied to the ionizing radiation response. Proc. Natl. Acad. Sci. U.S.A. 98, 5116-5121 (2001).
Wang et al., Cancer stem cells: lessons from leukemia. Trends in Cell Biology 15, 494-501 (2005).
Wang, X. et al. Overexpression of HMGA2 promotes metastasis and impacts survival of colorectal cancers. Clin. Cancer Res. 17, 2570-2580 (2011).
Wang, T. et al., Sequential expression of putative stem cell markers in gastric carcinogenesis. British Journal of Cancer 105, 658-665 (2011).
Wang, X.-Y. et al., Musashi1 regulates breast tumor cell proliferation and is a prognostic indicator of poor survival. Mol Cancer 9, 221 (2010).
Wu, J., Irizarry with contributions from James MacDonald, R. & Gentry, J. gcrma: Background Adjustment Using Sequence Informatin. R package version 2.37.0).
Yachida et al., "The pathology and genetics of metastatic pancreatic cancer", Arch. Pathol. Lab. Med. 133, 413-422 (2009).

\* cited by examiner

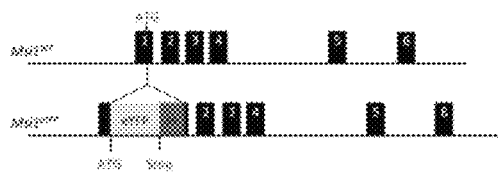
FIG. 1A REM1
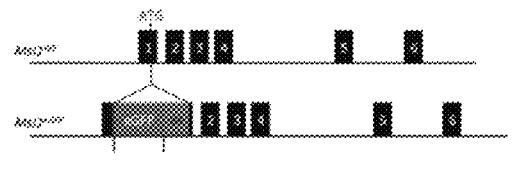
FIG. 1B REM2
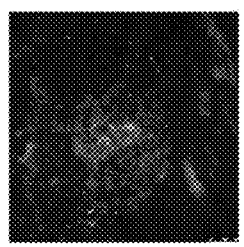
FIG. 1C REM1-KP$^{fC}$
FIG. 1D
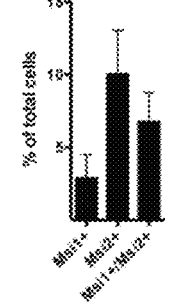
FIG. 1G
Msi1/Msi2 Overlap
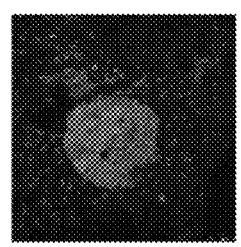
REM2-KP$^{fC}$
FIG. 1E
FIG. 1F
FIG. 1H
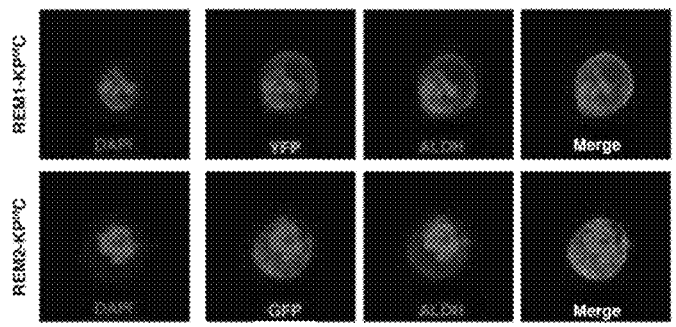
FIG. 1I
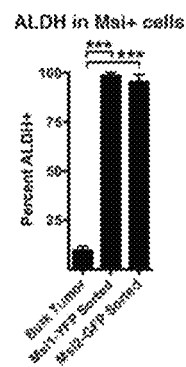
ALDH in Msi+ cells
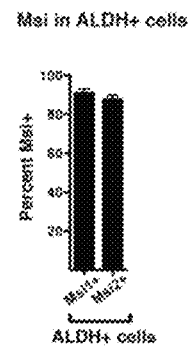
Msi in ALDH+ cells
FIG. 1J
FIG. 1K FIG. 1L
Msi1 Reporter+ cells
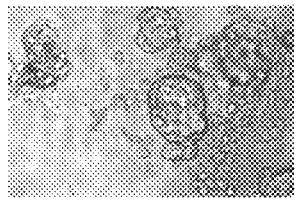
FIG. 1M
Msi1 Reporter- cells
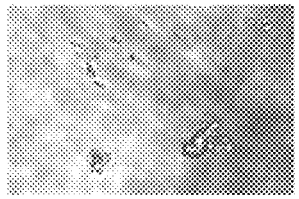
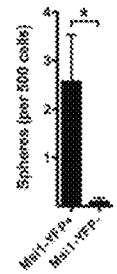
FIG. 1N
FIG. 1O
Msi2 Reporter+ cells
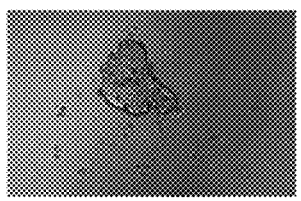
FIG. 1P
Msi2 Reporter- cells
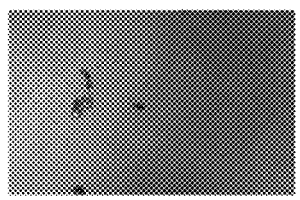
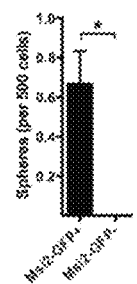
FIG. 1Q
FIG. 1R
100 cells
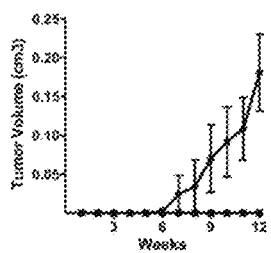
FIG. 1S
500 cells
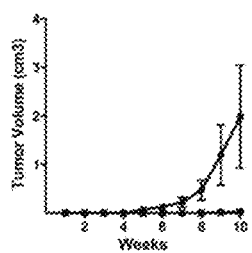
FIG. 1T
1000 cells
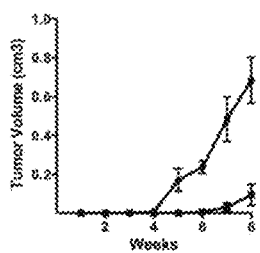
FIG. 1U
10,000 cells
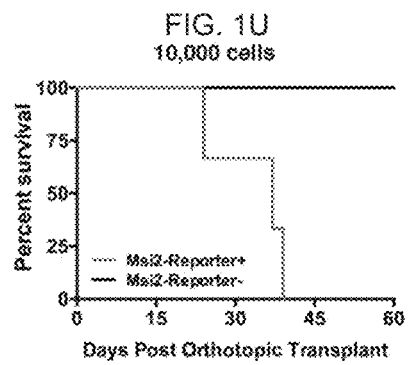
1,000 cells    FIG. 1V
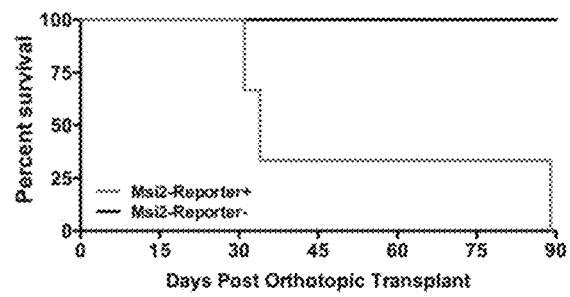

FIG. 1W
Reporter Frequency
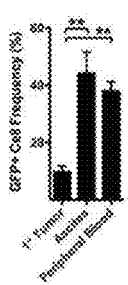
FIG. 1X
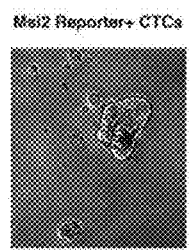
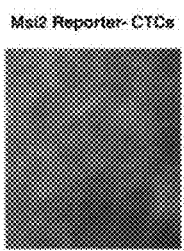
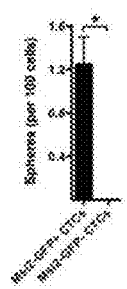
FIG. 1Y
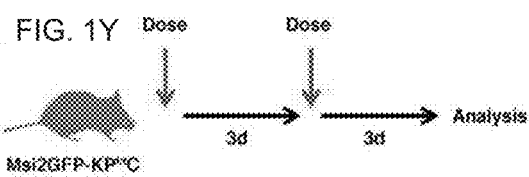
FIG. 1Z
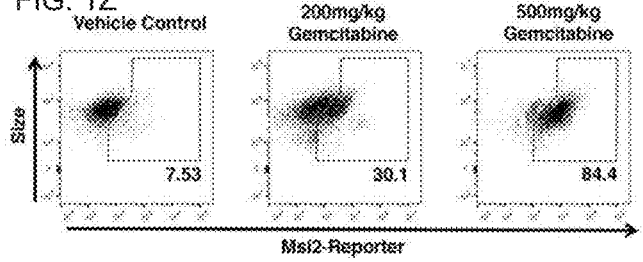
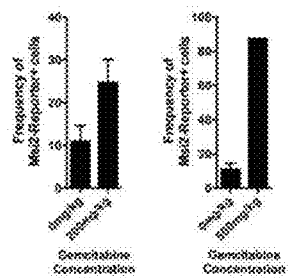

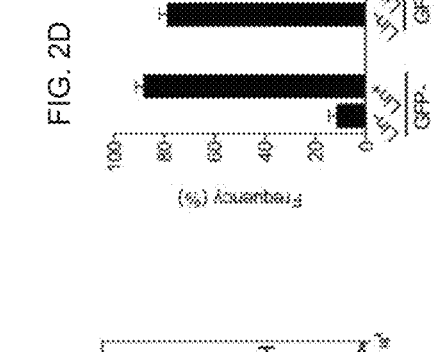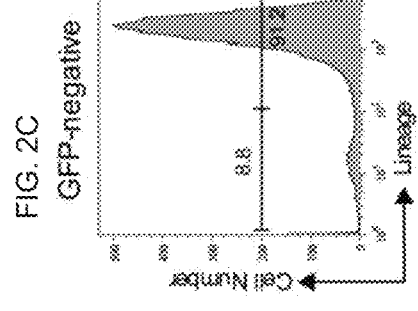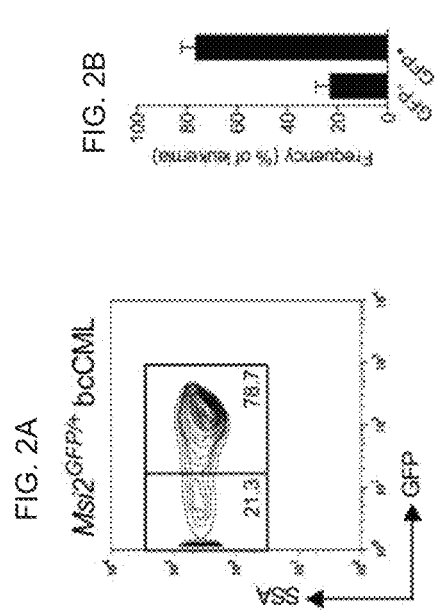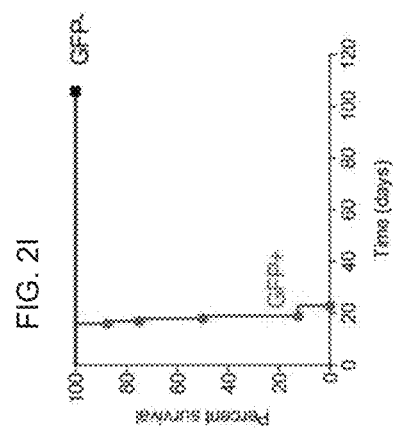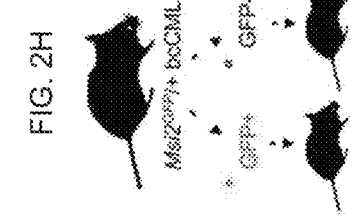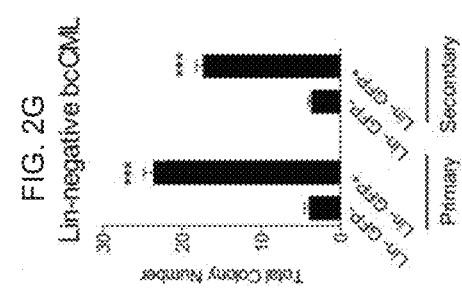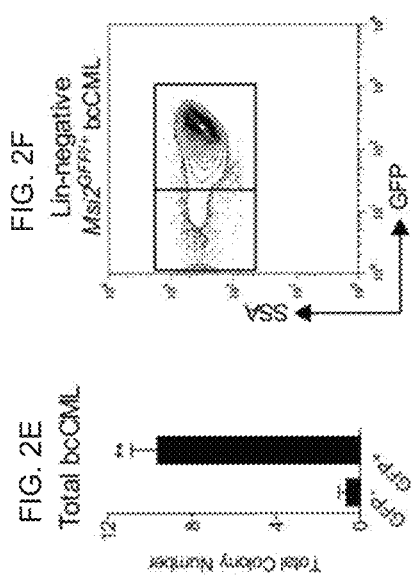

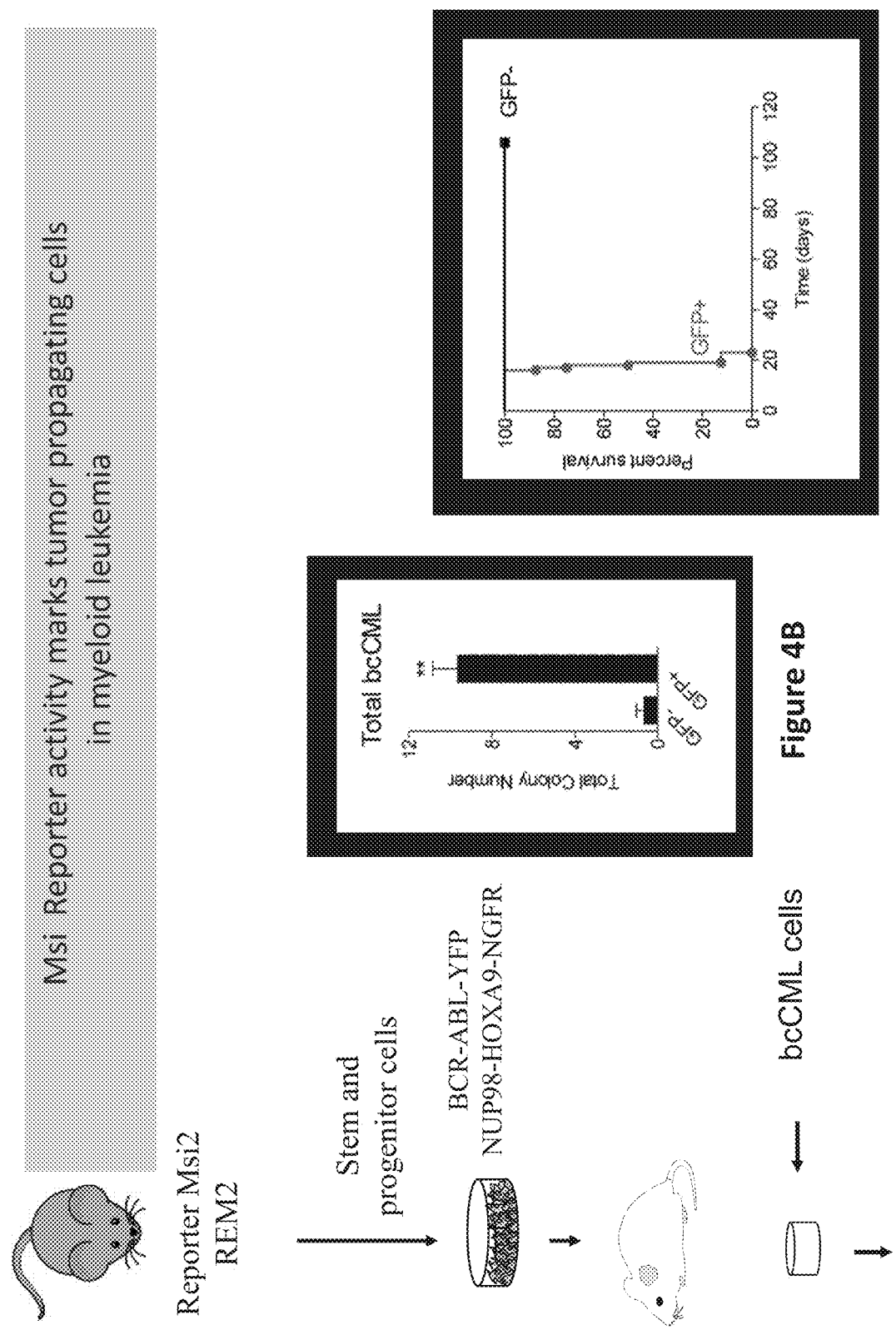

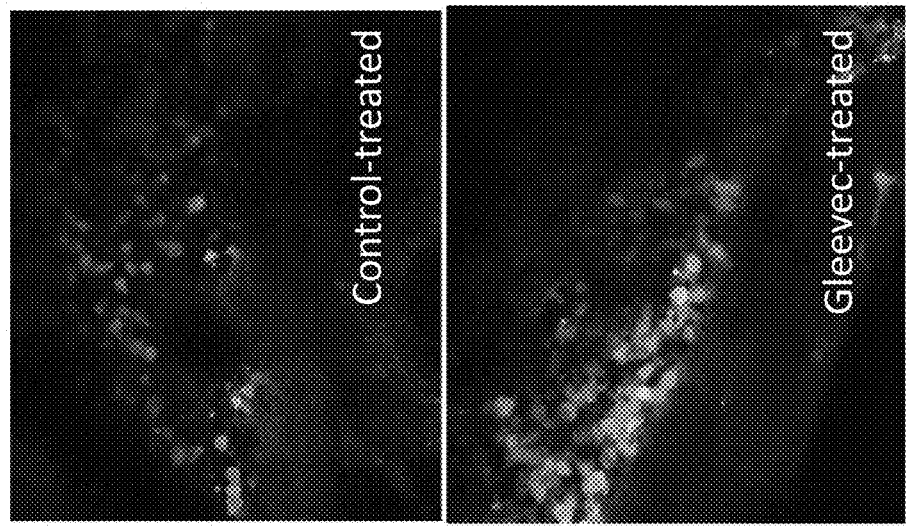
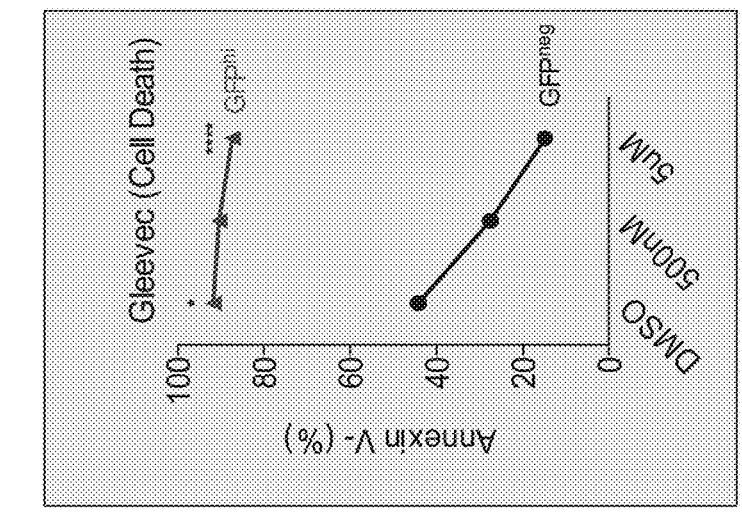
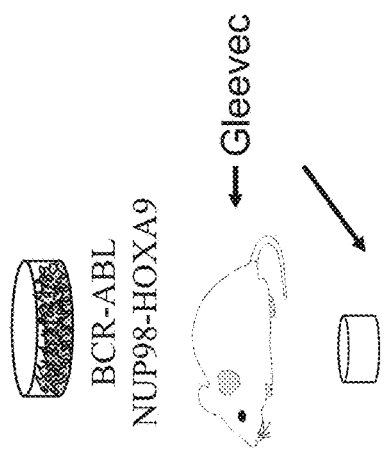
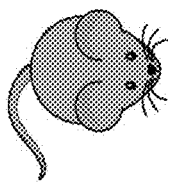
Figure 5A
Figure 5B
Figure 5C

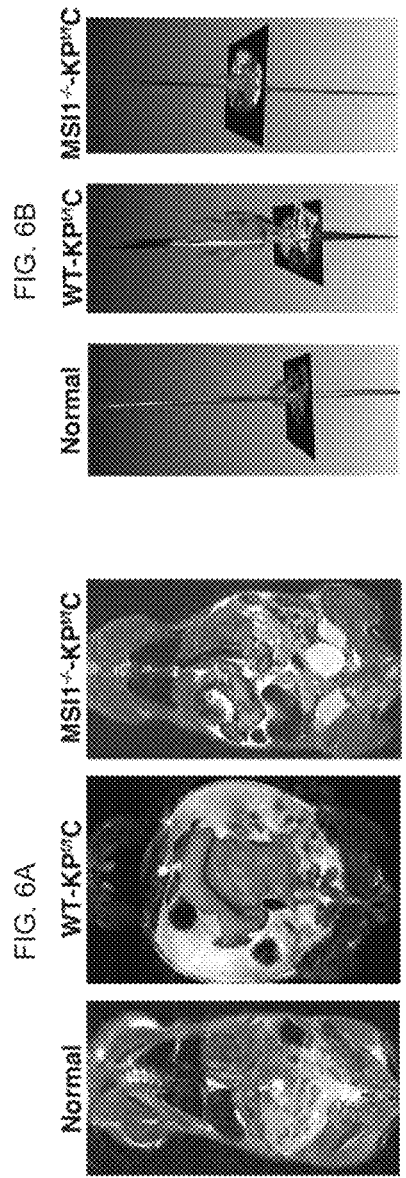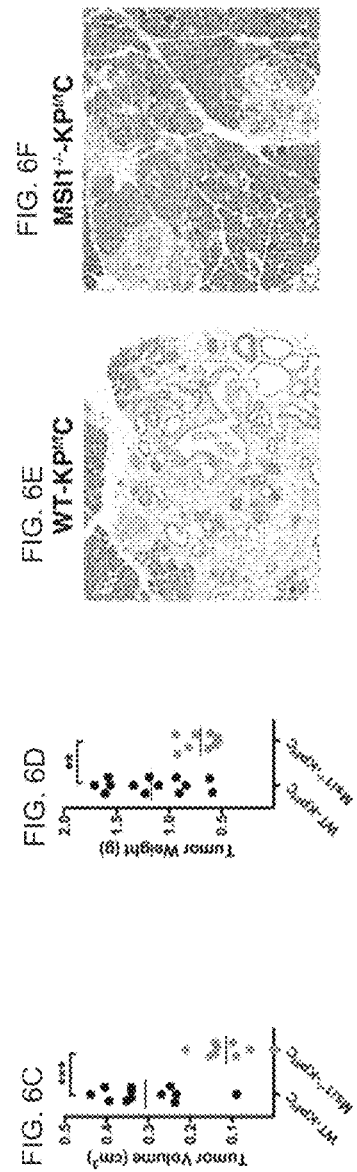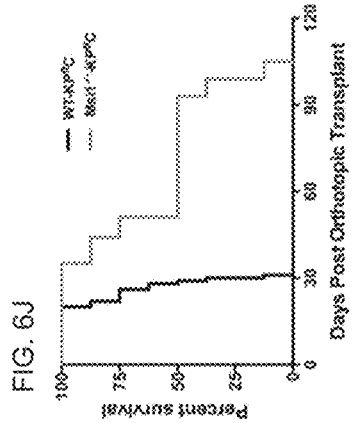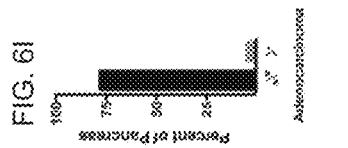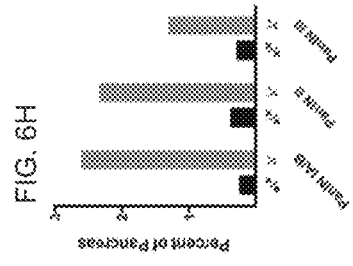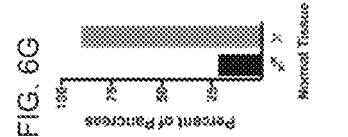

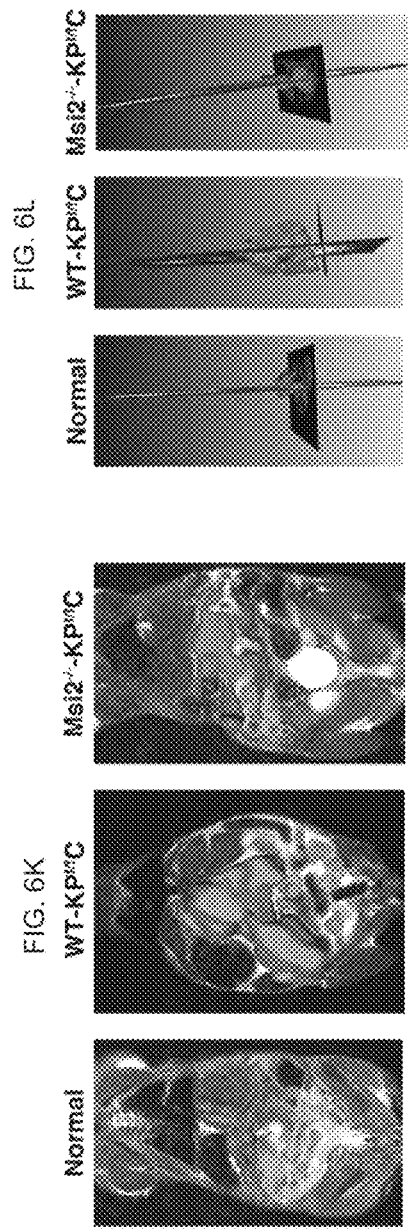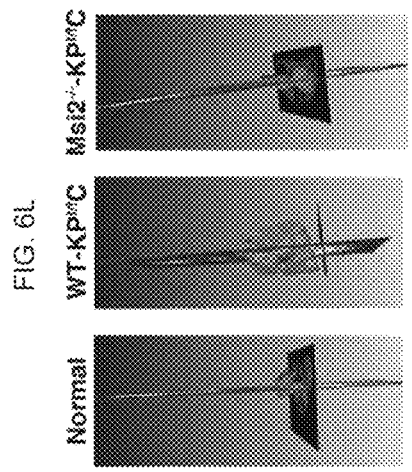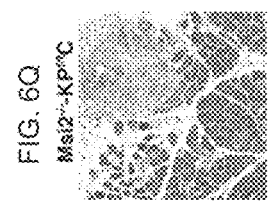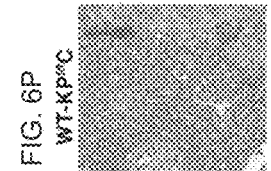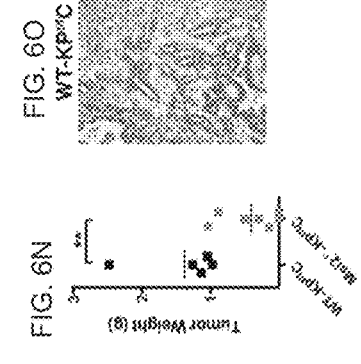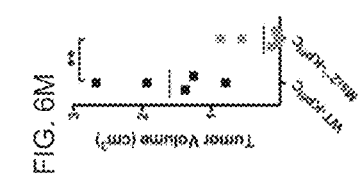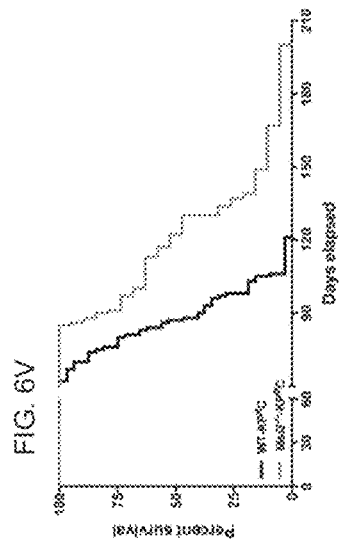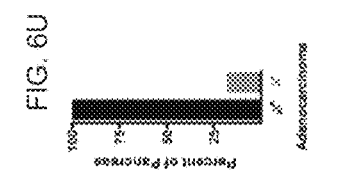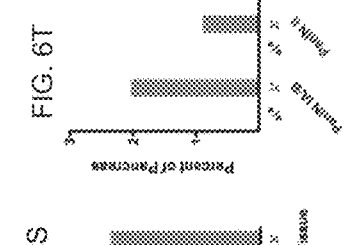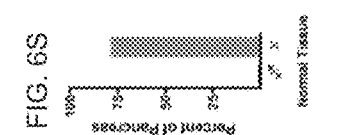

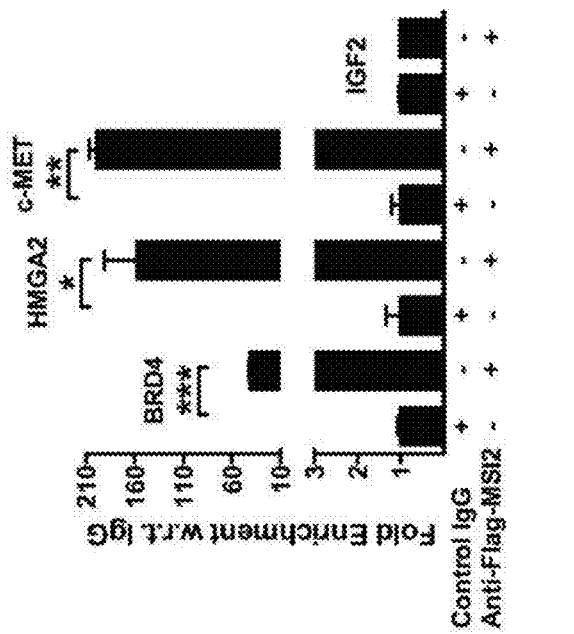
FIG. 7A
FIG. 7B
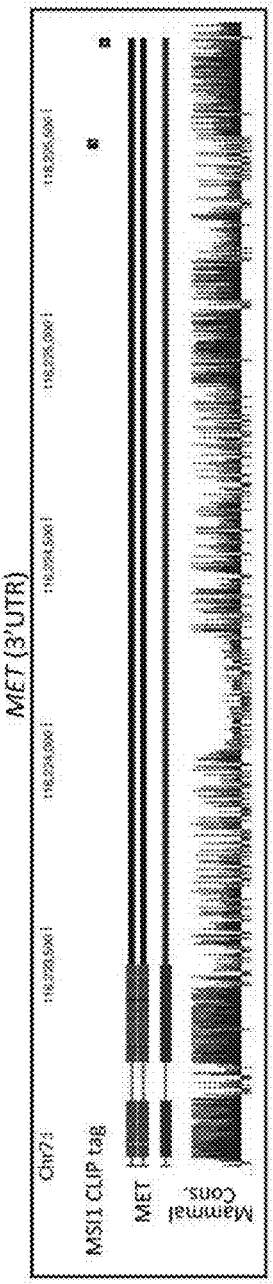
FIG. 7C

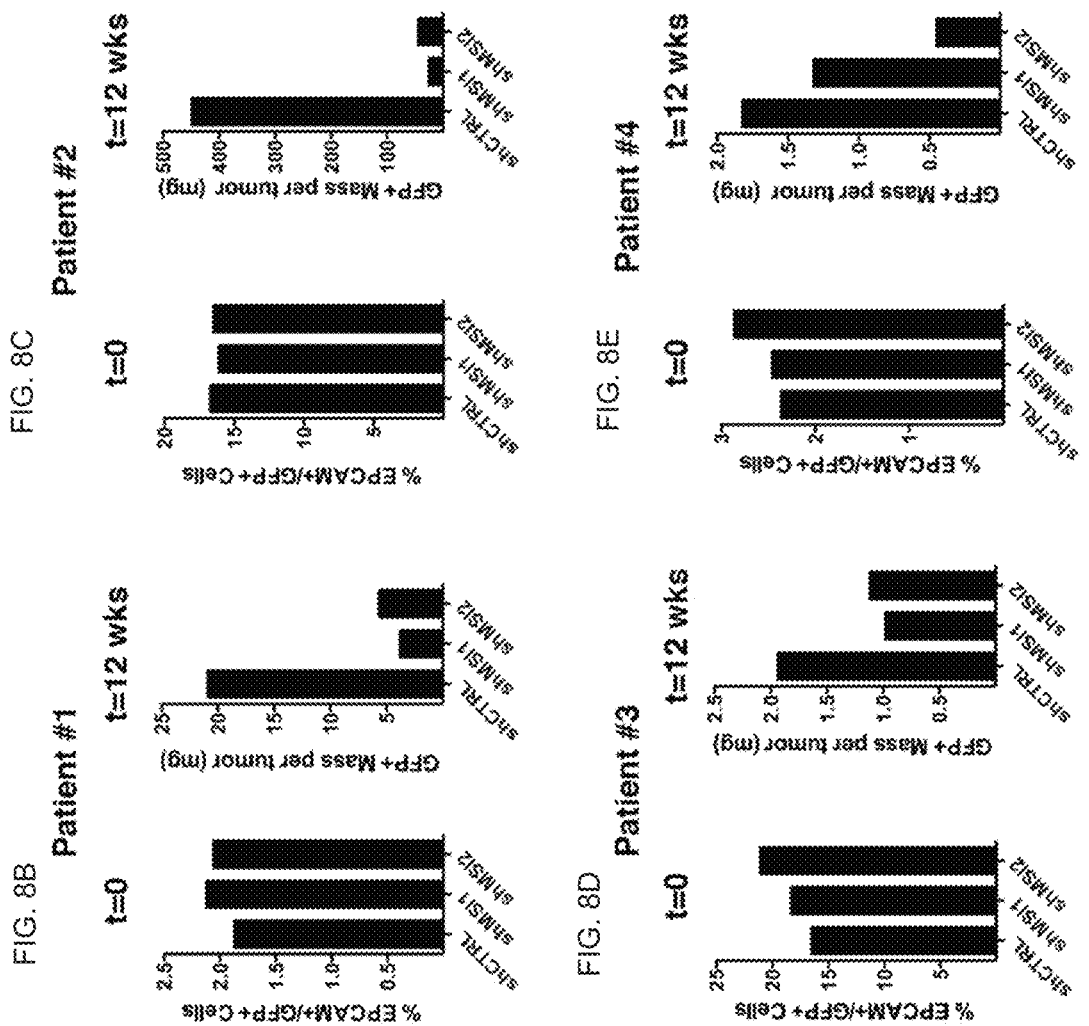
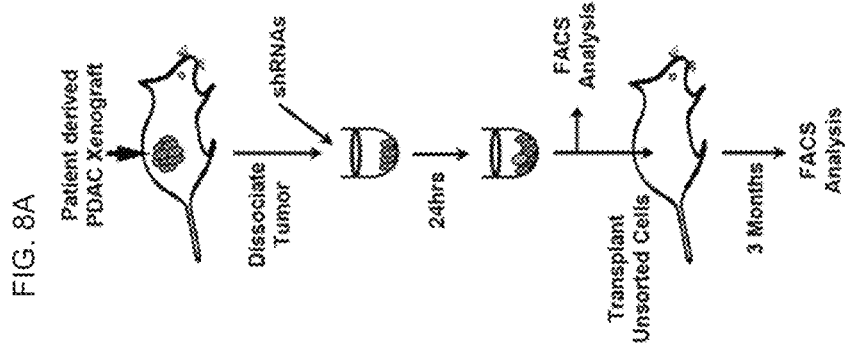

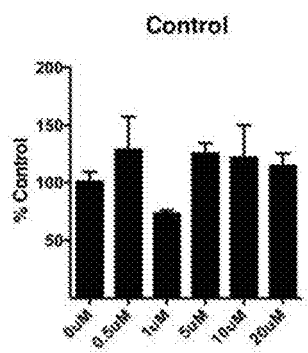

FIG. 8F Control

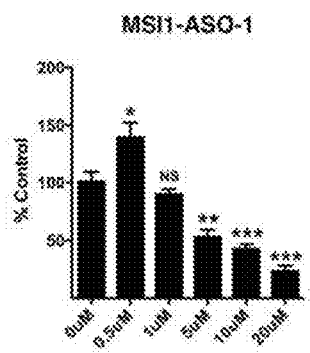

FIG. 8G MSI1-ASO-1

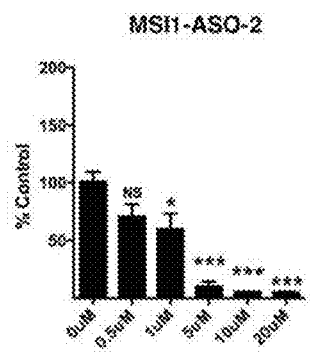

FIG. 8H MSI1-ASO-2

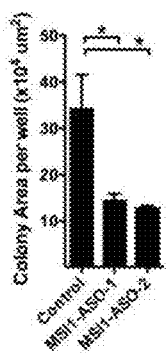

FIG. 8I
Colony Formation In Vitro
(pancreatic cancer cell line)

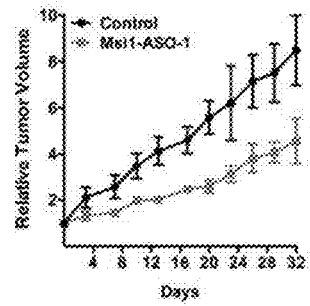

FIG. 8J
Impact on growth
of established tumors
In Vivo
(pancreatic cancer cell line)

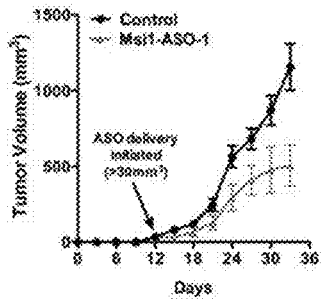

FIG. 8K
Impact on growth
of established tumors
In Vivo
(primary KPC cells)

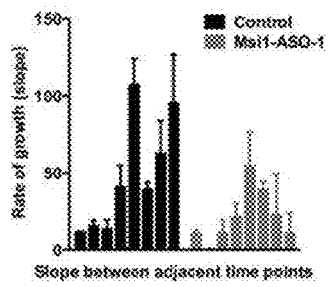

FIG. 8L
Rate of Tumor Growth
In Vivo
(primary KPC cells)

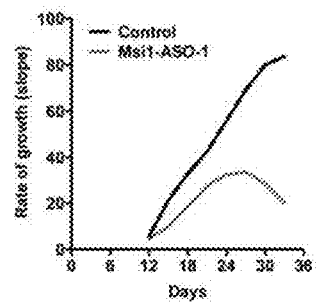

FIG. 8M
Best Fit Curve of
Rate of Tumor Growth
(primary KPC cells)

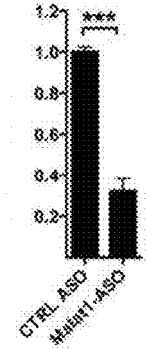

FIG. 8N
Systemic delivery of
optimized Malat ASO
(endogenous mouse
pancreatic tumor)

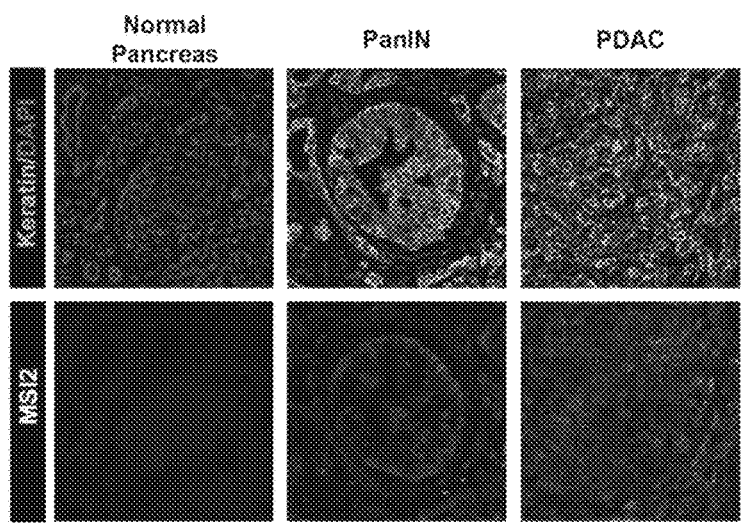
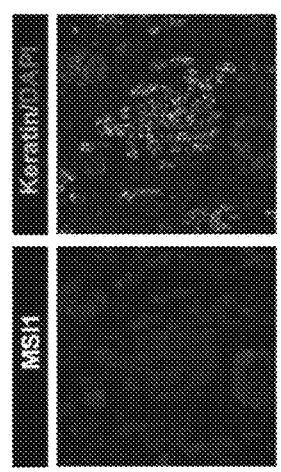
FIG. 9A
FIG. 9B
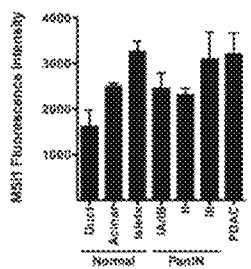
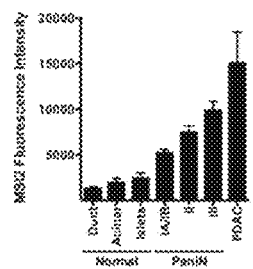
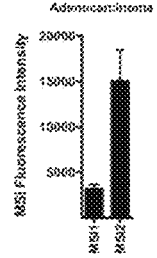
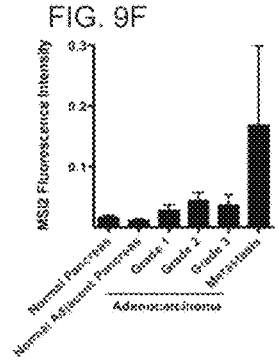
FIG. 9C
FIG. 9D
FIG. 9E
FIG. 9F
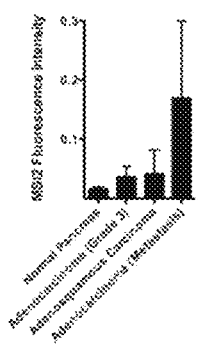
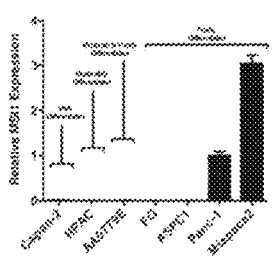
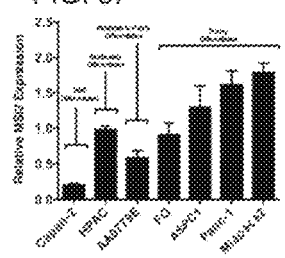
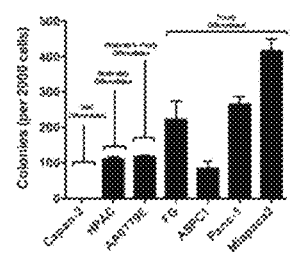
FIG. 9G
FIG. 9H
FIG. 9I
FIG. 9J

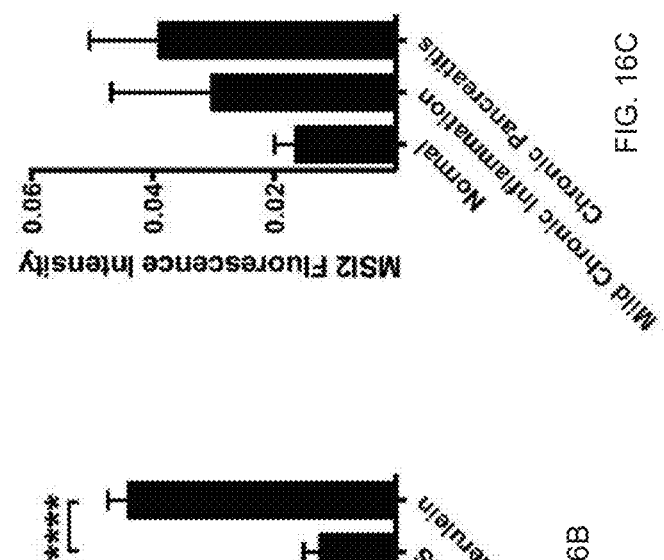
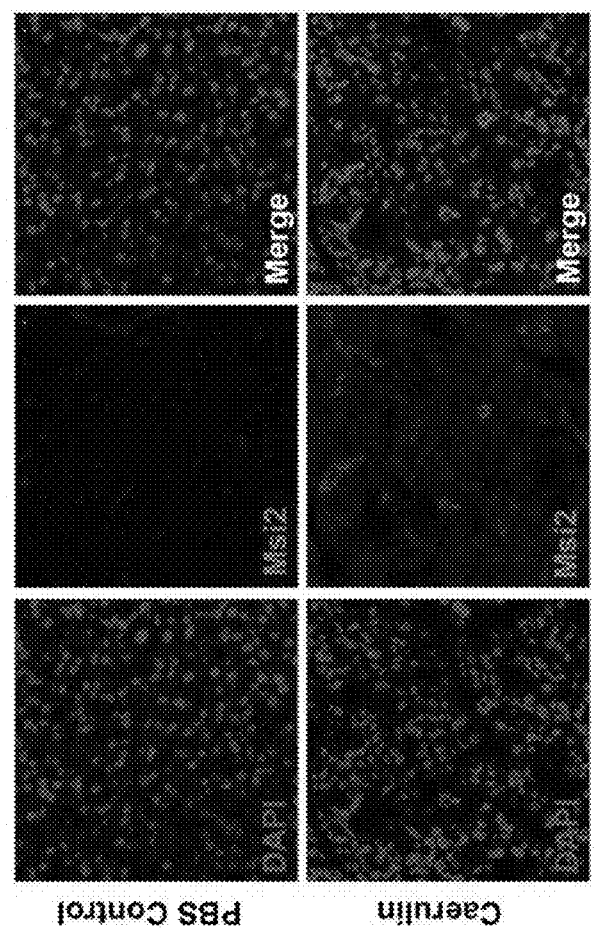
FIG. 16A
FIG. 16B
FIG. 16C

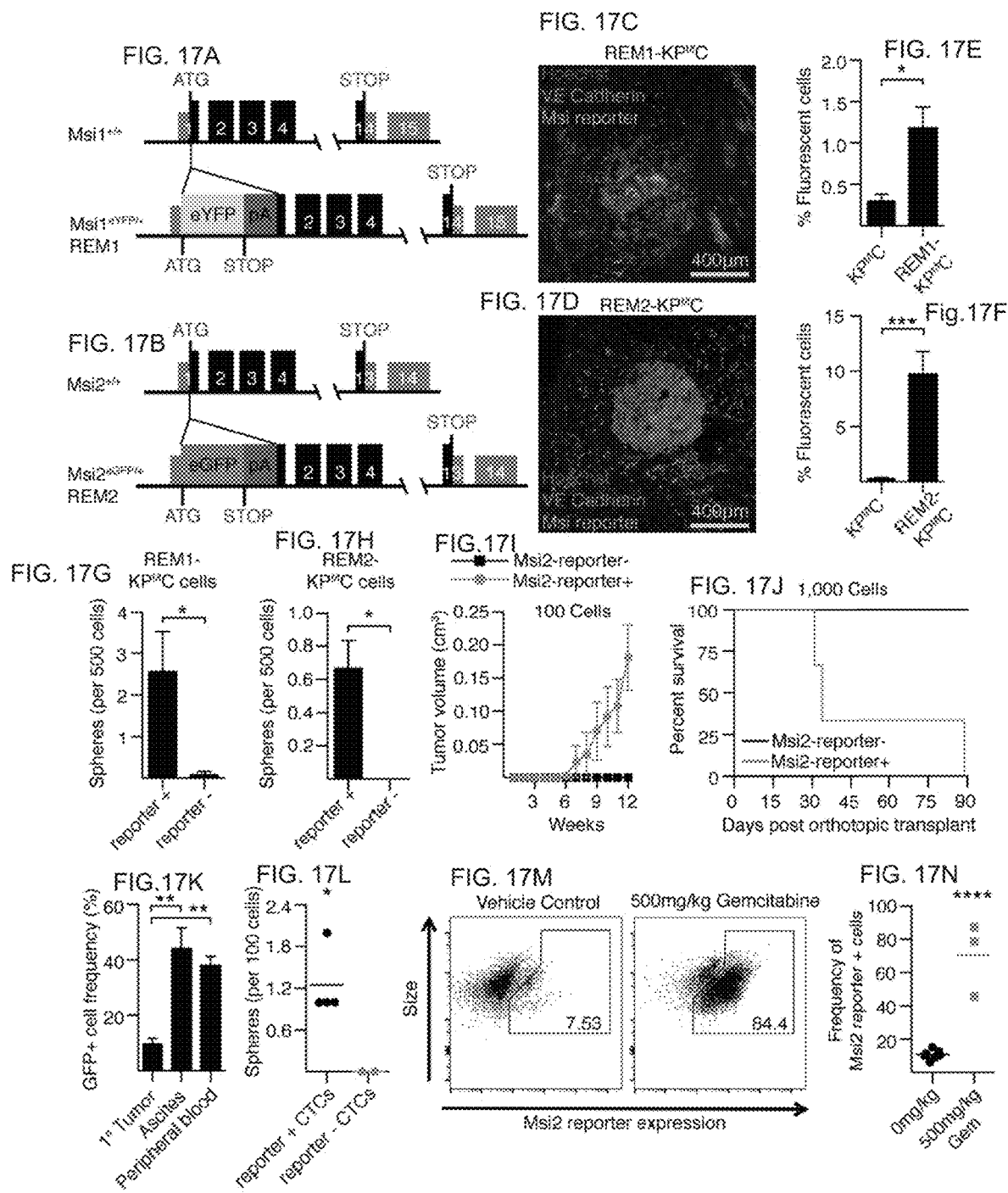

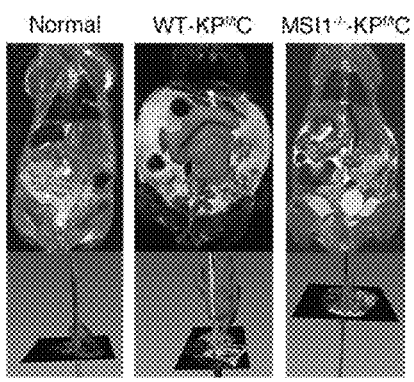
FIG. 18A
FIG. 18B
FIG. 18C
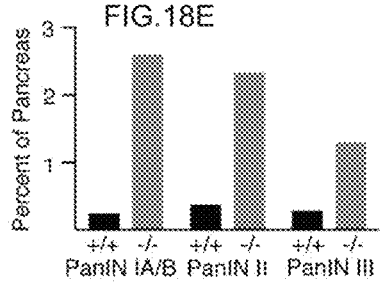
FIG. 18E
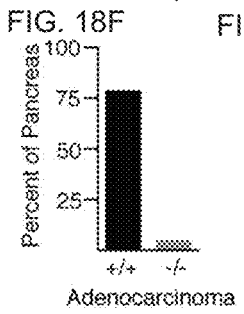
FIG. 18F
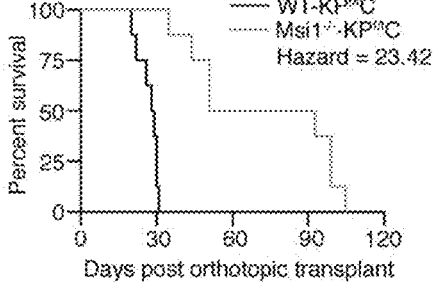
FIG. 18G
FIG. 18D
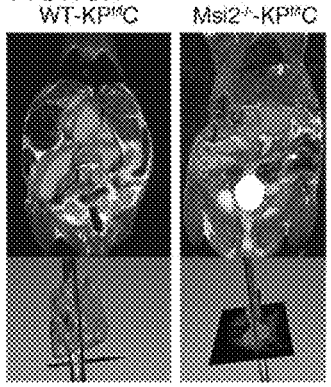
FIG. 18H
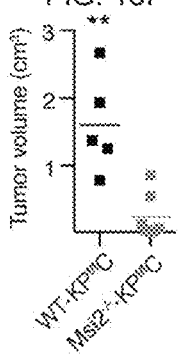
FIG. 18I
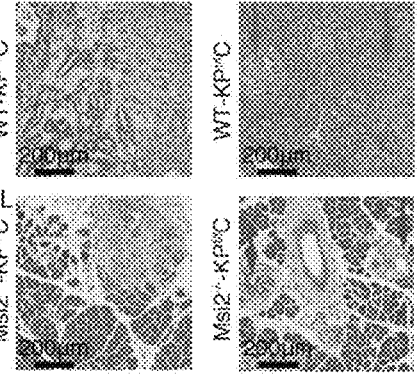
FIG. 18J  FIG. 18K
FIG. 18L  FIG. 18M
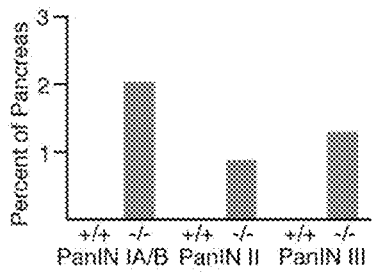
FIG. 18N
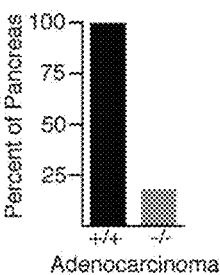
FIG. 18O
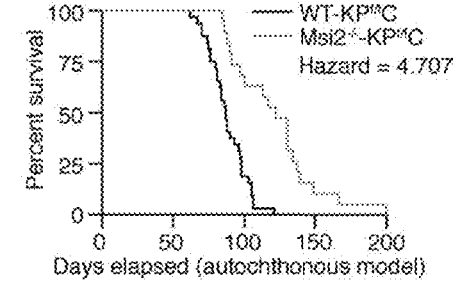
FIG. 18P

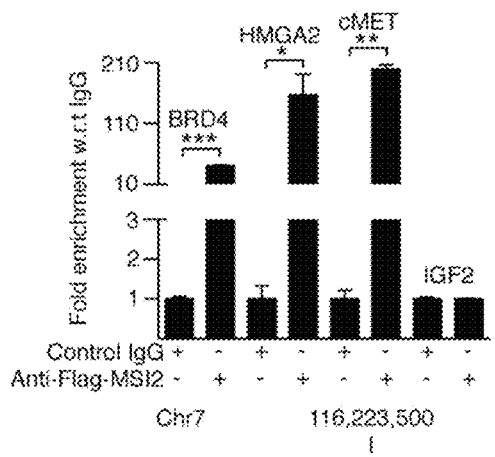
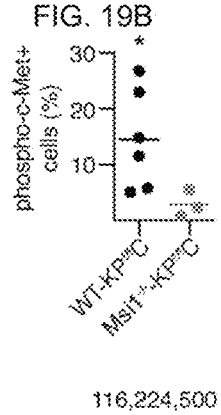
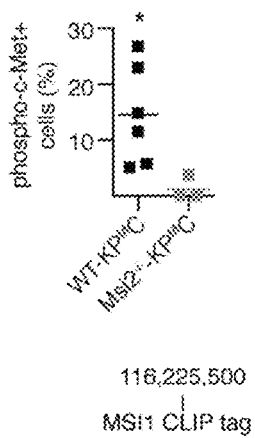
FIG. 19A
FIG. 19B
FIG. 19C
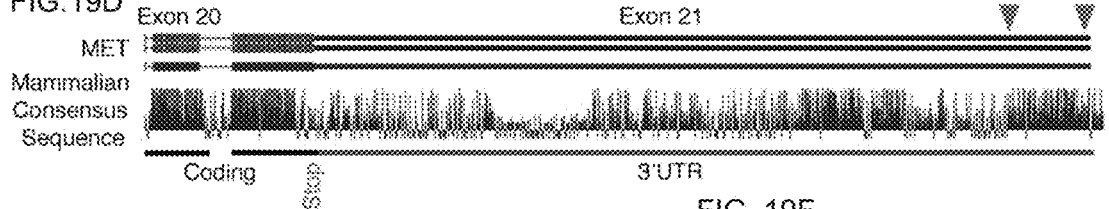
FIG. 19D
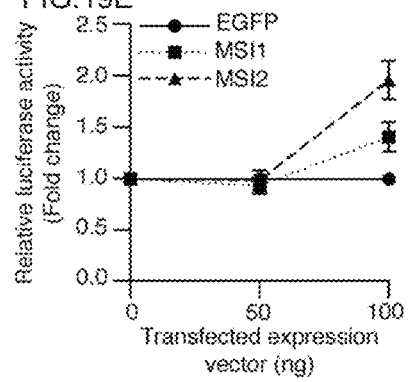
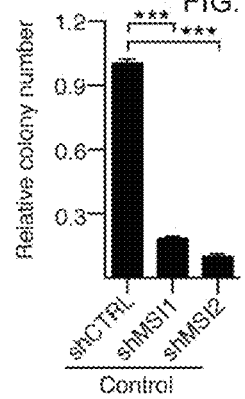
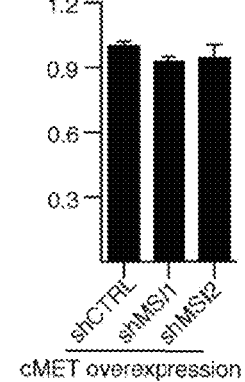
FIG. 19E
FIG. 19F
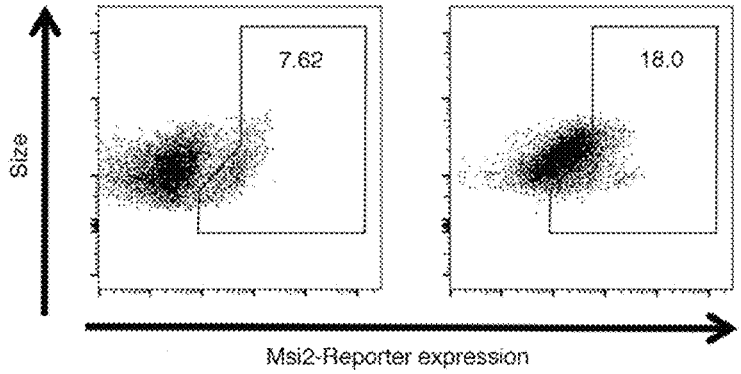
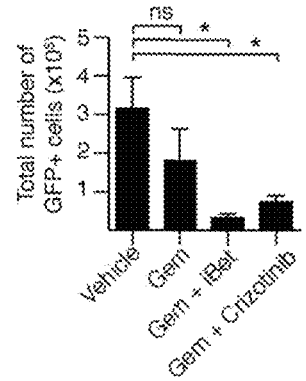
FIG. 19G
FIG. 19H

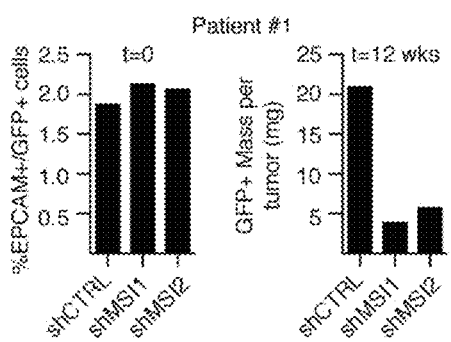
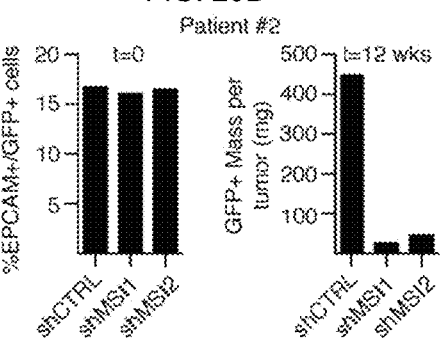
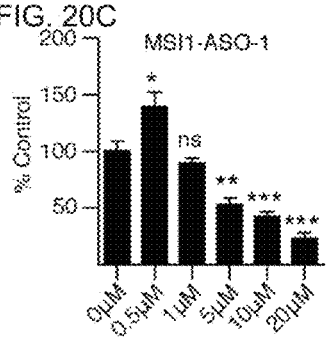
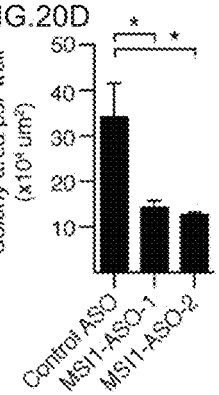
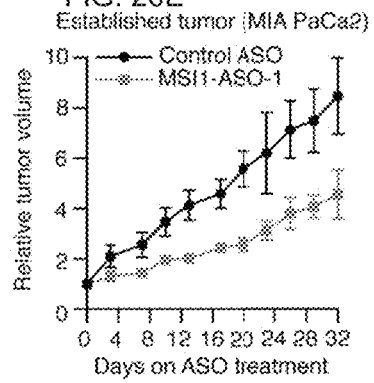
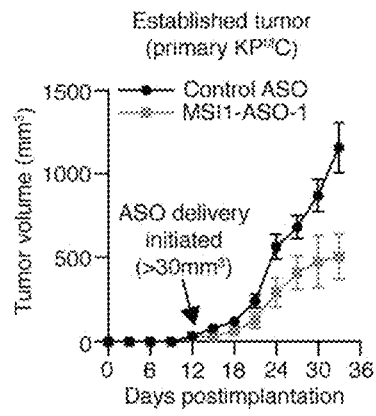
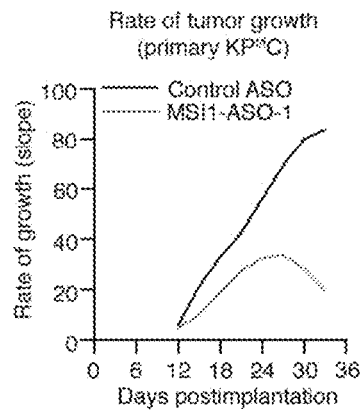
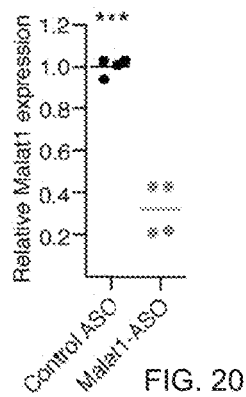

FIG. 22A
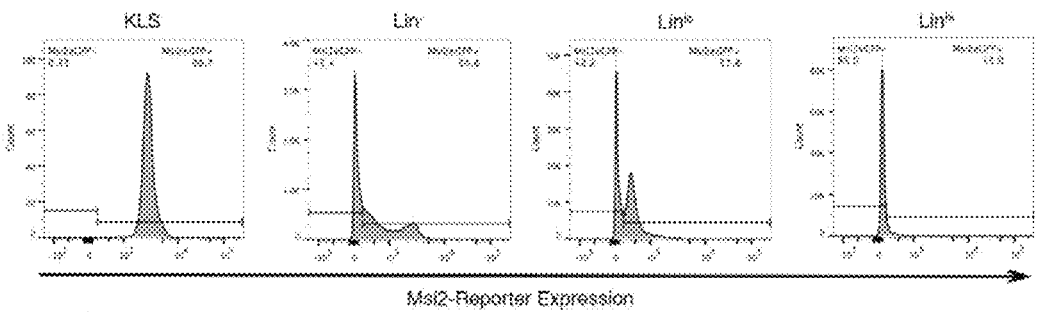
FIG. 22B
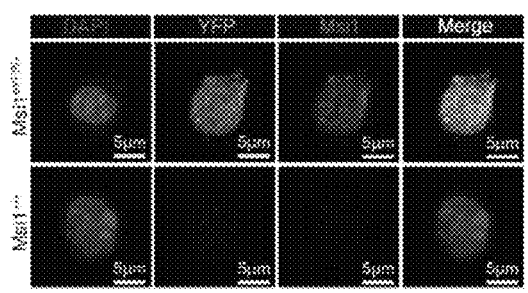
FIG. 22C
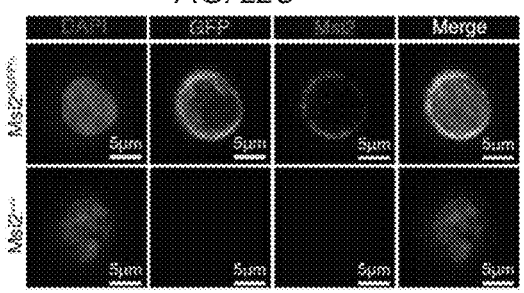
FIG. 22D
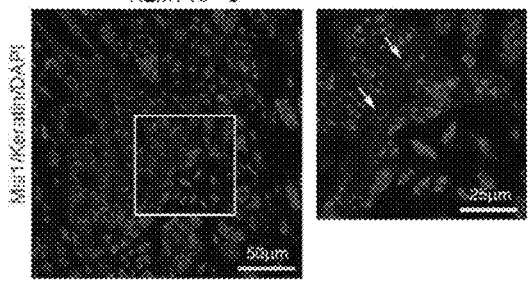
FIG. 22E
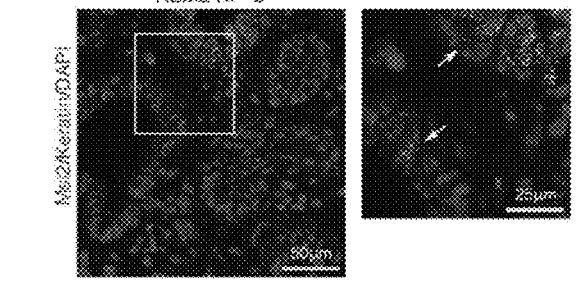
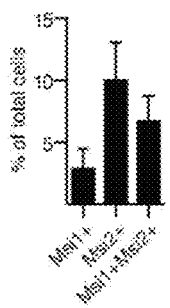
FIG. 22F
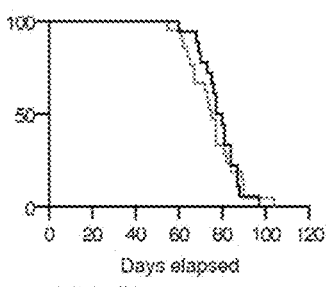
FIG. 22G
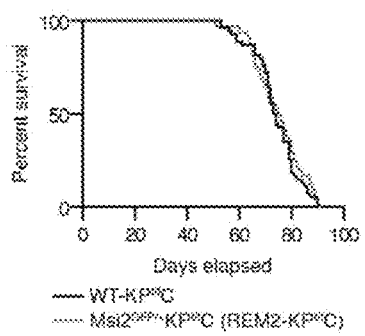
FIG. 22H
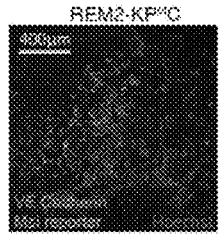
FIG. 22I

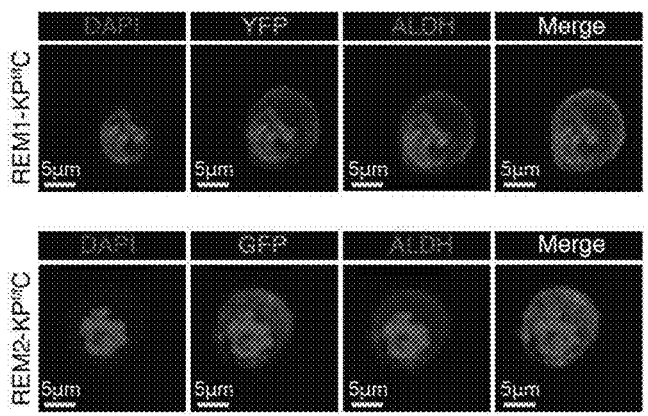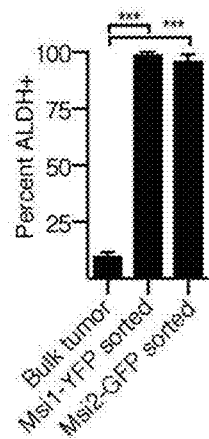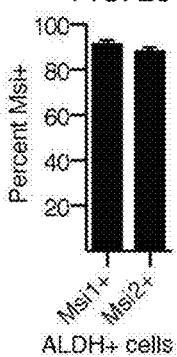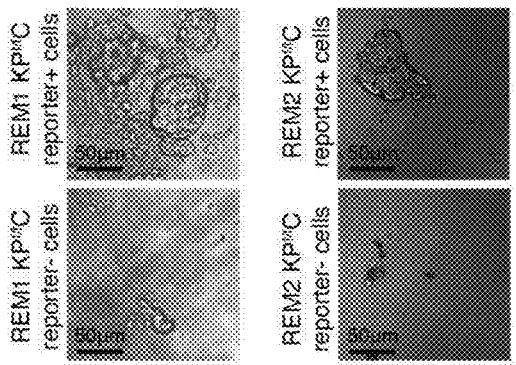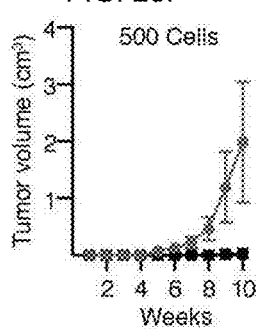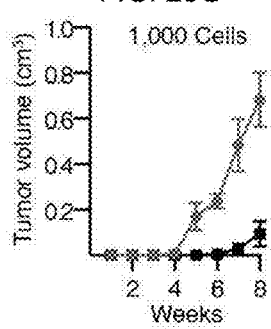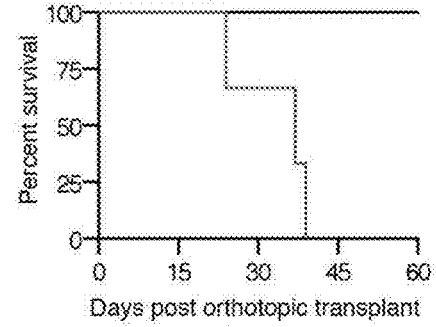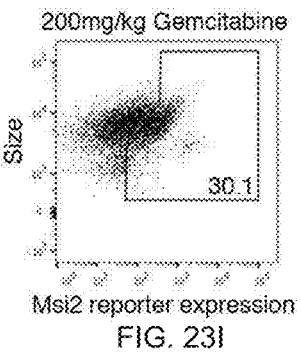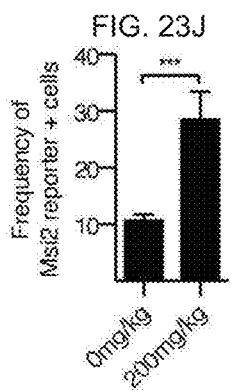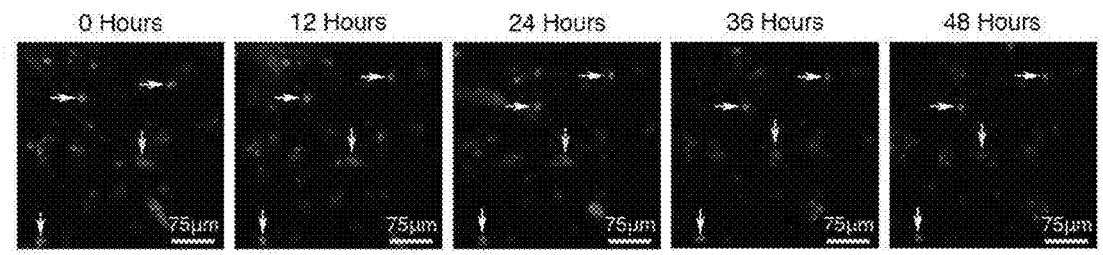

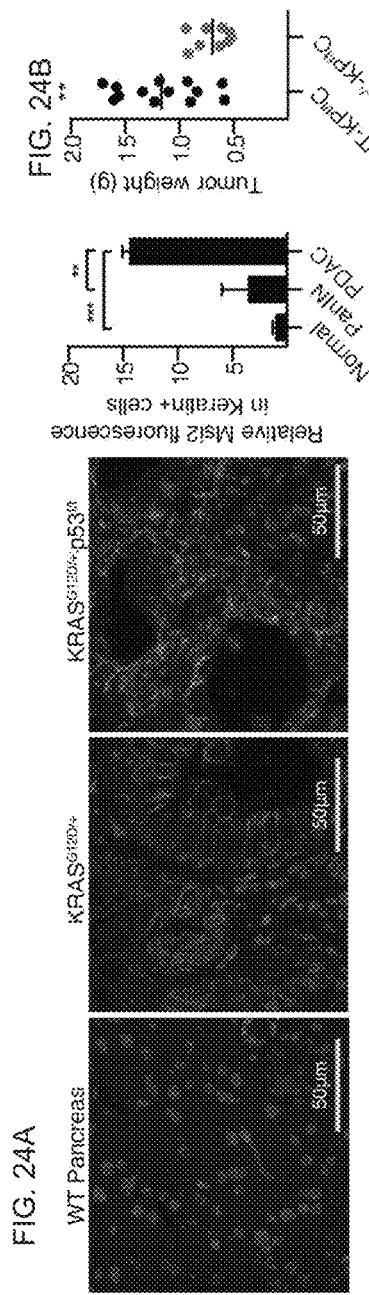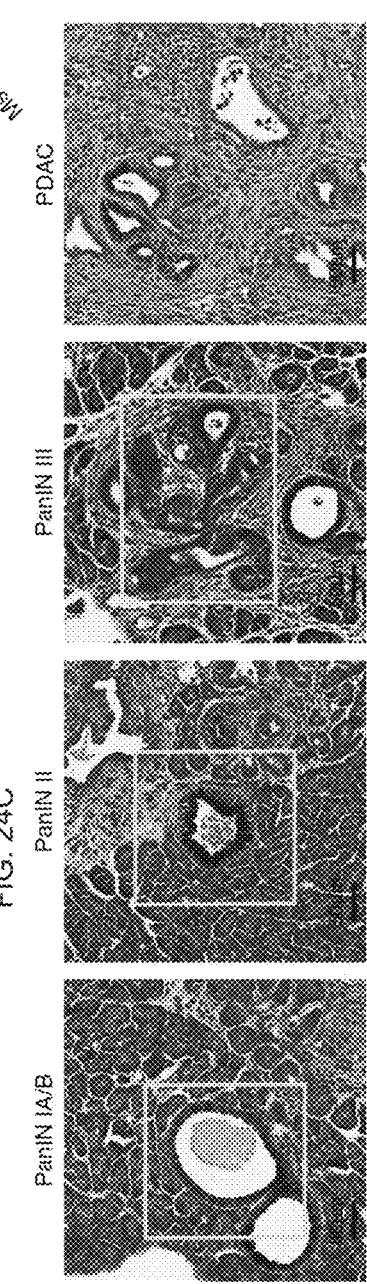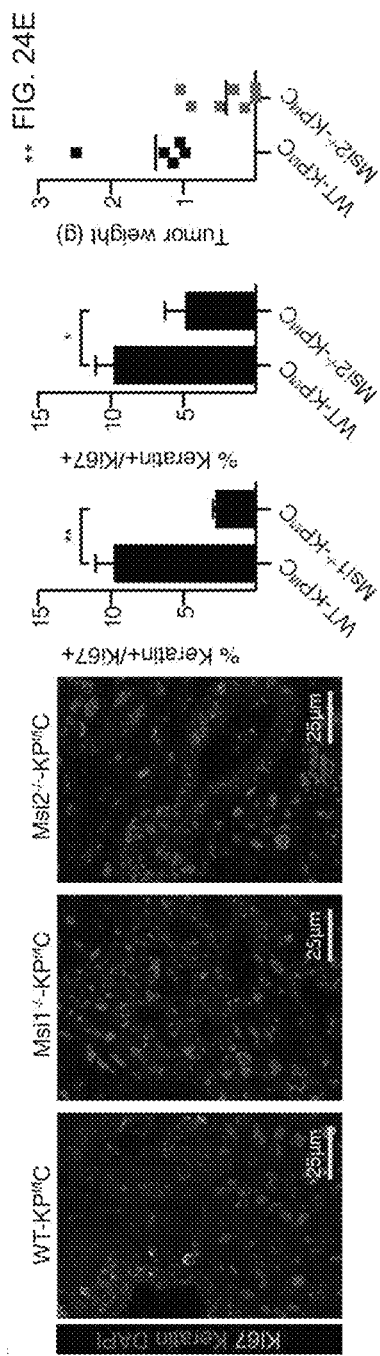
FIG. 24A  FIG. 24B  FIG. 24C  FIG. 24D  FIG. 24E

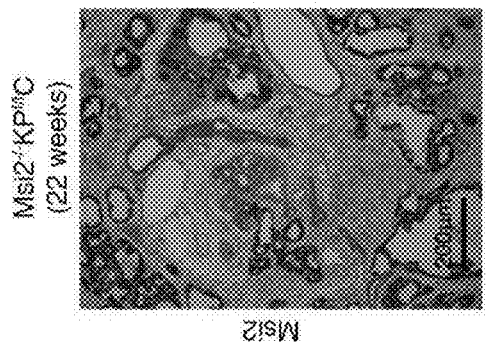
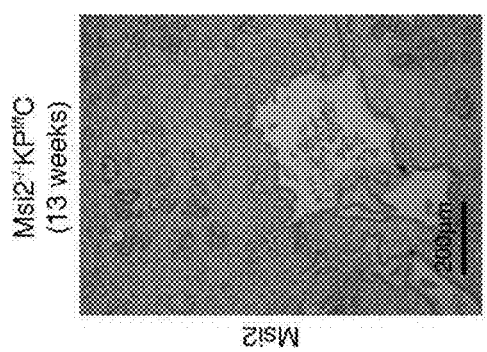
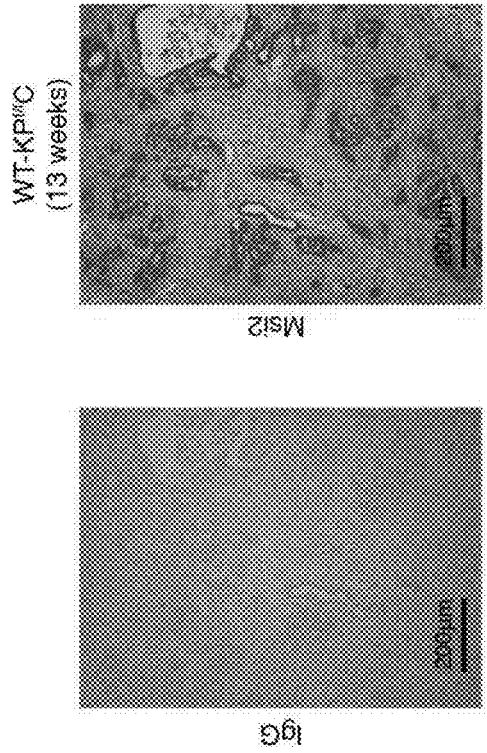
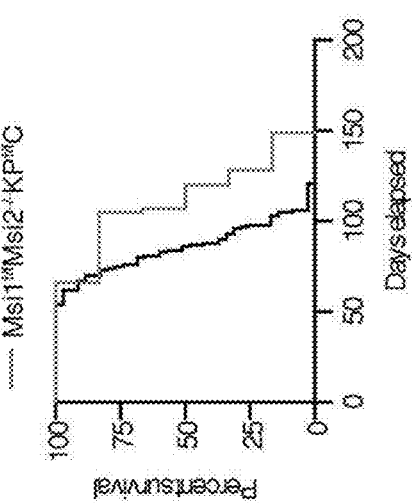
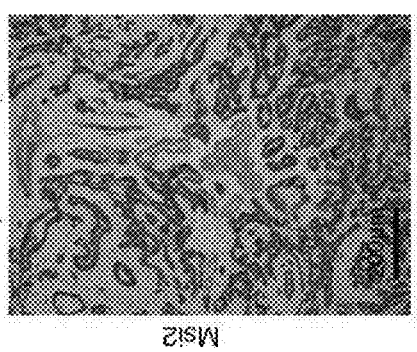
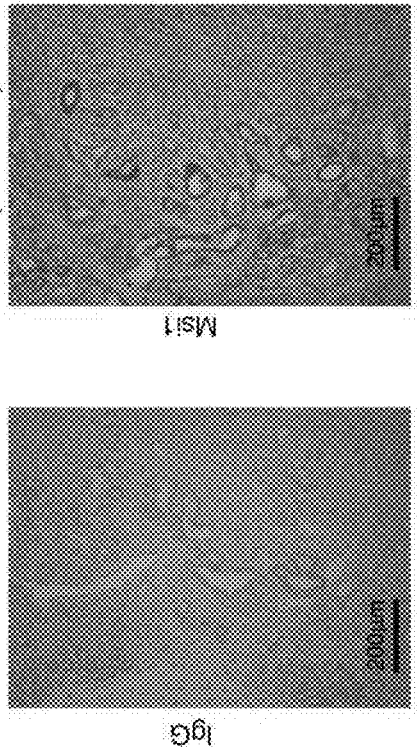

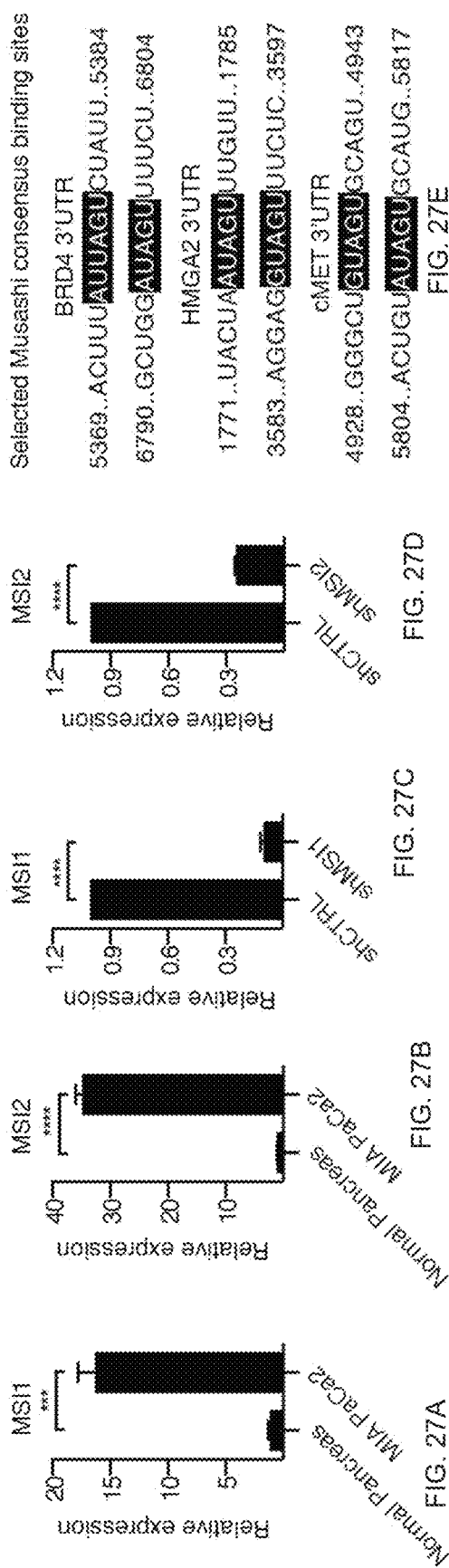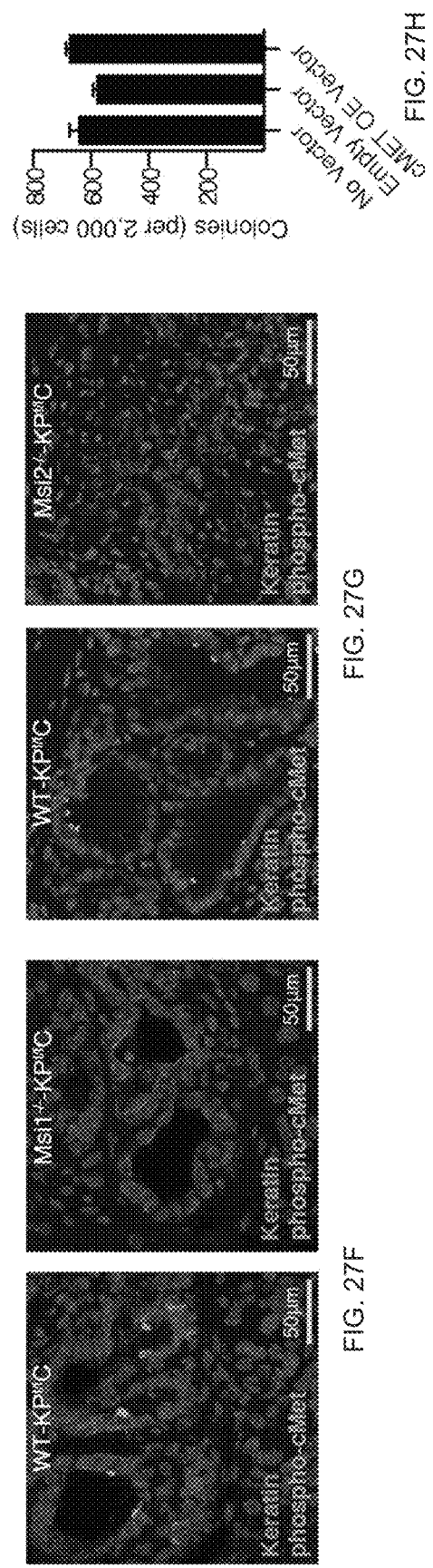

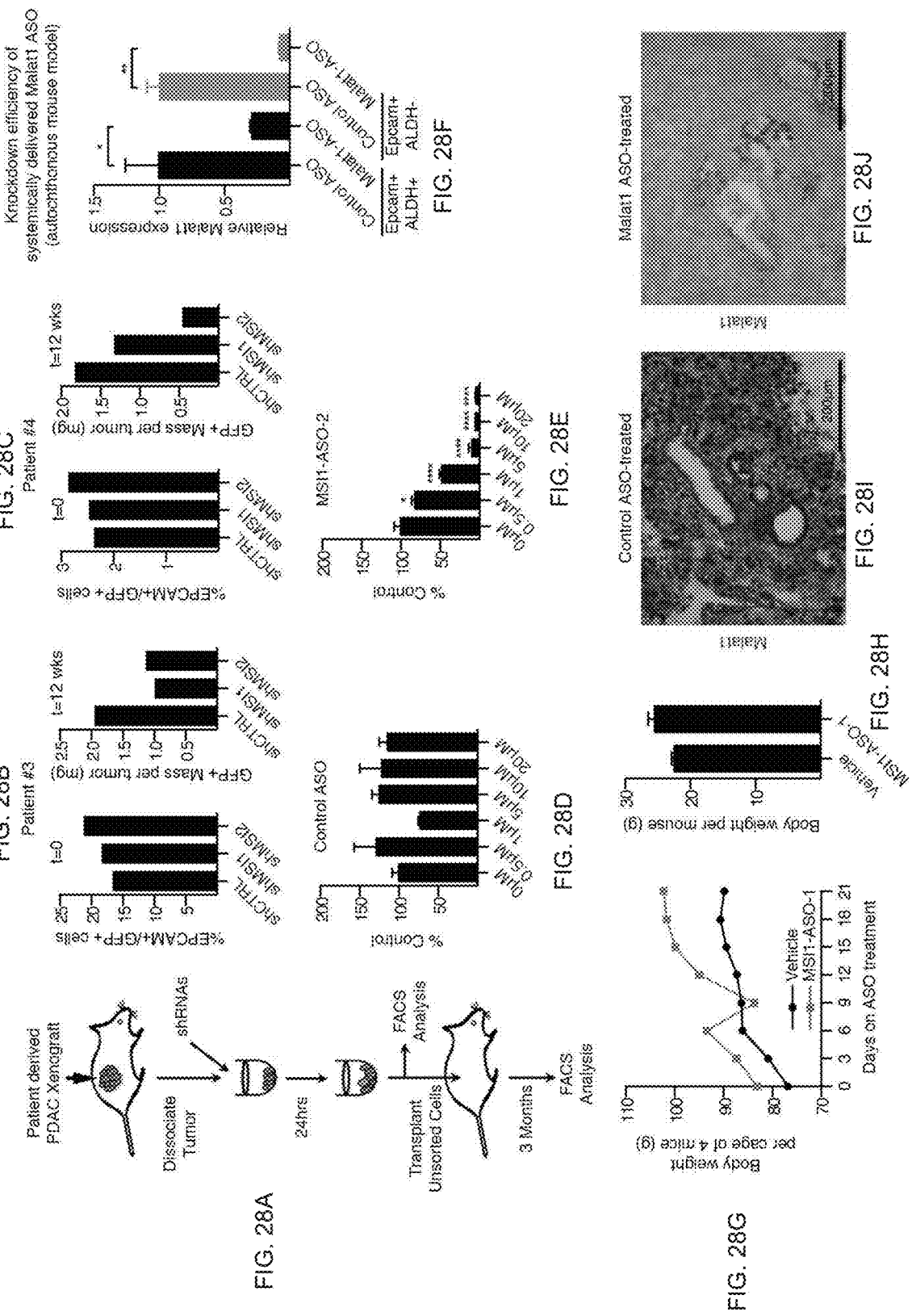

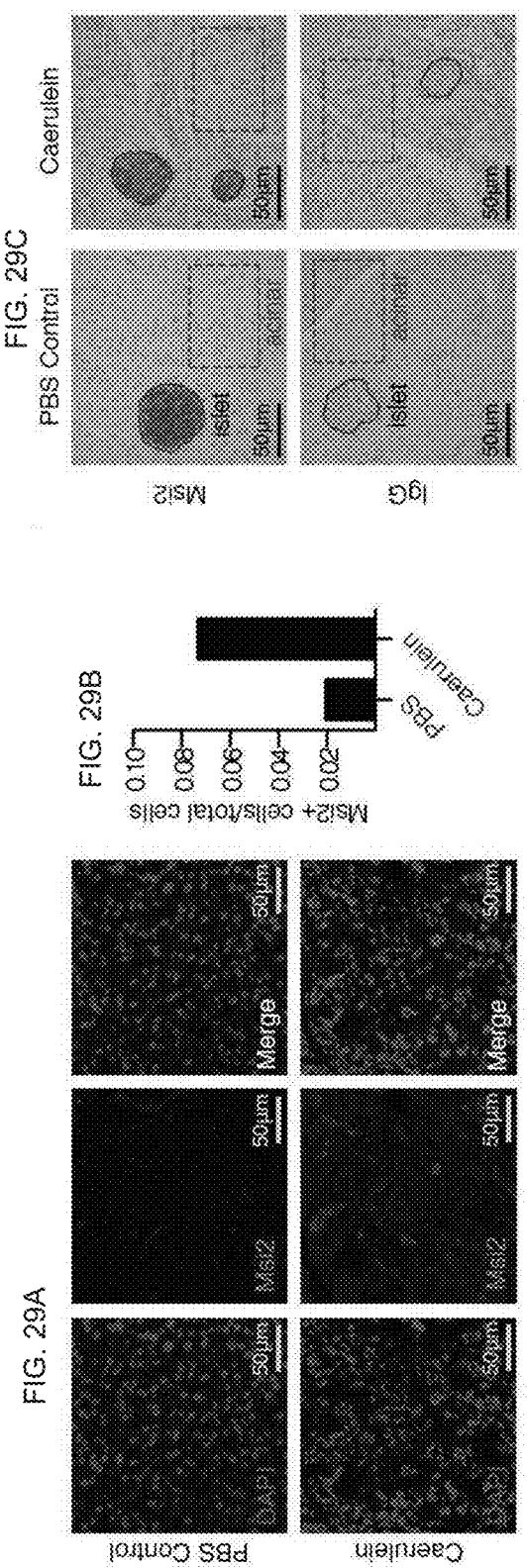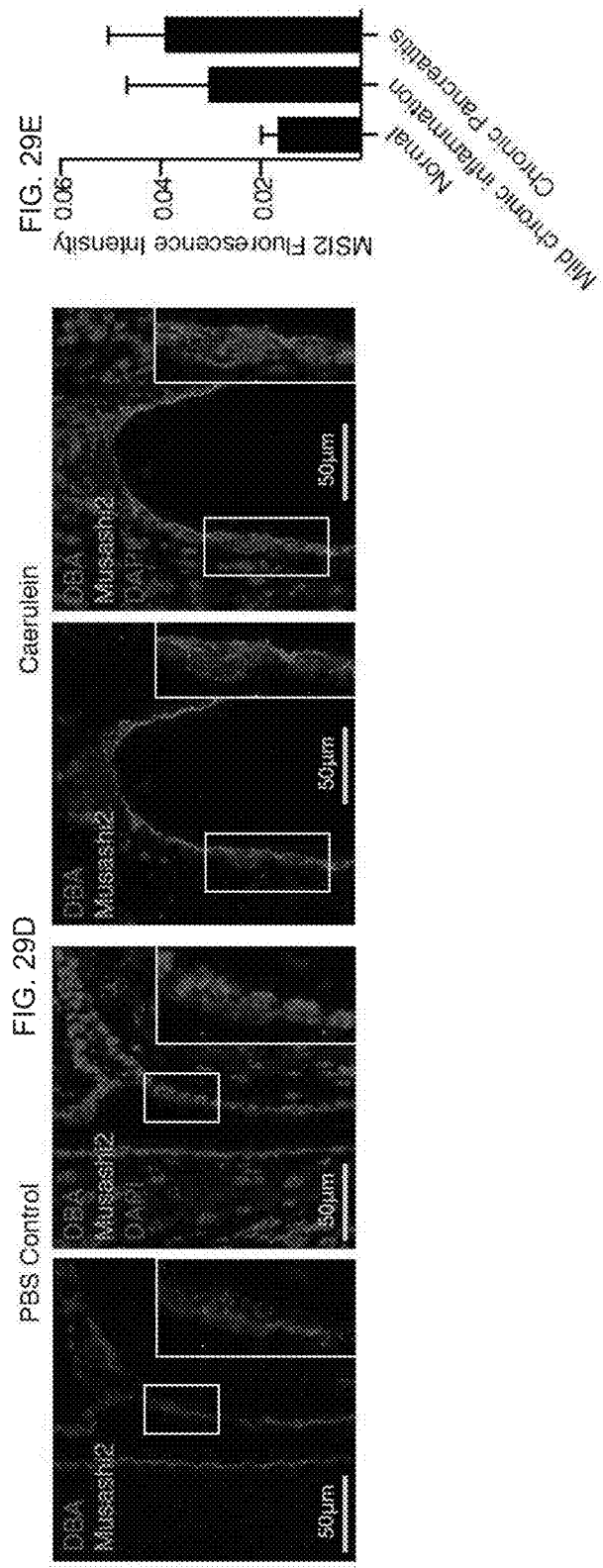

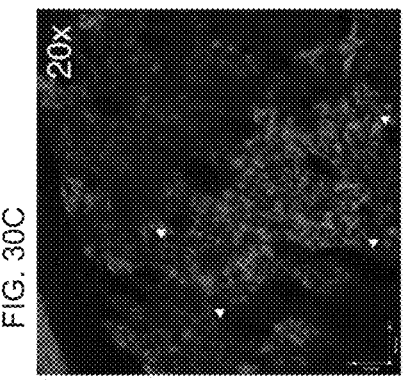
FIG. 30C
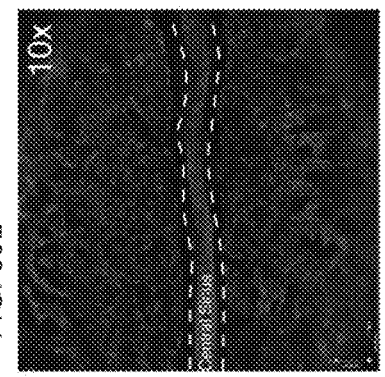
FIG. 30B
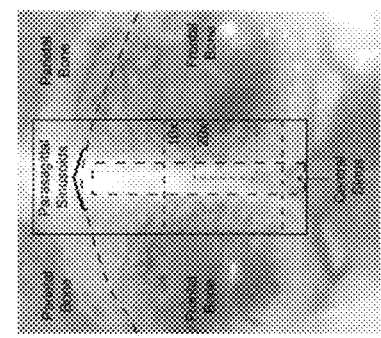
FIG. 30A
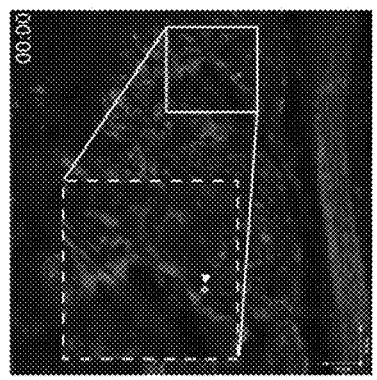
FIG. 30D
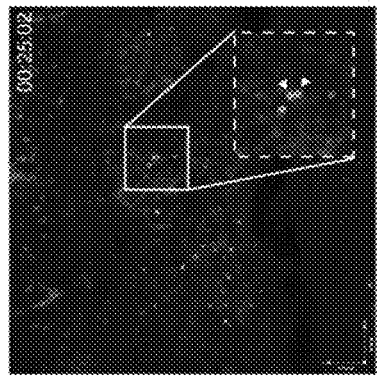
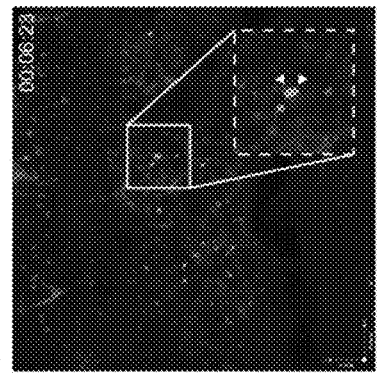
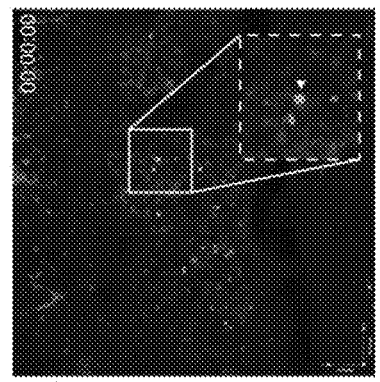
FIG. 30E

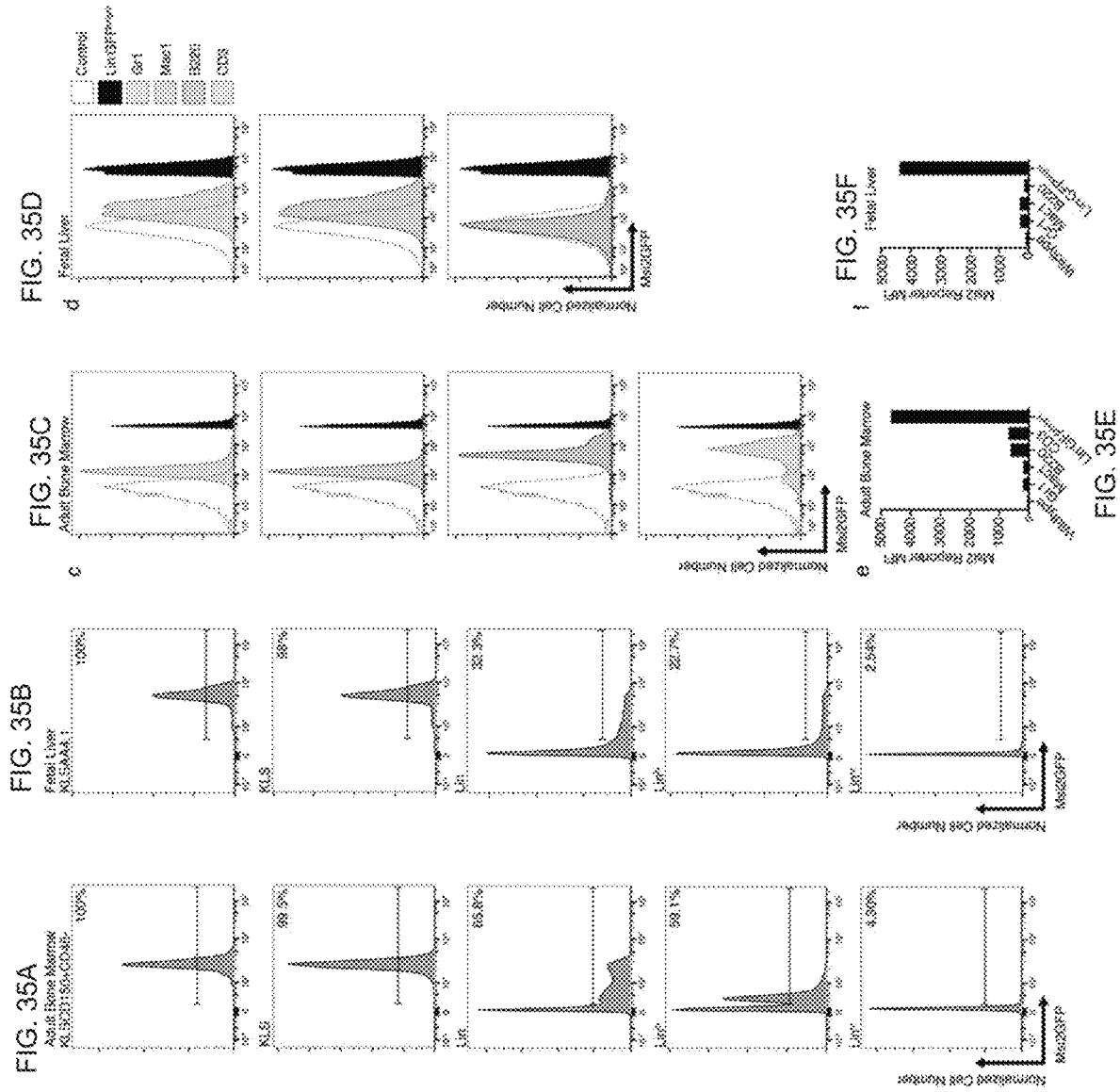

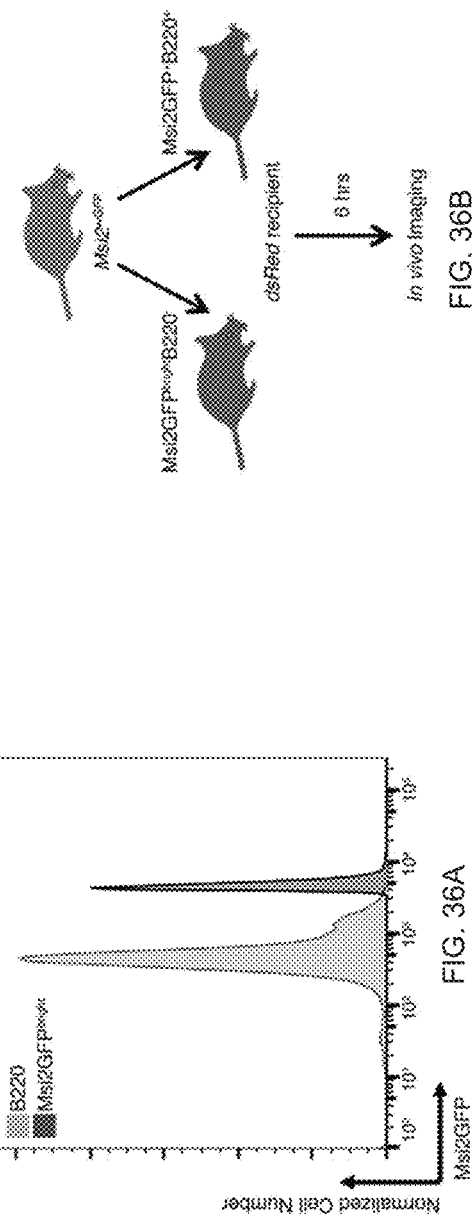
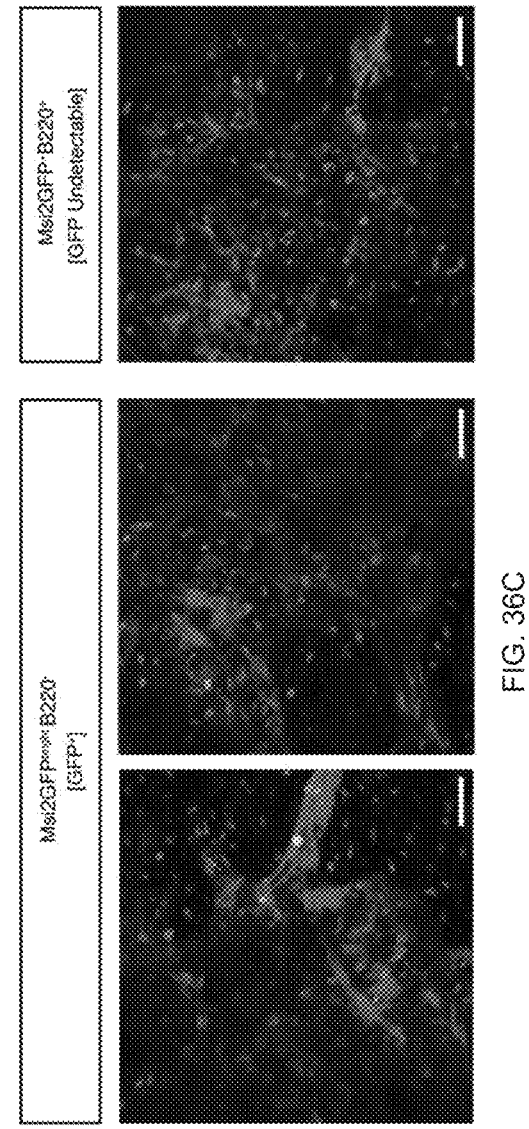
FIG. 36A
FIG. 36B
FIG. 36C

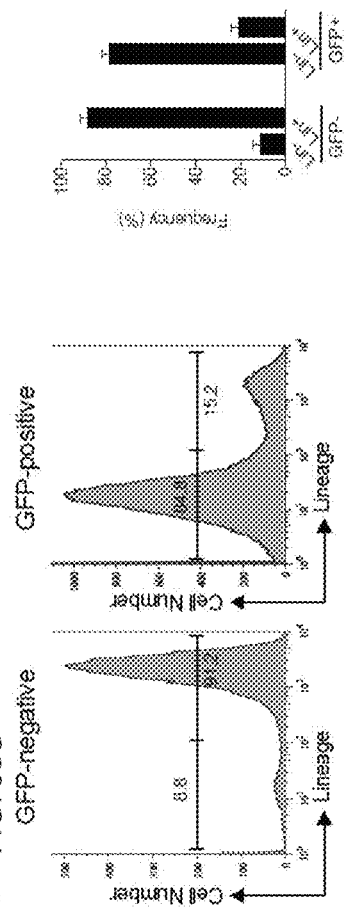
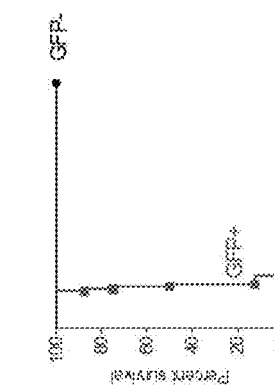
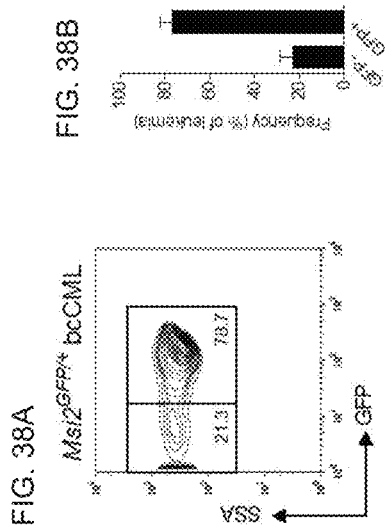
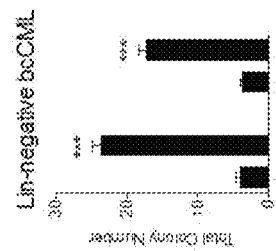
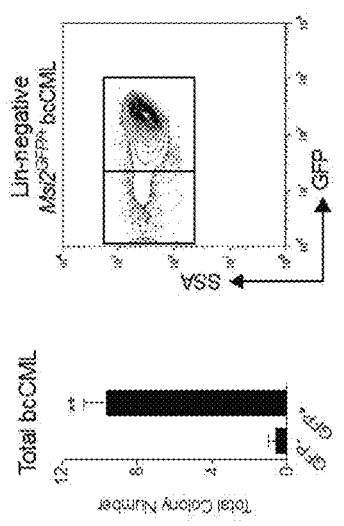

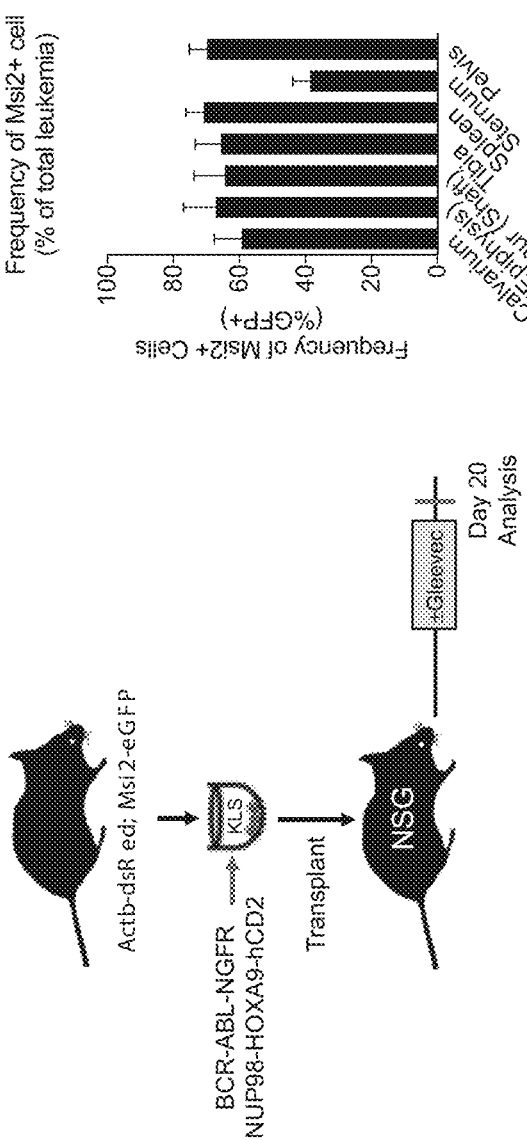
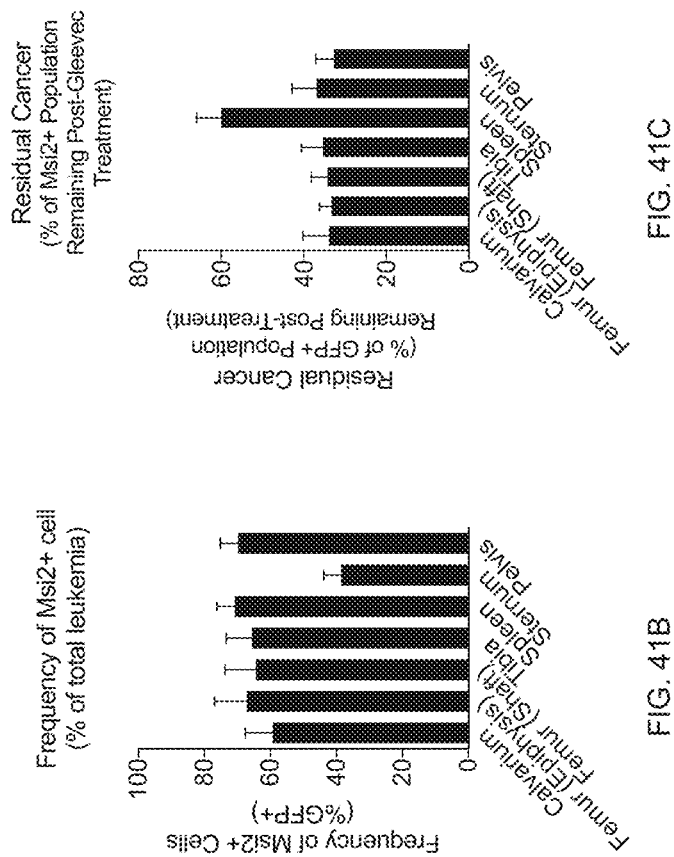
FIG. 41C
FIG. 41B
FIG. 41A

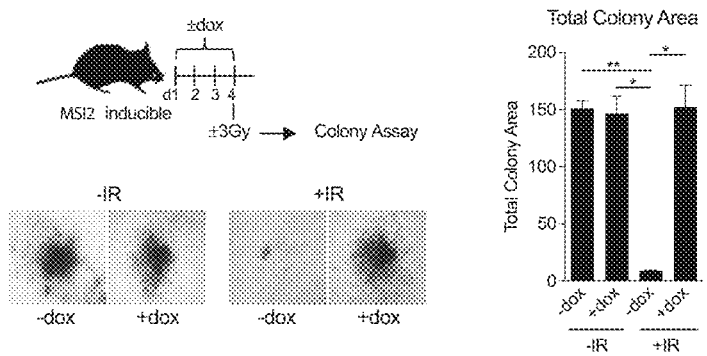
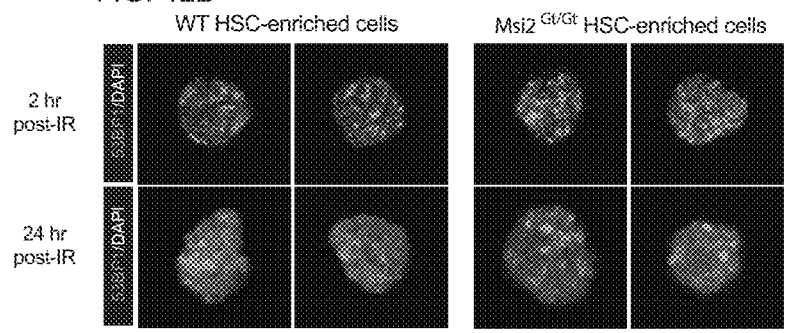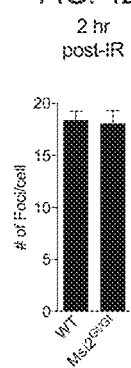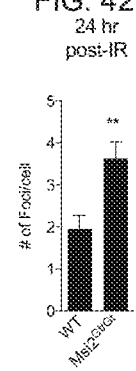
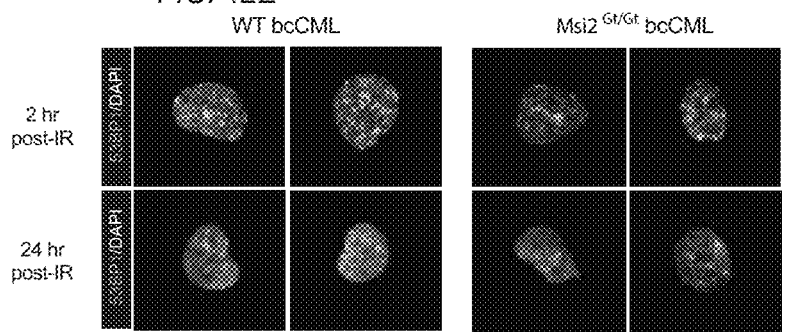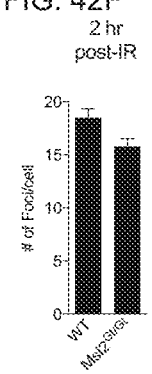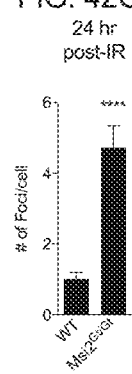

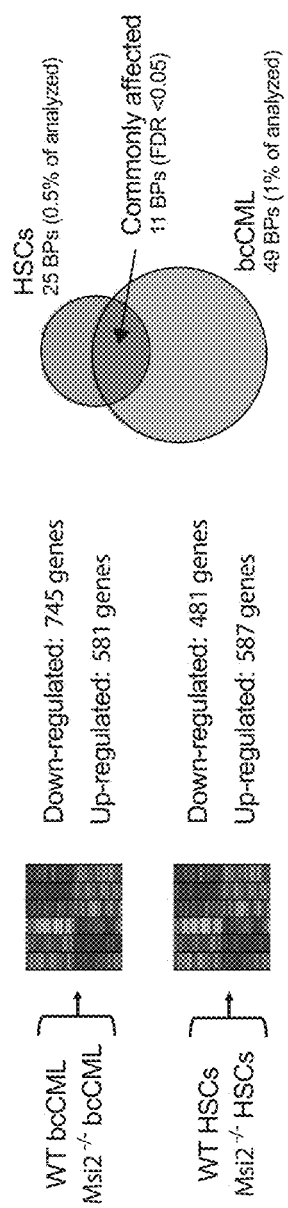
FIG. 44A
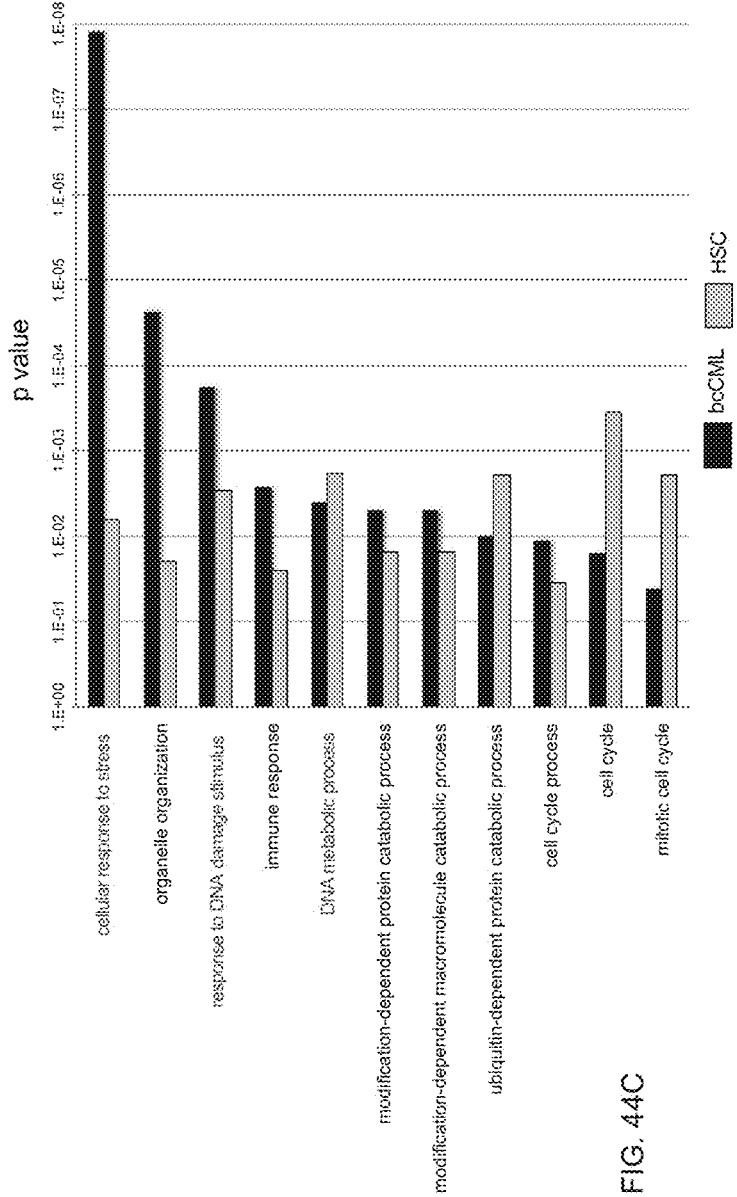
FIG. 44B
FIG. 44C

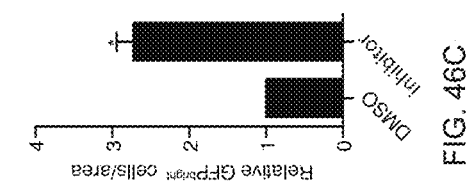
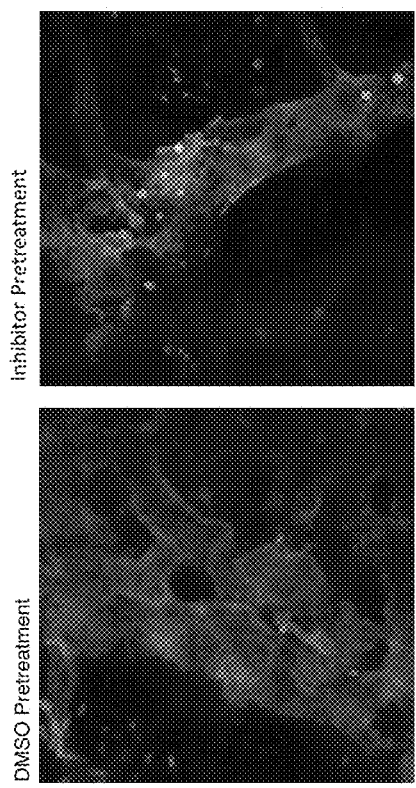
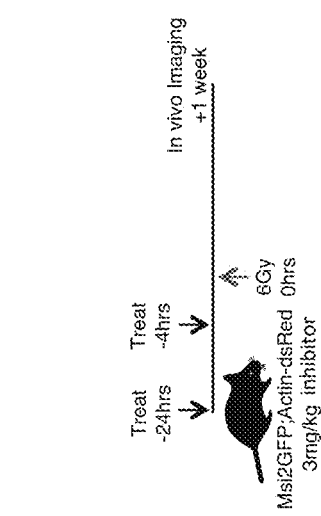
FIG. 46A
FIG. 46B
FIG. 46C

Aerial View

Side View

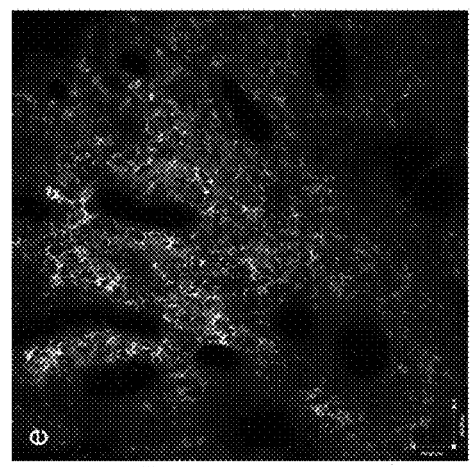
FIG. 48A
FIG. 48B
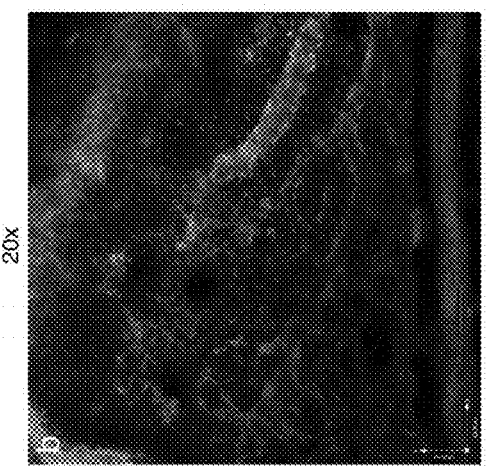
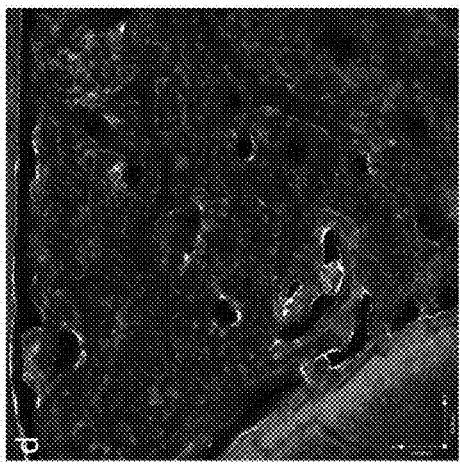
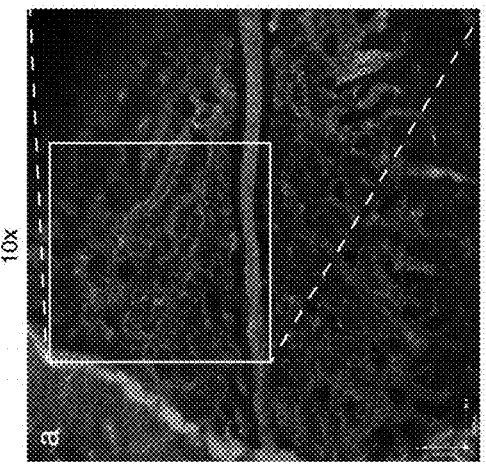
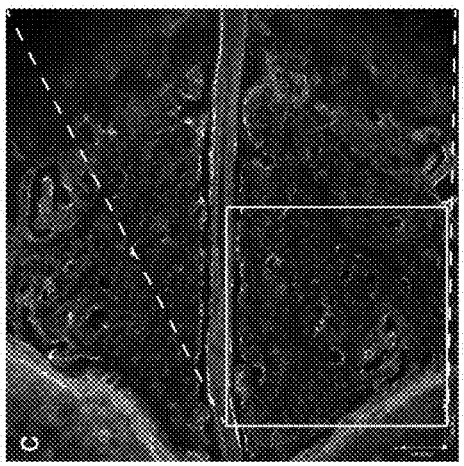

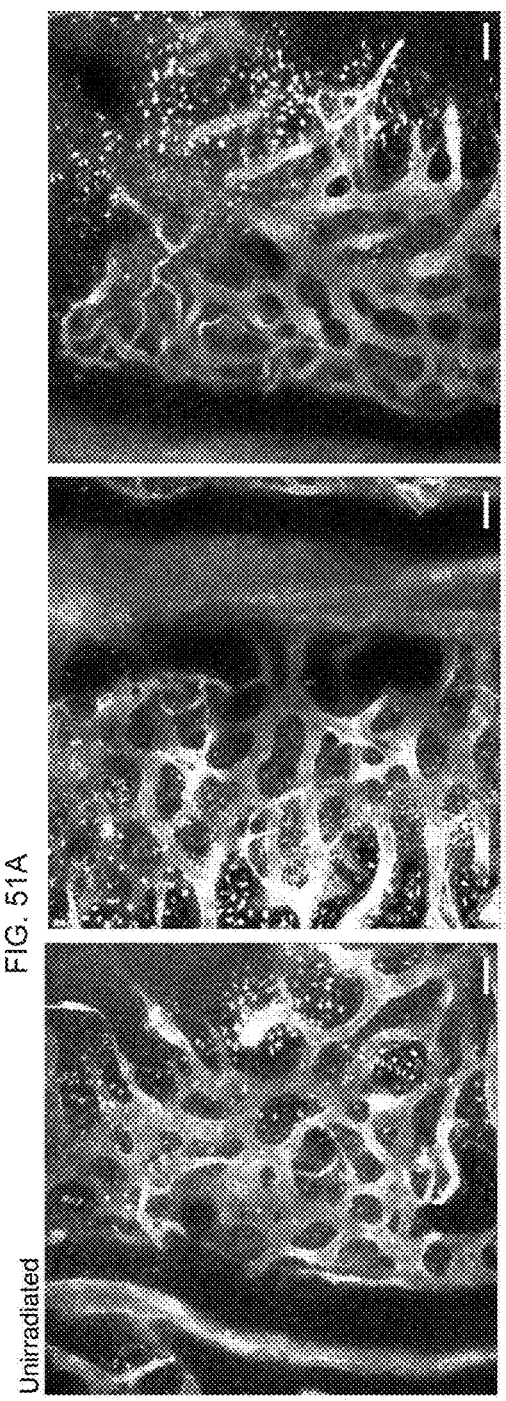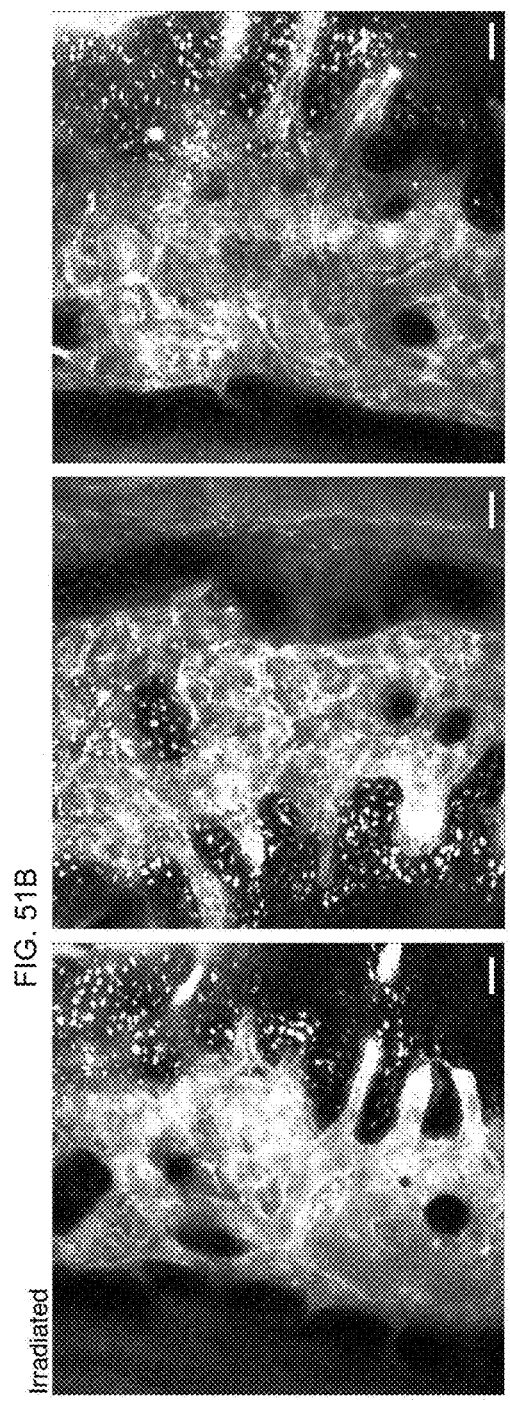
FIG. 51A  Unirradiated
FIG. 51B  Irradiated

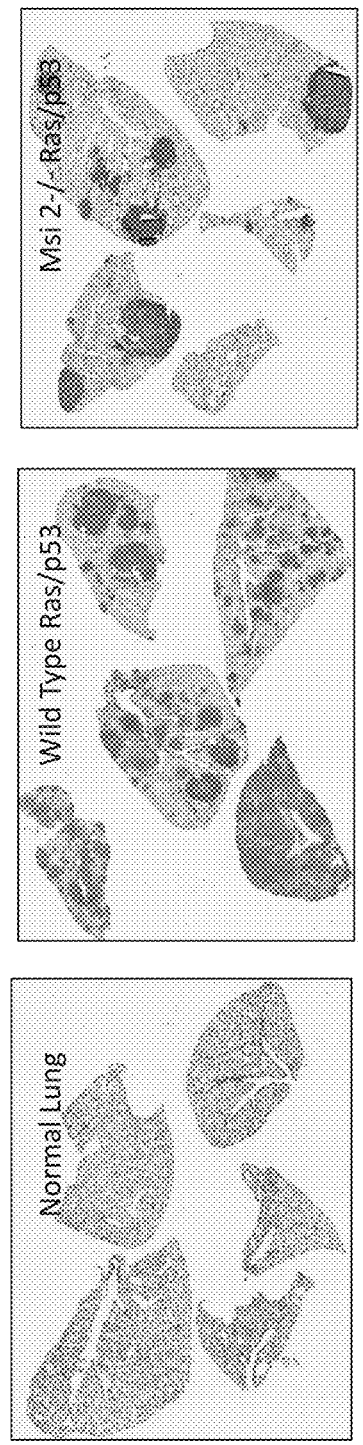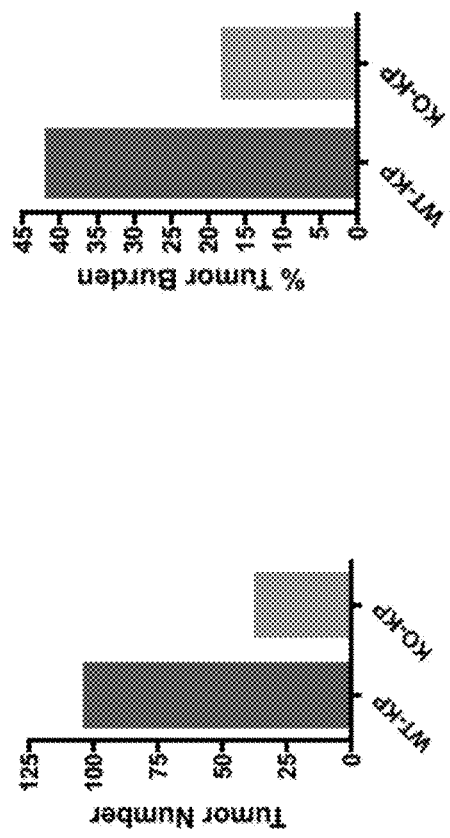
Figure. 53

US 10,578,608 B1

TOOLS TO DETECT, TRACK AND TARGET CANCER CELLS IN VIVO

CROSS-REFERENCED TO RELATED APPLICATIONS

The present application claims priority to U.S. Provisional Application Ser. No. 62/242,190, entitled "Tools To Detect, Track And Target Cancer Cells In Vivo" filed Oct. 15, 2015, the contents of which are hereby expressly incorporated by reference in their entirety.

STATEMENT REGARDING FEDERALLY SPONSORED R&D

This invention was made with government support under CA017442 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled UCSD095.001A.TXT, created Oct. 13, 2016, which is 7 Kb in size. The information in the electronic format of the Sequence Listing is incorporated herein by reference in its entirety.

REFERENCE TO COLOR DRAWINGS

The patent of application file contains at least one drawing executed in color. Copies of this patent or patent application publication with color drawings will be provided by the Office upon request and payment of the necessary fee.

BACKGROUND OF THE INVENTION

Field of the Invention

Some embodiments described herein include a genetically engineered cell comprising a nucleic acid encoding a detectable polypeptide operably linked to the Msi1 or Msi2 promoter and genetically engineered organisms comprising these genetically engineered cells.

Description of the Related Art

Detection of drug resistant residual disease is currently a major technical challenge since the cells can hide in low numbers at any spatial location and cannot always be detected in blood draws or aspirates. This residual disease, while dormant for long periods, can reinitiate tumor growth and lead to disease relapse.

Currently, there is no reliable way to visualize and track cancer stem cells and therapy resistant cancer cells in vivo. Moreover, there is a need for the development of methods to specifically target drug resistant residual disease, and to detect cancers at earlier stages. To this end, the compositions and methods provided herein provide valuable resources that can be used for a wide variety of applications, including, for example, to identify and track drug resistant cells in drug development (which would provide a powerful and sophisticated complement to traditional screens that usually assess de-bulking), to develop strategies aimed at identifying the spatial location of therapy resistant cancer cells (which could allow regional targeting and minimize collateral damage in normal tissues), identify and radiosensitize resistant tumor cells (which could improve locoregional targeting and improve disease outcomes), and develop methods for early detection of cancer (which has the potential to dramatically improve survival rates).

SUMMARY OF THE INVENTION

Some embodiments are described in the following numbered paragraphs:

1. A genetically engineered cell comprising a nucleic acid encoding a detectable polypeptide operably linked to the Msi1 promoter.

2. The genetically engineered cell of Paragraph 1 wherein said nucleic acid encoding said detectable polypeptide is inserted into an exon of the Msi1 promoter such that said detectable polypeptide is expressed in a form which allows to be detected.

3. The genetically engineered cell of any one of Paragraphs 1 and 2, in which the level or activity of one or more oncogenic polypeptides has been increased.

4. The genetically engineered cell of any one of Paragraphs 1-3, wherein said one or more oncogenic polypeptides are associated with lung, adenocarcinoma, pancreatic cancer or leukemia.

5. The genetically engineered cell of any one of Paragraphs 1-4, wherein the level or activity of the Kras polypeptide has been increased.

6. The genetically engineered cell of any one of Paragraphs 1-5, wherein the level or activity of the BCR-ABL polypeptide has been increased.

7. The genetically engineered cell of any one of Paragraphs 1-6 wherein the level or activity of the Nup98-HoxA9 transactivator polypeptide has been increased.

8. The genetically engineered cell of any one of Paragraphs 1-7 wherein said cell comprises the KRASG12D allele.

9. The genetically engineered cell of any one of Paragraphs 5 or 8, wherein the Kras oncogene is under the control of the Ptf1a promoter.

10. The genetically engineered cell of any one of Paragraphs 1-9, wherein said cell comprises a genetic modification which reduces the level or activity of or inactivates one or more tumor suppressor proteins.

11. The genetically engineered cell of Paragraph 10, wherein said one or more tumor suppressor protein is selected from the group consisting of p53, p16/INK4A, and SMAD4.

12. The genetically engineered cell of any one of Paragraphs 10-12, wherein said tumor suppressor is encoded by a nucleic acid which can be conditionally deleted.

13. The genetically engineered cell of any one of Paragraphs 1-12, wherein the detectable polypeptide comprises a fluorescent polypeptide.

14. The genetically engineered cell of Paragraph 13, wherein said fluorescent polypeptide comprises eYFP or eGFP.

15. The genetically engineered cell of any one of Paragraphs 1-14, wherein said cell is capable of forming a tumor.

16. The genetically engineered cell of any one of Paragraphs 1-15, wherein said cell is a tumor stem cell.

17. A genetically engineered cell comprising a nucleic acid encoding a detectable polypeptide operably linked to the Msi2 promoter.

18. The genetically engineered cell of Paragraph 17 wherein said nucleic acid encoding said detectable polypeptide is inserted into an exon of the Msi2 promoter such that said detectable polypeptide is expressed in a form which allows to be detected.

19. The genetically engineered cell of any one of Paragraphs 17 or 18, in which the level or activity of one or more oncogenic polypeptides has been increased.

20. The genetically engineered cell of any one of Paragraphs 17-19, wherein said one or more oncogenic polypeptides are associated with lung, adenocarcinoma, pancreatic cancer or leukemia.

21. The genetically engineered cell of any one of Paragraphs 17-20, wherein the level or activity of the Kras polypeptide has been increased.

22. The genetically engineered cell of any one of Paragraphs 17-21, wherein the level or activity of the BCR-ABL polypeptide has been increased.

23. The genetically engineered cell of any one of Paragraphs 17-22 wherein the level or activity of the Nup98-HoxA9 transactivator polypeptide has been increased.

24. The genetically engineered cell of any one of Paragraphs 17-23 wherein said cell comprises the KRASG12D allele.

25. The genetically engineered cell of any one of Paragraphs 21 or 24, wherein the Kras oncogene is under the control of the Ptf1a promoter.

26. The genetically engineered cell of any one of Paragraphs 17-25, wherein said cell comprises a genetic modification which reduces the level or activity of or inactivates one or more tumor suppressor proteins.

27. The genetically engineered cell of Paragraph 26, wherein said one or more tumor suppressor protein is selected from the group consisting of p53, p16/INK4A, and SMAD4.

28. The genetically engineered cell of any one of Paragraphs 27 or 28, wherein said tumor suppressor is encoded by a nucleic acid which can be conditionally deleted.

29. The genetically engineered cell of any one of Paragraphs 17-28, wherein the detectable polypeptide comprises a fluorescent polypeptide.

30. The genetically engineered cell of Paragraph 29, wherein said fluorescent polypeptide comprises eYFP or eGFP.

31. The genetically engineered cell of any one of Paragraphs 17-30, wherein said cell is capable of forming a tumor.

32. The genetically engineered cell of any one of Paragraphs 17-31, wherein said cell is a tumor stem cell.

33. A genetically engineered cell comprising a first nucleic acid encoding a first detectable polypeptide operably linked to the Msi1 promoter and a second nucleic acid encoding a second detectable polypeptide operably linked to the Msi2 promoter.

34. The genetically engineered cell of Paragraph 33 wherein said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected.

35. The genetically engineered cell of any one of Paragraphs 33 or 34, in which the level or activity of one or more oncogenic polypeptides has been increased.

36. The genetically engineered cell of any one of Paragraphs 33-35, wherein said one or more oncogenic polypeptides are associated with lung, adenocarcinoma, pancreatic cancer or leukemia.

37. The genetically engineered cell of any one of Paragraphs 33-36, wherein the level or activity of the Kras polypeptide has been increased.

38. The genetically engineered cell of any one of Paragraphs 33-37, wherein the level or activity of the BCR-ABL polypeptide has been increased.

39. The genetically engineered cell of any one of Paragraphs 33-38 wherein the level or activity of the Nup98-HoxA9 transactivator polypeptide has been increased.

40. The genetically engineered cell of any one of Paragraphs 33-39 wherein said cell comprises the KRASG12D allele.

41. The genetically engineered cell of any one of Paragraphs 37 or 40, wherein the Kras oncogene is under the control of the Ptf1a promoter.

42. The genetically engineered cell of any one of Paragraphs 33-41, wherein said cell comprises a genetic modification which reduces the level or activity of or inactivates one or more tumor suppressor proteins.

43. The genetically engineered cell of Paragraph 42, wherein said one or more tumor suppressor protein is selected from the group consisting of p53, p16/INK4A, and SMAD4.

44. The genetically engineered cell of any one of Paragraphs 42 or 43, wherein said tumor suppressor is encoded by a nucleic acid which can be conditionally deleted.

45. The genetically engineered cell of any one of Paragraphs 33-44, wherein at least one of the first detectable polypeptide and the second detectable polypeptide comprises a fluorescent polypeptide.

46. The genetically engineered cell of Paragraph 45, wherein said fluorescent polypeptide comprises eYFP or eGFP.

47. The genetically engineered cell of any one of Paragraphs 33-46, wherein said cell is capable of forming a tumor.

48. The genetically engineered cell of any one of Paragraphs 33-47, wherein said cell is a tumor stem cell.

49. A genetically engineered organism comprising the genetically engineered cell of any one of Paragraphs 1-48 and 68.

50. A method for determining the location of cancerous cells in an organism comprising:
   determining the location of the detectable polypeptide in a genetically engineered organism of Paragraph 48.

51. The method of Paragraph 50, wherein the location of the detectable polypeptide is determined using in vivo imaging.

52. A method for identifying cancer therapy resistant cancer cells comprising:
   administering a cancer therapeutic agent to a genetically engineered organism of Paragraph 48 using a therapeutic regimen sufficient to kill cells which are not resistant to said cancer therapeutic agent; and
   detecting the location of genetically engineered cells producing the detectable polypeptide in said genetically engineered organism following the completion of said therapeutic regimen.

53. A method for identifying a candidate therapeutic agent which targets cancer therapy resistant cancer cells comprising:
   contacting a genetically engineered cell of any one of Paragraphs 1-47 and 68 which is cancer therapy resistant or a genetically engineered organism of Paragraph 48 comprising genetically engineered cells which are cancer therapy resistant with a candidate therapeutic agent; and determining whether said candidate therapeutic agent is able to kill or inhibit the replication of said cancer therapy resistant genetically engineered cell or cancer therapy resistant genetically engineered cells in said genetically engineered organism.

54. The method of Paragraph 53 wherein said cancer therapy resistant genetically engineered cell comprises a genetically engineered cell comprising a nucleic acid encoding a detectable polypeptide operably linked to the Msi2 promoter or said genetically engineered organism comprising cancer therapy resistant genetically engineered cells comprising a nucleic acid encoding a detectable polypeptide operably linked to the Msi2 promoter.

55. The method of any one of Paragraphs 53 or 54 wherein said cancer therapy resistant genetically engineered cells are resistant to radiation or Gleevec therapy or said said genetically engineered organism comprises cancer therapy resistant genetically engineered cells which are resistant to radiation or Gleevec therapy.

56. A method for monitoring eradication of cancer therapy resistant cancer cells comprising:

contacting a genetically engineered organism comprising genetically engineered cells of any one of Paragraphs 1-47 and 68 which are cancer therapy resistant with a candidate therapeutic agent; and monitoring the rate of proliferation of said cancer therapy resistant genetically engineered cells in said genetically engineered organism over a period of time.

57. A method for identifying a candidate therapeutic agent comprising:

contacting a genetically engineered cell of any one of Paragraphs 1-47 and 68 or a genetically engineered organism of Paragraph 48 with a candidate therapeutic agent; and determining whether said candidate therapeutic agent is able to kill or inhibit the replication of said genetically engineered cell or genetically engineered cells in said genetically engineered organism.

58. A method for identifying a candidate therapeutic agent comprising:

contacting a genetically engineered cell of any one of Paragraphs 1-47 and 68 or a genetically engineered organism of Paragraph 48 with a candidate therapeutic agent; and determining whether said candidate therapeutic agent is able reduce the level of expression or activity of Msi1 or Msi2 in said genetically engineered cell.

59. A method for identifying a molecular probe indicative of cancer comprising:

identifying nucleic acids or polypeptides which have differential levels or activity in in cancerous cells generated from any of the genetically engineered cells of any one of Paragraphs 1-47 and 68 or generated from genetically engineered cells in a genetically engineered organism of Paragraph 48; and identifying a molecular probe which specifically recognizes said nucleic acids or polypeptides.

60. The method of Paragraph 59, wherein said molecular probe comprises a nucleic acid which specifically binds to said nucleic acids which have differential levels or activity in said cancerous cells or an antibody or portion thereof which specifically recognizes said polypeptides which have differential levels or activity in said cancerous cells.

61. A method for detecting cancer comprising contacting a sample obtained from a subject with a molecular probe which specifically binds to a nucleic acid or polypeptide which has differential levels or activity in in cancerous cells generated from any one of the genetically engineered cells of any one of Paragraphs 1-47 and 68 or generated from genetically engineered cells in a genetically engineered organism of Paragraph 48.

62. A method for monitoring cancer comprising monitoring the growth or location of said genetically engineered cells in a genetically engineered organism of Paragraph 48.

63. A method for tracking circulating cancer cells comprising tracking the location of said genetically engineered cells in a genetically engineered organism of Paragraph 48.

64. A method for identifying a candidate therapeutic agent which increases the proliferation of stem cells comprising:

contacting a genetically engineered cell of any one of Paragraphs 1-47 and 68 wherein said cell is a stem cell or a genetically engineered organism of Paragraph 48 wherein said genetically engineered cells are stem cells with a candidate therapeutic agent; and determining whether said candidate therapeutic agent is able to increase the proliferation of said genetically engineered stem cell or said genetically engineered stem cells in said genetically engineered organism.

65. A method for ameliorating cancer comprising reducing the level or activity of a nucleic acid encoding the Msi1 polypeptide or the Msi2 polypeptide or reducing the level or activity of Msi1 polypeptide or the Msi2 polypeptide.

66. A method of reducing the level or activity of a nucleic acid encoding the Msi1 polypeptide or the Msi2 polypeptide or reducing the level or activity of Msi1 polypeptide or the Msi2 polypeptide comprising contacting a cell with a nucleic acid which is complementary to at least a portion of a nucleic acid encoding the Msi1 polypeptide or the Msi2 polypeptide.

67. A method for diagnosing lung, adenocarcinoma, pancreatic cancer, or leukemia comprising contacting a sample obtained from a subject with an agent which specifically binds to a nucleic acid encoding Msi1 or Msi2 or which specifically binds to the Msi1 or Msi2 polypeptide, and determining whether said sample comprises an elevated level of said nucleic acid encoding Msi1 or Msi2 or said Msi1 or Msi2 polypeptide relative to the level of said nucleic acid encoding Msi1 or Msi2 or said Msi1 or Msi2 polypeptide in individuals who do not have adenocarcinoma, pancreatic cancer or leukemia.

68. The genetically engineered cell of any one of paragraphs 1-48, wherein the cell is a human cell.

BRIEF DESCRIPTION OF THE DRAWINGS

FIG. 1A to FIG. 1Z. Msi reporter positive pancreatic tumor cells are enriched for tumor initiating capacity.

Part I: (FIG. 1A and FIG. 1B) Msi reporter mice were generated by knocking-in a YFP cassette into the $1^{st}$ exon of the Msi1 gene locus (REM1, Msi1$^{eYFP}$) and a GFP cassette into the $1^{st}$ exon of the Msi2 gene locus (REM2, Msi2$^{eGFP}$). (FIG. 1C and FIG. 1E) Live image of Msi1 reporter+ cells in pancreatic tumors of REM1-KP$^{f/f}$C mice (FIG. 1C); live image of Msi2 reporter+ cells in pancreatic tumors of REM2-KP$^{f/f}$C mice (FIG. 1E); VE-cadherin (magenta), Hoescht (blue) and Msi reporter (Msi1 yellow, Msi2 green). (FIG. 1D and FIG. 1F) Average Msi1 and Msi2 reporter expression in dissociated tumors (n=3 for each). (FIG. 1G) Immunofluorescence analysis of Msi1 and Msi2 expression overlap in isolated EpCAM+KP$^{f/f}$C cells (FIG. 1H-1I)

Immunofluorescence analysis of ALDH expression in reporter positive tumor cells sorted from REM1-KP$^{f/f}$C (FIG. 1H) and REM2-KP$^{f/f}$C (FIG. 1I) mice; ALDH1 (red), DAPI (blue) and GFP or YFP (green). (FIG. 1J) Average ALDH expression in bulk or Msi1 and Msi2 reporter positive tumor cells; n=3 for REM1-KP$^{f/f}$C and n=3 for REM2-KP$^{f/f}$C. (FIG. 1K) Average Msi expression in ALDH+ cells from REM1-KP$^{f/f}$C and REM2-KP$^{f/f}$C tumors.

Part II: Analysis of sphere forming capacity of Msi reporter+ cells. (FIG. 1L-FIG. 1Q) Representative images of spheres formed from Msi1 reporter+ and Msi1 reporter− tumor cells (FIG. 1L and FIG. 1M) and Msi2 reporter+ and Msi2 reporter− tumor cells (FIG. 1O and FIG. 1P). (FIG. 1N) Average frequency of spheres generated from Msi1 reporter+ and reporter− cells. (FIG. 1Q) Average frequency of spheres generated from Msi2 reporter+ and reporter− cells, n=3 for each condition. In vivo flank tumor growth of Msi2 reporter+ cells transplanted with (FIG. 1R) 100 cells, (FIG. 1S) 500 cells, or (FIG. 1T) 1000 cells and tumor volume measured over time; n=4 for each dose. (FIG. 1U-1V) Survival curves of mice orthotopically transplanted with 10,000 (FIG. 1U) or 1000 (FIG. 1V) Msi2 reporter+ and reporter− KP$^{f/f}$C tumor cells; n=3 for each dose. Log-rank (Mantel-Cox) test was used to determine the difference in survival curves between mice transplanted with reporter+ and reporter− tumor cells (p<0.5).

Part III: (FIG. 1W) Average reporter frequency in primary tumor (n=3), peripheral blood (n=4), and ascites (n=3). (FIG. 1X) Representative images and quantification of spheres formed from Msi2 reporter+ and Msi2 reporter− CTCs. (FIG. 1Y) Schematic of in vivo Gemcitabine administration into KP$^{f/f}$C mice. (FIG. 1Z) FACS plots and average reporter frequency of primary tumors from REM2-KP$^{f/f}$C mice treated with vehicle (n=3), 200 mg/kg (n=3), or 500 mg/kg (n=1) Gemcitabine. Data are represented as mean±SEM. *P<0.05, P<0.01, and *P<0.001 by Student's t-test or One-way ANOVA.

FIG. 2A to FIG. 2I. Msi2 marks cancer stem cells in a mouse model of blast crisis CML.

(FIG. 2A) Representative FACS plot shows GFP expression in the spleen of terminally-ill mice transplanted with KLS cells isolated from REM2 mice and co-infected with BCR-ABL and NUP98-HOXA9. (FIG. 2B) Average frequency of GFP-negative (GFP−) and GFP-positive (GFP+) leukemic spleen cells (n=4 mice). (FIG. 2C) Representative histograms show lineage expression in GFP− and GFP+ leukemic spleen cells. (FIG. 2D) Average frequency of lineage-negative (Lin−) and lineage-positive (Lin+) cells within either the GFP− or GFP+ fraction (n=4 mice). (FIG. 2E) Number of colonies generated from GFP− and GFP+ blast crisis CML cells. P=0.0020 (n=3 technical replicates). (FIG. 2F) Representative FACS plot shows GFP expression within the lineage-negative (Lin−) fraction of the spleen from leukemic mice. (FIG. 2G) Number of colonies generated from Lin− GFP− and Lin− GFP+ blast crisis CML cells after primary and secondary plating. P=0.0001 (n=3 technical replicates each). (FIG. 2H) Schematic illustrates experimental approach to test the ability of established GFP+ and GFP− blast crisis CML cells to drive disease development in secondary recipient mice. GFP+ or GFP− cells from established blast crisis CML were transplanted into secondary recipients and (FIG. 2I) survival was monitored (n=8 for GFP+ and 10 for GFP−).

(FIG. 3A and FIG. 3B) Msi2-expressing (GFP$^{hi}$) cells are highly resistant to imatinib-induced cell death (FIG. 3A) Representative histograms show frequency of live (Annexin V−) GFP$^{neg}$, GFP$^{lo}$ and GFP$^{hi}$ established lineage-negative blast crisis CML cells after 7 hours of imatinib (5 μM) or DMSO control treatment. (FIG. 3B) Average frequency of live (Annexin V−) GFP$^{hi}$ and GFP$^{neg}$ cells after 7 hours of imatinib (500 nM or 5 μM) or DMSO control treatment. *P=0.0139 for DMSO, **P<0.0001 for imatinib at 5 μM (n=2-4 for each treatment condition). (FIG. 3C and FIG. 3D) Msi2-expressing (GFP$^{hi}$) cells are highly resistant to radiation-induced cell death. (FIG. 3C) Representative histograms show frequency of live (Annexin V−) GFP$^{neg}$, GFP$^{lo}$ and GFP$^{hi}$ established lineage-negative blast crisis CML cells 7 hours following radiation (5 Gy). (FIG. 3D) Average frequency of live (Annexin V−) GFP$^{hi}$ and GFP$^{neg}$ cells 7 hours following radiation (0, 5, or 10 Gy). P=0.0095 at 0 Gy and **P=0.0034 at 5 Gy (n=1-3 for each treatment condition).

FIG. 4A to FIG. 4C illustrates (FIG. 4A) the process for obtaining bcCML cells, (FIG. 4B) the number of colonies generated from GFP− and GFP+ blast crisis CML cells. **P=0.0020 (n=3 technical replicates) and (FIG. 4C) the survival periods for mice with GFP+ or GFP− transplants (n=8 for GFP+ and 10 for GFP−).

FIG. 5A to FIG. 5C illustrates (FIG. 5A) the process for obtaining therapy resistant leukemia cells, (FIG. 5B) the average frequency of live (Annexin V−) GFP$^{hi}$ and GFP$^{neg}$ cells after 7 hours of imatinib (500 nM or 5 μM) or DMSO control treatment. *P=0.0139 for DMSO, ****P<0.0001 for imatinib at 5 μM (n=2-4 for each treatment condition, and (FIG. 5C) the reporter positive cells in control treated and Gleevec treated samples.

FIG. 6A to FIG. 6V. Loss of Msi 1 or Msi2 impairs tumor initiation and progression in a genetic mouse model of pancreatic cancer.

Part I: (FIG. 6A to FIG. 6D) Comparison of WT-KP$^{f/f}$C and Msi1$^{-/-}$-KP$^{f/f}$C mice at 11 weeks of age. (FIG. 6A to FIG. 6B) Coronal and sagittal images acquired in vivo using 7 Tesla MRI of normal, WT-KP$^{f/f}$C and Msi1$^{-/-}$-KP$^{f/f}$C mice, with 3-dimensional volume rendering of the tumor mass shown in red. (FIG. 6C) Average volumes of tumors resected from WT-KP$^{f/f}$C (n=12) and Msi1$^{-/-}$-KP$^{f/f}$C (n=9). (FIG. 6D) Average weights of tumors resected from WT-KP$^{f/f}$C (n=13) and Msi1$^{-/-}$-KP$^{f/f}$C (n=9). (FIG. 6E-FIG. 6I) Comparison of WT-KP$^{f/f}$C and Msi1$^{-/-}$-KP$^{f/f}$C mice at 6.5 weeks of age. (FIG. 6E and FIG. 6F) Representative images of H&E stained tumor sections from WT-KP$^{f/f}$C and Msi1$^{-/-}$-KP$^{f/f}$C mice. Representative analysis of WT-KP$^{f/f}$C and Msi1$^{-/-}$-KP$^{f/f}$C sections that consist of (FIG. 6G) normal tissue, (FIG. 6H) PanIN IA/B, PanIN II, PanIN III, and (FIG. 6I) adenocarcinoma; n=12 per genotype. PAS and Alcian Blue staining (FIG. 13A and FIG. 13B) was used to determine the percentage of total area that was normal tissue, PanIN or adenocarcinoma. (FIG. 6J) Survival curves of NSG mice orthotopically grafted with Msi1$^{-/-}$-KP$^{f/f}$C or WT-KP$^{f/f}$C tumors (n=8 per group). Log-rank (Mantel-Cox) test was used to determine the difference in survival curves between WT-KP$^{f/f}$C and Msi1$^{-/-}$-KP$^{f/f}$C mice (p<0.0001).

Part II: (FIG. 6K-FIG. 6N) Comparison of WT-KP$^{f/f}$C and Msi2$^{-/-}$-KP$^{f/f}$C mice at 13 weeks of age. (FIG. 6K to FIG. 6L) Coronal and sagittal images acquired in vivo using 7 Tesla MRI of normal, WT-KP$^{f/f}$C and Msi2$^{-/-}$-KP$^{f/f}$C mice, with 3-dimensional volume rendering of the tumor mass shown in red. (FIG. 6M) Average volumes of tumors resected from WT-KP$^{f/f}$C (n=5) and Msi2$^{-/-}$-KP$^{f/f}$C (n=7) mice. (FIG. 6N) Average weights of tumors resected from WT-KP$^{f/f}$C (n=5) and Msi2$^{-/-}$-KP$^{f/f}$C (n=7) mice. (FIG. 6O-FIG. 6R) Representative images of H&E stained sections from WT-KP^(f/f)C (FIG. 6O-FIG. 6P) and Msi2^(−/−)-KP^(f/f)C (FIG. 6Q-FIG. 6R) pancreatic tumors at 40× magnification. Green arrows in (FIG. 6P) denote areas of adenocarcinoma and liver invasion; yellow arrows in (FIG. 6Q) mark adenocarcinoma; blue arrows in (FIG. 6R) mark PanINs. Representative analysis of WT-KP^(f/f)C and Msi2^(−/−)-KP^(f/f)C sections that consist of (FIG. 6S) normal tissue, (FIG. 6T) PanIN IA/B, PanIN II, PanIN III, and (FIG. 6U) adenocarcinoma; n=3 per genotype. (FIG. 6V) Survival curves of Msi2^(−/−)-KP^(f/f)C (n=19) or WT-KP^(f/f)C tumors (n=32). Log-rank (Mantel-Cox) test was used to determine the difference in survival between WT-KP^(f/f)C and Msi2^(−/−)-KP^(f/f)C mice ($p<0.0001$). Data are represented as mean±SEM. $P<0.01$ and *$P<0.001$ by Student's t-test.

FIG. 7A to FIG. 7G. Msi controls key oncogenic signals, and mediates tumor growth through c-MET.

Part I: (FIG. 7A) Selected Musashi consensus binding sites located in the human 3'UTRs of BRD4, c-MET, and HGMA2. (FIG. 7B) RNA immunoprecipitation for MSI2 in 293T cells followed by qPCR for BRD4, HMGA2, c-MET, and IGF2. (FIG. 7C) CLIP-Seq analysis showing identification of c-MET sequences following Msi1 IP in MIA PaCa-2 cells.

Part II: (FIG. 7D) Phospho-c-Met staining in WT-KP^(f/f)C and Msi1^(−/−)-KP^(f/f)C mice with average percent of Keratin+ (magenta), phospho-c-Met+ (green) cells per tumor section (n=3 each genotype). (FIG. 7E) Phospho-c-Met staining in WT-KP^(f/f)C and Msi2^(−/−)-KP^(f/f)C mice with average percent of Keratin+ (magenta), phospho-c-Met+ (green) cells per tumor section (n=3 each genotype). (FIG. 7F) c-MET 3'UTR luciferase reporter activity in MIA PaCa-2 cells co-transfected with 50 ng of c-MET 3'UTR and MSI1 or MSI2 expression vectors. (FIG. 7G) Colony formation of MIA PaCa-2 cells infected with control shRNA or shRNA targeting human MSI1 or MSI2 followed by rescue of colony formation by over expression of c-MET. Data are represented as mean±SEM. *$P<0.05$, $P<0.01$, and *$P<0.001$ by Student's t-test or One-way ANOVA.

FIG. 8A to FIG. 8N.

Figure 3A:
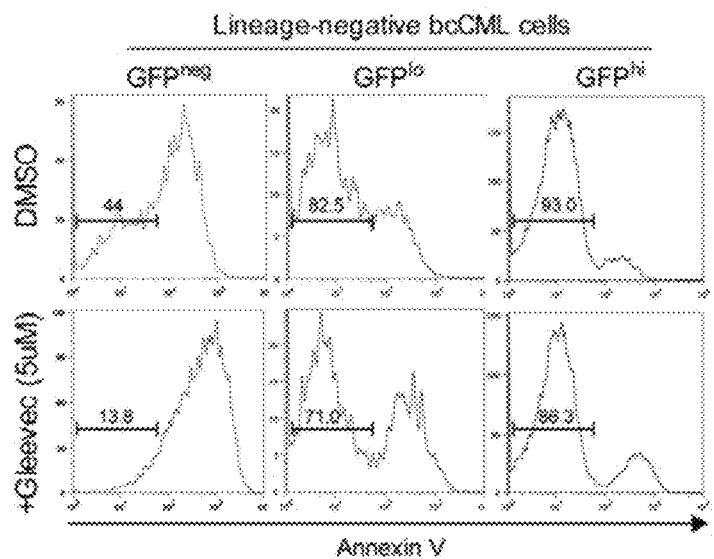
FIG. 3A to FIG. 3D. Msi2 marks blast crisis CML cells that are highly resistant to radiation and imatinib treatment.

Part I: Inhibition of MSI blocks human patient-derived xenograft pancreatic cancer growth.

(FIG. 8A) Schematic for inhibiting MSI in adenocarcinoma from primary patient-derived xenografts. Early passage xenografted tumors were dissociated and infected with GFP tagged shCTRL, shMSI1 or shMSI2. A combination of shRNA infected and uninfected cells were subcutaneously transplanted into NSG recipient mice. (FIG. 8B to FIG. 8E) Musashi inhibition was tested in four separate patient tumors. GFP frequency of tumor cells prior to transplantation (t=0) and GFP+ mass per tumor at 12 weeks post-transplantation.

Part II: Antisense oligonucleotide (ASO)-mediated targeting of Msi expression inhibits pancreatic cancer cell growth.

(FIG. 8F to FIG. 8H) Real time PCR analysis of Msi expression following ASO free uptake in MIA PaCa-2 cells. MIA PaCa-2 cells were treated with 2 Gen 2.5 cEt ASOx target MSI1 or Control Gen 2.5 ASO for 24 hours, RNA was isolated and target knockdown (MSI1 RNA level) was determined by q-RT-PCR. $IC_{50}$ values for each ASO were calculated using GraphPad Prism software; each treatment condition was performed in triplicate. (FIG. 8I) Colony formation assay in MSI1 ASO-treated MIA PaCa-2 cells after weekly delivery of control or MSI1 ASOs; colonies were counted after 4 weeks; n=3 for each ASO tested. (FIG. 8J) In vivo tracking of tumor volume in MSI1 ASO treated MIA PaCa-2 tumors with intratumoral delivery of control or MSI1 ASOs every day for 5 days followed by 2 days off; n=5 for each ASO tested. Nonlinear regression was used to determine the difference in slope between Control ASO and MSI1-ASO-1 ($p<0.001$). (FIG. 8K) In vivo tracking of tumor volume of primary KP^(f/f)C tumors with intratumoral delivery of control ASO or MSI1 ASOs following tumor establishment (n=4). (FIG. 8L) Rate of growth (slope between adjacent timepoints from k) of control ASO or MSI1 ASO treated KP^(f/f)C tumors, and (FIG. 8M) best fit curve for control ASO and MSI1 ASO treated; n=4 for each ASO. (FIG. 8N) Optimized ASOs can target signals in pancreatic tumors in autochthonous model. Target knockdown efficiency of a systemically delivered optimized ASO for Malat1 relative to an optimized control ASO. Data are represented as mean±SEM. *$P<0.05$, $P<0.01$, and *$P<0.001$ by One-way ANOVA. NS—not significant.

FIG. 9A to FIG. 9J. The Musashi genes MSI1 and MSI2 are expressed in human pancreatic adenocarcinoma. (FIG. 9A) Representative images of primary patient normal pancreas, pancreatic intraepithelial neoplasia, and pancreatic adenocarcinoma samples stained with anti-keratin (green), DAPI (blue), and anti-MSI2 (yellow) antibodies (FIG. 9B) Representative image of pancreatic adenocarcinoma samples stained with anti-keratin (green), DAPI (blue), and anti-MSI1 (yellow) antibodies. (FIG. 9C) MSI1 expression in normal pancreas, pancreatic intraepithelial neoplasia, and pancreatic adenocarcinoma samples. (FIG. 9D) MSI2 expression in normal pancreas, pancreatic intraepithelial neoplasia, and pancreatic adenocarcinoma samples. (FIG. 9E) Relative MSI1 and MSI2 expression levels in pancreatic adenocarcinoma samples. (FIG. 9F) Quantification of MSI2 expression from a human tissue array comparing Grade 1 (well-differentiated), Grade 2 (moderately differentiated), Grade 3 (poorly differentiated), and Metastatic adenocarcinoma relative to normal pancreas. (FIG. 9G) Quantification of MSI2 expression from a human tissue array comparing Grade 3 adenocarcinoma, adenosquamous carcinoma, and metastatic adenocarcinoma. MSI1 (FIG. 9H) and MSI2 (FIG. 9I) expression in well-differentiated, moderately differentiated, and poorly differentiated human pancreatic cancer cell lines. (FIG. 9J) Colony formation of well-differentiated, moderately differentiated, and poorly differentiated human pancreatic cancer cell lines. Data are represented as mean±SEM. Total Magnification 200× A-B.

Figure 10:
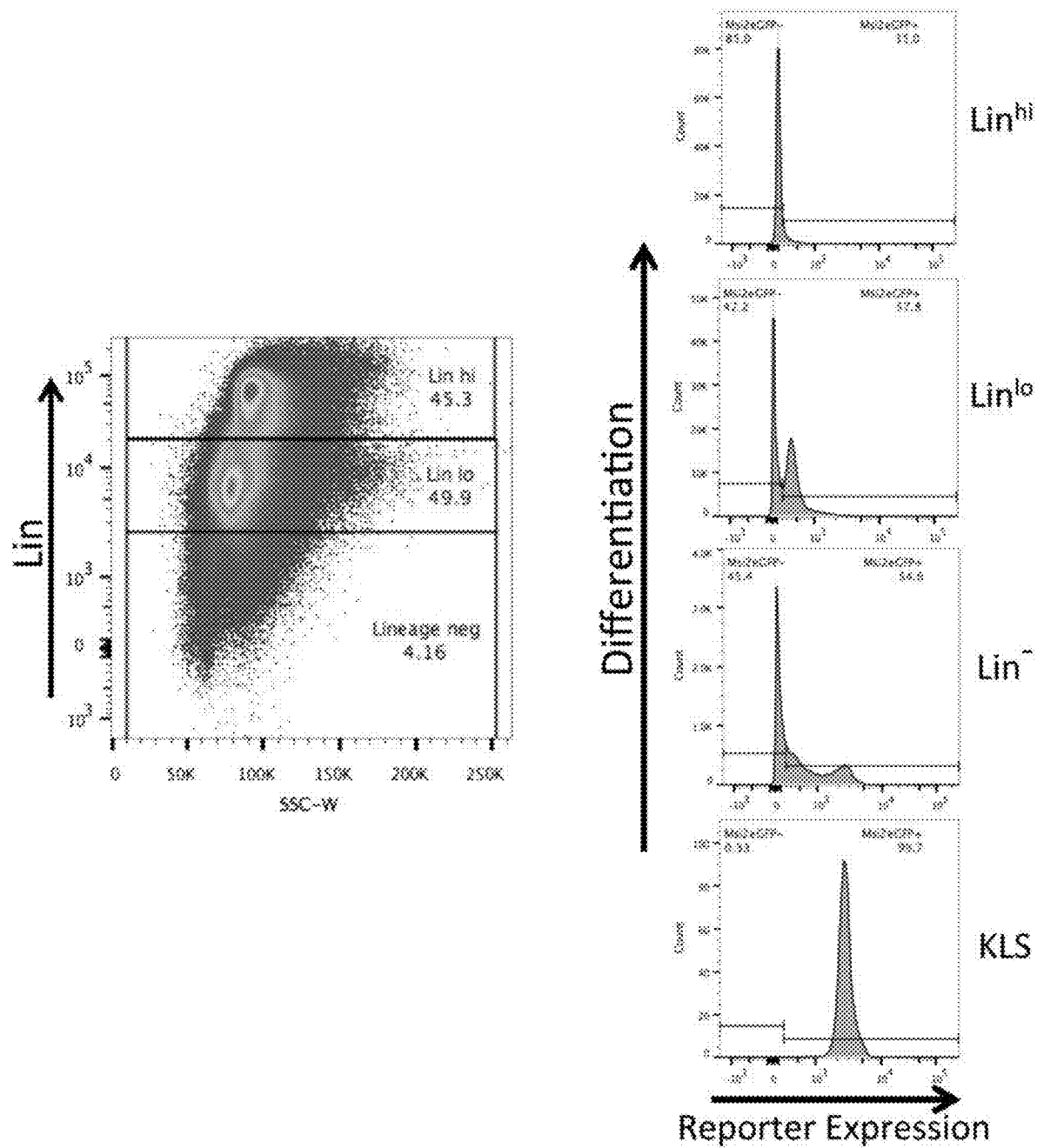

FIG. 10. FACs analysis of Msi2 reporter expression in hematopoietic stem cells, progenitors and lineage-positive differentiated cells.

Figure 11A:
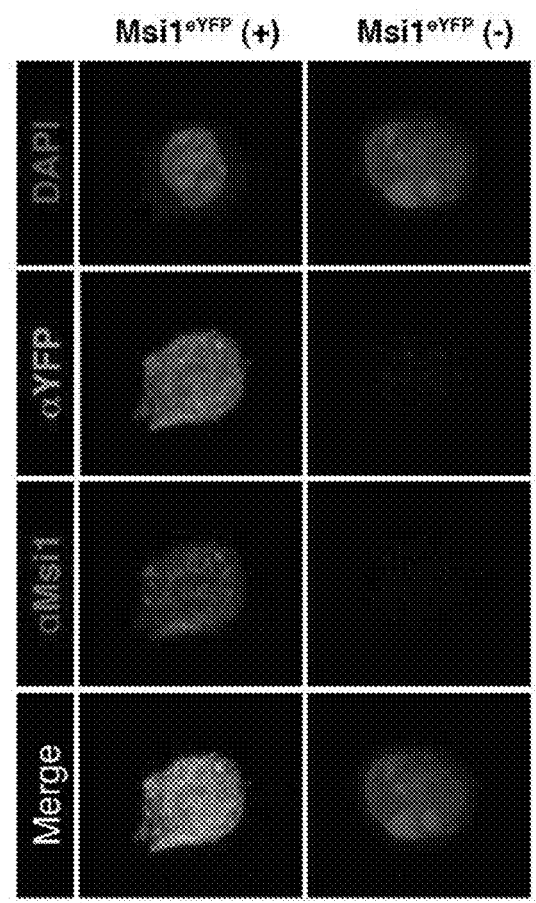
Figure 11B:
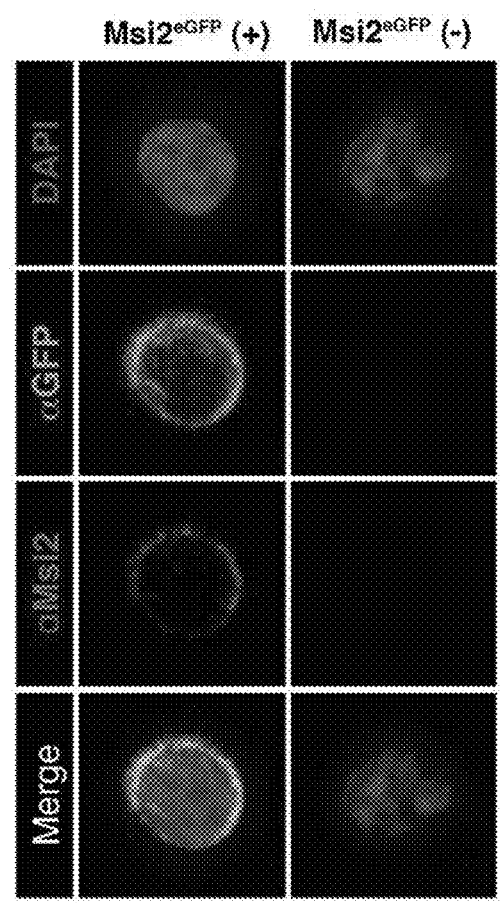

FIG. 11A and FIG. 11B. (FIG. 11A) Immunofluorescence analysis of Msi1 expression in FACs sorted YFP+ neuronal cells; YFP (green), Msi1 (red), and DAPI (blue). (FIG. 11B) Immunofluorescence analysis of Msi2 expression in FACs sorted GFP+ hematopoietic cells; GFP (green), Msi1 (red), and DAPI (blue).

Figure 12A:
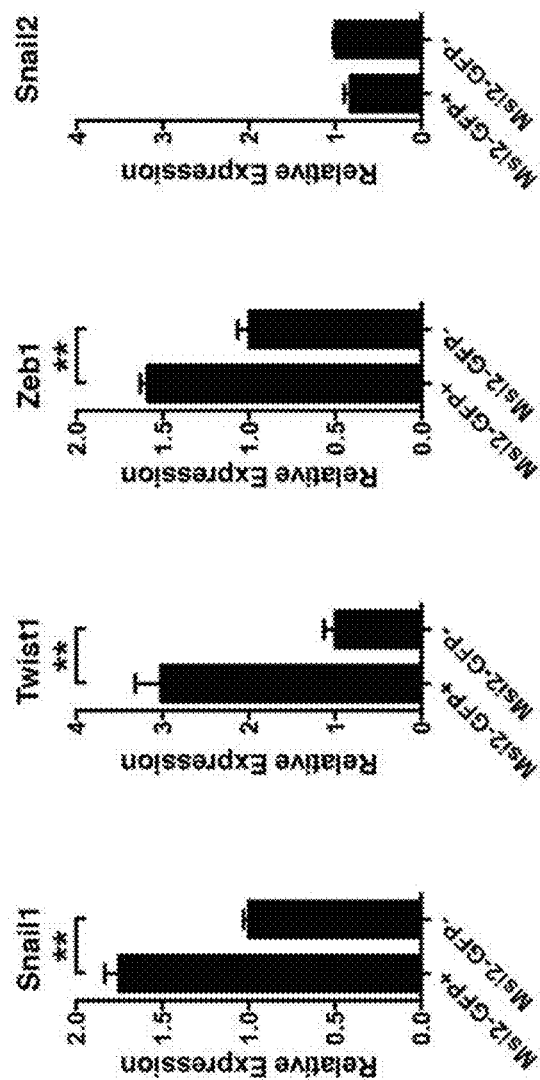
Figure 12B:
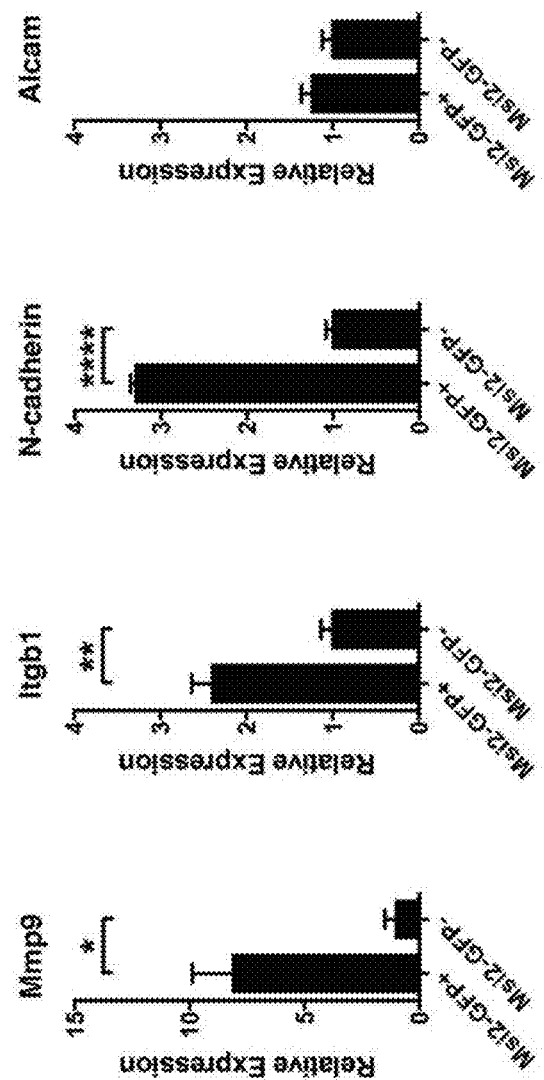

FIG. 12A and FIG. 12B. Relative expression of EMT-associated genes (FIG. 12A), and migration- or invasion-associated genes (FIG. 12B) in EpCAM+/Msi2+ and EpCAM+/Msi2− cells. Data are represented as mean±SEM. *$P<0.05$, $P<0.01$, *$P<0.001$, ****$P<0.0001$ by Student's t-test.

Figure 13A:
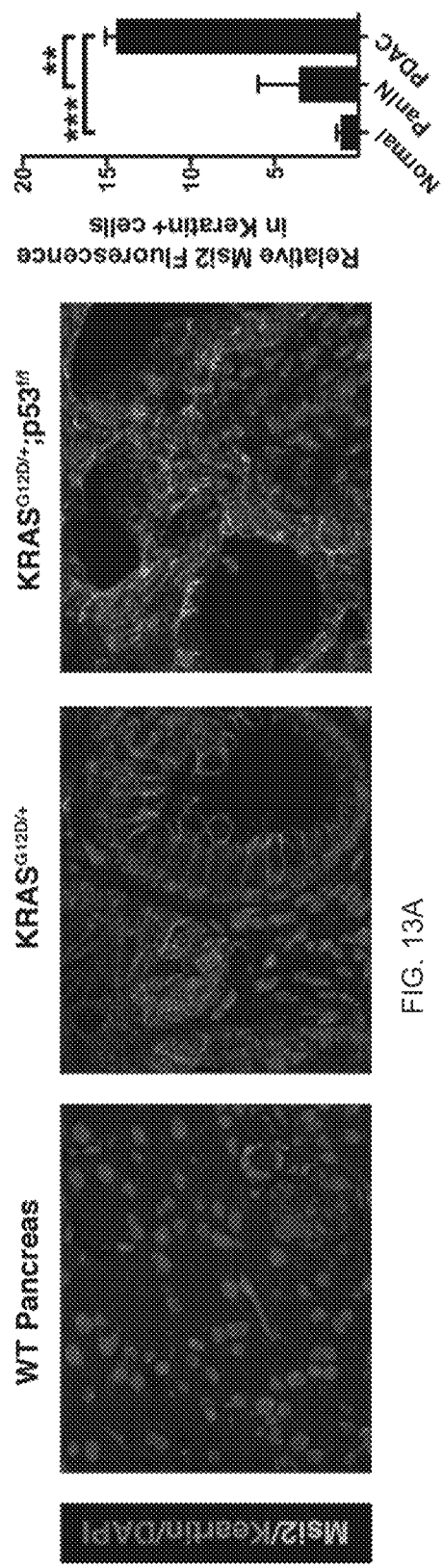
Figure 13B:
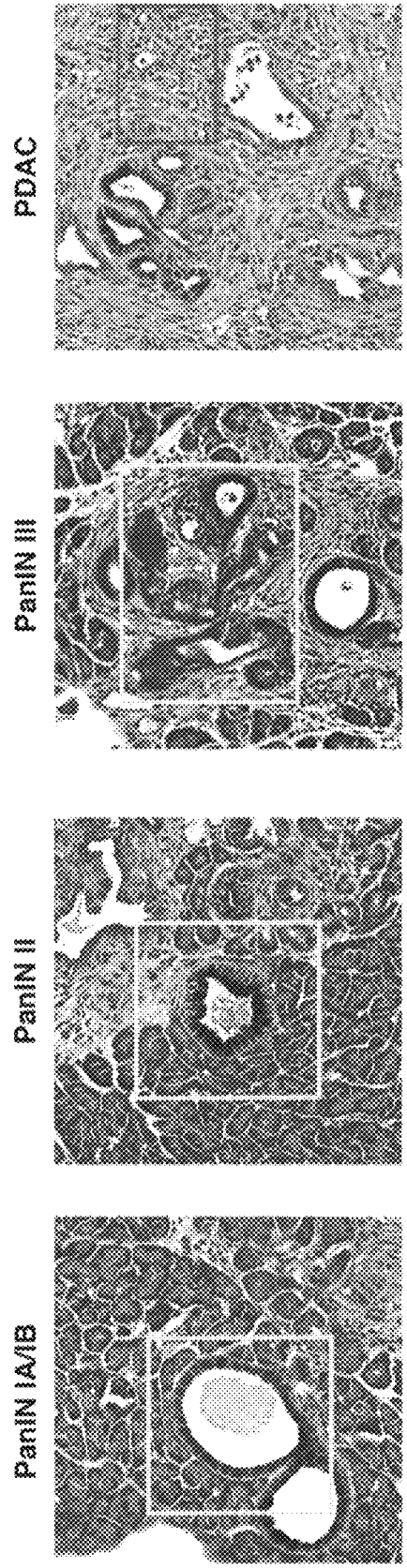

FIG. 13A and FIG. 13B. (FIG. 13A) Msi2 (green) and Keratin (red) immunofluorescent staining was performed on tissue sections from WT pancreas (Normal), KRAs^(G12D/+) (PanIN), and KRAS^(G12D/+); p53^(f/f) (PDAC) mice with quantification of Msi2 fluorescence in Keratin positive cells. (FIG. 13B) PAS and Alcian Blue stained sections of pancreata isolated from WT-KP^(f/f)C and Msi1^(−/−)-KP^(f/f)C at different time points to identify and quantify areas of PanIN (yellow boxes) and adenocarcinoma (red box). Data are represented as mean±SEM. P<0.01 and *P<0.001 by Student's t-test.

Figure 14:
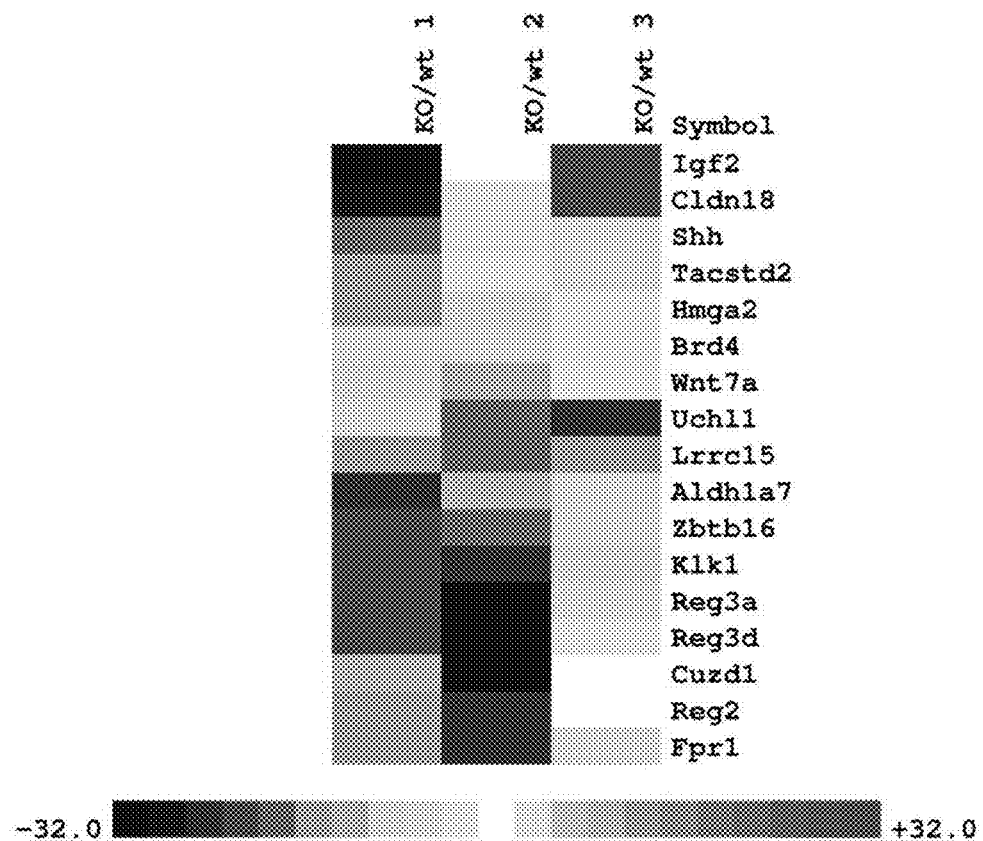

FIG. 14. Genome wide expression analysis of dissociated pancreatic tumors. Microarray analysis was performed on RNA from 3 WT-KP$^{f/f}$C and Msi1$^{-/-}$-KP$^{f/f}$C matched littermates. Heat map shows differential expression of selected mRNAs identified as part of a stem cell associated gene signature.

Figure 15A:
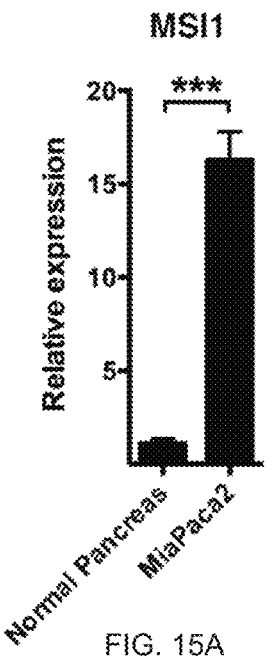
Figure 15B:
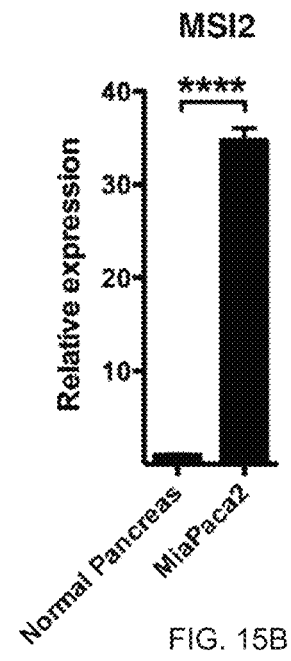
Figure 15C:
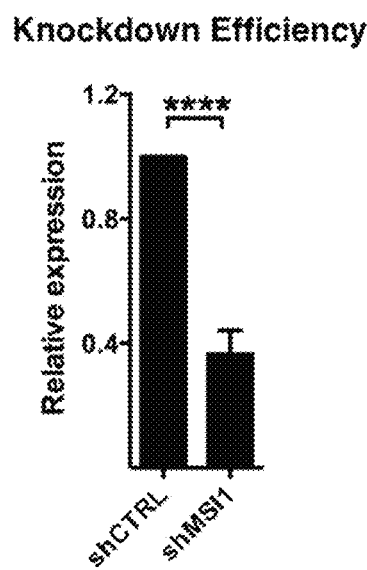
Figure 15D:
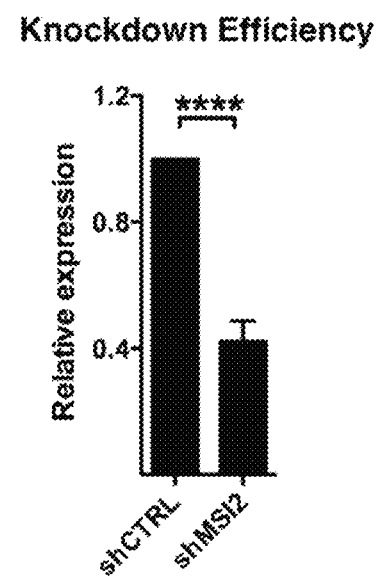

FIG. 15A to FIG. 15D. (FIG. 15A-FIG. 15B) Real-time PCR analysis of Msi1 and Msi2 expression in MIA PaCa-2 human pancreatic cancer cells relative to normal pancreas. Analysis of shRNA knockdown efficiency in human pancreatic cancer cells infected with GFP tagged lentiviral shRNA against scrambled control sequences, MSI1 (FIG. 15C) or MSI2 (FIG. 15D). GFP+ cells were sorted and Msi expression analyzed by real time PCR. Data are represented as mean±SEM. *P<0.001 and **P<0.0001 by Student's t-test.

FIG. 16A to FIG. 16C. Elevation of Msi in a caerulein induced mouse model of pancreatitis, and in human pancreatitis. (FIG. 16A) Msi expression in PBS treated (top panels) and Caerulein treated mice (bottom panels). (FIG. 16B) Quantification of Msi expression in caerulein induced pancreatitis. (FIG. 16C) Msi expression in human tissue arrays from patients presenting with mild chronic inflammation and chronic pancreatitis compared normal pancreas. Data are represented as mean±SEM. ****P<0.0001 by Student's t-test.

FIG. 17A to FIG. 17N. Msi reporter+ pancreatic cancer cells are enriched for tumour-initiating capacity. FIG. 17A and FIG. 17B, Design of Msi reporter constructs (REM1, Msi1eYFP/+; REM2, Msi2eGFP/+). FIG. 17C and FIG. 17D, Live images of Msi reporter cells in (FIG. 17C) REM1-KPf/fC and (FIG. 17D) REM2-KPf/fC tumours; VE-cadherin (magenta), Hoechst (blue), Msi reporter (green). FIG. 17E and FIG. 17F, Msi1 and Msi2 reporter expression in dissociated tumours (n=6). FIG. 17G and FIG. 17H Sphere-forming ability of Msi reporter+ and reporter– cells (FIG. 17G, n=8; h, n=6). FIG. 17I, In vivo growth of Msi2 reporter+ tumour cells (n=8). FIG. 17J, Survival of mice orthotopically transplanted with Msi2 reporter+ and reporter– KPf/fC tumour cells (n=6). Log-rank (Mantel-Cox) survival analysis (P<0.05). FIG. 17K, Reporter frequency in primary tumours (n=3), and circulating tumour cells from ascites (n=3) or peripheral blood (n=4). FIG. 17L, Average frequency of tumour-spheres from Msi2 reporter+ and reporter– circulating tumour cells (n=2-4 technical replicates). FIG. 17M and FIG. 17N, Reporter frequency in REM2-KPf/fC mice treated with vehicle or 500 mg per kg (body weight) gemcitabine (n=6). Data are represented as mean±s.e.m. *P<0.05, P<0.01, *P<0.001, ****P<0.0001 by Student's t-test or one-way analysis of variance (ANOVA). Source data for all panels are available online.

FIG. 18A to FIG. 18P. Loss of Msi1 or Msi2 impairs tumour initiation and progression in a genetic mouse model of pancreatic cancer. FIG. 18A, Coronal and sagittal MRI images of normal, WT-KPf/fC, and Msi1–/–-KPf/fC mice with three-dimensional volume rendering of tumour mass (red). FIG. 18B, Average volumes of isolated WT-KPf/fC (n=13) and Msi1–/–-KPf/fC tumours (n=9). FIG. 18C and FIG. 18D, Histology and (FIG. 18E and FIG. 18F) quantification of PanIN and/or adenocarcinoma areas in WT-KPf/fC and Msi1–/–-KPf/fC tumours. FIG. 18G, Survival of mice orthotopically grafted with Msi1–/–-KPf/fC or WT-KPf/fC tumours (n=16). Analysis of Msi2–/–-KPf/fC tumours (FIG. 18H) by MRI and (FIG. 18I) after isolation, WT-KPf/fC (n=5), Msi2–/–-KPf/fC (n=7). FIG. 18J to FIG. 18M, Histology of WT-KPf/fC and Msi2–/–-KPf/fC pancreatic tumours (x40 magnification); FIG. 18K, adenocarcinoma, liver invasion (green arrows); FIG. 18L, adenocarcinoma (yellow arrows); m, PanINs (blue arrows). FIG. 18N to FIG. 18O, Quantification of PanIN and/or adenocarcinoma areas in WT-KPf/fC and Msi2–/–-KPf/fC tumours (n=6). FIG. 18P, Survival of autochthonous Msi2–/–-KPf/fC (n=19) or WT-KPf/fC (n=32) mice. Log-rank (Mantel-Cox) survival analysis (P<0.0001). Data represented as mean±s.e.m. P<0.01, *P<0.001 by Student's t-test. Source data for all panels are available online.

FIG. 19A to 19H. Msi controls expression of key oncogenic and epigenetic signals. FIG. 19A, Msi RIP-PCR for indicated transcripts. FIG. 19B and FIG. 19C, Frequency of phospho-cMet+ cells in WT-KPf/fC, Msi1–/–-KPf/fC, and Msi2–/–-KPf/fC mice (FIG. 19B, n=8; FIG. 19C, n=6). FIG. 19D, Schematic of cMET exons and 3' UTR. CLIP tags (red triangles) indicate MSI1 binding in 3' UTR. FIG. 19E, cMET 3' UTR luciferase reporter activity in the presence or absence of MSI1 or MSI2 (n=3 independent experiments). FIG. 19F, Colony formation of MSI1 or MSI2 knockdown cells with or without cMET (n=4 independent experiments). FIG. 19G and FIG. 19H, Fluorescence-activated cell sorting (FACS) analysis of tumours from gemcitabine-treated REM2-KPf/fC mice, in the presence or absence of crizotinib and iBet762; vehicle (n=7), gemcitabine (n=3), gemcitabine+iBet762 (n=3), gemcitabine+crizotinib (n=3). Data represented as mean±s.e.m. *P<0.05, P<0.01, *P<0.001 by Student's t-test or one-way ANOVA. NS, not significant. Source data for all panels are available online.

FIG. 20A to FIG. 20H. Targeting MSI inhibits pancreatic cancer growth in patient derived xenografts. FIG. 20A and FIG. 20B, Frequency of green fluorescent protein-positive (GFP+) tumour cells before and after transplantation. FIG. 20C, MSI1 expression after MSI1-ASO free uptake in human pancreatic cancer line (n=3 independent experiments per dose). FIG. 20D, Colony formation of control or MSI1-ASO-treated human pancreatic cancer line (n=3 independent experiments). FIG. 20E, In vivo growth of human cell-line-derived tumours in control or MSI1-ASO treated mice (n=10). FIG. 20F, Relative tumour volume and (FIG. 20G) rate of growth of KPf/fC-derived tumours in control or MSI1– ASO-treated mice (n=8). FIG. 20H, Malat1 expression in autochthonous KPf/fC tumours after systemic delivery of control or lead-optimized Malat1– ASO (n=6). Data represented as mean±s.e.m. *P<0.05, P<0.01, *P<0.001 by one-way ANOVA. NS, not significant. Source data for all panels are available online.

Figure 21A:
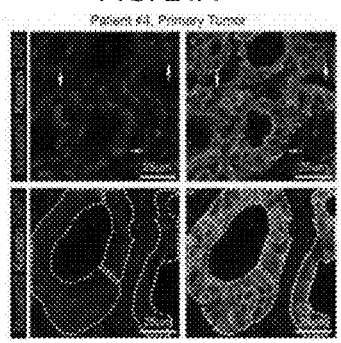
Figure 21B:
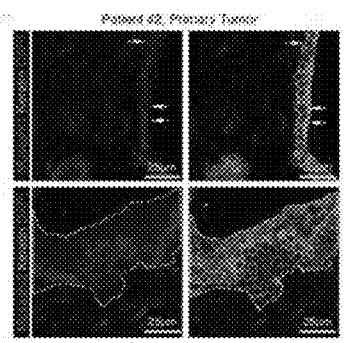
Figure 21C:
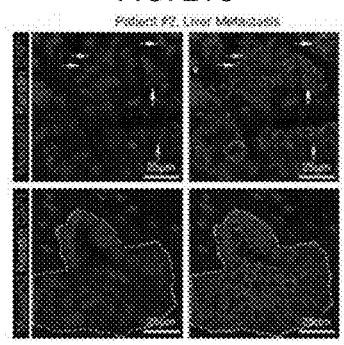
Figure 21D:
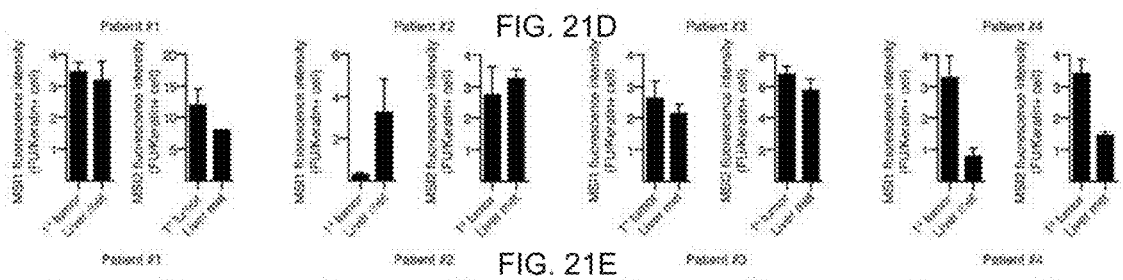
Figure 21E:
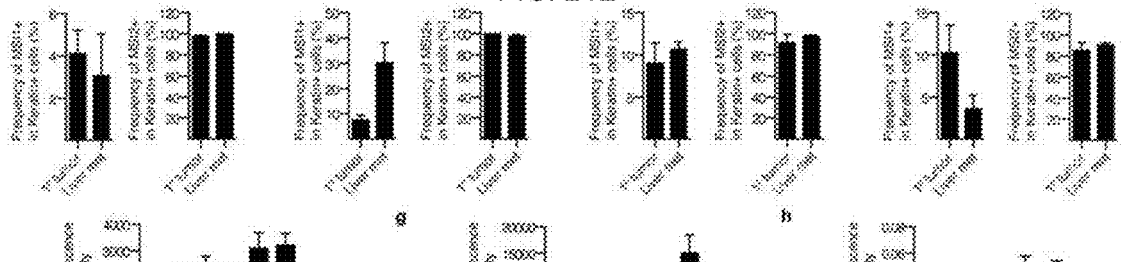
Figure 21F:
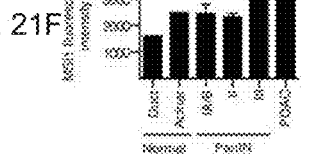
Figure 21G:
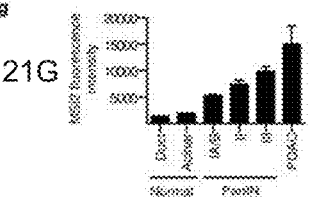
Figure 21H:
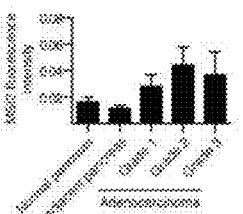
Figure 21I:
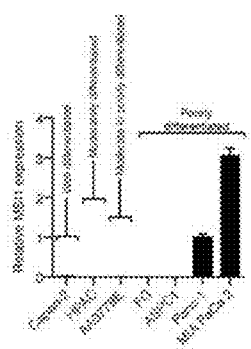
Figure 21J:
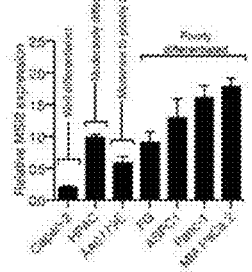
Figure 21K:
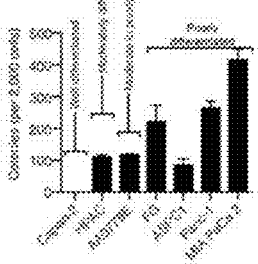

FIG. 21A to FIG. 21K. The Musashi genes MSI1 and MSI2 are expressed in human pancreatic adenocarcinoma. FIG. 21A, Top row: representative images of a primary patient pancreatic adenocarcinoma sample stained with anti-keratin (green), DAPI (blue), and anti-MSI1 (red) antibodies. White arrows indicate MSI1– cells; yellow arrow indicates a MSI1+ cell. FIG. 21A, Bottom row: representative images of a primary patient pancreatic adenocarcinoma sample stained with anti-keratin (green), DAPI (blue), and anti-MSI2 (red) antibodies. White dotted regions indicate MSI2– cells while yellow dotted regions indicate MSI2+ cells. FIG. 21B, Top row: representative images of a primary patient pancreatic adenocarcinoma sample stained with anti-keratin (green), DAPI (blue), and anti-MSI1 (red) antibodies. White arrows indicate MSI1– cells; yellow arrow indicates a MSI1+ cell. FIG. 21B, Bottom row: representative images of a primary patient pancreatic adenocarcinoma sample stained with antikeratin (green), DAPI (blue), and anti-MSI2 (red) antibodies. Yellow dotted region indicates MSI2+ cells. FIG. 21C, Top row: representative images of a matched liver metastasis from a patient with pancreatic adenocarcinoma stained with anti-keratin (green), DAPI (blue), and anti-MSI1 (red) antibodies. White arrows indicate MSI1– cells; yellow arrows indicate MSI1+ cells. FIG. 21C, Bottom row: representative images of a matched liver metastasis from a patient with pancreatic adenocarcinoma stained with The Musashi genes MSI1 and MSI2 are expressed in human pancreatic adenocarcinoma. FIG. 21A, Top row: representative images of a primary patient pancreatic adenocarcinoma sample stained with anti-keratin (green), DAPI (blue), and anti-MSI1 (red) antibodies. White arrows indicate MSI1– cells; yellow arrow indicates a MSI1+ cell. FIG. 21A, Bottom row: representative images of a primary patient pancreatic adenocarcinoma sample stained with anti-keratin (green), DAPI (blue), and anti-MSI2 (red) antibodies. White dotted regions indicate MSI2– cells while yellow dotted regions indicate MSI2+ cells. FIG. 21B, Top row: representative images of a primary patient pancreatic adenocarcinoma sample stained with anti-keratin (green), DAPI (blue), and anti-MSI1 (red) antibodies. White arrows indicate MSI1– cells; yellow arrow indicates a MSI1+ cell. FIG. 21B, Bottom row: representative images of a primary patient pancreatic adenocarcinoma sample stained with antikeratin (green), DAPI (blue), and anti-MSI2 (red) antibodies. Yellow dotted region indicates MSI2+ cells. FIG. 21C, Top row: representative images of a matched liver metastasis from a patient with pancreatic adenocarcinoma stained with anti-keratin (green), DAPI (blue), and anti-MSI1 (red) antibodies. White arrows indicate MSI1– cells; yellow arrows indicate MSI1+ cells. FIG. 21C, Bottom row: representative images of a matched liver metastasis from a patient with pancreatic adenocarcinoma stained with anti-keratin (green), DAPI (blue), and anti-MSI2 (red) antibodies. Yellow dotted region indicates MSI2+ cells. FIG. 21D, Quantification of MSI1 and MSI2 expression in four patients comparing primary pancreatic adenocarcinoma to the patient-matched liver metastasis; four images analysed per patient. FIG. 21E, Quantification of the frequency of MSI1+ and MSI2+ cells in four patients comparing primary pancreatic adenocarcinoma to the patientmatched liver metastasis; four images analysed per patient. FIG. 21F, MSI1 and (FIG. 21G) MSI2 expression in normal pancreas (n=1), PanIN (n=9), and pancreatic adenocarcinoma samples (n=9). FIG. 21H, Quantification of MSI2 expression from a human tissue array comparing grade 1 (well-differentiated, n=9), grade 2 (moderately differentiated, n=12), and grade 3 (poorly differentiated, n=16) adenocarcinoma relative to normal pancreas (n=14) and normal adjacent pancreas (n=16). FIG. 21I, MSI1 and (FIG. 21J) MSI2 expression in well-differentiated, moderately differentiated, and poorly differentiated human pancreatic cancer cell lines (n=3 independent experiments). FIG. 21K, Colony formation of well-differentiated, moderately differentiated, and poorly differentiated human pancreatic cancer cell lines (n=3 independent experiments). Data are represented as mean±s.e.m. Total magnification ×200 (FIG. 21A to FIG. 21C). Source data for all panels are available online.

FIG. 22A to FIG. 22I. Validation of Msi1 and Msi2 reporter mice. FIG. 22A, FACS analysis of Msi2 reporter expression in haematopoietic stem cells, progenitors, and lineage-positive differentiated cells. FIG. 22B, Representative image of Msi1 expression in FACS-sorted YFP+ neuronal cells; YFP (green), Msi1 (red), and DAPI (blue). FIG. 22C, Representative image of Msi2 expression in FACS-sorted GFP+ haematopoietic cells; GFP (green), Msi1 (red), and DAPI (blue). FIG. 22D and FIG. 22E, Msi-expression in keratin+ cells. d, Msi1-YFP reporter (green, white arrows) and keratin (red) staining was performed on tissue sections of REM1-KPf/fC mice; FIG. 22E, Msi2-GFP reporter (green, white arrows) and keratin (red) staining was performed on tissue sections of REM2-KPf/fC mice. DAPI staining is shown in blue. Rare cells (<5%) were found to be keratin– (possibly mesenchymal population). FIG. 22F, Immunofluorescence analysis of Msi1 and Msi2 expression overlap in isolated EpCAM+ KPf/fC cells (n=3, 1,000 total cells analysed from 3 independent experiments). Data are represented as mean±s.e.m. FIG. 22G and FIG. 22H, Survival of Msi reporter-KPf/fC and WT-KPf/fC mice. Survival curves of (FIG. 22G) Msi1YFP/+-KPf/fC (REM1-KPf/fC, n=21) or WT-KPf/fC (n=18) mice and (FIG. 22H) Msi2GFP/+-KPf/fC (REM2-KPf/fC, n=65) or WT-KPf/fC (n=54) mice. FIG. 22I, Live image of Msi2 reporter cells in REM2-KPf/fC tumour; VE-cadherin (magenta), Hoescht (blue), Msi reporter (green). See also FIG. 17C and FIG. 17D. Source data for all panels are available online.

FIG. 23A to FIG. 23K. Analysis of stem cell traits in Msi1 and Msi2 reporter+ KPf/fC populations. FIG. 23A, ALDH expression in reporter+ tumour cells sorted from REM1-KPf/fC (top row) and REM2-KPf/fC (bottom row) mice; ALDH1 (red), DAPI (blue), and GFP or YFP (green). FIG. 23B, Average ALDH expression in bulk or Msi1 and Msi2 reporter+ tumour cells (n=3 each; 90 total cells analysed from 3 REM1-KPf/fC and 150 total cells analysed from 3 REM2-KPf/fC). (FIG. 23C) Average Msi expression in ALDH+ cells from REM1-KPf/fC and REM2-KPf/fC tumours (n=3 independent experiments for each genotype). FIG. 23D and FIG. 23E, Representative images of spheres formed from (FIG. 23D) Msi1 and (FIG. 23E) Msi2 reporter+ and reporter– tumour cells. See also FIG. 17G, 17H, 17F, In vivo tumour growth of Msi2 reporter+ or Msi reporter– KPf/fC cells at (FIG. 23F) 500 or (FIG. 23G) 1,000 cells (n=16). See also FIG. 17I. (FIG. 23H) Survival of mice orthotopically transplanted with 10,000 Msi2 reporter+ and reporter– KPf/fC tumour cells (n=6). See also FIG. 17J. Log-rank (Mantel-Cox) survival analysis (P<0.05). FIGS. 23I and 23J, Reporter frequency in REM2-KPf/fC mice treated with vehicle or 200 mg per kg (body weight) gemcitabine (n=3 each). See also FIG. 17M and FIG. 17N for high-dose (500 mg per kg (body weight)) gemcitabine. Data are represented as mean±s.e.m. ***P<0.001 by Student's t-test or one-way ANOVA. FIG. 23K, Msi2 reporter– KPf/fC cells do not turn on Msi2 expression after in vitro gemcitabine treatment, suggesting that Msi-reporter+ cells are differentially resistant to gemcitabine. Low-passage Msi2 reporter KPf/fC cells loaded with DiI were live-imaged continuously for up to 48 h. Representative series of images from 10 μM gemcitabine treatment. Reporter– cells (red); GFP reporter+ cells (green); tracking of Msi2 reporter– cells (white arrows); tracking of Msi2 reporter+ cells (yellow arrows) (n=3 independent experiments). Source data for all panels are available online.

FIG. 24A to FIG. 24E. Analysis of tumours from Msi null KPf/fC mice. FIG. 24A, Msi2 (green) and Keratin (red) immunofluorescent staining was performed on tissue sections from WT pancreas (normal, n=3 samples), KRASG12D/+; Ptf1aCre/+ (PanIN, n=2 samples), and KRASG12D/+; p53f/f; Ptf1aCre/+ (pancreatic ductal adenocarcinoma, n=3 samples) mice with quantification of Msi2 fluorescence in keratin+ cells. FIG. 24B, Average weights of WT-KPf/fC (n=13) and Msi1–/–-KPf/fC tumours (n=9). See also FIG. 18A and FIG. 18B for tumour volume analysis. FIG. 24C, PAS and Alcian blue stained sections of pancreata isolated from WT-KPf/fC represent areas used to identify the stages of PanINs (yellow boxes) and adenocarcinoma (red box). FIG. 24D, Tumours from 11- to 13-week-old WT-KPf/fC (n=6), Msi1−/−-KPf/fC (n=3), and Msi2−/−-KPf/fC (n=3) mice were stained and quantified for percentage of Keratin+ tumour cells (red) expressing Ki67 (green); DAPI staining is shown in blue. FIG. 24E, Average weights of WT-KPf/fC (n=5) and Msi2−/−-KPf/fC tumours (n=7). See also FIG. 18H, i for tumour volume analysis. Data are represented as mean±s.e.m. *P<0.05, P<0.01, *P<0.001 by Student's t-test or one-way ANOVA. Source data for all panels are available online.

FIG. 25A to FIG. 25H. Selection for escaper Msi-expressing cells in Msi1, Msi2 single and double knockout KPf/fC mice. FIG. 25A to FIG. 25C, Immunohistochemical staining for (FIG. 25A) IgG control (n=4) or (FIGS. 25B and 25C, red) Msi2 in 13-week-old WT-KPf/fC (n=4) and Msi2−/−-KPf/fC (n=4) mice. FIG. 25D, Immunohistochemical staining for Msi2 (red) in 22-week-old Msi2−/−KPf/fC mouse (n=1). e-g, Immunohistochemical staining for (FIG. 25E) IgG control, (FIG. 25F, red) Msi1, and (FIG. 25G, red) Msi2 in a 15-week-old Msi1f/fMsi2−/− double knockout KPf/fC mouse (n=1). FIG. 25H, Survival curves of Msi1f/fMsi2−/−-KPf/fC (n=6) or WT-KPf/fC tumours (n=35). Source data for all panels are available online.

Figure 26A:
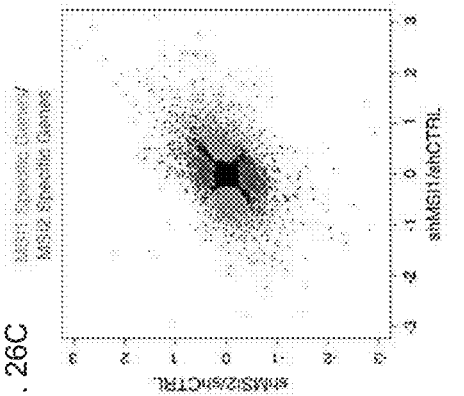
Figure 26B:
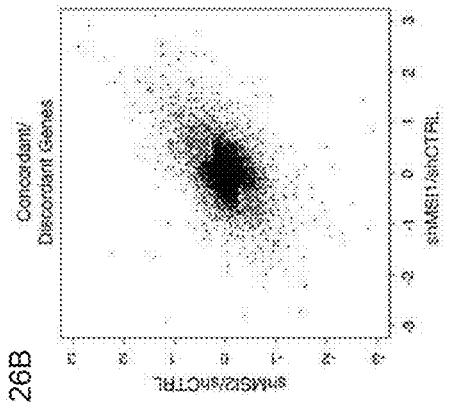
Figure 26D:
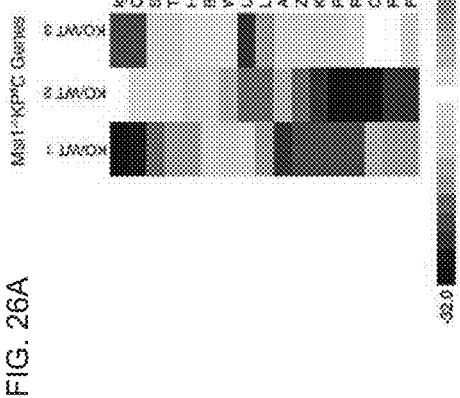
Figure 26C:
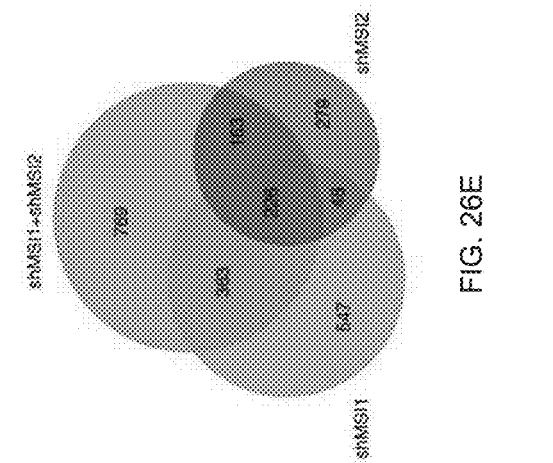
Figure 26E:
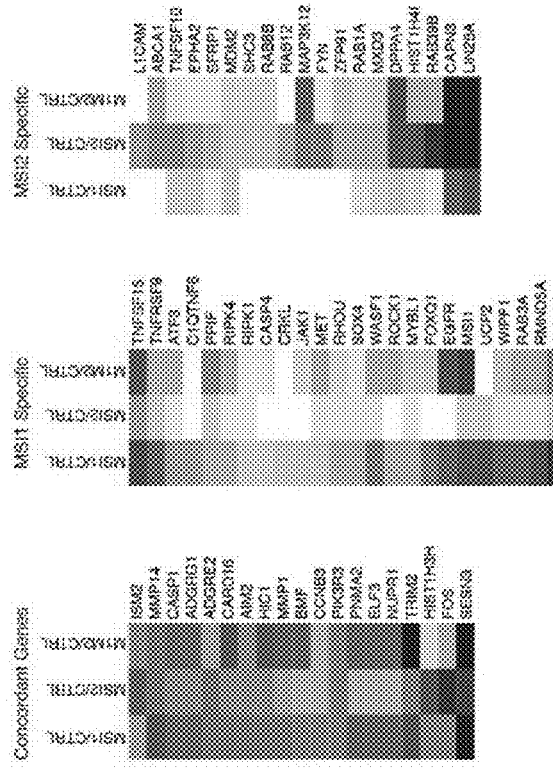

FIG. 26A to FIG. 26E. Genome-wide analysis of Msi controlled programs in pancreatic cancer. FIG. 26A, Genome-wide expression analysis of dissociated pancreatic tumours. Microarray analysis was performed on RNA from three pairs of WT-KPf/fC and Msi1−/−-KPf/fC matched littermates. Heat map shows differential expression of selected mRNAs identified as part of a stem-cell-associated gene signature. FIG. 26B, Concordantly (upper right and lower left quadrants) and discordantly (upper left and lower right quadrants) regulated genes (red) in MSI1-knockdown and MSI2-knockdown MIA PaCa-2 cells. FIG. 26C, Gene changes specific to MSI1-knockdown (turquoise) or MSI2-knockdown (purple) in MIA PaCa-2 cells. FIG. 26D, Heat maps indicating concordant, MSI1-specific, and MSI2-specific genes. FIG. 26E, Venn diagram displaying the intersection of probe sets that are differentially regulated in MSI1-knockdown, MSI2− knockdown, and double knockdown of MSI1 and MSI2 in MIA PaCa-2 cells. Within scatterplots, lighter colour corresponds to a probability >0.5 and the darker colour corresponds to a probability >0.75. Source data for all panels are available online.

FIG. 27A to FIG. 27G. Molecular targets of Msi signaling. FIG. 27A and FIG. 27B, Quantitative PCR analysis of (FIG. 27A) Msi1 and (FIG. 27B) Msi2 expression in MIA PaCa-2 human pancreatic cancer cells relative to normal pancreas (n=3 independent experiments). FIG. 27C and FIG. 27D, Analysis of shRNA knockdown efficiency in GFP+-sorted MIA PaCA-2 cells infected with GFP-tagged lentiviral shRNA against scrambled control sequences, (FIG. 27C) MSI1, or (FIG. 27D) MSI2 (n=3 independent experiments). FIG. 27E, Analysis of direct Msi targets: Msi consensus binding sites in 3' UTR of BRD4, HMGA2, and cMET transcripts. FIG. 27F and FIG. 27G, Phospho-cMet staining in WT-KPf/fC and (FIG. 27F) Msi1−/−-KPf/fC, (FIG. 27G) Msi2−/−-KPf/fC mice; keratin (magenta), phosphocMet (green), DAPI (blue). See FIG. 19B to FIG. 19C for quantified data. FIG. 27H, Colony formation of MIA PaCa-2 cells infected with empty vector or cMET overexpression vector (three independent experiments) shows no impact of overexpressed cMet on control MIA PaCa-2 (control for cMet-mediated rescue of MSI knockdown in FIG. 19F). Data are represented as mean±s.e.m. *P<0.001, **P<0.0001 by Student's t-test. Source data for all panels are available online.

FIG. 28A to FIG. 28J. Analysis of impaired pancreatic cancer growth with shMSI and MSI1-ASOs. FIG. 28A, Schematic for inhibiting MSI in primary patient-derived xenografts. FIG. 28B and FIG. 28C, Frequency of GFP+ patient tumour cells before and after transplantation. See also FIG. 20A and FIG. 20B for patients 1 and 2. FIG. 28D and FIG. 28E, MSI1 expression after free uptake of (FIG. 28D) control ASO or (FIG. 28E) MSI1-A502 in human pancreatic cancer line (n=3 per condition). See also FIG. 20C for impact of MSI1-ASO1. FIG. 28F to FIG. 28J, ASO delivery in vivo. FIG. 28F, Target knockdown efficacy of lead-optimized ASO in KPf/fC stem cells. Malat1 expression in EpCAM+/ALDH+ and EpCAM+/ALDH− cells after systemic delivery of control ASO or lead-optimized Malat1-ASO in autochthonous KPf/fC model (n=3 independent experiments). See also FIG. 20H for target knockdown in unfractionated EpCAM+ cells. FIGS. 28G and 28H, Analysis of potential toxicity of MSI-ASO: g, cage weight of mice receiving daily treatment of MSI1 ASO-1 (50 mg per kg (body weight)) or vehicle by intraperitoneal injection; four mice per cage; cage weight was measured every 3 days; h, average body weight of mice after 3 weeks of daily treatment with MSI1 ASO-1 (50 mg per kg (body weight)) or vehicle by intraperitoneal injection (n=4 mice/cohort). In vivo delivery of MSI1 ASOs (50 mg per kg (body weight)) had no deleterious impact on body weight and maintained plasma chemistry markers (AST, ALT, BUN, T.Bil) within 3× upper limit of normal. FIG. 28I and FIG. 28J, Representative images of in situ hybridization for Malat1 (purple) in pancreatic tumours isolated from KPf/fC mice treated by daily intraperitoneal injection with (FIG. 28I) control ASO (50 mg per kg (body weight)) or (FIG. 28A to 28I) Malat1-ASO (50 mg per kg (body weight)) for 14 days. Source data for all panels are available online.

FIG. 29A to FIG. 29E. Elevated expression of Msi in pancreatitis. Msi2 expression in a caerulein-induced mouse model of pancreatitis, and in human pancreatitis. FIG. 29A, Msi2 staining and (FIG. 29B) quantification of ten images per group in pancreas from PBS-treated (FIG. 29A, top panels, n=1) and caerulein-treated mice (FIG. 29A, bottom panels, n=1). FIG. 29C, Msi2 immunohistochemical staining in islets (black dotted outlines) and acinar cells (blue squares) in caerulein-treated or PBS-treated mice (n=1 for each group). FIG. 29D, Immunofluorescent staining of Msi2 (green) in DBA+ ductal cells (red) treated with PBS (left panels) or caerulein (right panels) (n=1 for each group); DAPI is shown in blue. FIG. 29E, MSI2 expression in human tissue arrays from patients presenting with mild chronic inflammation (n=4) and chronic pancreatitis (n=6) compared with normal pancreas (n=14). Data are represented as mean±s.e.m. ****P<0.0001 by Student's t-test. Source data for all panels are available online.

FIG. 30A to FIG. 30E. Real-Time imaging (FIG. 30A) Representative photo showing architecture of imaging area in mouse calvarium. Red-dashed boxes indicate representative areas imaged. Black dashed box highlights the central sinus. Parasagittal sinusoids flank either side of the central sinus. (FIG. 30B) Representative 10× image of transgenic dsRed mouse calvarium. White dashed lines highlight the central sinus. Scale bar=150 μm. (FIG. 30C) Representative 20× image of dsRed bone marrow. Closed triangles depict transplanted Lin−GFP+ cells in microenvironment. Scale bar=80 μm. (FIG. 30D) Still image of a Lin−GFP+ hematopoietic cell (closed triangle) rolling along the vessel wall in a dsRed recipient mouse, shown are images taken at t=0 (left panel) and at endpoint t=05:41 (right panel). Inlay=1.5× zoom, scale bar=80 μm. (FIG. 30E) Still image of a Lin⁻GFP⁺ hematopoietic cell in division. t=0: arrow identifies cell preparing to divide, t=6:23: arrows indicate cell in the midst of division and t=25:02: arrows indicate two daughter cells. Scale bar=80 μm, box 1.5× zoom of field.

FIG. 31A to FIG. 31E. Multi-color analysis. (FIG. 31A) Representative three-color analysis of a dsRed recipient transplanted with GFP⁺ and CFP⁺ whole bone marrow cells. Corresponding movie shows a z-stack step through the marrow microenvironment. Scale bar=80 μm, box 1.5× zoom of field. (FIG. 31B) Representative image of dsRed mouse crossed to TNR showing Notch signaling domains within the bone marrow microenvironment; green signal reflects Notch reporter activity within the microenvironment (asterisks). (FIG. 31C) Representative image of dsRed⁺ WBM transplanted into TNR.CFP mouse. Green reflects Notch reporter activity within the microenvironment. Images (FIG. 31A to FIG. 31C) were obtained with a 20× objective. Scale bar=80 μm. (FIG. 31D and FIG. 31E) dsRed mice (red) transplanted with GFP⁺Lin⁻ cells (green) and co-labeled with conjugated probes to (FIG. 31D) endothelial cells (anti-VE-cadherin antibody) and (FIG. 31E) the endosteal surface (Osteosense). Scale bar=70 μm.

FIG. 32A to FIG. 32F. Computational image analysis of spatial dynamics (FIG. 32A) Automated analysis enables tracking of individual cells (green) over time, and determination of the distance from the vascular (outlined in red) and endosteal (outlined in gray) regions. (FIG. 32B) For the same cell shown in (FIG. 32A), the distance to the endosteal (gray line) and vascular (red line) regions as well as the cell velocity (green line) are shown. (FIG. 32C and FIG. 32D) Histograms containing the distance to the vascular (FIG. 32C) and endosteal (FIG. 32D) regions for all cells analyzed at all time points assessed. Three "zones" were determined from these histograms: contact, proximal and distal. (FIG. 32E) The same data shown in (FIG. 32B), but with the three zones highlighted. (FIG. 32F) Average cellular velocity for all cells observed in the bone marrow (regardless of lineage status), compared to the average velocity of two cells quantitated in a blood vessel.

FIG. 33A to FIG. 33F. Comparative temporal dynamics of hematopoietic cells (FIG. 33A) Histogram showing duration of all the interactions (instances where cells were in contact with or proximal to a given region) calculated by this software. Two categories of interaction duration were identified: short (<60 minutes) and long (>60 minutes). (FIG. 33B) Cell trace depicting a short contact with the vascular region. Distance to the endosteal (gray line) and vascular (red line) regions as well as cell velocity (green line) for a representative cell is shown, highlighting a short contact interaction (dashed gates) with the vascular region. (FIG. 33C to FIG. 33F) Categorization of the interactions of KLS (black) and Lin⁻ (gray) cells by region and duration. (FIG. 33C) The incidence of interactions per cell found in the vascular region, sorted by duration. P=0.10 for KLS (n=33 cells) and **P=0.0126 for Lin– (n=31 cells) by Student's t test. (FIG. 33D) The incidence of interactions per cell found in the endosteal region, sorted by duration. P=0.09 for KLS (n=33 cells) and P=0.09 for Lin– (n=31 cells) by Student's t-test. Data represented as mean+SEM. (FIG. 33E) For each cell, the fraction of observation time (shown as percent) spent near (<25 microns; in contact or proximal to) the vascular (x-axis) and endosteal (y-axis) regions is plotted as a single point. Point overlap is indicated in the parentheses, where the first number represents KLS (black circle) and the second number Lin⁻ (gray diamond) cells that fall in that point. (FIG. 33F) Histogram containing the normalized average displacement for KLS and Lin⁻ cells, where displacement is defined as the distance between a current cell position and its first recorded position, and the displacement is normalized by the total time a given cell was observed.

FIG. 34A to FIG. 34E. Comparative associations of hematopoietic cells with vascular and endosteal regions (FIG. 34A) The relative fraction of time (shown as percent) in contact with the vascular or endosteal niche. P=0.0016 for Lin–. **P<0.0001 for KLS by Student's t-test. Data represented as mean+SEM. (FIG. 34B) The relative contact frequency (vasculature/endosteal) of KLS (black), Lin⁻ (gray) and Lin⁺ (solid hatched line) cells. (FIG. 34C) The relative fraction of time in proximal interactions with the vascular or endosteal niche. *P=0.0137 for Lin+ by Student's t-test. Data represented as mean+SEM. (FIG. 34D) The relative proximal frequency (vascular/endosteal) of KLS (black), Lin⁻ (gray) and Lin⁺ (solid hatched line) cells. (FIG. 34E) Model showing microenvironmental regions enriched for progenitor cell (Lin–) associations in homeostasis as an example. Cells are preferentially in contact with or proximal to the vascular niche but mostly proximal to, rather than in contact with, the endosteal region. Warmer colors (red) identify areas with a high probability of associations and cooler colors (blue) identify areas with a low probability of associations.

FIG. 35A to FIG. 35F. Msi2 reporter expression in stem/progenitor and differentiated hematopoietic cell populations (FIG. 35A) Representative flow cytometry plots show histograms of Msi2GFP fluorescence intensity in KLSCD150+CD48-, KLS, Lin⁻, $Lin^{lo}$ and $Lin^{hi}$ cells from adult bone marrow. (FIG. 35B) Representative flow cytometry plots show histograms of Msi2GFP fluorescence intensity in KLSAA4.1⁺, KLS, Lin⁻, $Lin^{lo}$ and $Lin^{hi}$ cells derived from E15.5 fetal liver. (FIG. 35C) Representative flow cytometry plots showing GFP expression in control (wildtype, non-reporter) bone marrow (light grey, dashed), $Msi2GFP^{bright}Lin^-$ cells (black), and differentiated cells from Msi2GFPreporter mouse (colored). (FIG. 35D) Representative flow cytometry plots showing GFP expression in control (wildtype, non-reporter) fetal liver cells (light grey, dashed), $Msi2GFP^{bright}Lin^-$ cells (black), and differentiated cells from Msi2GFP reporter mouse (colored). (FIG. 35E) Quantification of mean fluorescence intensity (MFI) of Msi2GFP in control bone marrow (wildtype, non-reporter), differentiated lineages and $Msi2GFP^{bright}Lin^-$ immature cells. (FIG. 35F) Quantification of mean fluorescence intensity (MFI) of Msi2GFP in control fetal liver, differentiated cells and $Msi2GFP^{bright}Lin^-$ undifferentiated cells.

FIG. 36A to FIG. 36C. Imaging $Msi2GFP^{bright}$ cells in vivo enables tracking of endogenous immature cells (FIG. 36A) Representative flow cytometry plot showing Msi2 reporter fluorescence intensity in B220+ cells (light grey) and $Msi2GFP^{bright}$ cells (dark grey). (FIG. 36B) Experimental design to image and compare fluorescence intensity of Msi2GFP⁺B220+ cells and $Msi2GFP^{bright}B220^-$ cells in vivo. (FIG. 36C) Representative images showing visible transplanted $Msi2GFP^{bright}B220^-$ cells after voltage-gated thresholding so Msi2GFP⁺B220+ cells were undetectable. Scale bar=40 μm.

FIG. 37A to FIG. 37I. Comparative associations of endogenous undifferentiated hematopoietic cells with vascular and endosteal regions using Msi2 knock-in reporter mouse Representative image of Msi2GFP (green); dsRed (red) mice showing $Msi2GFP^{bright}$ cells localized near vasculature (FIG. 37A) (white) and endosteum (FIG. 37D) (white). Scale bar=40 µm. 37 (FIG. 37B) Quantification showing the incidence of Msi2GFP$^{bright}$ cells localized in contact with, proximal, or distal to vasculature (n=43 cells from 5 mice). (FIG. 37C) Quantification of the mean distance to vasculature within contact, proximal, and distal regions. **P<0.0001 (n=43 cells from 5 mice) by Student's t-test. (FIG. 37E) Quantification showing the incidence of Msi2GFP$^{bright}$ cells localized in contact with, proximal, or distal to endosteum (n=33 cells from 5 mice). (FIG. 37F) Quantification of the mean distance to endosteum within contact, proximal, and distal regions. *P=0.0003 (n=33 cells from 5 mice) by Student's t-test. (FIG. 37G) Representative image of E15.5 Msi2GFP fetal liver showing Msi2GFP$^{bright}$ cells (green) localized near vasculature (white). Scale bar=40 µm. (FIG. 37H) Quantification showing the incidence of Msi2GFP$^{bright}$ cells localized in contact with, proximal, or distal to vasculature. (FIG. 37I) Quantification of the mean distance to vasculature within contact, proximal, and distal regions. ****P<0.0001 (n=52 cells) by Student's t-test. Data represented as mean+SEM.

FIG. 38A to FIG. 38I. Msi2 marks cancer stem cells in a mouse model of blast crisis CML. (FIG. 38A) Representative FACS plot shows GFP expression in the spleen of a terminally ill mouse transplanted with KLS cells isolated from REM2 mice and co-infected with BCR-ABL and NUP98-HOXA9. (FIG. 38B) Average frequency of GFP-negative (GFP$^-$) and GFP-positive (GFP$^+$) leukemic spleen cells (n=4 mice). (FIG. 38C) Representative histograms show lineage expression in GFP$^-$ and GFP$^+$ leukemic spleen cells. (FIG. 38D) Average frequency of lineage-negative (Lin$^-$) and lineage-positive (Lin$^+$) cells within either the GFP$^-$ or GFP$^+$ fraction (n=4 mice). (FIG. 38E). Number of colonies generated from GFP$^-$ and GFP$^+$ blast crisis CML cells. P=0.0020 (n=3 technical replicates). (FIG. 38F) Representative FACS plot shows GFP expression within the lineage-negative (Lin$^-$) fraction of the spleen from a leukemic mouse. (FIG. 38G) Number of colonies generated from Lin$^-$ GFP$^-$ and Lin$^-$ GFP$^+$ blast crisis CML cells after primary and secondary plating. *P=0.0001 (n=3 technical replicates each). (FIG. 38H) Schematic illustrates experimental approach to test the ability of established GFP$^+$ and GFP$^-$ blast crisis CML cells to drive disease development in secondary recipient mice. GFP$^+$ or GFP$^-$ cells from established blast crisis CML were transplanted into secondary recipients and (FIG. 38I) survival was monitored (n=8 for GFP and 10 for GFP$^-$).

Figure 39A:
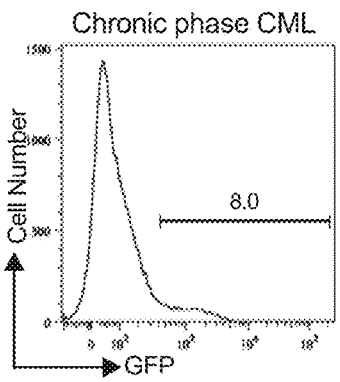
Figure 39B:
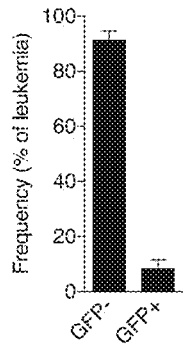
Figure 39C:
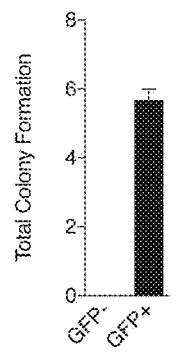
Figure 39D:
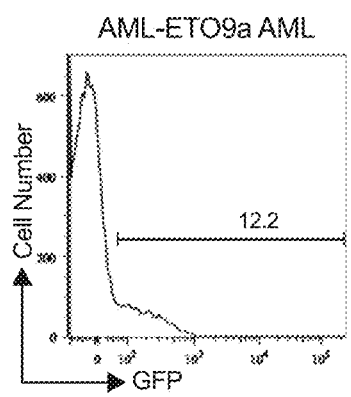
Figure 39E:
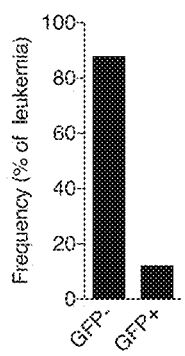
Figure 39F:
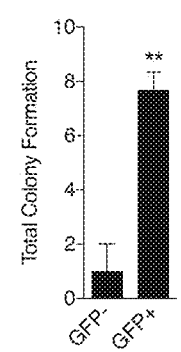
Figure 39G:
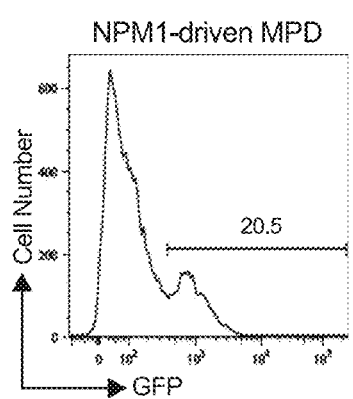
Figure 39H:
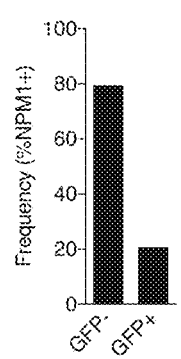
Figure 39I:
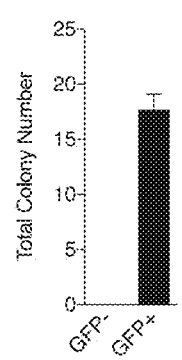

FIG. 39A to 39I. Msi2 reporter can be used broadly, as it marks the cancer stem cells in diverse hematologic malignancies. (FIG. 39A-FIG. 39C) Msi2 marks cancer stem cells in chronic phase CML. (FIG. 39A) Representative histogram shows GFP expression in leukemic spleen cells from a mouse with chronic phase CML. (FIG. 39B) Average frequency of GFP$^-$ and GFP$^+$ leukemic spleen cells from mice with chronic phase CML (n=4 mice). (FIG. 39C) Number of colonies generated from GFP$^-$ and GFP$^+$ chronic phase CML cells (n=3 technical replicates). (FIG. 39D-FIG. 39F) Msi2 marks cancer stem cells in AML-ETO9a/NRAS$^{G12V}$-driven AML. (FIG. 39D) Representative histogram shows GFP expression in leukemic spleen cells from a mouse with AML-ETO9a/NRAS$^{G12V}$-driven AML. (FIG. 39E) Frequency of GFP$^-$ and GFP$^+$ AML-ETO9a+/NRAS+ spleen cells from a mouse with AML-ETO9a/NRAS$^{G12V}$-driven AML. (FIG. 39F) Number of colonies generated from GFP$^-$ and GFP$^+$ AML-ETO9a+/NRAS+ cells. **P=0.0052 (n=3 technical replicates). (FIG. 39G-FIG. 39I). Msi2 marks disease-propagating cells in NPM1-driven MPD. (FIG. 39G) Representative histogram shows GFP expression in NPM1c+ spleen cells from a mouse with MPD. (FIG. 39H) Frequency of GFP$^-$ and GFP$^+$ NPM1c+ spleen cells from a mouse with MPD. (FIG. 39I) Number of colonies generated from GFP$^-$ and GFP$^+$ NPM1c+ cells (n=3 technical replicates).

FIG. 40A to FIG. 40D. Msi2 marks blast crisis CML cells that are highly resistant to radiation and imatinib treatment. (FIG. 40A and FIG. 40B) Msi2-expressing (GFP$^{hi}$) cells are highly resistant to imatinib-induced cell death. (40A) Representative histograms show frequency of live (Annexin V–) GFP$^{neg}$, GFP$^{lo}$ and GFP$^{hi}$ established lineage-negative blast crisis CML cells after 7 hours of imatinib (5 µM) or DMSO control treatment. (FIG. 40B) Average frequency of live (Annexin V–) GFP$^{hi}$ and GFP$^{neg}$ cells after 7 hours of imatinib (500 nM or 5 µM) or DMSO control treatment. *P=0.0139 for DMSO, **P<0.0001 for imatinib at 5 µM (n=2-4 for each treatment condition). (FIG. 40C and FIG. 40D) Msi2-expressing (GFP$^{hi}$) cells are highly resistant to radiation-induced cell death. (FIG. 40C) Representative histograms show frequency of live (Annexin V–) GFP$^{neg}$, GFP$^{lo}$ and GFP$^{hi}$ established lineage-negative blast crisis CML cells 7 hours following radiation (5 Gy). (FIG. 40D) Average frequency of live (Annexin V–) GFP$^{hi}$ and GFP$^{neg}$ cells 7 hours following radiation (0, 5, or 10 Gy). P=0.0095 at 0 Gy and **P=0.0034 at 5 Gy (n=1-3 for each treatment condition).

FIG. 41A to 41C. Msi2 reporter can be used to track cancer stem cells and identify sites that have an enhanced ability to protect therapy-resistant cells.

(FIG. 41A) The strategy used to track residual leukemia cells in vivo. KLS cells isolated from Msi2$^{GFP}$/Actb-DsRed mice were co-infected with BCR-ABL1 and NUP98-HOXA9 and subsequently transplanted into NOD-Scid IL2Rg$^{null}$ (NSG) recipient mice. Fourteen days post-transplantation (D14), recipient mice were treated daily with Gleevec or vehicle alone (control) for four consecutive days (D14 to D19) and analyzed by flow cytometry on D20. (FIG. 41B) Average frequency of Msi2+ (% GFP$^+$) leukemia cells determined at various anatomic sites from mice with blast crisis CML (n=3 mice). (FIG. 41C) Extent of residual disease at different anatomic sites following Gleevec treatment. Graph shows the average percentage of GFP$^+$ population (determined in (FIG. 41B)) remaining post-treatment (n=5 mice).

FIG. 42A to FIG. 42G. Msi2 confers resistance by facilitating effective repair following exposure to DNA damaging agents. (FIG. 42A) MSI2 inducible mice (doxycycline (dox)-inducible transgenic mice, which harbor the human MSI2 gene at the Col1a1 locus) were treated with dox for 3 days and subsequently whole body irradiated (3 Gy). Seven hours post-irradiation, KLS cells were sorted and plated in semi-solid methylcellulose media. Representative images of single colonies (lower left) and average total colony area (µm; right) generated following secondary plating ±dox and ±irradiation (IR) are given (n=3 technical replicates for each condition). (FIG. 42B-FIG. 42D) Loss of Msi2 impairs and/or delays the DNA damage response in HSC-enriched cells. (FIG. 42B) Representative images (63×; zoomed) show the nucleus of individual KLS cells isolated from irradiated (3 Gy) Msi2 mutant (Msi2$^{Gt/Gt}$) or wild-type (WT) mice stained with antibody to 53BP1 (green) and DAPI (gray) at 2 hrs (top) and 24 hrs (bottom) post-irradiation. (FIG. 42C-FIG. 42D) Average number of 53BP1+ foci in individual wild-type (WT) or Msi2-deficient HSC-enriched cells at 2 hrs (FIG. 42C) and 24 hrs (FIG. 42D) post-irradiation. P=0.0015 at 24 hrs (n=43-55 cells analyzed for each genotype at each time point). (FIG. 42E-FIG. 42G) Loss of Msi2 impairs and/or delays the DNA damage response in established blast crisis CML cells. (FIG. 42E) Representative images (63×; zoomed) show the nucleus of individual Propidium Iodide (PI)-negative live Msi2-deficient or wild-type established blast crisis CML cells that were irradiated (3 Gy) and stained with antibody to 53BP1 (green) and DAPI (gray) at 2 hrs (top) and 24 hrs (bottom) post-irradiation. (FIG. 42F-FIG. 42G) Average number of 53BP+ foci in individual wild-type (WT) or Msi2-deficient established blast crisis CML cells at 2 hrs (F) and 24 hrs (FIG. 42G) post-irradiation. **P<0.0001 at 24 hrs (n=51-65 cells analyzed for each genotype at each time point).

FIG. 43A to FIG. 43E. Msi2 does not mark cancer stem cells in MLL-AF9/NRAS$^{G12V}$-driven AML. (FIG. 43A) Representative histogram shows GFP expression in leukemic spleen cells from mice with MLL-AF9/NRAS$^{G12V}$ AML. (FIG. 43B) Average frequency of GFP$^-$ and GFP$^+$ leukemic spleen cells from mice with MLL-AF9/NRAS$^{G12V}$ AML (n=3 mice). (FIG. 43C) Number of colonies generated from GFP$^-$ and GFP$^+$ MLL-AF9/NRAS$^{G12V}$ AML cells in primary and secondary plating (n=3 technical replicates for both primary and secondary plating). (FIG. 43D) Kaplan-Meier plot showing survival of recipient mice transplanted with either GFP$^+$ or GFP$^-$ MLL-AF9/NRAS$^{G12V}$ AML cells (n=7 for GFP$^+$ and 6 for GFP$^-$). (FIG. 43E) Representative FACS profile showing c-Kit$^+$ expression versus GFP expression in MLL-AF9/NRAS$^{G12V}$ AML cells (n=3 mice).

FIG. 44A to FIG. 44C. Expression of DNA damage-related genes are significantly affected following the loss of Msi2. (FIG. 44A) Comprehensive gene expression analysis of Msi2-deficient leukemia and hematopoietic stem cells. For blast crisis CML, KLS cells from Msi2 mutant (Msi2$^{Gt/Gt}$; referred to as Msi2$^{-/-}$) or wild-type (WT) mice were co-infected with BCR-ABL and NUP98-HOXA9 and transplanted into recipient mice. After disease onset, established Lineage-negative (Lin$^-$) blast crisis CML cells were sorted from recipient mice and used for microarray analysis. For hematopoietic stem cell (HSC) cohorts, HSCs (KLS CD150+CD48$^-$) were sorted from Msi2 mutant (Msi2$^{Gt/Gt}$; referred to as Msi2$^{-/-}$) and wild-type (WT) mice. Microarray analysis was performed using three independent RNA samples for each genotype and cell type. In blast crisis CML, Msi2 deficiency resulted in 745 down-regulated and 581 up-regulated genes. Analysis revealed that 481 unique genes were down-regulated and 587 were up-regulated in HSCs by Msi2 loss (False Discovery Rate (FDR) p<0.05). (FIG. 44B) Gene Ontology analysis with the affected gene sets identified 25 and 49 unique Biological Processes (BPs) that were affected by Msi2 loss in HSCs and blast crisis CML, respectively. Among them, 11 BPs were commonly affected between the two different cell types. (FIG. 44C) The 11 commonly affected Biological Processes (BPs) by the loss of Msi2 gene in HSCs and leukemia. Only 3 BPs (highlighted in blue) were significantly affected in both cell types at FDR<0.01, suggesting that Msi2 loss affects the stress response pathway to DNA damage stimuli.

Figure 45:
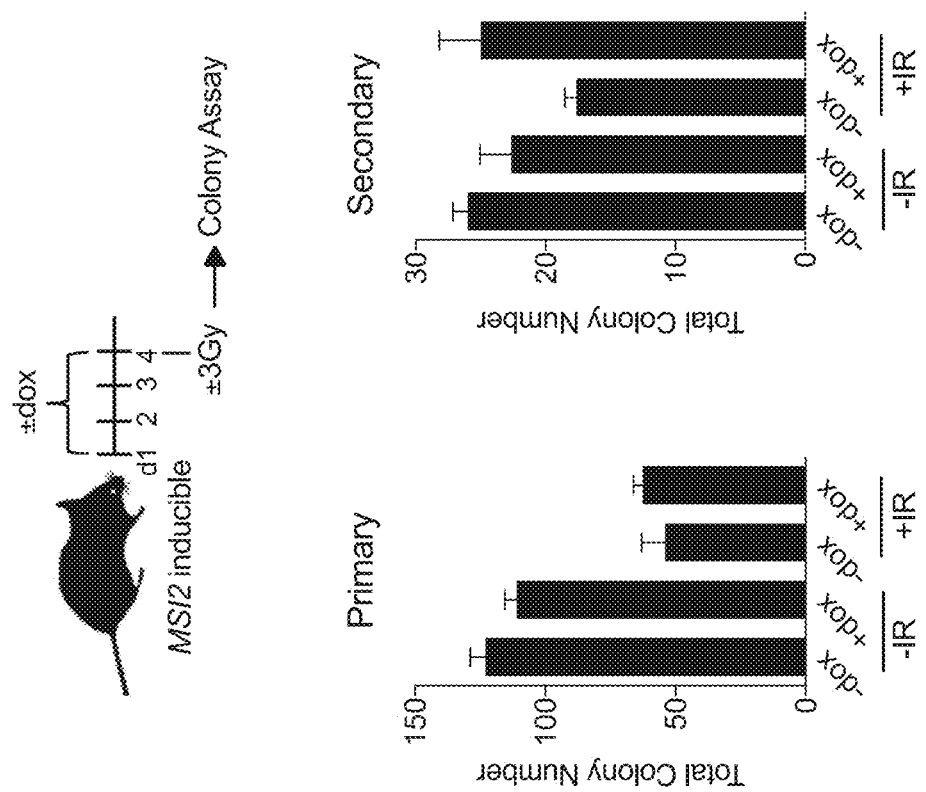

FIG. 45. Ectopic expression of MSI2 rescues impaired colony-forming ability of Msi2-deficient cells following irradiation. MSI2 inducible mice were treated with dox for 3 days followed by whole body irradiation at 3 Gy. Seven hours post-irradiation, KLS cells were sorted and plated in semi-solid methylcellulose media. Total number of colonies generated following primary and secondary plating ±dox and ±irradiation (IR) are given. (n=3 technical replicates for both primary and secondary plating).

FIG. 46A to FIG. 46C. A signaling pathway that when inhibited in HSCs improved stem cell function in vitro. Msi2$^{+/GFP}$ mice were pretreated with inhibitor before a 6 Gy sublethal irradiation and imaged one week after radiation (FIG. 46A). There was a clear enrichment of Msi2GFP$^{bright}$ immature hematopoietic cells (FIG. 46B). Quantification revealed a 2.7 fold increase in Msi2GFP$^{bright}$ cells within the bone marrow (FIG. 46C).

Figure 47B:
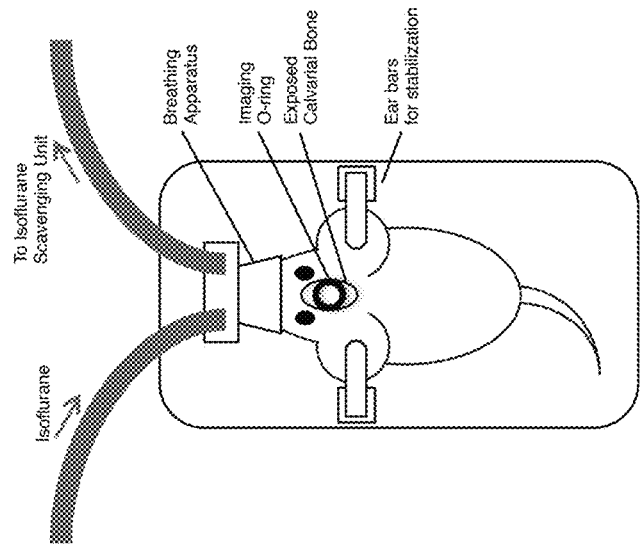
Figure 47A:
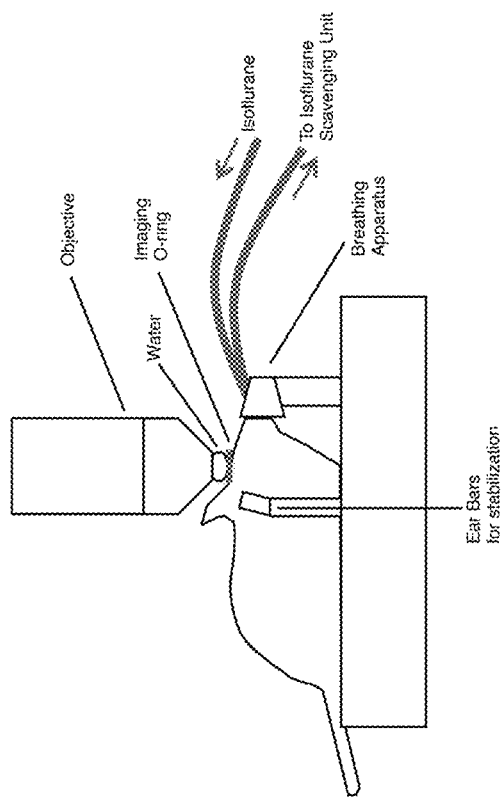

FIG. 47A and FIG. 47B. Schematic of intravital mouse imaging system. (FIG. 47A) A side view depicting an anesthetized mouse placed in a sterotactic holder prepared for confocal microscopy. Ear bars stabilize the mouse in the holder. A breathing apparatus keeps the mouse under anesthesia with isoflurane gas. An imaging O ring is secured to exposed calvarial bone. Water is placed in the O ring, through which the objective is able to image the calvarium. (FIG. 47B) An arial view depicting an anesthetized mouse placed in a stereotactic holder prepared for confocal microscopy.

FIG. 48A to 48E. Detection of vascular and endosteal surface in the bone marrow microenvironment. Representative 10× and 20× images of mice treated with Angiosense 680 prove (FIG. 48C and FIG. 48D), which marks the vasculature. Representative 10× and 20× image of mice treated with Osteosense 680 probe (FIG. 48C and FIG. 48D), which marks active osteoblasts (FIG. 48E). Still image of dsRed red recipient labeled in vivo with monoclonal antibody for tissue macrophage marker F4/80.

Figure 49C:
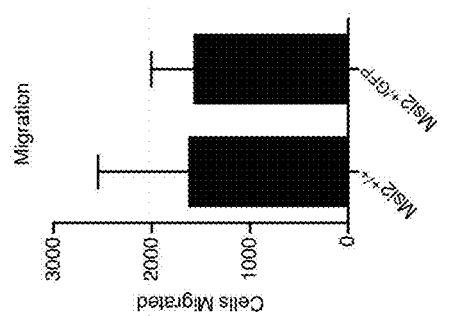
Figure 49B:
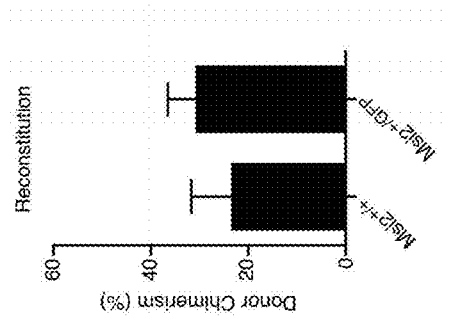
Figure 49A:
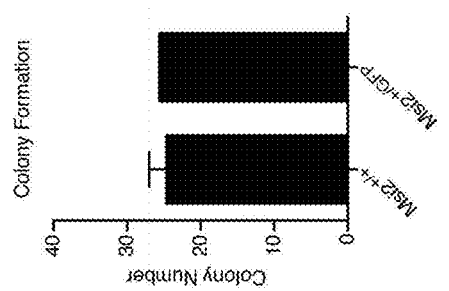

FIG. 49A to FIG. 49C. Functional Analysis of Msi2GFP hematopoietic cells. (FIG. 49A) Number of colonies generated from Msi2$^{+/+}$ and Msi2$^{+/GFP}$ LT-HSCs (KLSCD150+ CD48−) (Not significant by Student's t-test, n=3 technical replicates). (FIG. 49B) Average donor chimerism 4 weeks after transplantation (Not significant by Student's t-test, 3-5 mice per cohort). (FIG. 49C) Number of ckit+Lin− cells from Msi2$^{+/+}$ and Msi2$^{+/GFP}$ mice migrated in response to SDF1 (Not significant by Student's t-test, n=3 technical replicates). Data represented as mean+SEM.

Figure 50A:
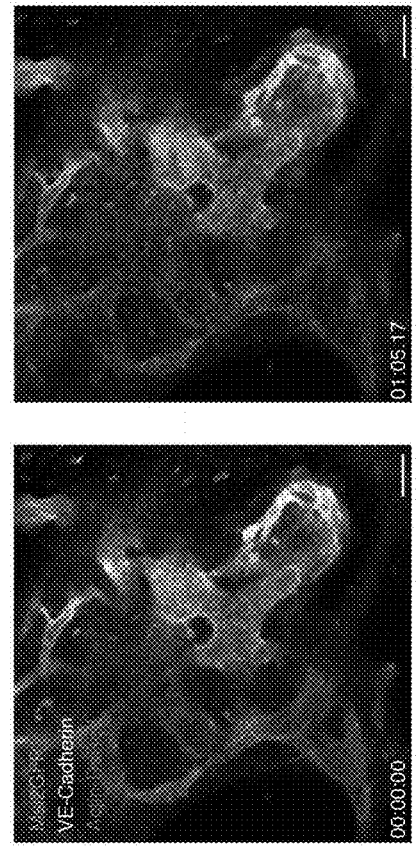
Figure 50B:
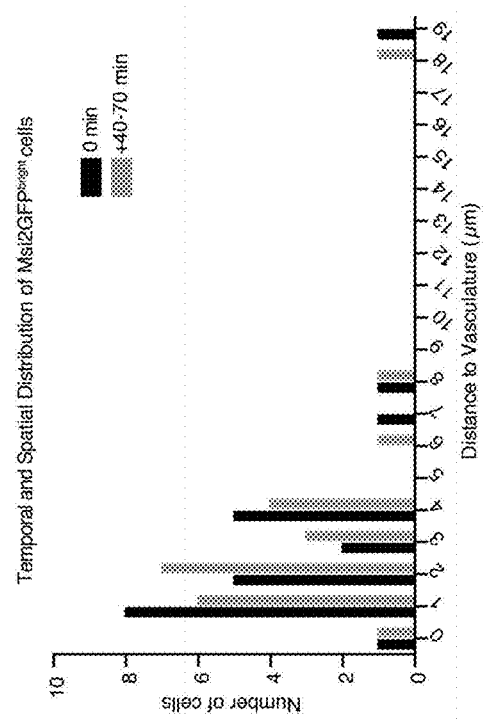

FIG. 50A and FIG. 50B. Temporal Analysis of Msi2 reporter interactions with the niche. (FIG. 50A) Representative image of a Msi2GFP$^{bright}$ cell (green) localized in contact with vasculature (white) shown are the images taken at t=0 (left panel) and at endpoint t=01:05:17 (right panel). Scale bar=40 μm. (FIG. 50B) Histogram showing the distance of Msi2GFP$^{bright}$ cells to vasculature at t=0 (black) and t=40-70 min later (grey) (n=24 cells from 3 mice).

FIG. 51A and FIG. 51B. Irradiation causes severe degradation of the bone marrow microenvironment. Representative images of bone marrow vasculature (white) in an unirradiated mouse (FIG. 51A) and a lethally irradiated (9.5 Gy) mouse (FIG. 51B) Scale bar=60 μm.

Figure 52:
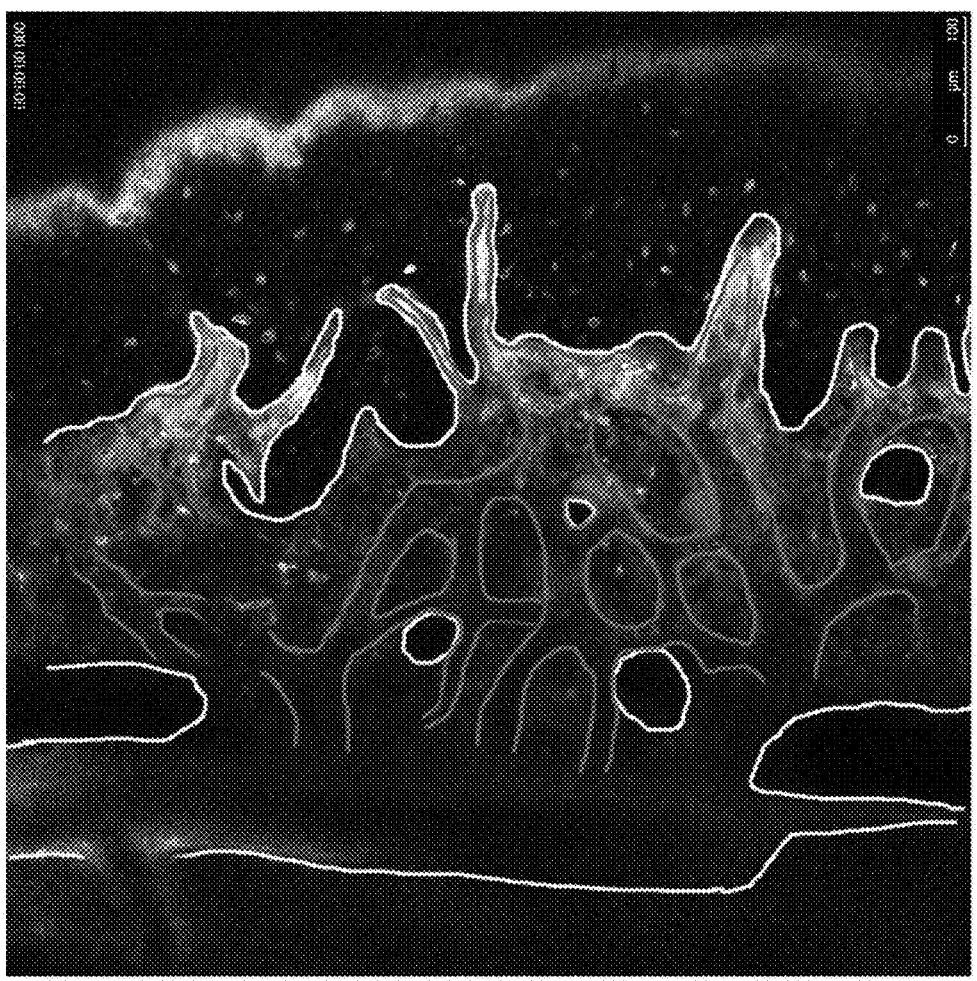

FIG. 52. Representative image of Niche Domain Mapping. A representative frame from a video of KLSGFP+ cells transplanted into a DsRed mouse. The location of domains was traced manually (vasculature in red, endosteum in white). This trace was used by software to determine the distance of cells in interest to microenvironmental domains. Scale bar=100 μm.

FIG. 53. Msi2 deletion leads to reduced tumor burden in a p53/Ras induced model of lung adenocarcinoma.

Figure 54:
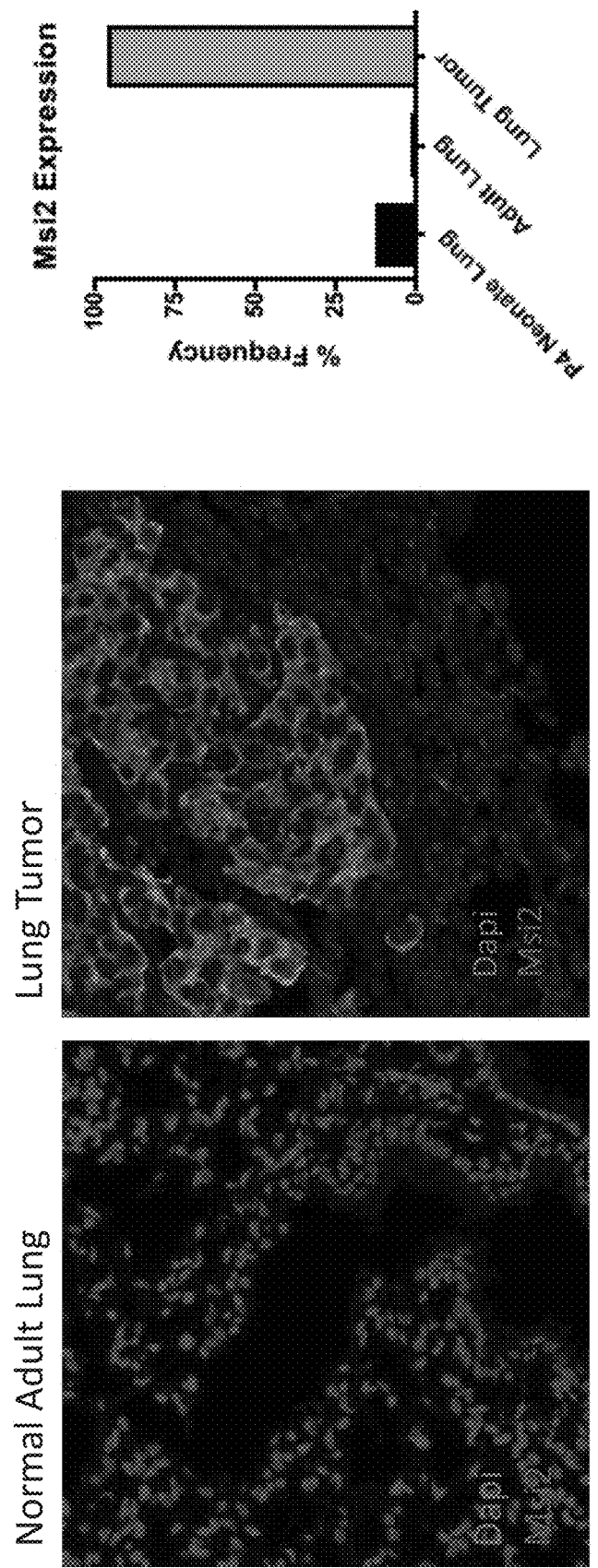

FIG. 54. Msi2 reporter expression in normal lung and lung cancer.

Figure 55:
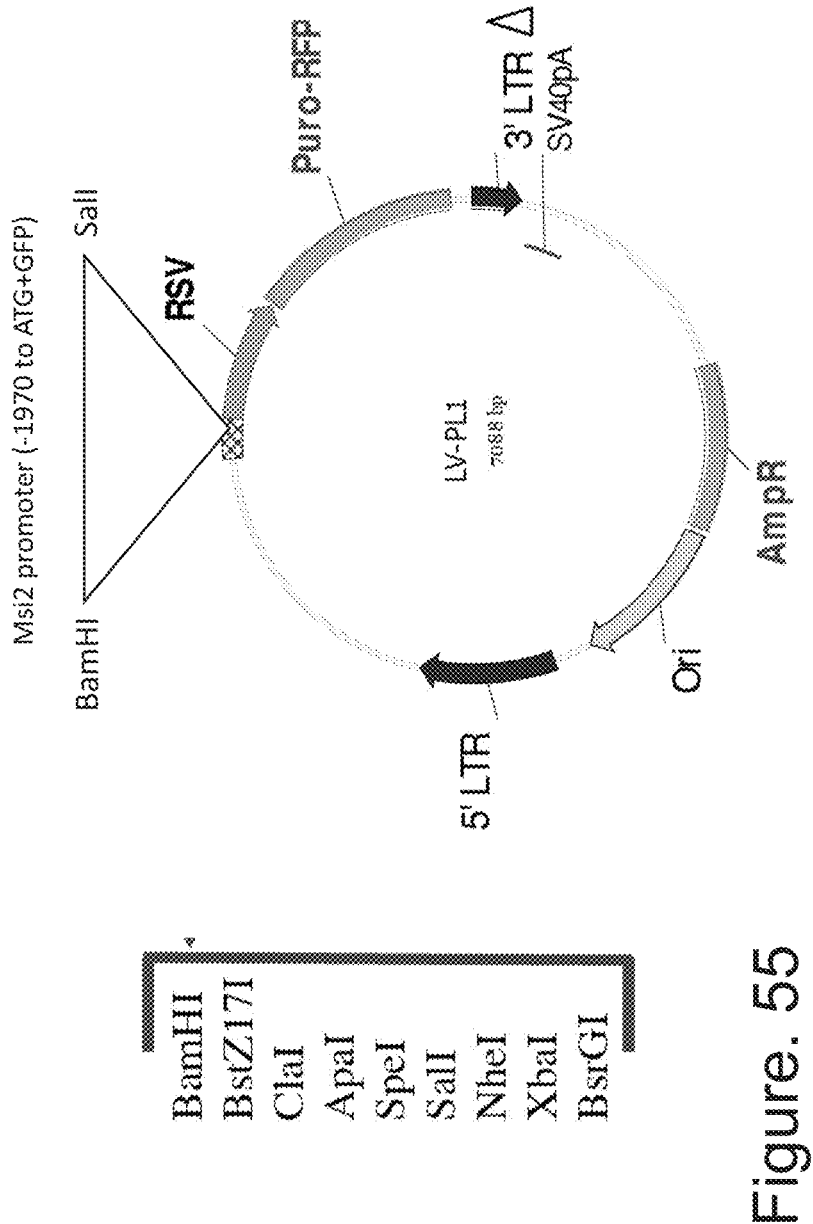

FIG. 55. Msi2 promoter reporter vector

Figure 56:
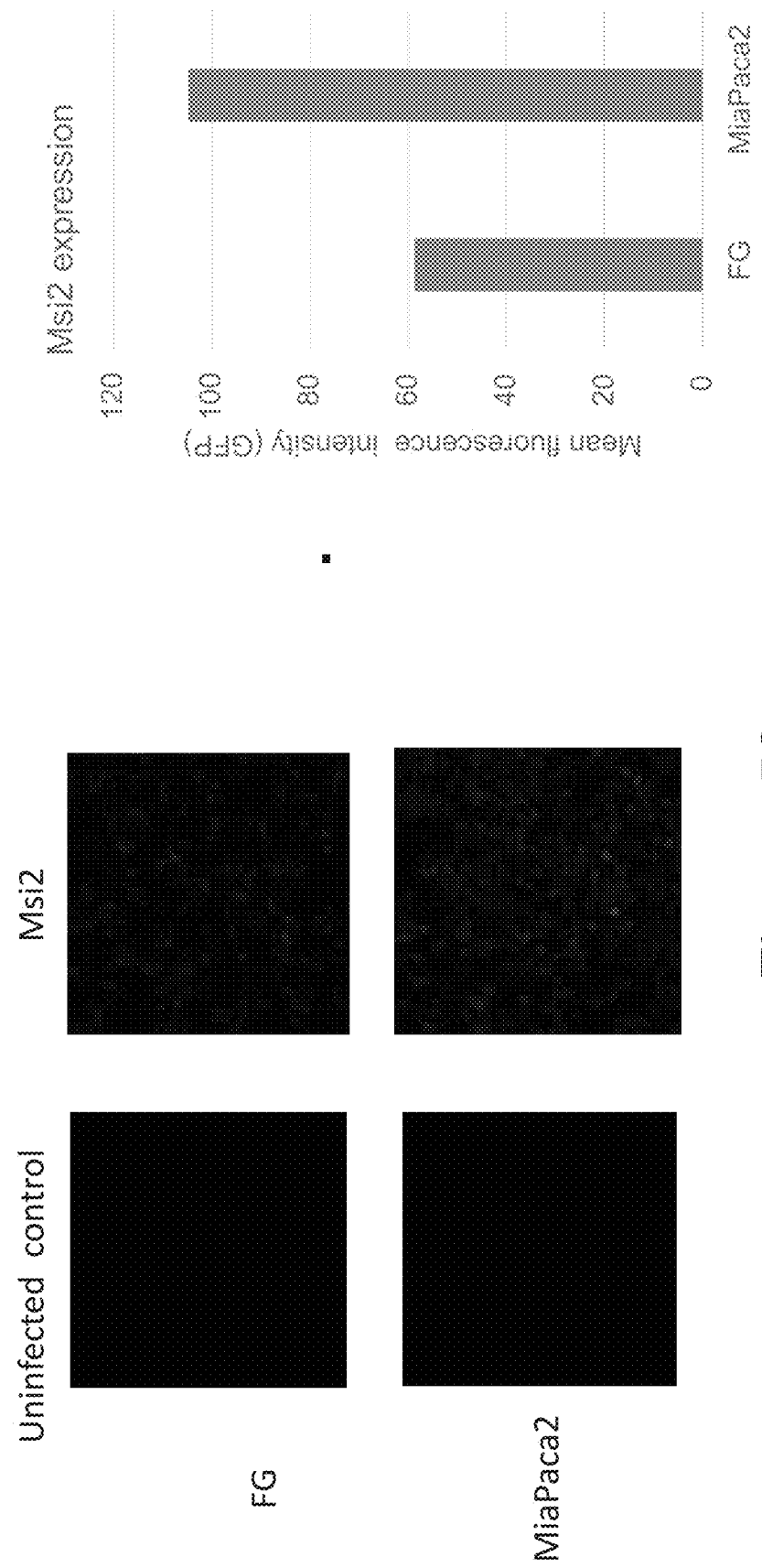

FIG. 56. Msi2 reporter expression: MP2 and FG cells

DEFINITIONS

"Genetic engineering," as described herein, is the direct manipulation of an organism's genome using biotechnology and is known to those skilled in the art. For example, it is a set of technologies used to change the genetic makeup of cells, including the transfer of genes within and across species boundaries to produce improved or novel organisms. Without being limiting, new DNA or other genetic material, can be inserted in the host genome by first isolating and copying the genetic material of interest using molecular cloning methods to generate a DNA sequence, or by synthesizing the DNA, and then inserting this construct into the host organism. Genes may be removed, or "knocked out", using a nuclease. Gene targeting is a different technique that uses homologous recombination to change an endogenous gene, and can be used to delete a gene, remove exons, add a gene, or introduce point mutations. A cell can be genetically engineered to provide a genetically engineered cell. In some embodiments, a genetically engineered cell comprising a nucleic acid encoding a detectable polypeptide operably linked to the Msi1 promoter, is provided.

In some embodiments, a genetically engineered cell is provided. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell. In some embodiments, the cells are from tissue stem cells. In some embodiments, the cells are pancreatic beta cells. In some embodiments, the cells are neural stem cells.

"Nucleic acid" as described herein, or nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery polynucleotide for stable insertion of a nucleic acid into a gene is provided. "Oligonucleotide" can be used interchangeable with nucleic acid and can refer to DNA or RNA, either double stranded or a single stranded piece or DNA or RNA.

"Operably linked" as used herein refers to functional linkage between a regulatory sequence and a heterologous nucleic acid sequence resulting in expression of the latter.

As described herein, a "polypeptide" is a long, continuous, and unbranched peptide chain. Hence, peptides fall under the broad chemical classes of biological oligomers and polymers, alongside nucleic acids, oligosaccharides and polysaccharides, etc.

"Coding for" or "encoding" are used herein refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Msi1" as described herein refers to Musashi1, a gene that encodes a protein containing two conserved tandem RNA recognition motifs. Similar proteins in other species function as RNA-binding proteins and play central roles in posttranscriptional gene regulation. Expression of this gene has been correlated with the grade of the malignancy and proliferative activity in gliomas and melanomas.

"Msi2" as described herein refers to Musashi 2 (Msi2), which is expressed as a RNA-binding protein in neuronal progenitor cells, including stem cells, and both normal and leukemic blood cells. Musashi2 can be found in a variety of tissues, such as, for example, stem cells, bulge region of the hair follicle, immature pancreatic β-cells and neural progenitor cells. In neural progenitor cells, Msi2 is expressed in early stages of development, in the ventricular and subventricular zone, in cells of the astrocyte lineage. Within the hematopoietic system, Msi2 is highly expressed in the most primitive progenitors, in stem cell compartments, and its overexpression has been found in myeloid leukemia cell lines. In neural cell lines, is exclusively located in the cytoplasm.

Kras polypeptide or Kras peptide as described herein, is the protein product of the normal KRAS gene performs an essential function in normal tissue signaling, and the mutation of a KRAS gene is an essential step in the development of many cancers. There are two protein products of the KRAS gene in mammalian cells that result from the use of alternative exon 4 (exon 4A and 4B respectively): K-Ras4A and K-Ras4B, these proteins have different structure in their C-terminal region and utilise different mechanisms to localize to cellular membranes including plasma membrane.

"BCR-ABL peptide or polypeptide" as described herein, is a product of a fusion gene created by juxtapositioning the Abl1 gene on chromosome 9 (region q34) to a part of the BCR ("breakpoint cluster region") gene on chromosome 22 (region q11).

"NUP98-HOXA9," as described herein, is the chimeric protein resulting from the t(7;11)(p15;p15) chromosomal translocation, and is a prototype of several NUP98 fusions that occur in myelodysplastic syndromes and acute myeloid leukemia.

"Tumor suppressor proteins" are expressed from tumor suppressor genes. In some embodiments herein, a cell comprises a genetic modification which reduces the level or activity of or inactivates one or more tumor suppressor proteins. Without being limiting, the tumor suppressor protein can be p53, p16/INK4A, and SMAD4, for example.

"Cancer," as described herein, is a group of diseases involving abnormal cell growth with the potential to invade or spread to other parts of the body. Subjects that can be addressed using the methods described herein include subjects identified or selected as having cancer. Such identification and/or selection can be made by clinical or diagnostic evaluation. In some embodiments, the tumor associated antigens or molecules are known, such as adenocarcinoma, lung, pancreatic cancer, chronic myelogenous leukemia or leukemia.

"Flourescent polypeptide" as described herein refers to a protein that can exhibit bright fluorescence when exposed to a specific light range.

Cancer therapeutics as described herein are drugs for the treatment of cancer. Without being limiting, therapeutics can include: Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine, and Zoledronic acid.

DETAILED DESCRIPTION OF THE PREFERRED EMBODIMENT

Detection of drug resistant residual disease is currently a major technical challenge since the cells can hide in low numbers at any spatial location and cannot always be detected in blood draws or aspirates. This residual disease, while dormant for long periods, can reinitiate tumor growth and lead to disease relapse. Currently, there is no reliable way to visualize and track cancer stem cells and therapy resistant cancer cells in vivo. Moreover, there is a critical need for the development of methods to specifically target drug resistant residual disease, and to detect cancers at earlier stages. To this end, the Msi reporter mice that are described herein represent unique and valuable resources that can be used to identify and track drug resistant cells in drug development (which would provide a powerful and sophisticated complement to traditional screens that usually assess de-bulking), develop strategies aimed at identifying the spatial location of therapy resistant cancer cells (which could allow regional targeting and minimize collateral damage in normal tissues), identify and radiosensitize resistant tumor cells (which could improve locoregional targeting and improve disease outcomes), and develop methods for early detection of cancer (which has the potential to dramatically improve survival rates).

The compositions and methods described herein provide a new and unique platform for drug discovery. For example, the compositions and methods described herein can be utilized (in vitro or in vivo) screens to identify compounds that can target cancer stem cells and therapy resistance cells. They can also be used for development of diagnostic and prognostic kits for these diseases, as the tumorigenic cells and CTCs can be visualized using a fluorescent marker. In addition, they can also be used to develop methods for early detection of cancer, as well as methods to monitor both tumor metastasis in cancer patients and the efficacy of cancer treatments. In some embodiments, a composition for use in identifying that can target cancer stem cells and therapy resistance cells is provided. In some embodiments, methods are provided for the identification of compounds that can target cancer stem cells and therapy resistance cells.

In addition to their application in cancer drug development, the compositions and methods described herein can be used to identify and screen compounds that can expand stem cell populations and trigger improved regeneration in a variety of tissues where Msi reporter activity marks stem and progenitor cells.

There are a number of different approaches to cancer therapy, including surgery, targeted drug delivery, chemotherapy and radiation. However, in many cases, these approaches have only limited effectiveness. For example, in pancreatic cancer, although surgical resection could be curative, only 20% of newly diagnosed cases are resectable. Even with macroscopic resection, residual microscopic disease remains high, triggering locoregional recurrence and, often times, metastases. And although radiation therapy is a tool often used to treat cancer in an attempt to improve local tumor control, a key challenge is the limitation of dose escalation due to toxicity of neighboring sensitive normal organs. In addition, one critical problem with many cancer treatments is that despite initial responses, cancers become resistant to conventional therapies, and the cells that persist after treatment drive disease relapse. Methods to specifically target drug resistant residual disease will assist in ending this pattern of recurrence.

Present day medicine relies heavily on imaging systems such as X-ray, MRI, and PET, which detect spatial abnormalities as a way to identify diseases such as cancer. Although these approaches diagnose 120 million Americans with cancer during their lifetimes, cancer continues to claim millions of lives worldwide. In some very significant part this extraordinary toll is due to the inability to detect the disease early. Early detection of cancer vastly increases the likelihood of effective and durable responses to therapy, and can make the difference between life and death. Thus, improved strategies for early detection of cancer are desperately needed.

Embodiment 1: Development of Msi Reporter Mice

To visualize, isolate and track the function of live Musashi (Msi)-expressing cells in vivo, Msi knock-in reporter strains were developed in which a fluorescent signal reflects endogenous expression of Msi. To preserve physiological regulation of expression, the Musashi1 (Msi1) reporter mouse was generated by knocking a eYFP cassette into the 1st exon of the Msi1 locus (Msi1eYFP, FIG. 1A), and the Musashi2 (Msi2) reporter was generated by knocking eGFP into the 1st exon of the Msi2 gene locus (Msi2eGFP, FIG. 1B). Msi1 reporter mice (referred to here as Reporter for Musashi1, or REM1) showed bright and circumscribed expression in the subventricular zone of the adult brain, an area that harbors neural stem and progenitor cells. In addition, all of the Msi1+ cells were Nestin+ and CD133+, consistent with Msi1 marking neural stem and progenitor cells. Msi2 reporter (REM2) mice also accurately reflected endogenous expression of Msi2; thus Msi2 reporter expression was high in hematopoietic stem cells and declined rapidly with maturation, consistent with previously reported RNA expression patterns. In both reporters, expression of Msi1 and Msi2 was concordant with expression of eYFP and eGFP, suggesting that persistence of eGFP or eYFP was not extensive.

The Musashi proteins are important genes, not only during normal development, but also during oncogenesis. Thus, genetically engineered Msi reporter organisms described herein, such as Msi reporter mice, can provide a platform to probe tumor heterogeneity and identify and track the cells responsible for propagating the tumor and for therapy resistance. Below is the work describing the use of Msi reporter mice in studies of pancreatic cancer and leukemia.

Embodiment 2: Tracking Msi-Expressing Cells in Pancreatic Cancer

In some embodiments, the genetically engineered Msi reporter organisms described herein can be used to define how Msi-expressing cells contribute to pancreatic cancer. Thus, to test if Msi-expressing cells preferentially harbor the ability to propagate pancreatic cancer, REM knock-in mice were crossed to the Kras-mutant/p53-null genetically engineered mouse model of pancreatic cancer. This model contains a lox-STOP-lox flanked KRASG12D allele, which is conditionally controlled by a Cre recombinase transgene driven by the pancreas-specific Ptf1a promoter. Ptf1a-Cre is also utilized to conditionally-delete the tumor suppressor p53. While the Kras mutation alone leads to PanIN formation, activation of Kras together with deletion of p53 drives progression to adenocarcinoma. KrasLSL-G12D/+; p53f/f; Ptf1aCRE/+ (referred to here as KPf/fC) were crossed to both REM1 and REM2 mice. In vivo imaging of live pancreatic tissue revealed clear Msi1 and Msi2 reporter activity within the tumors; interestingly, reporter positive cells were not disseminated throughout the tumor but in fact present in a spatially restricted manner (FIG. 1C and FIG. 1E).

Embodiment 3: Functional Heterogeneity Defined by Msi Reporter Expression in PDAC Flow cytometry-based quantification confirmed that Msi reporter activity was restricted to a minority cell population: Msi1 reporter was detected in 0.6-2.1% (FIG. 1D), and Msi2 in 5.6-12.2% of pancreatic cancer cells (FIG. 1F). Their expression overlapped in only 7% of EpCAM+ cells (FIG. 1G). Because cancer stem cells are similarly rare, it was tested if Msi-expressing cells can have preferential capacity for tumor initiation and self-renewal. While only 9.7% of the bulk tumor was ALDH+, a marker of pancreatic cancer stem cells, 98.4% of the Msi1-reporter+ cells and 95.6% of the Msi2-reporter+ cells co-expressed ALDH (FIG. 1H to FIG. 1K). Functionally Msi1 reporter+ cells gave rise to 31 fold higher numbers of colonies relative to Msi1 reporter− cells (FIG. 1L to FIG. 1N). Msi2 reporter+ cells were also highly enriched for their ability to form tumor spheres (FIG. 1O to FIG. 1Q).

The ability of Msi reporter+ and Msi reporter− cells to drive pancreatic cancer in vivo was tested. Msi1+ cells did not form tumors in vivo in small numbers (100, 1000), unlike Msi2+ cells (see below). Because Msi1+ cells are rare, sufficient cell numbers could not be retrieved to test their tumorigenic potential at higher numbers. This can imply that Msi1+ cells are less tumorigenic than Msi2+ cells, or Msi1+ cells are more quiescent than Msi2+ cells. Thus the focus was on the tumorigenic potential of Msi2 reporter cells in vivo. While as few as 100 Msi2-reporter⁺ cells could generate tumors, Msi2-reporter⁻ cells required a minimum of 1000 cells for tumor formation (FIG. 1R to FIG. 1T). Additionally, the tumors that did form with Msi2 reporter⁻ cells developed with a substantially longer latency and were 7-fold smaller than those generated by Msi2 reporter+ cells (FIG. 1T). In all, while 12/12 mice transplanted with GFP+ cells developed a tumor, only 3/12 mice displayed a tumor among the mice transplanted with GFP− cells. These data suggest that the Msi2-expressing cells surprisingly have significantly higher capacity to initiate adenocarcinoma growth. Further, reporter+ cells could recreate the heterogeneity as well as the histological characteristics of the original tumor. Importantly reporter+ cells were far more aggressive in causing lethal disease. 1000-10000 EpCAM+/Msi2+ or EpCAM+/Msi2− cells were transplanted orthotopically into recipients and survival monitored (FIG. 1U and FIG. 1V). While 100% (6/6) of mice that received GFP+ cells died (3 receiving 1,000 GFP+ cells, and 3 receiving 10,000 cells) none of the mice receiving GFP⁻ cells (0/6) showed signs of disease and remained healthy. Tumors derived from GFP+ cells invaded extensively into surrounding normal tissues; further Msi2+ cells were enriched in pro-EMT (epithelial-mesenchymal transition) and pro-invasion/migration genes. These studies strongly suggest that Msi2 reporter+ cells preferentially drive pancreatic cancer growth, invasion and lethality.

Since cells that disseminate from the primary lesion initiate growth at distant metastatic sites, Msi reporter expression in circulating tumor cells was analyzed. While Msi2+ cells comprised 9.7% of primary tumors from REM2-KPf/fC mice, they represented 38% and 44% of EpCAM+ circulating tumor cells in the peripheral blood and ascites, respectively (FIG. 1W), suggesting that Msi2 expression is 4-fold more enriched in cells that contribute to seeding secondary sites. Consistent with this, metastatic foci within the lung and liver contained a higher frequency of Msi2 reporter+ cells, and Msi1 was highly expressed in metastatic tumors in KPR172H/+C compared to the matched primary controls. Consistent with elevated Msi signaling in metastatic lesions, Msi2+ CTCs had much greater tumorigenic/colony forming capacity relative to Msi2− CTCs (FIG. 1X). These data, combined with the observations that Msi positive cells can preferentially drive tumor growth, suggest that Msi-expressing tumor cells can have enhanced capacity for driving tumor growth at new sites.

Embodiment 4: Tracking Therapy Resistance with Msi Reporter Mice in PDAC

The development of the reporter gave us a unique opportunity to determine whether it could be used as a new image based tool to identify therapy resistant cells in pancreatic cancer. The chemotherapeutic agent gemcitabine remains the standard of care for adjuvant treatment of pancreatic cancer and is the most commonly used single agent in the treatment of advanced disease. Despite this, clinical response rates to gemcitabine are below 10% and it fails to prevent relapse after surgery in 85% of patients. Gemcitabine was delivered to tumor-bearing REM2-KPf/fC mice in vivo at increasing doses to determine the composition of residual disease. Remarkably GFP− cells appeared sensitive to gemcitabine and were preferentially eliminated, while GFP+ cells were resistant and remained viable despite treatment with high doses of the drug (FIG. 1Z). Importantly, these experiments identify Msi reporter positive cells as the predominant gemcitabine resistant population. They further suggest that the newly developed Msi reporters could be an invaluable tool for tracking and visualization of drug resistant cells, and for testing therapeutic strategies designed to more effectively eliminate them.

Embodiment 5: Tracking Msi-Expressing Cells in Leukemia

It was previously shown that Msi2 plays an essential role in the development of blast crisis chronic myelogenous leukemia (CML), in part through its ability to block differentiation by repressing the expression of the cell fate determinant Numb (Ito et al., 2010). To examine if Msi2 reporter expression defines a distinct cell population within myeloid leukemia, blast crisis CML was modeled by transducing KLS cells isolated from REM2 mice with BCR-ABL and NUP98-HOXA9 and subsequently transplanting them into irradiated recipient mice. Flow cytometric analysis indicated that on average ~77% of the leukemia cells isolated from the spleen of terminally ill mice are GFP-positive (FIG. 2A and FIG. 2B). To determine whether GFP expression levels reflect cell differentiation status, leukemia cells were stained for mature hematopoietic lineage markers. It was found that whereas almost all of the GFP-negative cells (~91%) were positive for mature lineage markers (Lin+), on average ~85% of GFP-positive cells were negative for mature lineage markers (Lin−) (FIG. 2C and FIG. 2D), suggesting that GFP levels inversely correlate with the differentiation status of leukemia cells and thus, that GFP marks immature leukemia cells.

Embodiment 6: Functional Heterogeneity Defined by Msi Reporter Activity in Blast Crisis CML To define the cellular basis of the tumor heterogeneity observed with GFP levels, functional differences between GFP+ and GFP− leukemia cells were analyzed. To test this, the colony-forming ability of GFP+ and GFP− leukemia cells was first assessed and it was found that GFP+ cells formed on average 14.5-fold more colonies than GFP− cells (FIG. 2E and FIG. 4B). Since ~85% of GFP+ cells are Lin− (FIG. 2C), these data are consistent with previous work showing that all leukemia stem cell (LSC) activity resides in the immature Lin− compartment of BCR-ABL/NUP98-HOXA9-driven blast crisis CML. However, REM2 mice were used to further fractionate the Lin− compartment into a GFP+ and GFP− population (FIG. 2F). Interestingly, Lin− GFP+ cell formed on average ~6-fold more colonies than Lin− GFP− cells. The higher clonogenic activity of Lin− GFP+ was maintained after secondary plating, where Lin− GFP+ cells formed on average ~5-fold more colonies than Lin− GFP− cells (FIG. 2G). These data suggest functional heterogeneity exists even within the immature Lin− fraction of blast crisis CML. To determine whether GFP+ leukemia cells contain functional LSC activity in vivo, transplantation-based experiments were performed. To this end, established GFP+ or GFP− blast crisis CML cells were transplanted into irradiated mice. Whereas none of the mice transplanted with GFP− cells developed leukemia, 100% of mice transplanted with GFP+ cells succumbed to blast crisis CML and died within 23 days (FIGS. 2H, 2I and 4C), suggesting that all LSC activity in vivo resides within the Msi2-expressing GFP+ fraction of the leukemia. Overall, these data demonstrate that in a mouse model of blast crisis CML, GFP marks LSCs in vivo, and thus, that Msi2 reporter mice can be used to track tumor heterogeneity and identify the cells responsible for propagating blast crisis CML in vivo.

Figure 3B:
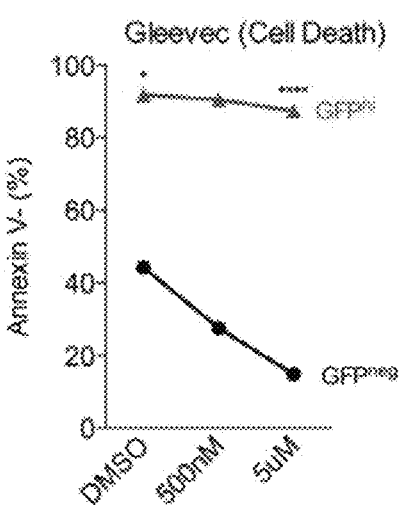

Embodiment 7: Therapy-Resistant Population Defined by Msi2GFP Reporter in Blast Crisis CML Previously it has been shown that LSCs are resistant to conventional anticancer therapies and thus, residual LSCs that persist after cessation of treatment inevitably drive disease relapse. To determine whether the Msi2-expressing population of blast crisis CML can mark such a therapy-resistant residual population, the resistance of Msi2-expressing leukemia cells to the BCR-ABL tyrosine kinase inhibitor was first tested, imatinib mesylate (also known as Gleevec), which is the gold-standard treatment for chronic phase CML. Although imatinib effectively induces a complete hematologic response in almost all chronic phase CML, imatinib is much less effective in treating blast crisis CML. This can be due to the fact that a higher fraction of blast crisis CML compared to chronic phase CML is composed of a population of cells largely insensitive to imatinib treatment. To test whether Msi2-expressing cells within blast crisis CML mark the imatinib-resistant population, blast crisis CML cells was treated with imatinib in vitro and cell death was analyzed by Annexin V staining 7 hours post-treatment. To account for any differences in cell survival between GFP+ and GFP− cells that is solely due to differences in differentiation status, we specifically analyzed cell survival of GFP+ and GFP− leukemia cells within the lineage-negative (Lin−) fraction. Interestingly, it was found that only a small fraction (~14%) of cells within the Lin− GFP− population were viable following exposure to imatinib at 5 µM (FIG. 3A and FIG. 3B). Surprisingly, however, more than 86% of the Lin− GFP+ cells remained viable following drug treatment at this high dose (FIGS. 3A, 3B and 5B), suggesting that GFP+ cells are highly resistant to imatinib-induced cell death. Importantly, while Lin− GFP+ cells displayed a 2-fold increase in cell viability compared to Lin− GFP− cells without treatment, differences in cell survival between Lin− GFP+ and Lin− GFP− cells increased 3-fold following imatinib treatment, indicating that Lin− GFP+ cells are indeed more resistant to imatinib (FIGS. 3B and 5B). Collectively, these data demonstrate that Msi2-expressing cells mark the targeted therapy-resistant cells within the leukemia.

Figure 3C:
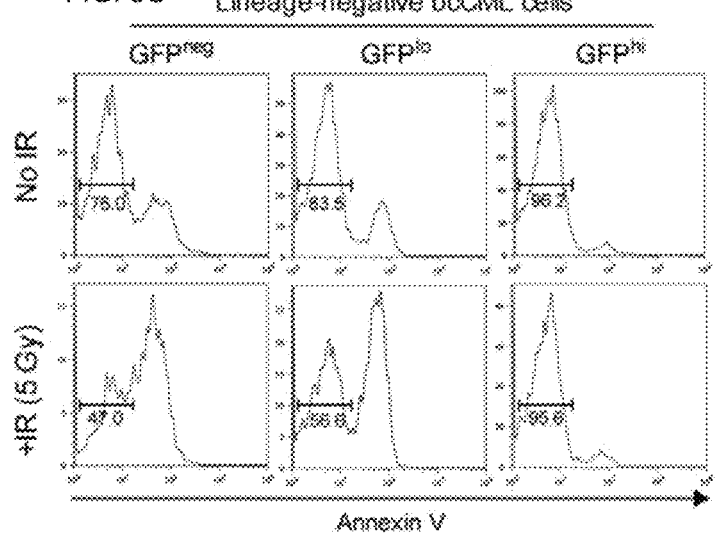
Figure 3D:
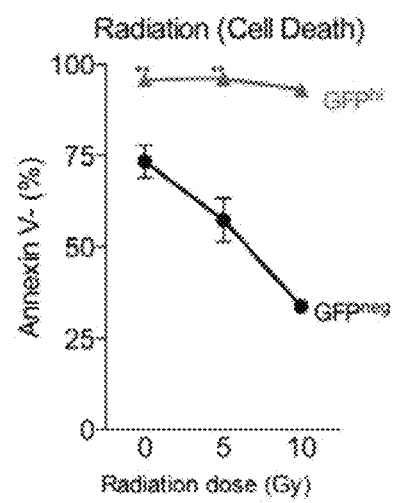
Figure 7D:
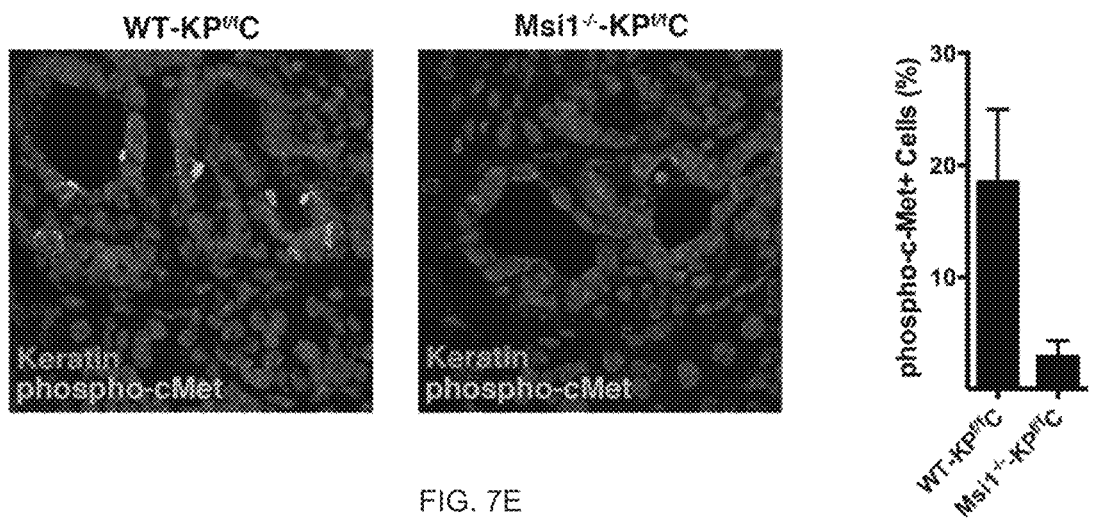
Figure 7E:
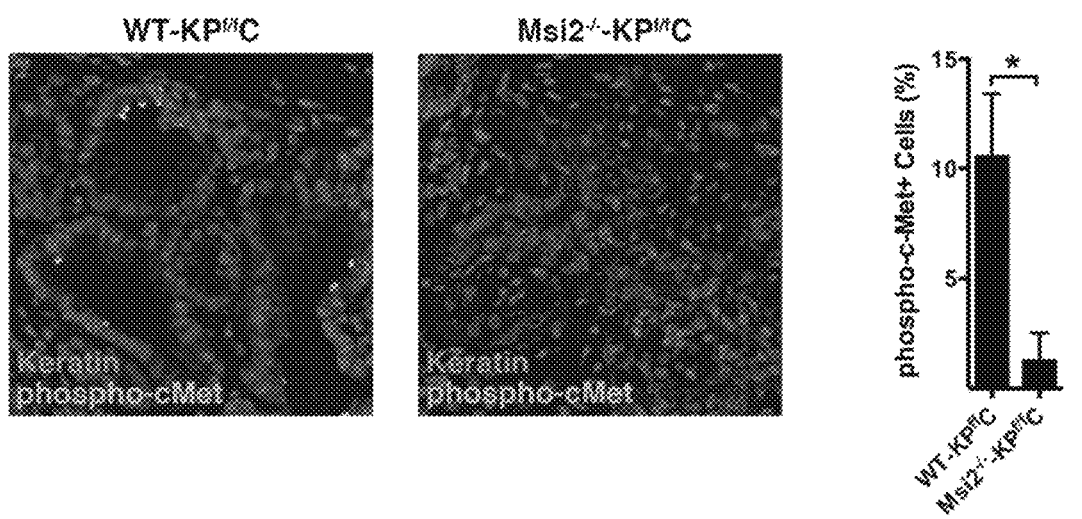
Figure 7F:
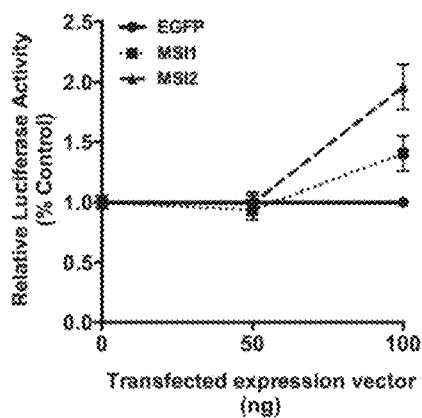
Figure 7G:
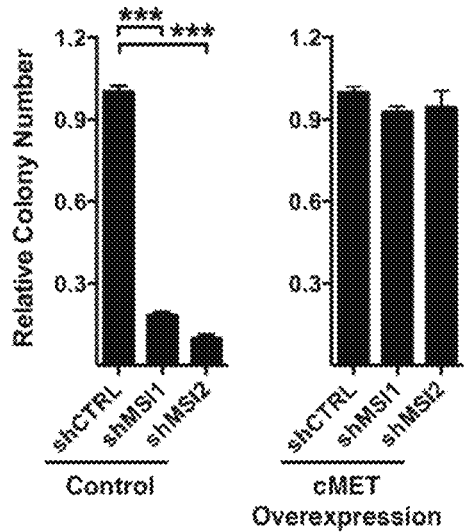

To further demonstrate that the Msi2-expressing population of blast crisis CML defines the therapy-resistant population, the irradiation (IR)-sensitivity of Msi2-expressing leukemia cells in vitro was also tested. Specifically, bulk established leukemia cells were irradiated in vitro at either 5 Gy or 10 Gy and cell survival was analyzed 7 hours post-irradiation. Following radiation insult at 5 Gy, it was found that only 47% of Lin− GFP⁻ cells were viable (Annexin V−) (FIG. 3C). In contrast, more than 95% of the Lin− GFP+ cells remained viable, suggesting that GFP+ cells are also resistant to radiation-induced cell death in vitro (FIG. 3C). In addition, it was found that with increasing radiation doses (0 to 10 Gy), GFP⁻ cells became increasingly more sensitive to radiation (FIG. 3D). However, GFP+ cells remained highly resistant to radiation, where even at the highest radiation dose tested (10 Gy), almost all (~93%) of the Lin− GFP+ cells remained viable (FIG. 3D). Collectively, these data demonstrate that Msi2-expressing leukemia cells are highly insensitive to radiation-induced cell death, and that the Msi2 reporter can be used to effectively mark therapy-resistant cells.

FIG. 1A to FIG. 1Z shows the structure of the Msi reporter constructs and highlights the ability to detect Msi-expressing cancer cells in solid tumors in vivo. Moreover, it was shown that Msi reporter+ cells in PDAC express stem cell markers and are enriched for tumor-initiating capacity in vitro and in vivo, and that they represent the predominant gemcitabine resistant population in PDAC. In FIG. 2A to FIG. 2I it was shown that Msi reporter+ cells mark the cancer stem cell population in blast crisis CML, and in FIG. 3 it was show that Msi reporter+ cells are highly resistant to radiation and imatinib treatment.

The compositions and methods described herein provide a new and unique platform for drug discovery. Specifically, they can be incorporated (in vitro or in vivo) into screens to identify compounds that can target cancer stem cells and therapy resistant cells. They can also allow for development of diagnostic and prognostic kits for these diseases, as the tumorigenic cells and CTCs can be visualized using a fluorescent marker. They can also be used to develop methods for early detection of cancer, as well as methods to monitor both tumor metastasis in cancer patients and the efficacy of cancer treatments.

In addition to their application in cancer drug development, the genetically engineered organisms described herein could be used to identify and screen compounds that can expand stem cell populations and trigger improved regeneration in a variety of tissues where Msi reporter activity marks stem and progenitor cells.

Pancreatic intraepithelial neoplasia (PanIN) is a premalignant lesion that can progress to pancreatic ductal adenocarcinoma, a highly lethal malignancy marked by its late stage at clinical presentation and profound drug resistance. As shown herein is a developed novel fluorescent reporter mice that show that the stem cell determinant, Musashi (Msi) is a critical element of pancreatic cancer progression. These reporters allowed functional and image based tracking of stem cell signals within cancers in vivo, revealing that Msi expression rises as PanINs progress to adenocarcinoma, and that Msi reporter+ tumor cells are the key drivers of pancreatic cancer: they preferentially harbor capacity to propagate adenocarcinoma, are enriched in circulating tumor cells, and are markedly drug resistant. This population could be effectively targeted by genetic deletion of either Msi 1 or Msi2 which led to a striking defect in progression from PanIN lesions to frank adenocarcinoma, and a significant improvement in survival. Msi inhibition also blocked the growth of primary patient-derived xenografts suggesting that this signal is required for human disease. To define the translational potential of this work we developed cET antisense oligonucleotides against Msi. These oligonucleotides showed reliable penetration, uptake and target inhibition, and effectively blocked the growth of pancreatic cancer cells in vitro and in vivo. Collectively, these studies highlight Msi reporters as a unique tool to identify cancer stem cells and drug resistance in vivo, and define Msi signaling as a central regulator of pancreatic cancer.

Pancreatic cancer is a disease for which treatment is rarely curative and in developed countries, it is the fourth leading cause of cancer-related deaths (Jemal, A. et al. Global cancer statistics. CA: *A Cancer Journal for Clinicians* 61, 69-90 (2011)). Because patients are asymptomatic at early stages, by the time a diagnosis is made, standard treatments have limited impact (Rhim, A. D. et al. EMT and dissemination precede pancreatic tumor formation. *Cell* 148, 349-361 (2012); Yachida, S. & Iacobuzio-Donahue, C. A. The pathology and genetics of metastatic pancreatic cancer. *Arch. Pathol. Lab. Med.* 133, 413-422 (2009); Paulson, A. S., Tran Cao, H. S., Tempero, M. A. & Lowy, A. M. Therapeutic advances in pancreatic cancer. *Gastroenterology* 144, 1316-1326 (2013)). Four genes are commonly altered in pancreatic cancer: activating mutations of KRAS2 are found in greater than 90% of tumors, while the tumor suppressors p16/INK4A, p53, and SMAD4 (Schutte, M. et al. Abrogation of the Rb/p16 tumor-suppressive pathway in virtually all pancreatic carcinomas. *Cancer Res.* 57, 3126-3130 (1997); Redston, M. S. et al. p53 mutations in pancreatic carcinoma and evidence of common involvement of homocopolymer tracts in DNA microdeletions. *Cancer Res.* 54, 3025-3033 (1994); Hahn, S. A. et al. DPC4, a candidate tumor suppressor gene at human chromosome 18q21.1. *Science* 271, 350-353 (1996); Almoguera, C. et al. Most human carcinomas of the exocrine pancreas contain mutant c-K-ras genes. *Cell* 53, 549-554 (1988); Jones, S. et al. Core signaling pathways in human pancreatic cancers revealed by global genomic analyses. Science 321, 1801-1806 (2008)) are frequently inactivated by mutation, deletion or epigenetic silencing. To date, it has been challenging to target these pathways therapeutically; thus the search for other key mediators of pancreatic cancer growth remains an important endeavour. Towards this goal we have investigated signals that control self-renewal, a key stem cell property which allows the sustained growth of undifferentiated cells and that is often hijacked in cancer. In particular, the role of Musashi, a highly conserved RNA binding protein originally identified in *drosophila* (Nakamura, M., Okano, H., Blendy, J. A. & Montell, C. Musashi, a neural RNA-binding protein required for *Drosophila* adult external sensory organ development. *Neuron* 13, 67-81 (1994)) was a main focus. Msi is expressed in stem and progenitor cells across many tissues, and long been used as a marker of undifferentiated cells (Okano, H., Imai, T. & Okabe, M. Musashi: a translational regulator of cell fate. *J. Cell. Sci.* 115, 1355-1359 (2002); Okano, H. et al. Function of RNA-binding protein Musashi-1 in stem cells. *Experimental Cell Research* 306, 349-356 (2005); Sutherland, J. M., McLaughlin, E. A., Hime, G. R. & Siddall, N. A. The Musashi family of RNA binding proteins: master regulators of multiple stem cell populations. *Adv. Exp. Med. Biol.* 786, 233-245 (2013)). However, its functional impact is only beginning to emerge: genetic loss of function models of Msi1 or Msi2 have shown that Msi signaling is important for maintaining stem cells in the mammalian nervous system (Sakakibara, S.-I. et al. RNA-binding protein Musashi family: roles for CNS stem cells and a subpopulation of ependymal cells revealed by targeted disruption and antisense ablation. *Proc. Natl. Acad. Sci. U.S.A.* 99, 15194-15199 (2002)), and, more recently, in normal and malignant hematopoiesis (Ito, T. et al. Regulation of myeloid leukaemia by the cell-fate determinant Musashi. *Nature* 466, 765-768 (2010); Hope, K. J. et al. An RNAi screen identifies Msi2 and Prox1 as having opposite roles in the regulation of hematopoietic stem cell activity. *Cell Stem Cell* 7, 101-113 (2010); de Andrés-Aguayo, L. et al. Musashi 2 is a regulator of the HSC compartment identified by a retroviral insertion screen and knockout mice. *Blood* 118, 554-564 (2011)). However, whether Msi is important in primary pancreatic cancers and whether it can be a viable therapeutic target remains unknown.

To address these issues, Msi expression in pancreatic cancer patient samples was first analyzed. Expression of MSI2 rose dramatically with PanIN progression to adenocarcinoma and metastatic disease (FIG. 9A to FIG. 9J). MSI1 expression was far weaker but trended upward with cancer progression (FIG. 9A to FIG. 9J). MSI1/MSI2 was not detectable in cancer-associated stroma (not shown). MSI1 and MSI2 was also high in human lines that generated poorly differentiated tumors and higher colony formation (FIG. 9A to FIG. 9J). These indicated that MSI1 and MSI2 are expressed in primary human pancreatic adenocarcinomas, and can play a role in oncogenesis.

To visualize and track the function of live Msi-expressing cells in vivo, Msi knock-in reporters in which fluorescent signals reflected endogenous Msi expression were developed (Msi1$^{eYFP}$, FIG. 1A, Msi2$^{eGFP}$, FIG. 1B). Msi1 reporter mice (Reporter for Musashi1, or REM1) showed expression in the stem cell enriched adult subventricular zone, and Msi1+ cells were Nestin+ and CD133+ (data not shown), consistent with Msi1 marking neural stem/progenitor cells (Kaneko, Y. et al. Musashi1: an evolutionarily conserved marker for CNS progenitor cells including neural stem cells. *Dev. Neurosci.* 22, 139-153 (2000)). Msi2 reporters (REM2) reflected endogenous expression of Msi2, being highest in hematopoietic stem cells and declining with maturation (Ito, T. et al. Regulation of myeloid leukaemia by the cell-fate determinant Musashi. *Nature* 466, 765-768 (2010); Kharas, M. G. et al. Musashi-2 regulates normal hematopoiesis and promotes aggressive myeloid leukemia. *Nat Med* 16, 903-908 (2010)) (FIG. 10). Msi expression was concordant with expression of eYFP and eGFP (FIG. 11A to FIG. 11B).

To define how Msi-expressing cells contribute to pancreatic cancer, REM mice were crossed to the Ptf1aCre (Kawaguchi, Y. et al. The role of the transcriptional regulator Ptf1a in converting intestinal to pancreatic progenitors. *Nat Genet* 32, 128-134 (2002)) driven KRAS$^{G12D}$ mutant (Jackson, E. L. et al. Analysis of lung tumor initiation and progression using conditional expression of oncogenic K-ras. *Genes & Development* 15, 3243-3248 (2001))/p53-null (Marino, S., Vooijs, M., van Der Gulden, H., Jonkers, J. & Berns, A. Induction of medulloblastomas in p53-null mutant mice by somatic inactivation of Rb in the external granular layer cells of the cerebellum. *Genes & Development* 14, 994-1004 (2000)) conditional model of pancreatic cancer. While Kras mutation alone leads to PanIN formation (Hingorani, S. R. et al. Preinvasive and invasive ductal pancreatic cancer and its early detection in the mouse. *Cancer Cell* 4, 437-450 (2003)), combined deletion of p53 drives progression to adenocarcinoma (Bardeesy, N. et al. Both p16Ink4a and the p19Arf-p53 pathway constrain progression of pancreatic adenocarcinoma in the mouse. *PNAS April, vol. no.* 103, 5947-5952 (2006)). Kras$^{LSL-G12D/+}$; p53$^{f/f}$; Ptf1a$^{CRE/+}$ (KP$^{f/}$$_f$C) were crossed to both REM1 and REM2 mice. In vivo imaging of live pancreas revealed Msi1 and Msi2 reporter activity within the tumors; interestingly, reporter+ cells were not disseminated throughout the tumor but distributed in a remarkably spatially restricted manner (FIG. 1C and FIG. 1E).

Msi expression was rare: Msi1 reporter was detected in 0.6-2.1% (FIG. 1D), and Msi2 in 5.6-12.2% of pancreatic cancer cells (FIG. 1F). Their expression overlapped in only 7% of EpCAM+ cells (FIG. 1G). Because cancer stem cells are similarly rare (Wang, J. C. Y. & Dick, J. E. Cancer stem cells: lessons from leukemia. *Trends in Cell Biology* 15, 494-501 (2005); Reya, T., Morrison, S. J., Clarke, M. F. & Weissman, I. L. Stem cells, cancer, and cancer stem cells. *Nature* 414(6859):105-11 (2001)), it was further tested if Msi-expressing cells can have preferential capacity for tumor propagation. Over 95% of Msi1-reporter+ and Msi2-reporter+ expressed ALDH, a marker of pancreatic cancer stem cells (Kim, M. P. et al. ALDH Activity Selectively Defines an Enhanced Tumor-Initiating Cell Population Relative to CD133 Expression in Human Pancreatic Adenocarcinoma. *PLoS ONE* 6, e20636 (2011); Marcato, P., Dean, C. A., Giacomantonio, C. A. & Lee, P. W. K. Aldehyde dehydrogenase: Its role as a cancer stem cell marker comes down to the specific isoform. cc 10, 1378-1384 (2011); Rasheed, Z. A. & Matsui, W. Biological and clinical relevance of stem cells in pancreatic adenocarcinoma. *Journal of Gastroenterology and Hepatology* 27, 15-18 (2012)) (FIG. 1H to FIG. 1K). Functionally both Msi1 and Msi2 reporter+ cells over 30 fold greater tumor sphere forming ability (Rovira, M. et al. Isolation and characterization of centroacinar/terminal ductal progenitor cells in adult mouse pancreas. *Proceedings of the National Academy of Sciences* 107, 75-80 (2010)) relative to reporter– cells (FIG. 1L to FIG. 1Q). In vivo, the focus was on the tumorigenic potential of Msi2 reporter cells since Msi1$^+$ cells were unable to form tumors in small numbers (100, 1000), possibly because they are less tumorigenic or more quiescent (data not shown). While as few as 100 Msi2-reporter+ cells could generate tumors, Msi2-reporter– cells required a minimum of 1000 cells to form tumors (FIG. 1R to FIG. 1T); even when they developed they did so with a longer latency and were 7-fold smaller (FIG. 1T). While 12/12 mice transplanted with GFP+ cells developed tumors, only 3/12 mice transplanted with GFP– cells displayed a tumor. Most importantly, reporter+ cells were far more aggressive in causing lethal disease. While 100% (6/6) of mice orthotopically transplanted with EpCAM+GFP+ cells died, none of the mice receiving EpCAM+/GFP– cells (0/6) showed signs of disease and remained healthy (FIG. 1U to 1V). Tumors from GFP+ cells recapitulated the heterogeneity of the original tumor, invaded extensively into surrounding normal tissues (not shown), consistent with enrichment of pro-EMT and pro-invasion/migration in Msi2+ cells (FIG. 12A and FIG. 12B). These studies strongly suggest that Msi2 reporter+ cells preferentially drive pancreatic cancer growth, invasion and lethality.

Since circulating tumor cells disseminate from the primary lesion and can be critical for driving growth at distant sites, Msi reporter expression in CTCs were analyzed. Msi2+ cells comprised 9.7% of primary tumors but represented 38% and 44% of EpCAM+ CTCs in blood and ascites (FIG. 1W), indicating a 4-fold enrichment of Msi2+ in cells that seed secondary sites. Importantly, Msi2+ CTCs had vastly greater tumorigenic/colony forming capacity relative to Msi2– CTCs (FIG. 1X), indicating that Msi+ CTCs can have enhanced functional capacity for driving tumor growth at new sites.

The reporter gave a unique opportunity to determine whether it could be a new image based tool to identify therapy resistance. Gemcitabine remains the standard of care for adjuvant treatment of pancreatic cancer and is the most commonly used single agent in the treatment of advanced disease. Despite this, clinical response rates to gemcitabine are below 10% and it fails to prevent relapse after surgery in 85% of patients. Gemcitabine was delivered to tumor-bearing REM2-KP$^{f/f}$C mice in vivo at increasing doses. Remarkably GFP$^-$ cells appeared sensitive to gemcitabine and were preferentially eliminated, while GFP+ cells were resistant and remained viable despite high doses of the drug (FIG. 1Z). These identify Msi-reporter+ cells as a predominant gemcitabine resistant population, and suggest that these reporters could be an invaluable tool for tracking and visualization of drug resistant cells, and testing therapeutic strategies to more effectively eliminate them.

The fact that Msi expression was sharply upregulated during progression (FIG. 9A to FIG. 9J and FIG. 13A), and marked the "high risk" therapy resistant tumor-propagating cells highlighted the need to develop ways to eradicate these cells. To define if targeting Msi signaling itself could contribute to this goal, both genetic and pharmacologic approaches were taken. Genetically, the KP$^{f/f}$C model to Msi1$^{-/-}$ or Msi2$^{-/-}$ mice were crossed (Sakakibara, S.-I. et al. RNA-binding protein Musashi family: roles for CNS stem cells and a subpopulation of ependymal cells revealed by targeted disruption and antisense ablation. *Proc. Natl. Acad. Sci. U.S.A.* 99, 15194-15199 (2002); Ito, T. et al. Regulation of myeloid leukaemia by the cell-fate determinant Musashi. *Nature* 466, 765-768 (2010)). Msi1 deletion led to a 5-fold reduction in MRI based tumor volume in KP$^{f/f}$C mice (FIG. 2A to FIG. 2B), concordant with direct measurements (FIG. 2C to FIG. 2D, n=12 wild type and n=9 Msi1$^{-/-}$ mice). Delays in tumor development were assessed in a temporal series in a larger cohort of mice (n=24). Periodic acid Schiff (PAS) and Alcian blue staining were used to identify and quantify areas of PanIN and adenocarcinoma (FIG. 13B). In 6.5 wk KP$^{f/f}$C mice 67% of the pancreas consisted of adenocarcinoma (FIG. 2E) whereas less than 10% of the Msi1$^{-/-}$ pancreas was adenocarcinoma (FIG. 2F to FIG. 2G). While Msi1 loss allowed early PanIN lesions to form, it largely blocked progression to adenocarcinoma (FIG. 2H to FIG. 2I). Most importantly, Msi1 loss clearly influenced survival. To avoid complications from reported cases of hydrocephaly in Msi1 null mice (Sakakibara, S.-I. et al. RNA-binding protein Musashi family: roles for CNS stem cells and a subpopulation of ependymal cells revealed by targeted disruption and antisense ablation. *Proc. Natl. Acad. Sci. U.S.A.* 99, 15194-15199 (2002)) Msi1−/− and WT-KP$^{f/f}$C pancreata were orthotopically grafted into NSG mice and monitored survival. Median survival for mice receiving WT-KP$^{f/f}$C grafts was 28.5 days, while that for Msi1$^{-/-}$-KP$^{f/f}$C grafts was 70.5 days, indicating a 2.5 fold increase in survival time (P<0.0001, FIG. 2J). These data collectively indicate that Msi1 is central to pancreatic cancer progression, such that its inhibition can significantly improve survival.

Because both Msi1 and Msi2 are expressed in pancreatic cancer, the impact of deleting Msi2 was also analyzed. MRI analysis at 13 weeks showed no detectable tumor mass in a majority (5/7) of the Msi2$^{-/-}$-KP$^{f/f}$C mice in contrast to controls (FIG. 2K). Msi2 deletion led to a 6.7-fold reduction in tumor volume and weight (n=7, FIG. 2M to FIG. 2N). Histologically control pancreata were predominantly replaced by adenocarcinoma (FIG. 2O, quantified in FIG. 2S to FIG. 2U) often accompanied by extracapsular invasion into surrounding structures (FIG. 2P, green arrows). In contrast, Msi2$^{-/-}$-KP$^{f/f}$C pancreas contained low-grade PanIN (FIG. 2R, blue arrows, quantified in FIG. 2S to FIG. 2U) with rare high-grade PanIN and microscopic foci of adenocarcinoma within mostly normal tissue (FIG. 2Q, yellow arrow). Importantly, the delay in progression with Msi2 loss led to a significant improvement in survival: while the median survival for WT-KP$^{f/f}$C mice was 87 days, the median survival for Msi2$^{-/-}$-KP$^{f/f}$C was 122 days, a 1.4 fold increase in survival (P<0.0001) (FIG. 2V). Collectively, the data show that Msi inhibition significantly improves disease trajectory, leading to an approximate doubling of survival in context of aggressive pancreatic cancer.

To define the molecular basis of Msi loss, the genes downstream of Msi were evaluated by genome wide analysis of Msi1$^{-/-}$ cancer (FIG. 14). Because Msi2$^{-/-}$-KP$^{f/f}$C mice fail to form tumors, it was too difficult to recover Msi2−/− tumor cells for such analysis, and thus used gene expression changes in Msi2−/− hematologic cancers (Kwon, H. Y. et al. Tetraspanin 3 Is Required for the Development and Propagation of Acute Myelogenous Leukemia. *Stem Cell* 17, 152-164 (2015)) as a surrogate, followed by confirmation and CLIPSeq in pancreatic cancer cells. Msi loss led to the down-regulation of many key genes such as Shh, Wnt7a and Aldh genes associated with stem cells (FIG. 14), c-Met (Kwon, H. Y. et al. Tetraspanin 3 Is Required for the Development and Propagation of Acute Myelogenous Leukemia. *Stem Cell* 17, 152-164 (2015)), a key proto-oncogene implicated in many cancers (Li, C. et al. c-Met is a marker of pancreatic cancer stem cells and therapeutic target. *Gastroenterology* 141, 2218-2227.e5 (2011); Hermann, P. C. et al. Distinct Populations of Cancer Stem Cells Determine Tumor Growth and Metastatic Activity in Human Pancreatic Cancer. *Cell Stem Cell* 1, 313-323 (2007); Delitto, D., Vertes-George, E., Hughes, S. J., Behrns, K. E. & Trevino, J. G. c-Met signaling in the development of tumorigenesis and chemoresistance: potential applications in pancreatic cancer. *World J. Gastroenterol.* 20, 8458-8470 (2014)), Igf2 and Hmga2, associated with poor prognosis in pancreatic cancer, as well as members of the Regenerating (Reg) gene family, associated with a variety of gastrointestinal cancers (Sayer, R. A. et al. High insulin-like growth factor-2 (IGF-2) gene expression is an independent predictor of poor survival for patients with advanced stage serous epithelial ovarian cancer. *Gynecologic Oncology* 96, 355-361 (2005); Wang, X. et al. Overexpression of HMGA2 promotes metastasis and impacts survival of colorectal cancers. *Clin. Cancer Res.* 17, 2570-2580 (2011); Kadowaki, Y. et al. Reg protein is overexpressed in gastric cancer cells, where it activates a signal transduction pathway that converges on ERK1/2 to stimulate growth. *FEBS Letters* 530, 59-64 (2002)). The focus was on genes that can broadly phenocopy Msi function, and analyzed their UTRs for Msi1/Msi2 consensus binding sites to define potential direct targets. Multiple binding sites were detected in BRD4, c-MET and HMGA2 (FIG. 3A). Using RIP-PCR, there was a 199-fold enrichment of c-MET, a 157-fold enrichment of HMGA2, and a 41-fold enrichment of BRD4 transcripts bound to Msi (FIG. 3B). In contrast, IGF2 transcripts were not detected, and served as a negative control consistent with lack of Msi2 binding sites (FIG. 3B).

c-MET transcripts were also identified by CLIP-seq as a direct target of MSI1 in pancreatic cancer cells (FIG. 3C). Thus it was functionally tested if c-MET can be a downstream mediator of Msi function. c-Met was markedly diminished in both Msi1/Msi2−/− pancreatic cancer, consistent with it being an Msi target (FIG. 3D to FIG. 3E). Analysis of MIAPaCa-2 cells transfected with the c-MET 3'UTR linked to a luciferase reporter revealed that at a molecular level MSI1/MSI2 controls c-MET through its 3'UTR (FIG. 3F). c-MET complementation of Msi loss was carried out in MIAPaCa-2 cells that express and are dependent on both MSI1 and MSI2 (FIG. 15A to 15D and FIG. 7G). While MSI1 or MSI2 knockdown impaired colony formation in semi solid media, ectopic expression of c-MET fully rescued the defect (FIG. 3G), demonstrating an unexpected functional connection between these two important genes. While the data strongly suggest that c-MET is an important functional downstream mediator of Msi function, it is highly likely that Msi utilizes many other key programs to mediate its influence on cancer. In fact, BRD4 and HMGA2 are attractive targets that should be pursued in the future as they could act at an epigenetic level together with c-MET to mediate the broad impact of Msi.

To complement the mouse models, the impact of MSI inhibition on primary patient samples was tested, which harbor complex mutations, and are uniformly drug resistant. Four patient-derived xenografts established from primary PDAC were isolated, dissociated and infected with lentiviral shMSI1, shMSI2, and scrambled controls. Following infection, unsorted mixtures of infected (GFP+) and uninfected (GFP−) cells were transplanted (FIG. 4A, schematic). At transplantation (t=0), the frequency of GFP+ cells was equivalent in all groups (FIG. 4B to FIG. 4E). Three months after transplantation, tumors were dissociated, and relative contribution of GFP+ cells tracked. Although there was an equivalent contribution of GFP+ cells at the time of transplant for each condition, in resulting tumors the GFP+ content of shMSI1 or shMSI2 tumors was reduced on average 6.5 and 4.9 fold, respectively, relative to the GFP+ content of shControl tumors (FIG. 4B to 3E). These experiments indicated that inhibition of either MSI1 or MSI2 results in marked suppression of primary human pancreatic adenocarcinoma growth.

Given that inhibition of Msi has profound effects on pancreatic cancer progression, exploring its potential as a therapeutic target seemed critical. To determine if Msi could be effectively targeted, antisense oligonucleotides (ASOs) specific for Msi1 were developed. ASOs are sequence-specific nucleotides that hybridize with the target RNA through Watson-Crick base pairing and mediate the selective cleavage of the target through the action of the cellular enzyme RNase H (Lee, R. G., Crosby, J., Baker, B. F., Graham, M. J. & Crooke, R. M. Antisense technology: an emerging platform for cardiovascular disease therapeutics. *J Cardiovasc Transl Res* 6, 969-980 (2013)). Because ASO inhibitors can be designed based on target RNA sequence information alone, they can be a powerful therapeutic approach for inhibiting proteins considered "undruggable"—those that have been difficult to target using traditional small molecule approaches (Li, N., Li, Q., Tian, X.-Q., Qian, H.-Y. & Yang, Y.-J. Mipomersen is a Promising Therapy in the Management of Hypercholesterolemia: A Meta-Analysis of Randomized Controlled Trials. *Am J Cardiovasc Drugs* 14, 367-376 (2014)), which include RNA binding proteins like Msi.

Generation 2.5 ASOs are highly potent next generation antisense compounds containing constrained ethyl (cEt) chemistry as previously described (Seth, P. P. et al. Short Antisense Oligonucleotides with Novel 2'-4' Conformationaly Restricted Nucleoside Analogues Show Improved Potency without Increased Toxicity in Animals. *J. Med. Chem.* 52, 10-13 (2009); Prakash, T. P. et al. Antisense Oligonucleotides Containing Conformationally Constrained 2',4'-(N-Methoxy)aminomethylene and 2',4'-Aminooxymethylene and 2'-0,4'-C-Aminomethylene Bridged Nucleoside Analogues Show Improved Potency in Animal Models. . . . medicinal chemistry (2010)). Although ASOs have been used to inhibit gene expression in a variety of tissues (Carroll, J. B. et al. Potent and Selective Antisense Oligonucleotides Targeting Single-Nucleotide Polymorphisms in the Huntington Disease Gene/Allele-Specific Silencing of Mutant Huntingtin. *Molecular Therapy* 19, 2178-2185 (2009); Hung, G. et al. Characterization of Target mRNA Reduction Through In SituRNA Hybridization in Multiple Organ Systems Following Systemic Antisense Treatment in Animals. *Nucleic Acid Therapeutics* 23, 369-378 (2013); Rigo, F. et al. Pharmacology of a central nervous system delivered 2'-O-methoxyethyl-modified survival of motor neuron splicing oligonucleotide in mice and nonhuman primates. *Journal of Pharmacology and Experimental Therapeutics* 350, 46-55 (2014)), whether pancreatic cancer cells can take up ASOs was not known. 400 candidate Msi1 ASOs were evaluated for the ability to inhibit MSI1 RNA levels in Panc1 cells at a single concentration, and the top 20 evaluated in dose-response experiments, from which the two most potent, ASO-1 and ASO-2, were identified. Control ASOs, which did not hybridize with any specific gene target, did not suppress MSI1 expression in cell lines (FIG. 4F); in contrast both MSI ASOs inhibited MSI1 expression (FIG. 4G to FIG. 4H). Functionally MSI1 ASOs led to a marked reduction in colony numbers as well as in colony size, with a cumulative reduction of ~2.5 fold in total growth (FIG. 4I). To test the impact of ASO mediated MSI1 inhibition in vivo, human pancreatic cancer cells were transplanted until growth was measurable. Subsequently, MSI1 inhibitors were delivered intratumorally for a period of four weeks (5 days on and 2 days off) and tumor growth monitored. While control treated tumors grew at a steady state, MSI1 ASO treatment resulted in a significant reduction in the rate of tumor growth (FIG. 4J). The ASO on primary $KP^{f/f}C$ driven tumors were also tested. $KP^{f/f}C$ pancreatic tumor cells were isolated, transplanted and monitored until measurable growth (30 mm$^3$). Subsequently, ASOs were delivered into established tumors daily. Remarkably anti-Msi1 ASOs effectively arrested primary tumor growth, in contrast to continued exponential growth seen in control treated tumors (FIG. 4K to 4M). Finally, the ASOs reported and used here have not undergone "lead optimization," a longer-term process needed for achieving therapeutic level efficacy with systemic delivery. To test whether a lead optimized ASO has the capacity to effectively penetrate pancreatic tumors when delivered systemically, an ASO against MALAT1 was also used. This was delivered by intraperitoneal injection followed by analysis of MALAT1 target knockdown in tumors in the autochthonous $KP^{f/f}C$ model. As shown (FIG. 4N), systemically delivered MALAT1 ASO was very effective in knocking down its target in endogenous pancreatic tumors, suggesting that ASOs can penetrate the stroma and be taken up by pancreatic tumor cells, and thus can be a reasonable new class of therapeutics to further explore in context of pancreatic tumors. Collectively, these studies provide proof of principle that effective deliverable inhibitors of Msi can antagonize pancreatic cancer growth in vivo.

The Msi reporters described here represent exciting new tools that could be broadly useful for studying cancer. Because Msi reporter activity can be visualized through live imaging these reporter mice can be uniquely used to image and track cancer stem cells in vivo, and can provide a dynamic view of endogenous cancer growth, tumor dissemination and metastasis in its native microenvironment. The fact that reporter positive cells are preferentially gemcitabine resistant, raises the exciting possibility that this could serve as a new platform to identify therapy resistance in vivo. The integration of such reporters in drug development can provide a powerful and sophisticated complement to traditional screens, by allowing the identification of therapies that are better able to target tumor propagating cells, and drug resistant residual disease. In addition, the spatially restricted distribution of Msi+ cells could have important implications for locoregional, aggressive targeting of driver cells that mediate resistance and disease relapse.

Combining this imaging strategy with genetic targeting revealed that abrogation of Msi signaling impaired cancer stem cell function, leading to a striking defect in adenocarcinoma progression and improving survival. It is intriguing that loss of either Msi1 or Msi2 affected pancreatic cancer suggesting both have distinct non-overlapping roles. The somewhat deeper defect in Msi2 null mice can be because Msi2 is more broadly expressed relative to Msi1; as a caveat, it should be noted that Msi1−/− mice express a residual gene fragment, which can have compensatory activity. Certainly, the fact that targeting either MSI1 or MSI2 in patient samples significantly inhibits in vivo tumor growth supports the conclusion that both MSI genes play distinct, non-redundant roles in cancer growth. Consistent with this, comparative molecular analysis of PDAC specific genes in the same cell line showed that MSI1 and MSI2 control overlapping and distinct downstream signals (data not shown). It is found that a remarkable number of critical cancer associated genes such as Brd4, Igf2, c-Met and Reg genes are direct or indirect downstream targets of Msi signaling. While the focus is on c-Met as a key functional target of Msi, undoubtedly many other genes contribute to Msi's broad impact. Although Msi proteins are highly expressed in multiple solid cancers (Wang, T. et al. Sequential expression of putative stem cell markers in gastric carcinogenesis. *British Journal of Cancer* 105, 658-665 (2011); Fan, L.-F. et al. Expression of putative stem cell genes Musashi-1 and β1-integrin in human colorectal adenomas and adenocarcinomas. *Int J Colorectal Dis* 25, 17-23 (2009); MacNicol, A. M., Wilczynska, A. & MacNicol, M. C. Function and regulation of the mammalian Musashi mRNA translational regulator. *Biochem. Soc. Trans* 36, 528 (2008); Shu, H.-J. et al. Expression of the Musashi1 gene encoding the RNA-binding protein in human hepatoma cell lines. *Biochem. Biophys. Res. Commun.* 293, 150-154 (2002); Wang, X.-Y. et al. Musashi1 regulates breast tumor cell proliferation and is a prognostic indicator of poor survival. *Mol Cancer* 9, 221 (2010); Nikpour, P., Mowla, S. J., Forouzandeh-Moghaddam, M. & Ziaee, S. A. The stem cell self-renewal gene, Musashi 1, is highly expressed in tumor and non-tumor samples of human bladder. *Indian J Cancer* 50, 214-218 (2013)), their role in growth and expansion of primary tumors remain poorly understood. Thus, understanding the mechanisms by which Msi regulates pancreatic cancer can not only have implications for developing strategies to control this disease in particular, but can also serve as a more general paradigm to define the role of Msi in other solid cancers.

One of the biggest disappointments in the development of new pancreatic cancer treatments has been the failure of targeted therapies to thus far make a meaningful impact. While therapies such as imatinib mesylate, trastuzamab and bevacuzimab have emerged as promising alternatives or adjuvants to traditional therapies, targeting RNA binding proteins poses unique challenges given the potential need to block binding function. The data as described in the embodiments herein, demonstrates that an effective approach to inhibiting Msi and other RNA binding proteins can be the use of cell-penetrating antisense oligonucleotides. Therapeutic antisense technology has advanced significantly during the 20 plus years since its inception, and the systemic delivery of ASOs has demonstrated robust human clinical activity in several disease areas (Li, N., Li, Q., Tian, X.-Q., Qian, H.-Y. & Yang, Y.-J. Mipomersen is a Promising Therapy in the Management of Hypercholesterolemia: A Meta-Analysis of Randomized Controlled Trials. *Am J Cardiovasc Drugs* 14, 367-376 (2014); Raal, F. J. et al. Mipomersen, an apolipoprotein B synthesis inhibitor, for lowering of LDL cholesterol concentrations in patients with homozygous familial hypercholesterolaemia: a randomised, double-blind, placebo-controlled trial. *The Lancet* 375, 998-1006 (2010); Saad, F. et al. Randomized phase II trial of Custirsen (OGX-011) in combination with docetaxel or mitoxantrone as second-line therapy in patients with metastatic castrate-resistant prostate cancer progressing after first-line docetaxel: CUOG trial P-06c. *Clin. Cancer Res.* 17, 5765-5773 (2011)). The data suggests that ASOs can penetrate pancreatic cancer and thus MSI ASOs should be considered for further development not only for potential use in pancreatic cancer but also in other aggressive cancers with high Msi expression such as glioblastoma and breast cancer. Finally, the rise of Msi in both human pancreatitis and in caerulein induced mouse models of the disease raises the intriguing possibility that blocking Msi via ASO delivery could prevent or reduce risk of progression from pancreatitis to pancreatic cancer and thus could contribute to prevention efforts as well (FIG. 16A to FIG. 16C). In the long term, defining Msi as a new target in pancreatic cancer together with methods to block this pathway could provide a new approach to control cancer growth and progression.

Methods:

Mice.

REM1 ($Msi1^{eYFP}$) and REM2 ($Msi2^{eGFP}$) reporter mice were generated by conventional gene targeting (Genoway, France; FIG. 2A to FIG. 2I). The Msi2 mutant mouse, B6; CB-$Msi2^{Gt(pU-21T)2Imeg}$ ($Msi2^{-/-}$) was made and established by gene trap mutagenesis (CARD, Kumamoto University). Mice were bred and maintained in the animal care facilities at the University of California San Diego. All animal experiments were performed according to protocols approved by the University of California San Diego Institutional Animal Care and Use Committee.

Tissue Dissociation and Cell Isolation.

(A) Mouse pancreatic tumors were washed in RPMI 1640 (Gibco, Life Technologies) and cut into 2-4 mm pieces immediately following resection. Dissociation into a single cell suspension was performed using the Miltenyi Biotec Mouse Tumor Dissociation Kit (130-096-730). Briefly, tumor pieces were collected into gentleMACS C tubes containing RPMI 1640 dissociation enzymes, and further homogenized using the gentleMACS Dissociator. Samples were incubated for 40 minutes at 37° C. under continuous rotation, then passaged through a 70 μm nylon mesh (Corning). Red blood cells were lysed using RBC Lysis Buffer (eBioscience), and the remaining tumor cells were used for FACS analysis and cell sorting. (B) Freshly resected mouse brains were rinsed in PBS, placed in accutase (Life Technologies), and cut into <2 mm pieces. Samples were incubated 15 minutes at 37° C., then passaged through a 70 μm nylon mesh (Corning). Red blood cells were lysed as above prior to FACS analysis and sorting of brain cells. (C) Bone marrow cells were suspended in HBSS (Gibco, Life Technologies) containing 5% FBS and 2 mM EDTA and were prepared for FACS analysis and sorting as previously described (Domen et al., 2000; Ito et al., 2010; Kharas et al., 2010). Analysis and cell sorting were carried out on a FACSAria III machine (Becton Dickinson), and data were analyzed with FlowJo software (Tree Star).

Immunofluorescence Staining.

(A) Human primary pancreatic cancer tissues were fixed in 10% neutral buffered formalin and paraffin embedded at the Moores Cancer Center at UCSD according to standard protocols. 7 μm sections were obtained and deparaffinized in Citrisolv. Antigen retrieval was performed for 20 minutes in 95-100° C. lx Citrate Buffer, pH 6.0 (eBioscience). Sections were blocked in TBS containing 0.1% Tween20 (Sigma-Aldrich), 10% Donkey serum (Invitrogen), and 5% bovine serum albumin (Invitrogen). Incubation with primary antibody was carried out overnight at 4° C. and incubation with Alexafluor-conjugated secondary antibodies (Molecular Probes) was performed for 1 hour at room temperature. DAPI (Molecular Probes) was used to detect DNA. Images were obtained with a Nikon Eclipse E600 fluorescent microscope. The following primary antibodies were used: rabbit anti-Msi 1:500 (Abcam, ab52865), rabbit anti-Msi2 1:500 (Abeam., ab50829), and mouse anti-pan cytokeratin 1:65

(Abcam, ab6401). (B) Single cell suspensions from mouse pancreatic tumors and brain. Cells isolated by FACS were suspended in DMEM (Gibco, Life Technologies) supplemented with 50% FBS and adhered to slides by centrifugation at 500 rpm. 24 hours later, cells were fixed with 4% paraformaldehyde (USB Corporation), permeabilized with PBS containing 0.1% Tween-20 (Sigma-Aldrich), and blocked with PBS containing 0.1% Triton X-100 (Sigma-Aldrich), 10% normal goat serum (Invitrogen), and 5% bovine serum albumin (Invitrogen). (C) Single cell suspensions from mouse bone marrow. Cells were allowed to settle onto chambered cover glass (LabTek) coated with poly-1-lysine (Sigma) at 37° C., fixed with 4% paraformaldehyde (USB Corporation), permeabilized with 1× Dako wash buffer (Dako), and blocked with 10% normal goat serum (Invitrogen) in 1× Dako wash buffer. Incubation with primary antibody was carried out overnight at 4° C. The following primary antibodies were used to stain mouse tissues: rabbit anti-ALDH1 (Abcam, ab24343) 1:200; rabbit anti-cMet (Abcam, ab5662) 1:250; chicken anti-GFP (Abcam, ab13970) 1:250 (for pancreatic tumors and brain) or 1:200 (for bone marrow); rabbit anti-Msi2 (Abcam, ab76148) 1:500 (for pancreatic tumors and brain) or 1:200 (for bone marrow); and rat anti-Msi1 (eBioscience, 14-9896-82) 1:500. Incubation with secondary antibody was performed for 1 hour at room temperature. DAPI (Molecular Probes) was used to detect DNA. Images were obtained with a Confocal Leica TCS SP5 II (Leica Microsystems).

Pancreatic Tumorsphere Formation Assay.

(A) Pancreatic tumorsphere formation assays were performed on fresh mouse pancreatic tumor cells as previously described (Domen et al., 2000; Jackson et al., 2001; Rovira et al., 2010). Briefly, pancreatic tumors from 10-13 week old REM1- or REM2-KP$^{f/f}$C mice were dissociated and FACS sorted for reporter+ (YFP+ or GFP+, respectively) and reporter− cells. 500 cells were suspended in 100 μl DMEM F-12 (Gibco, Life Technologies) containing 1×B-27 supplement (Gibco, Life Technologies), 3% FBS, 100 mM □-mercaptoethanol (Gibco, Life Technologies), 1× non-essential amino acids (Gibco, Life Technologies), 1×N2 supplement (Gibco, Life Technologies), 20 ng/ml EGF (Gibco, Life Technologies), 20 ng/ml FGF2 (Gibco, Life Technologies), and 10 ng/ml ESGRO mLIF (Millipore). Cells in media were plated in 96-well ultra-low adhesion culture plates (Costar) and incubated at 37° C. for 7 days. Sphere images were obtained with a Nikon80i. Sphere size was measured using ImageJ 1.47v software. (B) Glioblastoma cells, kindly provided by Paul Mischel (UCSD), and were dissociated in TripLe (Gibco, Life Technologies) for 5 min at 37° C. then resuspended in DMEM F12 (Gibco, Life Technologies) containing 1×N2 supplement (Gibco, Life Technologies), 20 ng/ml EGF (Gibco. Life Technologies), 20 ng/ml FGF2 (Gibco, Life Technologies), and 1 μg/ml Heparin (Sigma). Cells were plated in a 24-well ultra-low adhesion plate (Corning) at a density of 5000 cells per well. ASOs were added to growth medium at a concentration of 0 μM, 2 μM, or 10 μM. Spheres were counted 5 days later.

Lentiviral Constructs and Production.

Short hairpin RNA (shRNA) constructs were designed and cloned into plenti-hU6BX vector by Cellogenetics. The target sequences are 5′-CCCAGATAGCCTTAGAGACTAT-3′ (SEQ ID NO: 1) for MSI1, 5′-CCCAGATAGCCTTAGA-GACTAT-3′ (SEQ ID NO: 2) for MSI2 and 5′-CTGTGC-CAGAGTCCTTCGATAG-3′ (SEQ ID NO: 3) for the control scrambled sequence. Virus was produced in 293T cells transfected with plenti-shRNA constructs along with pRSV/REV, pMDLg/pRRE, and pHCMVG constructs. Viral supernatants were collected for three days followed by ultracentrifugal concentration at 50,000×g for 2 h.

Agarose Colony Formation Assays.

MIA PaCa-2 cells were infected with GFP-tagged lentiviral particles containing shRNAs for MSI1, MSI2, and a scrambled control. Positively infected cells were sorted 72 hours after transduction. For colony assays, 24-well plates were first coated with 0.6% agarose in DMEM without supplements. Cells were plated at a density of 2000 cells per well in 0.3% agarose containing DMEM, 10% FBS, NEAA, PS, and Glutamax. Growth medium was placed over the solidified agarose layers and was supplemented every three days. Colonies were counted 14 days after plating.

MRI.

Magnetic resonance imaging was used to determine the pancreatic volumes of the mice in vivo. Mice were anesthetized using 1.5% isoflurane and imaged in a 7.0 Tesla small animal scanner (Bruker-Biospin, Ettlingen, Germany). Contiguous coronal slices were acquired using a multi-slice, RARE sequence: repetition time/echo time=4826 ms/33 ms, Field of View=6×3 cm, and Matrix=126×128 with up to 44 slices with a thickness of 0.5 mm. Segmentation and volume rendering were performed using Amira software (FEI Visualization Sciences Group, Burlington, Mass.).

Histological Analysis/Quantification of PanIN and PDAC.

Msi1$^{-/-}$-KP$^{f/f}$C and Msi2$^{-/-}$-KP$^{f/f}$C mice were euthanized between 4.5 and 13 weeks of age for tumor isolation and temporal analysis. Mouse tumors were fixed in 4% paraformaldehyde and paraffin embedded according to standard protocols. 5 μm sections were obtained for hematoxylin and eosin and periodic acid-Schiff/Alcian Blue staining. To quantify tumor areas, each slide was digitally scanned with an Aperio slide scanner. Imagescope software was used to measure PDAC area, PanIN area, and normal pancreas area.

Gene Expression Microarray and Data Analysis.

WT-KP$^{f/f}$C or Msi1$^{-/-}$-KP$^{f/f}$C mice were euthanized at 11 weeks of age. Tumors were harvested and total cellular RNAs were purified, labeled and hybridized onto Affymetrix GeneChip Mouse Genome 430 2.0 Arrays and raw hybridization data were collected (VA/VMRF Microarray & NGS Core, UCSD). Expression level data were extracted using R package gcrma (Kawaguchi, Y. et al. The role of the transcriptional regulator Ptf1a in converting intestinal to pancreatic progenitors. *Nat Genet* 32, 128-134 (2002); Team, R. C. R: A language and environment for statistical computing. R Foundation for Statistical Computing, Vienna, Austria (2012); Wu, J., Irizarry with contributions from James MacDonald, R. & Gentry, J. gcrma: Background Adjustment Using Sequence Informatin. R package version 2.37.0), and normalized using a multiple-loess algorithm as previously described (Marino, S., Vooijs, M., van Der Gulden, H., Jonkers, J. & Berns, A. Induction of medulloblastomas in p53-null mutant mice by somatic inactivation of Rb in the external granular layer cells of the cerebellum. *Genes & Development* 14, 994-1004 (2000); Sasik, R., Woelk, C. H. & Corbeil, J. Microarray truths and consequences. *J. Mol. Endocrinol.* 33, 1-9 (2004)). Probes whose expression levels exceed a threshold value in at least one sample were considered detected. The threshold value is found by inspection from the distribution plots of log 2 expression levels. Detected probes were sorted according to their q-value, which is the smallest false discovery rate (FDR) at which a probe is called significant (Hingorani, S. R. et al. Preinvasive and invasive ductal pancreatic cancer and its early detection in the mouse. *Cancer Cell* 4, 437-450 (2003); Benjamini, Y. & Hochberg, Y. Controlling the false discovery rate: a practical and powerful approach to multiple testing. *Journal of the Royal Statistical Society. Series B (Methodological)* 289-300 (1995)). An FDR value of a is the expected fraction of false positives among all genes with q ≤α. FDR was evaluated using Significance Analysis of Microarrays (SAM) and its implementation in the official statistical package samr (Bardeesy, N. et al. Both p16Ink4a and the p19Arf-p53 pathway constrainprogression of pancreatic adenocarcinomain the mouse. *PNAS April*, vol. no. 103, 5947-5952 (2006); Tusher, V. G., Tibshirani, R. & Chu, G. Significance analysis of microarrays applied to the ionizing radiation response. *Proc. Natl. Acad. Sci. U.S.A.* 98, 5116-5121 (2001)). The samples were treated as "Two class paired" according to the date of RNA extraction. No genes reached a significance level of α=0.1. A heat map of selected genes was created using in-house software.

RT-PCR Analysis.

RNA was isolated using RNeasy Micro and Mini kits (Qiagen) and converted to cDNA using Superscript III (Invitrogen). Quantitative real-time PCR was performed using an iCycler (BioRad) by mixing equal amounts of cDNAs, iQ SYBR Green Supermix (BioRad) and gene specific primers. Primer sequences are available upon request. All real time data was normalized to actin.

In Vivo Transplantation Assay and Analysis.

Pancreatic tumors from 10-13 week-old REM2-KP$^{f/f}$C mice were dissociated and FACS sorted for reporter+ (GFP+) and reporter- (GFP-) cells. 100, 500, 1000, or 5000 GFP+ and GFP- cells were suspended in DMEM (Gibco, Life Technologies) containing 10% FBS, then mixed 1:1 with matrigel (BD Biosciences). Cells were injected subcutaneously into the left or right flank of 5-8 week-old NOD/SCID Il2ry$^{-/-}$ (NSG) recipient mice. Tumor dimensions were measured with calipers every 7 days for 8-12 weeks. Tumor volume was calculated using the standard modified ellipsoid formula, $1/2(Length \times Width^2)$. At endpoint, mice were anesthetized and perfused with 5 ml saline. Flank tumors, liver, and lungs were removed, rinsed in PBS, and cut into <2 mm pieces. Tumors were dissociated as described above. Tumor cells were stained with anti-mouse EpCAM PE antibody (eBiosciences) then analyzed for GFP expression by flow cytometry on a FACSAria III machine (Becton Dickinson), and data analyzed with FlowJo software (Tree Star). Liver and lungs were incubated for 30 minutes at 37° C. in PBS containing 0.5 mg/ml Collagenase IV (Sigma) and 0.005 MU/ml DNase I (Millipore). Cells were then passaged through a 70 μm nylon mesh (Corning) and red blood cells were lysed using RBC Lysis Buffer (eBioscience). Remaining lung and liver cells were plated into a 96-well plate at a concentration of 100,000 cells/well. Cells were permeabilized and fixed using the Cytofix/Cytoperm Fixation/Permeabilization Solution Kit (BD Biosciences). Following permeabilization, cells were incubated in rabbit anti-Cre antibody 1:250 (Covance) then in goat anti-rabbit AlexaFluor 647 1:1000 (eBiosciences). Primary and secondary antibodies were diluted in 1×Perm/Wash buffer (BD Biosciences) and incubated for 20 minutes at room temperature. Analysis was carried out on a FACSAria III machine (Becton Dickinson), and data were analyzed with FlowJo software (Tree Star).

Patient-Derived Xenograft Infection and In Vivo Transplant.

Patient samples were obtained from Moores UCSD Cancer Center from Institutional Review Board-approved protocols with written informed consent in accordance with the Declaration of Helsinki. All knockdown experiments were conducted with the construct shCTRL (scrambled), shMSI1, and shMSI2. Briefly, freshly dissociated (GentleMACS Dissociator, Miltenyi) patient-derived xenograft cells were plated in RPMI-1640 with 20% FBS, 1× glutamax, 1× non-essential amino acids, 100 IU/ml penicillin, and 100μg/ml streptomycin. Cells were transduced with GFP-tagged lentiviral shRNAs, and FACS analysis was performed after 24 hours on a portion of the cells; the remaining cells were transplanted into the flank of NSG mice. Tumor size was monitored by caliper measurement, and mice were euthanized when tumors reached 2 cm. Tumors were harvested, dissociated, and analyzed by FACS.

RIP-qPCR.

HEK 293T cells were transfected with MSCV-Flag-Msi2-IRES-tNGFR and lysed 72 hours post-transfection. RNA-immunoprecipitation was carried out with anti-Flag antibody (Sigma-Aldrich) or control IgG using the EZ-Magna RIP kit as per the manufacturers' protocol (Millipore). Immunoprecipitated RNA was converted to cDNA and analyzed for the expression of indicated genes by real-time PCR.

MET Rescue Assay.

Using gateway technology, pENTR-Human c-MET was engineered into the pLENTI-PGK-PURO DEST vector. MIA PaCa-2 cells were infected with pLENTI PGK-MET or pLENTI PGK-EMPTY virus. Following the establishment of the stable cell line over expressing c-MET; lentiviruses containing shRNAs for Control, MSI1, or MSI2 were delivered. Cells were sorted for GFP expression and plated into a soft agar colony assay. Colonies were counted 14 days after plating.

ASO Inhibitors.

To identify human Msi ASO inhibitors, rapid throughput screens were performed to identify effective ASOs as previously described (Wang, J. C. Y. & Dick, J. E. Cancer stem cells: lessons from leukemia. *Trends in Cell Biology* 15, 494-501 (2005); Reya, T., Morrison, S. J., Clarke, M. F. & Weissman, I. L. Stem cells, cancer, and cancer stem cells. *Nature* 414(6859):105-11 (2001); Carroll, J. B. et al. Potent and Selective Antisense Oligonucleotides Targeting Single-Nucleotide Polymorphisms in the Huntington Disease Gene/Allele-Specific Silencing of Mutant Huntingtin. *Molecular Therapy* 19, 2178-2185 (2009); Samuel, V. T. et al. Targeting foxo1 in mice using antisense oligonucleotide improves hepatic and peripheral insulin action. *Diabetes* 55, 2042-2050 (2006)). ASOs were tested in full dose-response experiments to determine potency. The top 2 most effective ASOs were chosen to test free uptake and verify target knockdown in MIA PaCa-2 cells. (A) In Vitro: MIA PaCa-2 cells were treated with 0.5 uM-20 uM of antisense compound for 24 hours, after which cells were lysed and RNA isolated. Gene expression was assessed with taqman probes for MSI1 and MSI2. Actin was used to normalize all real time data. For functional testing, MIA PaCa-2 cells were plated in the colony assay as previously described. The growth medium was supplemented with 0.25 uM-10 uM of ASO. Cells were supplemented weekly with fresh antisense compound. Colonies were counted 21 days after the first ASO treatment. (B) In Vivo: $5 \times 10^5$ MIA PaCa-2 cells were transplanted into the flank of NSG mice. Once tumors were measurable at 2 weeks post transplant, 50 ug of either Control ASO or MSI1 ASO-1 in PBS was administered intratumorally. ASOs were delivered for 5 days with 2 days off. Tumor measurements were recorded every 3 days.

Tumor Imaging.

11-12 week old REM-KP$^{f/f}$C mice were anesthetized by intraperitoneal injection of ketamine and xylazine (100/20 mg/kg). In order to visualize blood vessels, each mouse was injected retro-orbitally with AlexaFluor 647 anti-mouse CD144 (VE-cadherin) antibody immediately following anesthesia induction. Pancreatic tumors were removed and placed in HBSS containing 5% FBS and 2 mM EDTA. 80-100 micron images in 1024×1024 format were acquired with an HCX APO L20× objective on an upright Leica SP5 confocal system using Leica LAS AF 1.8.2 software. Movies were generated using Volocity 3D Image Analysis Software and compressed using Microsoft Video 1 compression.

Circulating Tumor Cell Analysis.

10-13 week old REM2-KP$^{f/f}$C mice were anesthetized and approximately 100 μl of peripheral blood and ascites was collected in PBS containing 5 mM EDTA and 2% Dextran. Samples were incubated at 37° C. and red blood cells were lysed using RBC lysis buffer (eBiosciences). Remaining cells were stained with anti-mouse EpCAM PE (eBiosciences) and anti-mouse CD45 PE Cy7 (eBiosciences) antibodies. Analysis was carried out on a FACSAria III machine (Becton Dickinson) and data analyzed with FlowJo software (Tree Star).

Statistical Analysis.

Statistical analyses were carried out using GraphPad Prism software version 6.0d (GraphPad Software Inc.). Data are shown as the mean±SEM. Two-tailed unpaired Student's t-tests with Welch's correction or One-way analysis of variance (ANOVA) for multiple comparisons when appropriate were used to determine statistical significance (*P<0.05, P<0.01, *P<0.001, ****P<0.0001).

Embodiment 8: Image Based Detection and Targeting of Therapy Resistance in Pancreatic Adenocarcinoma Pancreatic intraepithelial neoplasia (PanIN) is a premalignant lesion that can progress to pancreatic ductal adenocarcinoma, a highly lethal malignancy marked by its late stage at clinical presentation and profound drug resistance. The genomic alterations that commonly occur in pancreatic cancer include activation of KRAS2 and inactivation of p53, and SMAD. To date, however, it has been challenging to target these pathways therapeutically; thus the search for other key mediators of pancreatic cancer growth remains an important endeavor. Here it is shown that the stem cell determinant Musashi (Msi) is a critical element of pancreatic cancer progression in both genetic models and patient derived xenografts. Specifically, Msi reporter mice were developed that allowed image based tracking of stem cell signals within cancers, revealing that Msi expression rises as PanIN progresses to adenocarcinoma, and that Msi-expressing cells are key drivers of pancreatic cancer: they preferentially harbor the capacity to propagate adenocarcinoma, are enriched in circulating tumor cells, and are markedly drug resistant. This population could be effectively targeted by deletion of either Msi1 or Msi2, which led to a striking defect in PanIN progression to adenocarcinoma and an improvement in overall survival. Msi inhibition also blocked the growth of primary patient-derived tumors, suggesting that this signal is required for human disease. To define the translational potential of this work, antisense oligonucleotides against Msi were developed; these showed reliable tumor penetration, uptake and target inhibition, and effectively blocked pancreatic cancer growth. Collectively, these studies highlight Msi reporters as a unique tool to identify therapy resistance, and define Msi signaling as a central regulator of pancreatic cancer.

To understand the mechanisms that underlie pancreatic cancer development and progression, signals that control self-renewal were investigated, a key stem cell property often hijacked in cancer. In particular, the focus was on the role of Musashi (Msi), a highly conserved RNA binding protein originally identified in *drosophila*. While Msi has long been used as a marker of stem/progenitor cells, the breadth of its functional impact is only beginning to emerge: genetic loss-of-function models have shown that Msi signaling is important for maintaining stem cells in the mammalian nervous system, and more recently in normal and malignant hematopoiesis. However, the role of Msi in pancreatic cancer biology and whether it can be a viable therapeutic target remains unknown.

To address these questions, MSI expression in human pancreatic cancers was first analyzed. MSI1 and MSI2 were expressed in all primary tumor samples analyzed, with expression increasing during progression (FIG. 2L). To track the function of Msi-expressing cells, Msi knock-in reporters were developed (Reporter for Musashi, REM) in which fluorescent signals reflected endogenous Msi expression (FIG. 17A to 17B; FIG. 21A to FIG. 21C). To define if Msi-expressing cells contribute to pancreatic cancer, REM mice were crossed to the Kras$^{LSL-G12D/+}$; p53$^{f/f}$; Ptf1a$^{CRE/+}$ model (FIG. 22D to FIG. 22H). In vivo imaging of living tumors revealed clear Msi1 and Msi2 reporter activity within remarkable spatially restricted domains frequently surrounded by blood vessels (FIG. 17C to 17D; FIG. 22I). Cells with high levels of Msi reporter expression were rare, and detected in 1.18% and 9.7% of REM1 and REM2 cancers (FIG. 17E to FIG. 17F). Because cancer stem cells can be similarly rare, it was tested if Msi-expressing cells have preferential capacity for tumor propagation. Consistent with this possibility, Msi+ cells expressed ALDH, and were dramatically more tumorigenic in vitro and in vivo (FIG. 17G to FIG. 17I; FIG. 23A to FIG. 23G). Most importantly, Msi2+ cells were highly lethal: while 100% of mice orthotopically transplanted with Msi2+ cells developed invasive tumors and died, none of the mice receiving Msi2$^-$ cells showed signs of disease (FIG. 17J; FIG. 23H). Given the suggestion that certain markers can not consistently enrich for tumor propagating ability, the findings indicate that Msi-expression can identify cancer stem cells at least in some contexts, and that Msi2+ cells preferentially drive pancreatic cancer growth, invasion and lethality.

Msi2+ cells also represented a high proportion of circulating tumor cells, and were more tumorigenic than Msi2$^-$ CTCs (FIG. 17K to FIG. 17L). While this suggests that Msi2$^+$ CTCs can pose a greater risk for tumor dissemination, the fact that Msi was not consistently elevated in metastatic patient-samples analyzed leaves the question of Msi's role in metastasis open. The Msi reporter also provided an opportunity to define if it could be used to identify therapy resistance. Exposure to gemcitabine led to preferential survival of Msi2+ cells even at high doses (FIG. 17M to FIG. 17N; FIG. 23I to FIG. 23K). These experiments show that Msi2+ cells are a predominant gemcitabine-resistant population, and suggest Msi reporters could serve as a tool to visualize drug resistant cells, and identify therapies to target them.

Because Msi expression rose during progression (FIG. 21F to FIG. 21K; FIG. 20A), and marked therapy resistant cells, it was tested if genetic or pharmacologic targeting of Msi could eradicate this 'high risk' population. Deletion of Msi1 led to a 5-fold reduction in tumor volume by MRI (FIG. 18A to FIG. 18B; FIG. 24B). Histologically, adenocarcinoma areas comprised 67% of WT-KP$^{f/f}$C but less than 10% of Msi1$^{-/-}$KP$^{f/f}$C pancreata; further while Msi1 loss allowed low grade PanINs to form, it largely blocked progression to adenocarcinoma (FIG. 18C to 18F; FIG. 24C to FIG. 24D). Finally, Msi1 deletion improved survival in orthotopic grafts: median survival for WT-KP$^{f/f}$C graft recipients was 28.5 days, and for Msi1$^{-/-}$-KP$^{f/f}$C grafts was 70.5 days, representing a 2.5-fold increase in survival time and a 23-fold decrease in risk of death (FIG. 18G).

Because both Msi1 and Msi2 are expressed in pancreatic cancer, the impact of deleting Msi2 was also analyzed. MRI showed no detectable tumor mass in most Msi2$^{-/-}$-KP$^{f/f}$C mice (FIG. 18H to FIG. 18I; FIG. 24E). Histologically, KP$^{f/f}$C pancreata were mostly replaced by adenocarcinoma, often accompanied by extracapsular invasion into surrounding structures; in contrast, Msi2$^{-/-}$-KP$^{f/f}$C pancreata contained low-grade PanIN with rare high-grade PanIN and microscopic foci of adenocarcinoma within predominantly normal tissue (FIG. 18J to FIG. 18O). Median survival, tracked in the autochthonous model, was 122 days for Msi2$^{-/-}$-KP$^{f/f}$C vs. 87 days for WT-KP$^{f/f}$C mice (FIG. 18P), representing a 4-fold decreased risk of death. Collectively, the data, as described in the embodiments herein show that Msi inhibition significantly improves disease trajectory, leading to an approximate doubling of survival. The fact that the mice ultimately succumbed to disease is likely due to the strong selection for escaper cells in Msi1 and Msi2 single, or double knockout mice (FIG. 25A to 25H). Additionally, some redundancy between Msi1 and Msi2, as well as a partial gene fragment present in Msi1$^{-/-}$ mice (data not shown) can also exert compensatory activity.

To understand the molecular basis of the effects of Msi loss, Msi deficient tumor cells were genomically profiled (FIG. 26A to FIG. 26E; FIG. 27A to FIG. 27D). Msi loss led to down-regulation of many key genes, including regulators of stem cell function (Wnt7a, Aldh, Lin28), proto-oncogenes (c-Met, Fos, Fyn) and Regenerating (Reg) family genes, linked to gastrointestinal cancers. Among these, analysis of 3'UTRs for Msi binding-sites and RIP-PCR identified BRD4, c-MET and HMGA2 as potential direct targets (FIG. 27E, FIG. 19A). c-MET$^{22}$ was the focus, which was diminished in Msi null pancreatic cancer and also bound MSI1 in CLIP-seq experiments (FIG. 19B to FIG. 19D; FIG. 27F to FIG. 27G). c-Met could not only be activated molecularly by MSI but also effectively complemented MSI loss (FIG. 19E to FIG. 19F; FIG. 27H). While these suggest that c-Met is a direct functional target of Msi, it is almost certainly one of many. In fact, Msi's powerful impact on cancer is probably because of its ability to control a broad range of programs (FIG. 26A to FIG. 26E). In this context, BRD4 and HMGA2 can be particularly attractive targets, as they could act at an epigenetic level with c-Met to collectively mediate Msi function. Underscoring such a potential convergence of epigenetic and oncogenic pathways, inhibitors of both Brd4 and c-Met effectively targeted gemcitabine-resistant Msi2$^+$ cells (FIG. 19G to FIG. 19H).

To complement the mouse models, the impact of MSI inhibition on primary patient samples was tested, which harbor more complex mutations, and are uniformly drug resistant. Primary pancreatic cancer cells were infected with MSI shRNAs and xenografted (FIG. 28A). While shMSI cells were equivalently present at time of transplant, their ability to contribute to the tumor mass in vivo was reduced by 4.9-6.5 fold (FIG. 20A to FIG. 20B; FIG. 28B to FIG. 28C), demonstrating that inhibition of either MSI1 or MSI2 results in marked suppression of primary human pancreatic cancer growth. Interestingly, MSI2 expression was more homogeneous in patients than in mouse models (FIG. 21A to FIG. 21B; FIG. 22D to FIG. 22E). This could be a consequence of selection due to treatment and end-stage disease in patients, or because MSI2 patterns differ between mouse models and human disease. However, regardless of the level of heterogeneity, the loss-of-function studies indicate that the mouse and human disease are both highly dependent on Msi signaling.

Given that inhibition of Msi has profound effects on pancreatic cancer progression, its potential as a therapeutic target by developing antisense oligonucleotides (ASOs) specific for MSI1 was explored. Because ASO inhibitors are designed based on target RNA sequences, they can be a powerful approach for inhibiting proteins like Msi, considered "undruggable" by traditional approaches. Of 400 candidate MSI1-ASOs screened, the two most potent markedly reduced colony formation, as well as human cell line and KP$^{f/f}$C derived tumor growth in vivo (FIG. 20C to FIG. 20G; FIG. 28D to FIG. 28E). The MSI1-ASOs have not yet been lead-optimized, a longer-term process designed to maximize therapeutic level efficacy with systemic delivery. To test if a lead-optimized ASO can penetrate the tumor microenvironment, a lead-optimized ASO against Malat1 was delivered intraperitoneally and was effective in knocking down its target in both stem and non-stem cell fractions (FIG. 20H; FIG. 28F to FIG. 28J). These studies provide proof-of-principle that deliverable Msi inhibitors can antagonize pancreatic cancer growth in vivo, and suggest that ASOs should be explored further as a new class of therapeutics in this disease.

The Msi reporters described herein can be broadly applicable for cancer diagnostic and therapeutic studies. Because Msi reporter activity can be visualized through live imaging, these mice can be used to track cancer stem cells in vivo, and provide a dynamic view of cancer growth and dissemination within the native microenvironment. The fact that reporter-positive cells are gemcitabine-resistant raises the exciting possibility that this could serve as a platform to visualize resistance in vivo. Integration of such reporters during drug development can provide a powerful complement to conventional screens, and allow identification of therapies that can better target therapy-resistant disease. Further, the spatially restricted distribution of Msi+ cells could have important implications for designing strategies to loco-regionally target cells that drive residual disease and relapse.

One of the biggest disappointments in pancreatic cancer therapy has been the failure of targeted agents to make a meaningful impact. The data demonstrate that Msi function is critical for growth and progression of pancreatic cancer, and Msi therefore represents an attractive therapeutic target. Here it is shown that cell-penetrating antisense oligonucleotides are able to antagonize Msi and inhibit growth of pancreatic cancer. These findings highlight the value of targeting Msi, and suggest that ASOs and other antagonists should be developed for pancreatic and other cancers marked by high Msi expression. Finally, the rise of Msi in pancreatitis (FIG. 29A to FIG. 29E) raises the possibility that Msi inhibition could serve as a strategy to decrease the risk of developing pancreatic cancer. In the long term, blocking Msi signaling could provide a new approach to controlling cancer establishment, progression, and therapy resistance.

Methods:

Mice.

REM1 (Msi1$^{eYFP/+}$) and REM2 (Msi2$^{eGFP/+}$) reporter mice were generated by conventional gene targeting (Genoway, France; FIG. 17A to FIG. 17N); all of the reporter mice used in experiments were heterozygous for the corresponding Msi allele. The Msi1$^{f/f}$ (Msi1$^{flox/flox}$) mice were generated by conventional gene targeting by inserting LoxP sites around Exons 1-4 (Genoway, France). The Msi2 mutant mouse, B6; CB-Msi2$^{Gt(pU-21T)2Imeg}$ (Msi2$^{-/-}$) was established by gene trap mutagenesis as previously described[9]. Dr. Hideyuki Okano provided the Msi1$^{-/-}$ mice as previously described. The LSL-Kras G12D mouse, B6.129S4-Kras$^{tm4Tyj}$/J (Stock No: 008179) and the p53flox/flox mouse, B6.129P2-Trp53$^{tm1Brn}$/J (Stock No: 008462), were purchased from The Jackson Laboratory. Dr. Maike Sander provided Ptf1a-Cre mice as previously described. Dr. Andrew Lowy provided Pdx1-Cre mice as previously described. Mice were bred and maintained in the animal care facilities at the University of California San Diego. All animal experiments were performed according to protocols approved by the University of California San Diego Institutional Animal Care and Use Committee. No sexual dimorphism was noted in all mouse models. Therefore males and females were equally used for experimental purposes and both sexes are represented in all data sets.

Tissue Dissociation and Cell Isolation.

(A) Mouse pancreatic tumors were washed in RPMI 1640 (Gibco, Life Technologies) and cut into 2-4 mm pieces immediately following resection. Dissociation into a single cell suspension was performed using the Miltenyi Biotec Mouse Tumor Dissociation Kit (130-096-730). Briefly, tumor pieces were collected into gentleMACS C tubes containing RPMI 1640 dissociation enzymes, and further homogenized using the gentleMACS Dissociator. Samples were incubated for 40 minutes at 37° C. under continuous rotation, then passaged through a 70 μm nylon mesh (Corning). Red blood cells were lysed using RBC Lysis Buffer (eBioscience), and the remaining tumor cells were used for FACS analysis and cell sorting. (B) Freshly resected mouse brains were rinsed in PBS, placed in accutase (Life Technologies), and cut into <2 mm pieces. Samples were incubated 15 minutes at 37° C., then passaged through a 70 μm nylon mesh (Corning). Red blood cells were lysed as above prior to FACS analysis and sorting of brain cells. (C) Bone marrow cells were suspended in HBSS (Gibco, Life Technologies) containing 5% FBS and 2 mM EDTA and were prepared for FACS analysis and sorting as previously described. Analysis and cell sorting were carried out on a FACSAria III machine (Becton Dickinson), and data were analyzed with FlowJo software (Tree Star).

Immunofluorescence and Immunohistochemical Staining.

(A) Human primary pancreatic cancer tissues were fixed in 10% neutral buffered formalin and paraffin embedded at the Moores Cancer Center at UCSD according to standard protocols. 7 μm sections were obtained and deparaffinized in xylene. The UNMC Rapid Autopsy Pancreas (RAP) Program provided a second cohort of human primary pancreatic cancer tissues and matched liver metastases. Pancreatic cancer tissue from KP$^{f/f}$C mice were fixed in 4% paraformaldehyde and paraffin embedded at the UCSD Histology and Immunohistochemistry Core at The Sanford Consortium for Regenerative Medicine according to standard protocols. 5 μm sections were obtained and deparaffinized in xylene. Antigen retrieval was performed for 20-40 minutes in 95-100° C. 1× Citrate Buffer, pH 6.0 (eBioscience). Sections were blocked in TBS or PBS containing 0.1% Triton X100 (Sigma-Aldrich), 10% Goat or Donkey Serum (Sigma Aldrich), and 5% bovine serum albumin. (B) Single cell suspensions from mouse pancreatic tumors and brain. Cells isolated by FACS were suspended in DMEM (Gibco, Life Technologies) supplemented with 50% FBS and adhered to slides by centrifugation at 500 rpm. 24 hours later, cells were fixed with 4% paraformaldehyde (USB Corporation), washed in PBS containing 0.1% Tween-20 (Sigma-Aldrich), and blocked with PBS containing 0.1% Triton X-100 (Sigma-Aldrich), 10% Goat serum (Invitrogen), and 5% bovine serum albumin (Invitrogen). (C) Single cell suspensions from mouse bone marrow. Cells were allowed to settle onto chambered cover glass (LabTek) coated with poly-1-lysine (Sigma) at 37° C., fixed with 4% paraformaldehyde (USB Corporation), washed in 1× Dako wash buffer (Dako), and blocked with Dako wash buffer containing 10% Goat serum (Invitrogen). All incubations with primary antibodies were carried out overnight at 4° C. For immunofluorescent staining, incubation with Alexafluor-conjugated secondary antibodies (Molecular Probes) was performed for 1 hour at room temperature. DAPI (Molecular Probes) was used to detect DNA and images were obtained with a Confocal Leica TCS SP5 II (Leica Microsystems) or with a Nikon Eclipse E600 fluorescent microscope. For immunohistochemical staining, endogenous peroxidase was blocked by incubating slides in 3% $H_2O_2$ for 15 minutes prior to primary antibody. Incubation with Biotinylated secondary antibodies (Vector Laboratories) was performed for 45 minutes at room temperature. ImmPACT NovaRED Kit (Vector Laboratories) was used per manufacturer's protocol. Sections were counterstained with hematoxylin. The following primary antibodies were used for human tissue sections: rabbit anti-Msi1 (Abcam, ab52865) 4 μg/ml; rabbit anti-Msi2 (Abcam, ab76148) 1 μg/ml; and mouse anti-Keratin (Abcam, ab8068) 1:20. The following primary antibodies were used to stain mouse tissues: rabbit anti-ALDH1 (Abcam, ab24343) 1:200; rabbit anti-cMet (Abcam, ab5662) 1:250; chicken anti-GFP (Abcam, ab13970) 1:250 (for pancreatic tumors and brain) or 1:200 (for bone marrow); rabbit anti-Msi2 (Abcam, ab76148) 1:500 (for pancreatic tumors and brain) or 1:200 (for bone marrow); rat anti-Ki67 (eBioscience, 14-5698) 1:1000; rat anti-Msi1 (eBioscience, 14-9896-82) 1:500; mouse anti-Keratin (Abcam, ab8068) 1:10; and biotinylated DBA (Vector Laboratories, B-1035) 1:1000.

Pancreatic Tumorsphere Formation Assay.

(A) Pancreatic tumorsphere formation assays were performed on freshly isolated mouse pancreatic tumor cells or circulating tumor cells from peripheral blood modified from Rovira, et al. Briefly, pancreatic tumors from 10-13 week old REM1-KP$^{f/f}$C or REM2-KP$^{f/f}$C mice were dissociated and FACS sorted for YFP+ and YFP− or EpCAM+/GFP+ and EpCAM+/GFP− cells, respectively. 100-500 cells were suspended in 1000 DMEM F-12 (Gibco, Life Technologies) containing 1×B-27 supplement (Gibco, Life Technologies), 3% FBS, 100 mM β-mercaptoethanol (Gibco, Life Technologies), 1× non-essential amino acids (Gibco, Life Technologies), 1×N2 supplement (Gibco, Life Technologies), 20 ng/ml EGF (Gibco, Life Technologies), 20 ng/ml FGF2 (Gibco, Life Technologies), and 10 ng/ml ESGRO mLIF (Millipore). Culture media for circulating tumor cells also contained 20 ng/ml mHGF (R&D Systems). Cells in media were plated in 96-well ultra-low adhesion culture plates (Costar) and incubated at 37° C. for 7 days. Sphere images were obtained with a Nikon80i. Sphere size was measured using ImageJ 1.47v software.

Lentiviral Constructs and Production.

Short hairpin RNA (shRNA) constructs were designed and cloned into plenti-hU6BX vector with a GFP tag by Cellogenetics. The target sequences are 5'-CCCAGATAGC-CTTAGAGACTAT-3' for MSI1 (SEQ ID NO: 1), 5'-CCCA-GATAGCCTTAGAGACTAT-3' for MSI2 (SEQ ID NO: 2) and 5'-CTGTGCCAGAGTCCTTCGATAG-3' for the control scrambled sequence (SEQ ID NO: 3). Additional (shRNA) target sequences were cloned into a plenty-FG12 vector with a Tomato Red tag. These target sequences are 5'-ATGAGTTAGATTCCAAGACGAT-3' (SEQ ID NO: 16) for MSI2 and 5'-AGGATTCCAATTCAGCGGGAGC-3' (SEQ ID NO: 17) for control scrambled sequence. Virus was produced in 293T cells transfected with plenti-shRNA constructs along with pRSV/REV, pMDLg/pRRE, and pHCMVG constructs. Viral supernatants were collected for three days followed by ultracentrifugal concentration at 50,000×g for 2 h.

Agarose Colony Formation Assays.

MIA PaCa-2, Panc-1, Capan-2, and HPAC human pancreatic cancer cell lines were purchased from ATCC, and cultured in the appropriate growth media as recommended by ATCC. ASPC1, FG, and AA0779E human pancreatic cancer cell lines were provided by Dr. Andrew Lowy, and grown in DMEM containing 10% FBS, 1× Glutamax, and 1×PS (pen/strep). Human pancreatic cancer cell lines were infected with GFP-tagged or TomatoRed-tagged lentiviral particles containing shRNAs for MSI1, MSI2, and a scrambled control. Positively infected cells were sorted 72 hours after transduction. For colony assays, 24-well plates were first coated with 0.6% agarose in DMEM without supplements. Cells were plated at a density of 2000 cells per well in 0.3% agarose containing DMEM, 10% FBS, NEAA, PS, and Glutamax. Growth medium was placed over the solidified agarose layers and was supplemented every three days. Colonies were counted 14 days after plating.

MRI.

Magnetic resonance imaging was used to determine the pancreatic volumes of the mice in vivo. Mice were anesthetized using 1.5% isoflurane and imaged in a 7.0 Tesla small animal scanner (Bruker-Biospin, Ettlingen, Germany). Contiguous coronal slices were acquired using a multi-slice, RARE sequence: repetition time/echo time=4826 ms/33 ms, Field of View=6×3 cm, and Matrix=126×128 with up to 44 slices with a thickness of 0.5 mm. Segmentation and volume rendering were performed using Amira software (FEI Visualization Sciences Group, Burlington, Mass.).

Histological Analysis/Quantification of PanIN and PDAC.

Mouse tumors from 4.5-13 week old Msi1$^{-/-}$-KP$^{f/f}$C, Msi2$^{-/-}$-KP$^{f/f}$C mice, and WT-KP$^{f/f}$C littermates were isolated, fixed in 4% paraformaldehyde, and paraffin embedded according to standard protocols. 5 µm sections were obtained for hematoxylin and eosin and periodic acid-Schiff/Alcian Blue staining. To quantify tumor areas, each slide was digitally scanned with an Aperio slide scanner. Imagescope software was used to measure PDAC area, PanIN area, and normal pancreas area.

Gene Expression Microarray, RNA-Seq, and Data Analysis.

(A) WT-KP$^{f/f}$C or Msi1$^{-/-}$-KP$^{f/f}$C mice were euthanized at 11 weeks of age. Tumors were harvested and total cellular RNAs were purified, labeled and hybridized onto Affymetrix GeneChip Mouse Genome 430 2.0 Arrays and raw hybridization data were collected (VA/VMRF Microarray & NGS Core, UCSD). Expression level data were extracted using R package gcrma, and normalized using a multiple-loess algorithm as previously described. Probes whose expression levels exceed a threshold value in at least one sample were considered detected. The threshold value is found by inspection from the distribution plots of log 2 expression levels. Detected probes were sorted according to their q-value, which is the smallest false discovery rate (FDR) at which a probe is called significant. An FDR value of a is the expected fraction of false positives among all genes with q≤α. FDR was evaluated using Significance Analysis of Microarrays (SAM) and its implementation in the official statistical package samr. The samples were treated as "Two class paired" according to the date of RNA extraction. No genes reached a significance level of α=0.1. A heat map of selected genes was created using in-house software. (B) MIA PaCa2 cells were infected with GFP-tagged or TomatoRed-tagged lentiviral particles containing shRNAs for MSI1, MSI2, MSI1+MSI2, and a scrambled control. At 72 hours post-infection, positively infected cells were sorted and total cellular RNAs were isolated using a Qiagen RNeasy mini kit. RNA-seq fastq files were processed into transcript-level summaries using kallisto, an ultrafast pseudo-alignment algorithm with expectation maximization. Transcript-level summaries were processed into gene-level summaries by adding all transcript counts from the same gene. Gene counts were normalized across samples using DESeq normalization, and the gene list was filtered based on mean abundance, which left 13,684 "detected" genes for further analysis. Differential expression was assessed with an R package limma[39] applied to log 2-transformed counts. Statistical significance of each test was expressed in terms of posterior error probability $p^E$ using the limina function eBayes. Posterior error probability, also called local false discovery rate, is the probability that a particular gene is not differentially expressed, given the prior probabilities of the model. The list of genes sorted by $p^E$ (in ascending order) were analyzed for over-represented biological processes and pathways using a non-parametric version of Gene Set Enrichment Analysis. Denoting $p^E(1)$ the probability that a gene is not differentially expressed in the Msi1 knockdown and $p^E(2)$ the probability that a gene is not differentially expressed in the Msi2 knockdown, the probability that a gene is differentially expressed in both samples was estimated as $[1-p^E(1)][1-p^E(2)]$. By the same token, the probability that a gene is differentially expressed in the Msi1 knockdown but not in the Msi2 knockdown was estimated as $[1-p^E(1)]p^E(2)$; likewise with indices 1 and 2 switched.

RT-PCR Analysis.

RNA was isolated using RNeasy Micro and Mini kits (Qiagen) and converted to cDNA using Superscript III (Invitrogen). Quantitative real-time PCR was performed using an iCycler (BioRad) by mixing cDNAs, iQ SYBR Green Supermix (BioRad) and gene specific primers. Primer sequences are available upon request. All real time data was normalized to actin or Gapdh.

In Vivo Transplantation Assay and Analysis.

In vivo the focus was on the tumorigenic potential of Msi2 reporter cells since Msi1+ cells were unable to form tumors in small numbers (100, 1000), possibly because they are less tumorigenic or more quiescent (data not shown). Pancreatic tumors from 10-13 week-old REM2-KP$^{f/f}$C mice were dissociated and FACS sorted for EpCAM+/reporter+ (GFP+) and EpCAM+/reporter– (GFP–) cells. 100, 500, 1000, or 5000 GFP+ and GFP– cells were suspended in DMEM (Gibco, Life Technologies) containing 10% FBS, then mixed 1:1 with matrigel (BD Biosciences). Cells were injected subcutaneously into the left or right flank or orthotopically into the tail of the pancreas of 5-8 week-old NOD/SCID Il2ry$^{-/-}$ (NSG) recipient mice. Subcutaneous tumor dimensions were measured with calipers every 7 days for 8-12 weeks. Tumor volume was calculated using the standard modified ellipsoid formula, 1/2(Length×Width$^2$). At endpoint, flank tumors were removed and dissociated as described above. Tumor cells were stained with anti-mouse EpCAM antibody (eBiosciences) then analyzed for GFP expression by flow cytometry on a FACSAria III machine (Becton Dickinson), and data analyzed with FlowJo software (Tree Star). Subcutaneous tumors did not exceed 2 cm in diameter as per the University of California San Diego Institutional Animal Care and Use Committee Policy on Experimental Neoplasia.

Patient-Derived Xenograft Infection and In Vivo Transplant.

Patient samples were obtained from Moores UCSD Cancer Center from Institutional Review Board-approved protocols with written informed consent in accordance with the Declaration of Helsinki. All knockdown experiments were conducted with the construct shCTRL (scrambled), shMSI1, and shMSI2. Briefly, freshly dissociated (GentleMACS Dissociator, Miltenyi) patient-derived xenograft cells were plated in RPMI-1640 with 20% FBS, 1× glutamax, 1× non-essential amino acids, 100 IU/ml penicillin, and 100µg/ml streptomycin. Cells were transduced with GFP-tagged lentiviral shRNAs, and FACS analysis was performed after 24 hours on a portion of the cells; the remaining cells were transplanted into the flank of 5-8 week-old NSG recipient mice. Tumor size was monitored by caliper measurement, and mice were euthanized when tumors reached 2 cm in diameter. Subcutaneous tumors did not exceed 2 cm in diameter as per the University of California San Diego Institutional Animal Care and Use Committee Policy on Experimental Neoplasia. Tumors were harvested, dissociated, and analyzed by FACS.

RIP-qPCR.

HEK 293T cells were transfected with MSCV-Flag-Msi2-IRES-tNGFR and lysed 72 hours post-transfection. RNA-immunoprecipitation was carried out with anti-Flag antibody (Sigma-Aldrich) or control IgG using the EZ-Magna RIP kit as per the manufacturers' protocol (Millipore). Immunoprecipitated RNA was converted to cDNA and analyzed for the expression of indicated genes by real-time PCR.

CLIP SEQ.

Briefly, MIA PaCa-2 cells were UV cross-linked with a Stratalinker (Model 2400, Stratagene). Cells were lysed and supernatant added to Dynabeads conjugated to MSI1 antibody (clone 14H1, eBiosciences). CLIP library preparation and sequencing, as well as sample preparation and sequencing, were performed as previously described[44]. 73,329 unique tags were obtained from MSI1-bound targets including tags with the binding core sequence "rUAG" site, as reported previously.

MET Rescue Assay.

Using gateway technology, pENTR-Human c-MET was engineered into the pLENTI-PGK-PURO DEST vector. MIA PaCa-2 cells were infected with pLENTI PGK-MET or pLENTI PGK-EMPTY virus. Following the establishment of the stable cell line over expressing c-MET; lentiviruses containing shRNAs for Control, MSI1, or MSI2 were delivered. Cells were sorted for GFP expression and plated into a soft agar colony assay. Colonies were counted 14 days after plating.

In Vivo and In Vitro Drug Therapy.

9-10 week old REM2-KP$^{f/f}$C mice were treated with Gemcitabine alone or in combination with Crizotinib or iBet762 for 6 days. On day 6, tumors were removed, dissociated (as described above), counted for total cellular content, stained with anti-mouse EpCAM antibody and analyzed for reporter expression by flow cytometry. Gemcitabine (Sigma, G6423) was resuspended in $H_2O$ at 20 mg/ml and delivered at 200 mg/kg or 500 mg/kg by IP injection twice over 6 days (on day 0 and 3). Crizotinib (Seleckchem PF-02341066) was resuspended in DMSO at 50 mg/ml, diluted 1:10 in $H_2O$, and delivered at 100 mg/kg/day for 6 days by oral gavage. iBet762 (Selleckchem S7189) was resuspended in DMSO at 50 mg/ml, diluted 1:10 in $H_2O$, and delivered at 30 mg/kg/day by IP injection for 6 days. For in vitro drug assay, low passage Msi2 Reporter KP$^{f/f}$C cells loaded with 2 µM DiI and imaged continuously for up to 48 hours while receiving 10 µM gemcitabine treatment.

ASO Inhibitors.

To identify human Msi ASO inhibitors, rapid throughput screens were performed to identify effective ASOs as previously described. ASOs were tested in full dose-response experiments to determine potency. The top 2 most effective ASOs were chosen to test free uptake and verify target knockdown in MIA PaCa-2 cells. The sequences of Gen 2.5 MSI1 ASOs used for the study were ASO-1, 5'-<u>ATA</u>TGATACAGGA<u>CGG</u>-3' (SEQ ID NO: 18), and ASO-2, 5'-<u>TTA</u>CATATGATAC<u>AGG</u>-3' (SEQ ID NO: 19), with underlined letters indicating cEt modified bases. The sequence of Gen 2.5 scrambled (5'-<u>GGC</u>TACTACGCCG<u>TCA</u>-3') (SEQ ID NO: 20) ASO with no perfect match for any known transcript was included as a negative control. (A) In Vitro: MIA PaCa-2 cells were treated with 0.5 µM-20 µM of antisense compound for 24 hours, after which cells were lysed and RNA isolated. Gene expression was assessed with Taqman probes for MSI1 and MSI2. Actin was used to normalize all real time data. For functional testing, MIA PaCa-2 cells were plated in the colony assay as previously described. The growth medium was supplemented with 0.25 µM-10µ µM of ASO. Cells were supplemented weekly with fresh antisense compound. Colonies were counted 21 days after the first ASO treatment. (B) In Vivo: 5×10$^5$ MIA PaCa-2 cells were transplanted into the flank of 5-8 week-old NSG recipient mice. Once tumors were measurable at 2 weeks post transplant, 50 µg of either Control ASO or MSI1 ASO-1 in PBS was administered intratumorally. ASOs were delivered daily over the course of the study. Tumor measurements were recorded every 3 days. Subcutaneous tumors did not exceed 2 cm in diameter as per the University of California San Diego Institutional Animal Care and Use Committee Policy on Experimental Neoplasia. (C) In Vivo: In 8 week-old WT-KPf/fC mice, either Control ASO or Malat1 ASO was delivered by intraperitoneal injection at a dose of 50 mg/kg. ASOs were delivered daily for 14 days. On day 15, mice were sacrificed and the tumor removed. Tumors were harvested and used as follows: (1) flash frozen for RNA isolation and qPCR analysis for Malat1; (2) placed into 4% paraformaldehyde for paraffin embedding, sectioning, and in situ hybridization analysis for Malat1; and (3) dissociated and sorted for RNA isolation to compare Malat1 expression in EpCAM+/ALDH+ and EpCAM+/ALDH− populations.

Tumor Imaging.

11-12 week old REM-KP$^{f/f}$C mice were anesthetized by intraperitoneal injection of ketamine and xylazine (100/20 mg/kg). In order to visualize blood vessels and nuclei, mice were injected retro-orbitally with AlexaFluor 647 anti-mouse CD144 (VE-cadherin) antibody and Hoechst 33342 immediately following anesthesia induction. Pancreatic tumors were removed and placed in HBSS containing 5% FBS and 2 mM EDTA. 80-100 micron images in 1024×1024 format were acquired with an HCX APO L20× objective on an upright Leica SP5 confocal system using Leica LAS AF 1.8.2 software. Videos were generated using Volocity 3D Image Analysis Software and compressed using Microsoft Video 1 compression.

Circulating Tumor Cell Analysis.

10-13 week old REM2-KP$^{f/f}$C mice were anesthetized and approximately 100 µl of peripheral blood and ascites was collected in PBS containing 5 mM EDTA and 2% Dextran. Samples were incubated at 37° C. and red blood cells were lysed using RBC lysis buffer (eBiosciences). Remaining cells were stained with anti-mouse EpCAM-PE (eBiosciences) and anti-mouse CD45-PE-Cy7 (eBiosciences) antibodies. Analysis was carried out on a FACSAria III machine (Becton Dickinson) and data analyzed with FlowJo software (Tree Star).

In Situ Hybridization.

Msi1 and Msi2 mRNA were detected in tumor samples using RNAscope, an RNA in situ hybridization method that permits signal amplification and background suppression. Human tissue was drop-fixed in neutral-buffered formalin and processed and embedded in paraffin. 4 µm tissue sections were collected in RNase-fee manner and dried at room temperature overnight. Staining was initiated by baking the slides for 32 min at 60 degrees, then they were deparaffinized, subjected to antigen retrieval and treated with protease (two sequential incubations at 65 and 75 degrees for 12 min each) to enhance probe penetration, as described by the manufacturer (Advanced Cell Diagnostics). Msi1-specific and Msi2-specific RNA target probe sets were generated and supplied by the manufacturer (Advanced Cell Diagnostics). Sequential amplification steps result in a large number of horseradish peroxidase molecules per mRNA. The probe was visualized by incubation with 3,3' diaminobenzidine (DAB). Sections were counterstained with hematoxylin. All steps of this procedure were performed using a Ventana Discovery Ultra (Roche). Slides were analyzed by conventional light microscopy.

Msi1$^{-/-}$KP$^{f/f}$C Survival Curve.

For the Msi1$^{-/-}$-KP$^{f/f}$C mice, tracking survival was complicated by the incidence of hydrocephaly observed in the knockout mice reported previously. To avoid confounding the data with deaths due to non-tumorigenic events, orthotopic transplants were carried out. Briefly, Msi1$^{-/-}$KP$^{f/f}$C and WT KP$^{f/f}$C mice at 8 weeks of age were sacrificed and tumors collected. Tumors were divided into four equal chunks, and then surgically transplanted into the pancreas of 8-week-old NSG mice. After surgery, the orthotopically transplanted mice were tracked for survival.

Luciferase Assay.

A Lightswitch Luciferase Assay System (Active Motif, Inc) was used for the assessment of MSI1 regulation of cMET. Briefly, 1×10$^4$ MIA PaCa-2 cells were plated into 96 well plates and cultured for 24 hours. 50 ng of cMET 3'UTR GoClone (S811259, Active Motif, Inc) plasmid DNA and increasing concentrations (0 ng, 50 ng, and 100 ng) of either PGK-GFP or PGK-MSI1 plasmid vector DNA were co-transfected into MIA PaCa-2 cells. After 24 hours, cells were lysed using the Lightswitch Luciferase Assay Reagent (LS100, Active Motif, Inc) and luciferase activity measured using a plate scanner (Infinite 200, Tecan).

Caerulein-Induced Pancreatitis.

4-week-old C57BL/6 mice received 8 injections of 50 µg/kg caerulein (Sigma-Aldrich) or PBS hourly each day for two consecutive days (for a total of 16 injections). Pancreata were isolated 2 days after the last injection, fixed in 4% paraformaldehyde and paraffin embedded according to standard protocols. 7 µm sections were obtained, deparaffinized in xylene, and stained as described above.

Statistical Analysis.

Statistical analyses were carried out using GraphPad Prism software version 6.0d (GraphPad Software Inc.). Sample sizes were determined based on the variability of pancreatic tumor models used. Tumor bearing animals within each group were randomly assigned to treatment groups. Data are shown as the mean±SEM. Two-tailed unpaired Student's t-tests with Welch's correction or One-way analysis of variance (ANOVA) for multiple comparisons when appropriate were used to determine statistical significance (*P<0.05, P<0.01, *P<0.001, ****P<0.0001).

Accession Codes.

Microarray and RNA-seq data reported here have been deposited in the Gene Expression Omnibus (accession GSE73312 and GSE75797).

Embodiment 9: High Resolution Imaging and Computational Analysis of Hematopoietic Cell Dynamics In Vivo Although a great deal about the phenotype and function of hematopoietic stem/progenitor cells is known, a major challenge has been mapping their dynamic behavior within living systems. A strategy to image cells in vivo with high spatial and temporal resolution and quantify their interactions using a high-throughput computational approach is described. Using these tools, and a new Msi2-reporter model, it is shown that hematopoietic stem/progenitor cells display high spatial affinity for contacting the vascular niche, and a temporal affinity for making stable associations with these cells. These preferences are markedly diminished as cells mature, suggesting that programs that control differentiation state are key determinants of spatiotemporal behavior, and thus dictate the signals a cell receives from specific microenvironmental domains. These collectively demonstrate that high-resolution imaging coupled with computational-analysis can provide new biological insight, and may in the long-term enable creation of a dynamic atlas of cells within their native microenvironment.

The hematopoietic system is responsible for generating all the cells of the blood and immune system. The development of fully mature cells from immature hematopoietic stem and progenitor cells occurs in a highly regulated manner within the bone marrow, the primary site of adult hematopoiesis. Here, cells integrate a multitude of soluble and cell contact-derived signals from their microenvironment or niche to achieve and maintain tissue homeostasis, as well as to initiate regeneration in response to injury. Defining the dynamic interactions of hematopoietic cells with the microenvironment over time and space is thus critically important to better understanding hematopoiesis.

Traditionally, studies of these interactions have been largely restricted to static analysis primarily due to limitations in imaging technology and tissue accessibility. Of note, advances in the field have improved the utility of this approach. For example, in a recent study, optical clearing of the bone marrow permitted deep confocal imaging of hematopoietic cells and digital reconstruction of the marrow cavity. However, the dynamic changes that occur as cells interact with components of the bone marrow microenvironment are not readily captured by these methods. To address this, several groups have used two-photon intravital imaging within the bone marrow cavity of the calvariumor the long bone. While these studies have provided valuable new ways to visualize the hematopoietic compartment and to generate three dimensional spatial models of the bone marrow microenvironment in living animals, there is a continued need for not only increasing spatiotemporal resolution, but also a strategy to track endogenous cells without transplantation and a means by which the 'big data' that is generated by such imaging approaches can be analyzed to reveal new biological patterns. This would enable us to better map the interactions, signals and mechanisms that govern hematopoietic cell behavior and function in vivo, and thereby understand how this can fail in disease and degeneration.

To address this need an approach that allows real-time imaging of hematopoietic cells in context of their living microenvironment with high spatial and temporal resolution is developed and described herein. Notably, the resolution achieved has allowed us to build a new analytic tool that permits in vivo tracking of individual cells and their temporal and spatial behavior relative to microenvironmental niches. In addition to tracking transplanted hematopoietic cells, endogenous immature hematopoietic cells using a newly developed Musashi2 (Msi2) knock-in reporter mouse was also tracked. This mouse reports endogenous expression of Musashi2 (Reporter for Musashi2, REM2) with enhanced green fluorescence protein (eGFP). Because Msi2 is highly expressed within hematopoietic stem and progenitor cells, Msi2GFP$^{bright}$ expression faithfully marks an immature hematopoietic population, which can be dynamically tracked in vivo. This reporter mouse in conjunction with high resolution live imaging makes it possible to dynamically track endogenous immature cells in vivo. These tools were used to identify spatial 'hotspots' within the microenvironment: areas where hematopoietic stem and progenitor cells preferentially reside and interact. Specifically it is found that immature hematopoietic cells have a significant preference for being in stable contact with vascular domains, while differentiated cells make more short-term interactions and frequently shuttle between the vascular and endosteal domains. These suggest that differentiation state can control the spatiotemporal behavior of hematopoietic cells and the programs that control cell fate also dictate the kinds of signals cells will be exposed to by virtue of their localization in specific microdomains. These data show that high-resolution imaging coupled with an effective high-throughput computational approach can be provide new biological insight into the dynamics of hematopoietic cells in their microenvironment, and can be used to establish a baseline to study changes in hematopoietic cell interactions within the niche during regeneration and oncogenesis.

Results

Real Time Imaging

To understand how hematopoietic stem and progenitor cells behave in living tissues, a real-time imaging strategy was developed and described herein to visualize cells in high resolution over extended periods of time. Fluorescent protein-expressing transgenic mice to observe the spatial orientation of the bone marrow cavity was used, and a typical confocal microscope to view the mouse calvarium (FIG. 30A). Mice were anesthetized, their calvaria exposed, and they were placed either inverted on an imaging apparatus or upright in a stereotactic device. Stabilization of animals was important for limiting breathing artifacts that can occur during an imaging session, and consistency of animal orientation was crucial for successful imaging of the same region (in the parasagittal sinusoids) between mice and between experiments over extended periods of time (FIG. 47A and FIG. 47B.

To highlight the features of the bone marrow microenvironment, mice with constitutive expression of dsRed under the control of a ubiquitous promoter were used[21]. This strategy provided a counterlabel and had a "backlighting" effect for visualizing microenvironment cells. A typical 10× image of the bone marrow of a dsRed mouse is shown in FIG. 30B. When analyzing hematopoietic cell movement, a higher magnification objective (20×) was used to achieve greater spatial resolution (FIG. 30C). The use of transgenic mice expressing dsRed.T3[22] to create a labeled microenvironment was particularly important in allowing tracking of hematopoietic cell encounters and associations with the niche at a single-cell level.

The high degree of temporal and spatial resolution allowed clear visualization of transplanted cells interacting for several minutes to several hours with specific niches. In these experiments, actin promoter-driven GFP$^+$ hematopoietic progenitor cells, as defined by the absence of lineage markers (Lineage negative or Lin$^-$), were transplanted into dsRed recipient mice (FIG. 30D). This strategy provided a way to distinguish associations that lasted short periods of time and those that were more stable, lasting several hours. Further, individual GFP$^+$ cells could be tracked rolling/crawling along the endothelium within the calvarial marrow (FIG. 30D, arrows). Finally, individual cells dividing in real-time were traced (FIG. 30E), a testament to the single cell resolution achieved in this system.

Figure 31C:
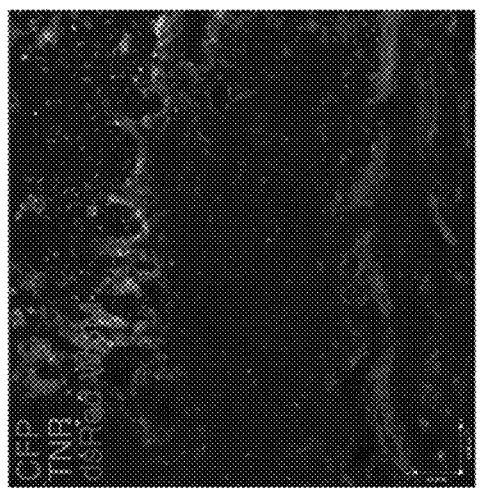
Figure 31B:
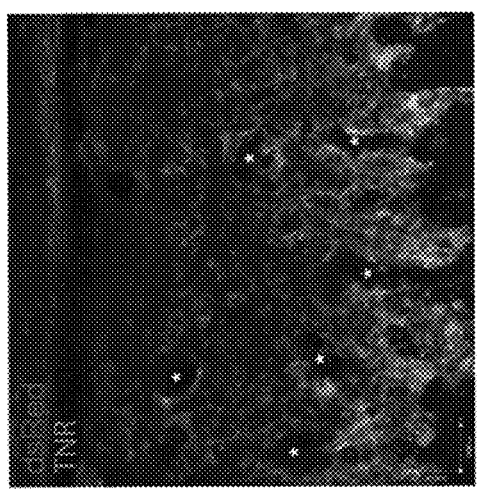
Figure 31A:
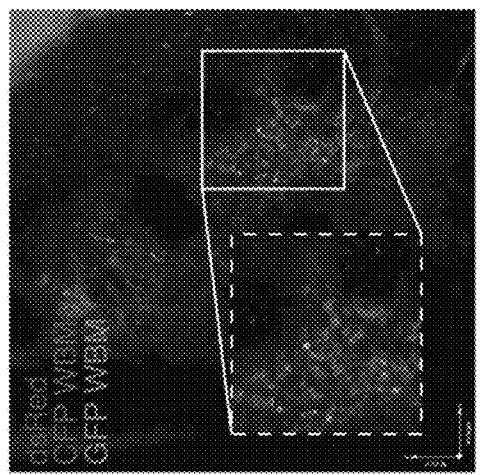

Different fluorescent proteins with multiple spectra were used to analyze distinct cell populations simultaneously. To test imaging in multiple colors, bone marrow cells from GFP and cyan fluorescent protein (CFP) donors wetr transplanted into dsRed recipients. As shown in the three-dimensional view of the recipient marrow, both GFP$^+$ and CFP$^+$ cells could be clearly distinguished within the dsRed backlit microenvironment (FIG. 31A). The use of multiple colors enabled comparative imaging of cells from distinct genetic backgrounds within the same niche. It was also tested if one could monitor the signaling status of niche cells. To this end, actin-dsRed mice were crossed to Transgenic Notch Reporter mice (TNR), in which GFP is predominantly expressed in cells responding to Notch signaling. Notch signaling was active in cells surrounding areas of bone and in the endosteal region within the microenvironment (FIG. 31B, asterisks). Further, the association of hematopoietic cells with reporter+ cells could be visualized by transplanting dsRed hematopoietic cells into TNR mice crossed to CFP mice (FIG. 31C). These data show that hematopoietic cells and their interactions with cells responsive to a specific signal can be traced at a single cell level in vivo.

Computational Analysis

The ability to clearly assess niches in real-time coupled with the spatial and temporal resolution can allow one to begin to generate a map of hematopoietic cell associations with the niche in homeostasis. To maintain the most flexibility, elements of the environment were visualized using ectopically-delivered antibodies and probes. Vascular endothelial cells and blood vessels were identified using anti-VE-cadherin antibodies and the in vivo probe angiosense, respectively (FIG. 31D, FIG. 48A to FIG. 48B), and the endosteal region was identified using the in vivo probe Osteosense (FIG. 31E; FIG. 48C to FIG. 48D). Other potential niche cells, such as tissue macrophages, could also be visualized using this strategy (FIG. 48E), and may be of future interest.

Figure 31E:
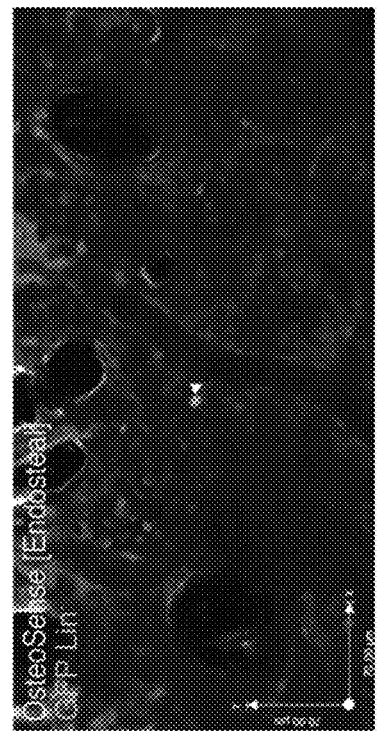
Figure 31D:
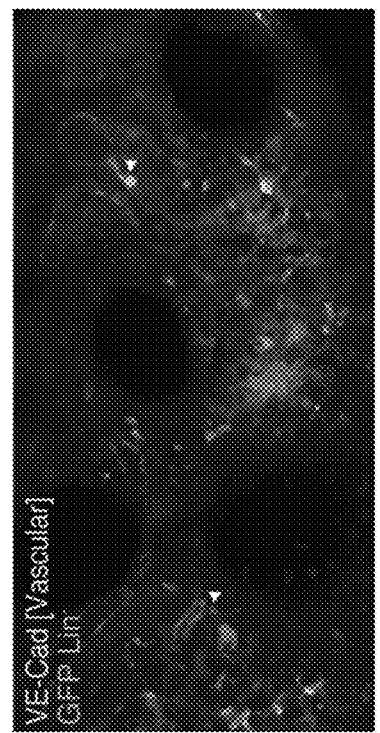
Figure 32A:
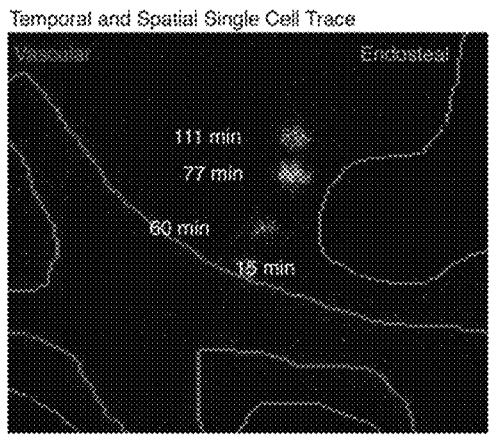
Figure 32B:
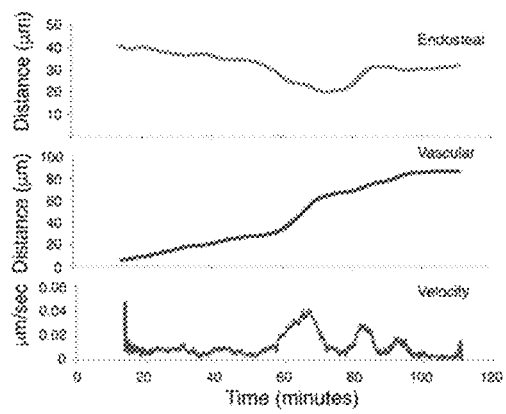

The spatial location of GFP$^+$ transplanted cells could be clearly viewed relative to the microdomain of interest (FIG. 31D to FIG. 31E, arrows). Beginning with the raw image set, the software automatically corrects for lateral drift between images, identifies individual cells, and tracks the position of each cell over time using particle tracking software (FIG. 32A). The program then records the x and y coordinates at each time point, as well as the distance traveled and cellular velocity. In addition, with defined endosteal and vascular microdomains (another input to the software), the program calculates the closest distance between these regions and each cell. For example, FIG. 32A shows how one cell, which initially localized close to a vascular (red) region, migrated over time towards an endosteal (gray) region. FIG. 32B is a trace depicting the quantitative data derived using the software.

Figure 32C:
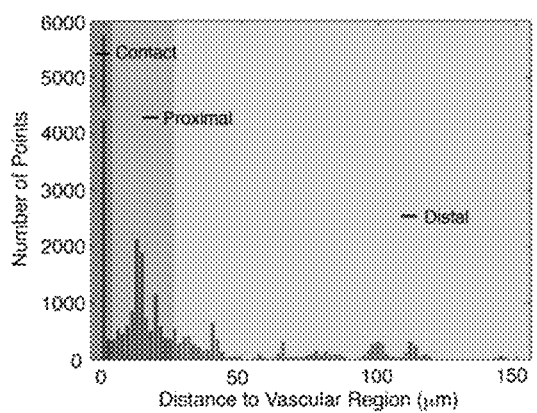
Figure 32D:
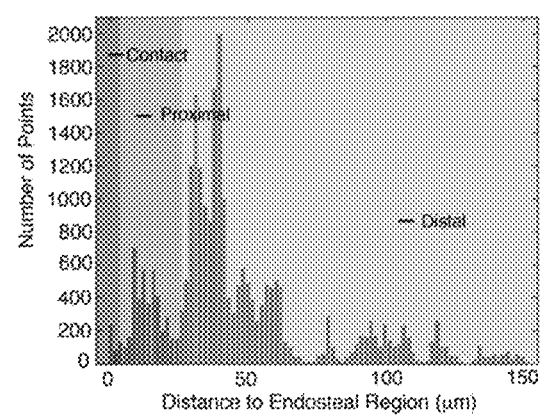

Using this approach, it was desired to determine if there were characteristic distances at which hematopoietic cells interacted with specific regions of the microenvironment. Thus, each cell's distance to the vasculature at every time point was first plotted (FIG. 32C). The resulting histogram suggested that a significant amount of cellular time was spent within five microns of the vasculature, and, based on visual confirmation, was designated as 'contact'. Interestingly, the region between 5 and 25 microns was also highly enriched in terms of cellular presence, and was designated as a 'proximal' zone. Distances greater than 25 µm from a niche of interest were designated as a 'distal' zone. These zones held true for the distribution of cells near the endosteum as well (FIG. 32D). These data cumulatively suggested that there are spatial hotspots of associations within the greater hematopoietic microenvironment and allowed us to define criteria for associations of hematopoietic cells with the niche.

Figure 32E:
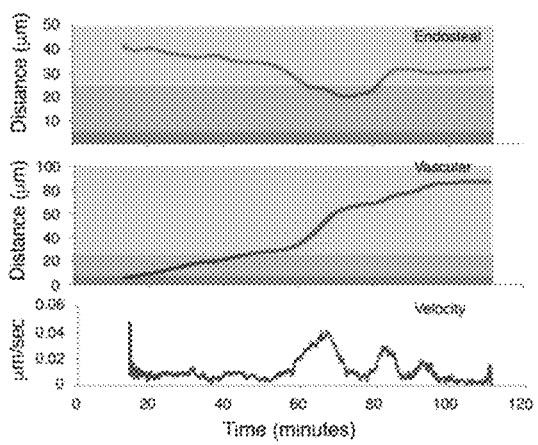
Figure 32F:
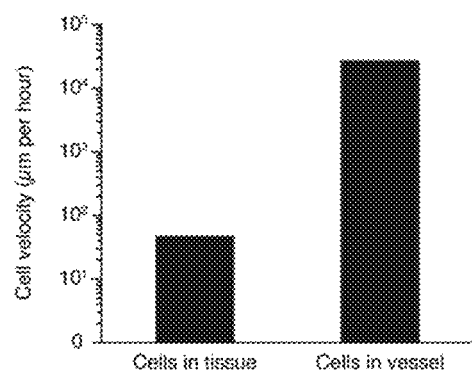

These spatial criteria were then imposed on the trace of the cell tracked in FIG. 32A; this analysis showed that the cell was initially in contact with the vasculature, followed by a proximal interaction with the vasculature and finally a proximal interaction with the endosteal region (FIG. 32E). Functionality was added to the software, which enabled one to identify, classify and quantify these interactions automatically (see Methods). Using this tool, it was found that the cells that were tracked had 95 periods of interaction with either the vascular or endosteal regions and 24 periods of no interaction (i.e., classified as distal to both regions) as a group. It is likely that other niche cells within the overall microenvironment can also serve as hotspots for associations and may be intermingled in the 'proximal' and 'distal' zones.

Figure 33A:
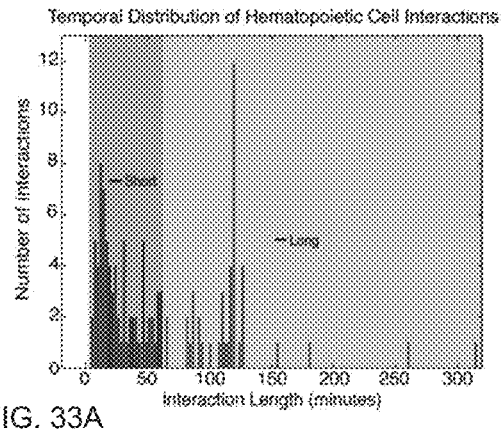
Figure 33B:
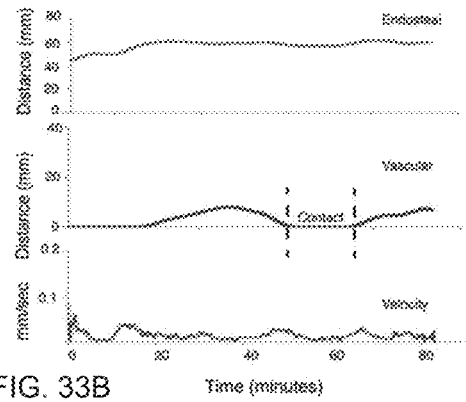

Interestingly, the duration of cell interactions varied from about four minutes to over five hours. Of the cells tracked, 7% moved through the blood vessels and 12% moved through the microenvironment in under 2 minutes (FIG. 32F); detailed measurements were thus extracted from the rest of the transplanted cells (n=95). Based on the distribution of duration of cell interactions, interactions could be categorized into two groups: the cluster of interactions lasting less than 60 minutes were termed 'short'; and interactions greater than 60 minutes were termed 'long' (FIG. 33A). In the cellular trace used as an example in FIG. 33B, imposing such temporal criteria shows that the cell tracked in this case made one short contact with the vasculature lasting less than thirty minutes and remained distal to the endosteal niche at all times.

Comparative Dynamics

Figure 33C:
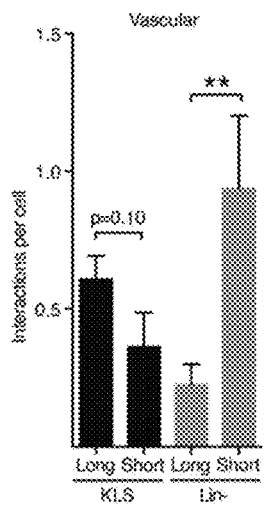
Figure 33D:
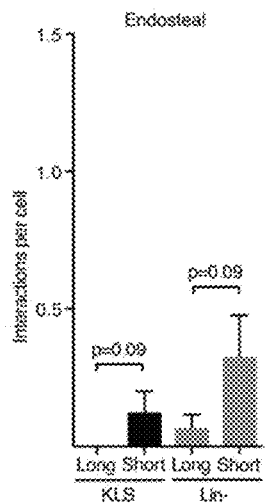
Figure 33E:
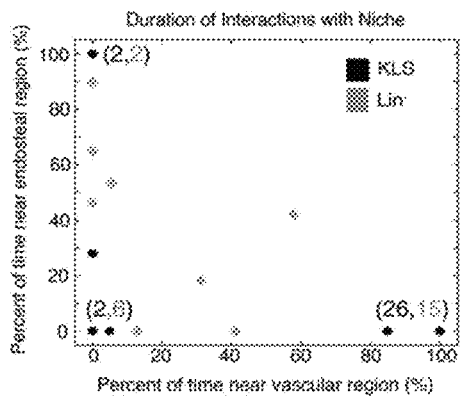
Figure 33F:
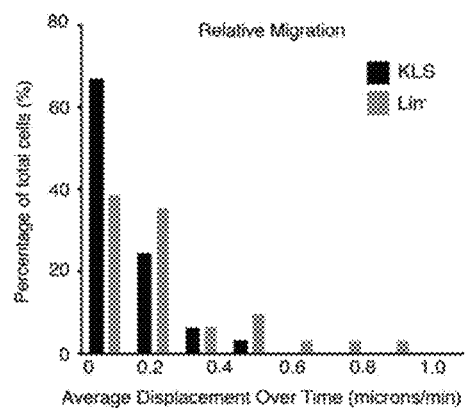

The ability to define interactions in terms of space and time provided suitable metrics for quantitatively comparing interactions made by distinct groups of cells. Using this approach the dynamics of transplanted hematopoietic cells at different stages of differentiation in a normal environment wetr compared. Specifically, the behavior of three cell populations were compared: 1) a stem cell enriched population using sorted c-Kit$^+$Lin$^-$ Sca-1$^+$ (KLS), 2) a progenitor cell enriched population using a Lineage depletion (Lin−) and 3) a fully differentiated Lineage positive fraction (Lin+) isolated from the bone marrow. This comparison revealed marked temporal and spatial differences in the interactions of mature and immature hematopoietic cells with their microenvironment. As shown in FIG. 33C, KLS cells made approximately 3-fold more long interactions per cell with the vascular niche than Lin− progenitors cells, which made mostly short associations. In contrast, both Lin− progenitors and KLS cells made more short-term interactions with the endosteal niche than they did long-term associations (FIG. 33D). Moreover, hematopoietic cells were found to associate with vascular niches the majority of the time (FIG. 33E) and, consistent with their ability to interact with several microenvironmental elements, progenitor cells showed greater displacement from their origin over time (FIG. 33F).

Figure 34A:
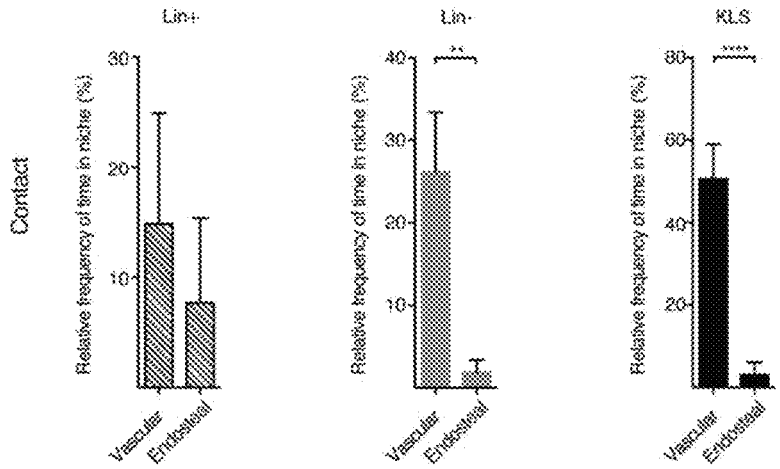
Figure 34B:
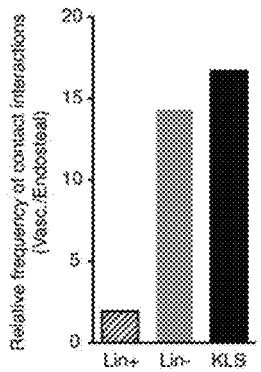
Figure 34C:
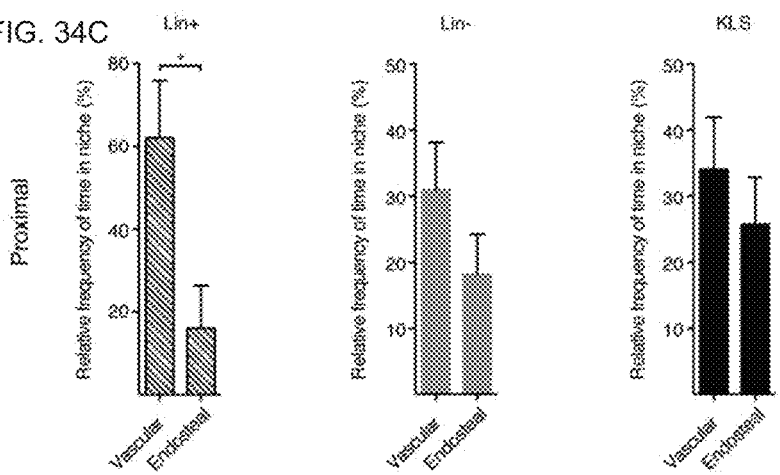
Figure 34D:
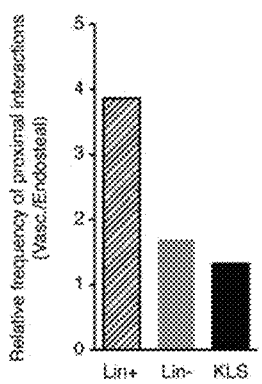
Figure 34E:
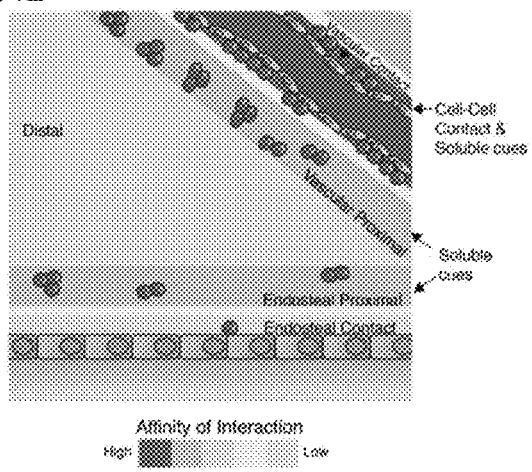

Although the nature of the temporal interactions differed between KLS and Lin− progenitor cells, both of these populations displayed highly significant spatial affinities for contacting the vascular area (FIG. 34A) compared to the endosteum. This preference was greatest in the most undifferentiated cells and decreased with differentiation (approximate 17-fold increase in affinity for KLS, 14-fold for Lin$^-$, and 2-fold for Lin$^+$ cells; FIG. 34B). Interestingly, cell interactions were more evenly distributed with the proximal domain of the vascular and endosteal niche (FIG. 34C and FIG. 34D). These data suggest a model where the programs that control lineage commitment and differentiation are closely linked to the spatial location and temporal interactions of cells within the niche, and that these molecular elements collectively ensure that the most immature cells receive cell-cell contact signals preferentially from the vascular endothelium, and soluble cues from both vascular and endosteal domains (e FIG. 34E).

Tracking Endogenous Hematopoietic Cells with a Msi2 Reporter Model

To track endogenous hematopoietic stem and progenitor cells in vivo, the newly developed REM2 knock-in reporter mouse were utilized. This reporter was created by knocking in the eGFP cassette into exon 1 of the Msi2 gene in frame with the ATG start codon. Because this is the first use of the Msi2GFP reporter mouse for imaging normal hematopoietic cells, it was desired to ensure that the disruption of one allele of the Msi2 gene caused by insertion of the reporter cassette did not impair stem/progenitor cell function. The experiments show that Msi2$^{+/+}$ and Msi2$^{+/GFP}$ LT-HSCs have equivalent colony forming ability in vitro (FIG. 49A) as well as reconstitution ability in vivo (FIG. 49B); further there was no detectable difference in the ability of Msi2+/+ and Msi2$^{+/GFP}$ stem and progenitor cells to migrate towards chemokines indicating the heterozygous cells likely reflect normal hematopoietic cell behavior (FIG. 49C). In accordance with the known pattern of Msi2 expression, reporter expression was highest in immature stem/progenitor cells and decreased with differentiation and lineage commitment. Specifically, KLS cells, which contain both stem and progenitor cells, and KLSCD150+CD48− cells which represent highly purified stem cells, were 99.5% and 100% positive for reporter expression, respectively, and contained within the Msi2GFP$^{bright}$ fraction (FIG. 35A). This pattern was also consistent during embryonic development: thus in the fetal liver, KLS cells and the more stem cell pure KLSAA4.1+ population were 98% and 100% positive for reporter expression, respectively (FIG. 35b), and expression dropped with differentiation. Overall, approximately 90% of the Msi2GFP$^{bright}$ population in the adult bone marrow, and 95% of the Msi2GFP$^{bright}$ population in the E15.5 fetal liver, were Lineage$^{negative/lo}$. Thus, Msi2GFP$^{bright}$ expression identified a nearly pure Lineage$^{negative/lo}$ population, one containing immature uncommitted cells that have not begun to express lineage markers and are thus not lineage committed. While there was some dim Msi2GFP expression in lineage committed cell populations in the bone marrow (B220, CD3, Gr1, Mac1), this expression was 7-28 fold dimmer than expression seen in immature cells, consistent with observations in the fetal liver (FIG. 35C to FIG. 35F).

Figure 37A:
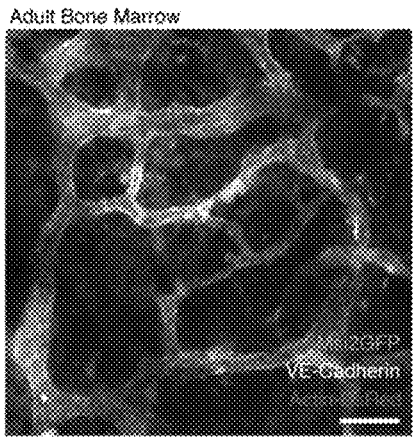
Figure 37B:
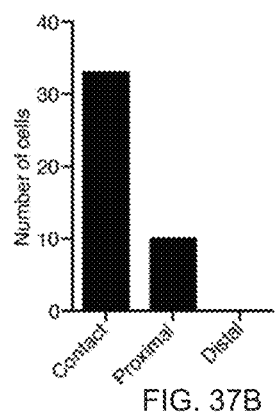
Figure 37C:
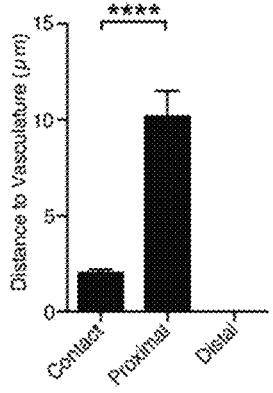
Figure 37D:
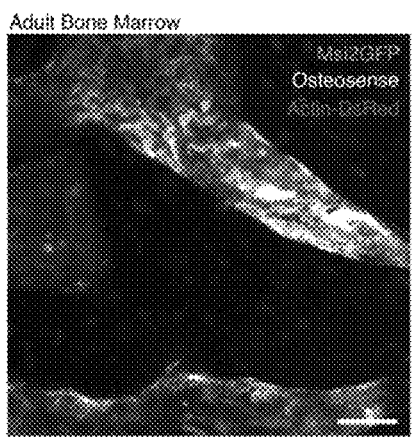
Figure 37E:
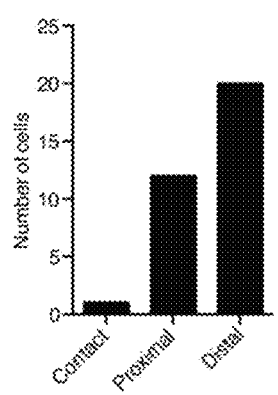
Figure 37F:
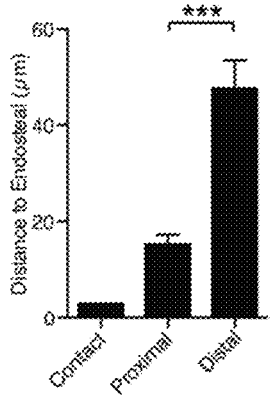
Figure 37G:
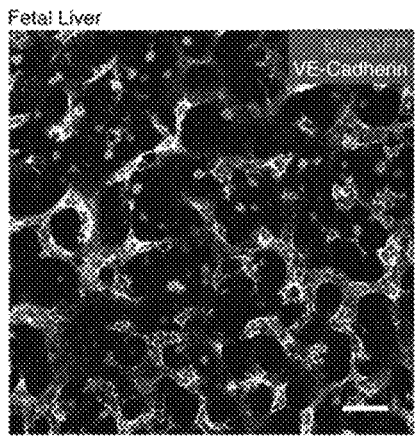
Figure 37H:
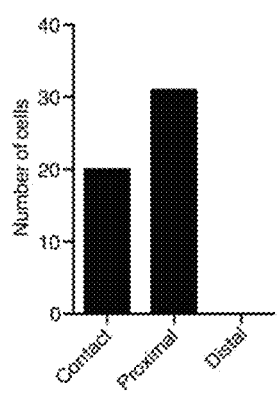
Figure 37I:
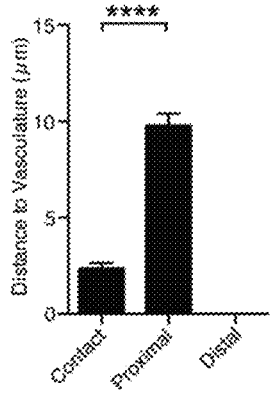

To set up the imaging parameters, the expression differential between differentiated B220+ cells and Msi2GFP$^{bright}$ cells were exploited. Specifically, the fact that B220+ cells were on average 8-fold dimmer (FIG. 36A), allowed one to threshold out the Msi2GFP$^{dim}$ cells and visualize only the Msi2GFP$^{bright}$ cells (FIG. 36B and FIG. 36C). The settings used were determined by transplanting Msi2GFP$^{bright}$ and B220+ (Msi2GFP$^{dim}$) cells into separate recipients and defining the voltage gates at which the B220+ cells were undetectable. To facilitate these studies, the Msi2GFP reporter mouse was crossed to a dsRed mouse to provide a counterlabel. Interestingly, all of the Msi2GFP$^{bright}$ cells were localized in contact or proximally to the vasculature, with the majority being in contact with the vascular cells (FIG. 37A to FIG. 27C). In contrast, the majority of Msi2GFP$^{bright}$ cells observed were localized distally from the endosteum (FIG. 37D to FIG. 37F). In addition to spatial analysis, Msi2GFP$^{bright}$ cells were also dynamically tracked over time. A representative Msi2GFP$^{bright}$ cell is shown in contact with the vasculature (FIG. 50A). When tracked relative to the vasculature, there was no change in the distribution of the distance over the time tracked (FIG. 50B). Consistent with this pattern, none of the Msi2GFP$^{bright}$ cells moved significantly enough to change the type of association (contact, proximal, or distal) they had with the microenvironment. The spatial interactions of endogenous immature hematopoietic cells within the fetal liver was also examined; here Msi2GFP$^{bright}$ cells associate with the vasculature via an even distribution of contact and proximal interactions (FIG. 37G to FIG. 37I). Importantly, these data are consistent with the interactions of transplanted immature cell populations, emphasizing the physiological relevance of the findings that native hematopoietic stem and progenitor cells are particularly dependent on niches set up by vascular domain.

Discussion

The approach provided herein provides a new framework for integrating very high-resolution long term in vivo imaging with high-throughput computational analysis (Table 1).

TABLE 1

Highlights and advantages of imaging strategy

|  | Microscope | Micro-environment Labelling | Number of Channels | Temporal Resolution | Spatial Resolution | High Throughput Computational Analysis |
|---|---|---|---|---|---|---|
| Highlights of imaging strategy | Leica SP5 II Conlocal | Genetic-Promoter-Driven Knock-in Msi2 Reporter (REM2) Transgenic Notch Reporter (TNR) Genetic-Backlit Microenvironment: Actin-dsRed, CFP and GFP In vivo Probe injection In vivo Antibody Injection Vascular Dye Injection | 4 | Hours (up to 12 hrs) | Can detect cell-cell interactions Can detect donor-host cell interactions. Can detect cell rolling and extravasabon. Can detect cell divisions, apoptosis Can detect microenvironment via antibody labeling in viva. | Can perform quantitiative single cell analysis providing detailed spatiotemporal information on position, motion and proximity to any niche cell. Enables rapid and efficient analysis of multiple parameters in vivo decreasing manual input time by 100-fold |
| Advantages over other systems | Commercially available, widely accessible and economic system | Backlighting and reporters allow the observation of multiple cell types in the microenvironment with the transplanted donor cells. Microenvironmental cells can be visualized clearly during long-term imaging at single cell resolution Msi2 reporter allows imaging of endogenous stem/progenitor hematopoietic cells | Allow concurrent visualization of multiple cell types thereby enabling mapping of interactions of hematopoietic cells with distinct elements of the niche. | Allows distinction between transient (seconds) and stable (up to 12 hours) interactions of hematopoietic cells with elements in the microenvironment | Allows tracking of a wide range of cellular behavior in vivo including asymmetric cell division and analysis of fine interactions in the microenvironment. | Provides a solution to the current difficulty in processing 'big data' large volumes of visual information derived from imaging. Analysis can precisely discern novel biological patterns of cellular dynamics in vivo. Approach can be broadly applied to studying cellular dynamics of other tissues (e.g. gut) and other processes (e.g. regeneration, oncogenesis) |

Table 1. Highlights and Advantages of Imaging Strategy.

The ability to use confocal microscopy makes this approach to real-time imaging significantly more accessible and provides far greater multichannel resolution relative to existing two-photon in vivo microscopy. This spatial clarity allowed visualization of fundamental biological processes such as cell migration, division, extravasation and intravasation. Imaging of both transplanted as well as endogenous hematopoietic cells from a Msi2GFP knock-in reporter mouse revealed that hematopoietic stem/progenitor cells are generally localized in contact with the vasculature, but distally from bone. Finally reported herein is a tool that enables high-throughput computational analysis of the 'big data' generated from in vivo imaging. A method to reliably automate spatiotemporal information from large volumes of imaging data does not exist at the current time; thus the publicly available MATLAB program developed and provided herein could be widely applicable, and thus a critical and novel contribution to the field.

The combination of the imaging resolution with the computational capacity provided, for the first time, quantitated information about the activity of single cells in space and time in vivo. Two microenvironmental elements implicated in hematopoiesis were analyzed and show that immature hematopoietic cells appear to interact with each in distinct ways, with preferential contact made with vascular domains, and equivalent levels of proximal associations made with vascular and endosteal domains. In the long term, overlaying the base spatio-temporal map with a map of molecular reporter activity may allow definition of the signals that are differentially activated in response to particular cell-niche associations. The strategy could be further expanded to further study the dynamics of cell responses to injury, oncogenesis or inflammation. The microenvironmental changes in each of these contexts will be unique and need to be tracked; for example after injury such as chemotherapy or radiation massive degeneration of microenvironmental structures occurs (FIG. 51A and FIG. 51B), indicating that associations may change dramatically in regeneration. The temporal resolution achieved could be useful in gaining insight into the dynamics of hematopoietic cells in biological processes such as regeneration that unfold over time.

Analyzing large amounts of image data have become a critical bottleneck in the discovery process. To resolve this, software was developed that allows efficient quantitative characterization of each cell in terms of its position, motion and proximity to important niches. Approximately 41,968 frames were analyzed in 20 minutes and required a total manual input time of about 3.5 hours. To compare it to manual analysis, it is estimated that a person would need at least 30-60 seconds per frame to measure the distance between a cell and each microenvironmental domain, and a total of 350-700 hours, indicating the software decreased manual work by 100-fold. The fact that the software provides a dramatic advantage over manual processing suggests it can serve as a more general high-throughput tool for spatio-temporal analysis of in vivo imaging data. The software also allowed calculation of the velocity of blood cells moving both within the bone marrow or flowing through a blood vessel. This capability could be useful for example in defining how closely 'induced' blood cells generated from directed differentiation strategies resemble 'naturally born' blood cells. In fact as the field of regenerative medicine matures, it is intriguing to speculate that this type of tool could prove important for in vivo assessment of cells derived from directed differentiation methods prior to clinical use.

The imaging analysis identified both spatial and temporal differences in the interactions of hematopoietic cells with vascular and endosteal regions in homeostasis. Further, it revealed that the dynamic behavior of hematopoietic cells in vivo is directly related to their differentiation state. Thus hematopoietic stem/progenitor cell enriched fractions have far higher spatial and temporal affinity for vascular domains, whereas differentiated cells shuttle more frequently between the vascular and endosteal domains, and exhibit less stable interactions. This suggests that immature cells are more dependent on the niches they are part of and thus retained more readily, and that this dependence diminishes with maturation, allowing cells to leave. In the longer term, the introduction of additional niche markers as well as other cell types could easily be accommodated by these techniques and allow the development of a comprehensive dynamic atlas of hematopoietic cell interactions within the bone marrow microenvironment.

The Msi2GFP reporter mouse is an exciting tool that can enabled one to dynamically track endogenous immature hematopoietic cells both temporally and spatially. Hematopoietic stem/progenitor cells in Msi2 reporter mice were largely localized in contact with the vasculature, and distally from the endosteum suggesting that the vascular niche is particularly supportive of these undifferentiated cells in this context as well. Interestingly, the association of Msi2GFP$^{bright}$ cells with the vascular domain was highly stable, with almost all encounters scored as 'long' interactions. The dominance of stable long interactions was in contrast to the more temporally distributed interactions (long and short) recorded from transplanted stem/progenitor cells. While the Msi2 reporters has been used to establish a baseline for normal hematopoietic stem and progenitor cells, they could be useful in multiple contexts: for example, this model has been used to track heterogeneity within aggressive solid cancers, and find it enables successful identification of tumor propagating cells, and therapy resistance in pancreatic cancer.

The work reported here highlights the power of visualizing tissues using high-resolution live microscopy to illuminate the bone marrow environment that is critical for the self-renewal and differentiation of hematopoietic stem and progenitor cells. The ability to observe different cell types simultaneously in vivo is a powerful tool for analyzing and understanding the nature of processes such as regeneration or oncogenesis, where new regulators may be difficult to discover with static approaches alone. Because the principles of the imaging paradigm and computational analysis developed and described herein, can be applied broadly, the work also raises the exciting possibility that use of this strategy may ultimately allow a dynamic view into an array of tissues and organs whose architecture and living physiology will be important areas of future investigation.

Methods

Animals and Cell Isolation

Hematopoietic stem and progenitor cells were isolated from 8-12 week old Actin-GFP mice (Jackson Labs, Bar Harbor, Me.). Whole bone marrow was lineage depleted via magnetic activated cell sorting (MACS; Miltenyi Biotec, Bergisch Gladbach, Germany) using an AutoMACS sorter (Miltenyi Biotec). Subsequent lineage-depleted cells were stained using PE-conjugated antibodies CD3e, CD4, CD8, B220, CD11b, Gr-1 and Ter119 (eBiosciences) and sorted for Lin$^+$ and Lin$^-$ fractions. Analysis and cell sorting were carried out on a FACSVantage sorter (Becton Dickinson, Mountain View, Calif.) at the Duke Cancer Center Flow Cytometry Core Facility. $1.5 \times 10^6$ GFP$^+$Lin$^-$ progenitors were transplanted via retro-orbital sinus into p15 DsRed2 or 8 week old mice (STOCK Tg(CAG-DsRed*MST)1Nagy/J, Jackson Labs). Mice were imaged between 1 to 12 hours after adoptive transfer of GFP$^+$Lin$^+$ and GFP$^+$Lin$^-$ progenitors. For KLS cell isolation, whole bone marrow was enriched for cKit via magnetic activated cell sorting (MACS; Miltenyi Biotec, Bergisch Gladbach, Germany) using an AutoMACS (Miltenyi Biotec). cKit enriched cells were labeled for PE-conjugated antibodies for CD3e, CD4, CD8, B220, CD11b, Gr-1 and Ter119, APC-conjugated antibody cKit, and PE-Cy5-conjugated antibody for Sca1 (eBiosciences). Analysis and cell sorting were carried out on a FACS AriaIII sorter (Becton Dickinson, Mountain View, Calif.). $1.5 \times 10^6$ GFP$^+$KLS cells were transplanted via retro-orbital sinus into 8 week old mice (STOCK Tg(CAG-DsRed*MST)1Nagy/J, Jackson Labs). Mice were imaged 24 hours after adoptive transfer of GFP$^+$KLS cells. REM2 (Msi2$^{+/GFP}$) reporter mice were generated by conventional gene targeting (Genoway, France). The eGFP cassette was knocked into exon 1 of the Msi2 gene in frame with the ATG start codon. Msi2GFP reporter mice imaged were between 3-8 weeks of age. Both male and female mice were used for experimental purposes. All animal experiments were performed according to protocols approved by the Duke University and University of California San Diego Institutional Animal Care and Use Committee.

Mouse Preparation and Imaging

Mice were anesthetized by intraperitoneal injection of ketamine and xylazine (100/20 mg/kg). Once mice were unresponsive to pedal reflex, heads were wiped down with 70% ethanol and hair was removed using Nair Hair Remover lotion (Church & Dwight Co., Inc., Princeton, N.J.). A midline incision was made using FST ToughCut Spring Scissors, 6 mm curved blade (Fine Science Tools (USA) Inc., Foster City, Calif.) and skin was removed to expose the calvarium. For inverted confocal microscopy using younger mice, the calvarium was kept moist with Aqua Poly/Mount (Polysciences, Inc., Warrington, Pa.) during the imaging session. Mice were inverted and secured onto a custom microscope rig by placing a rubber band (size 10) through the bit of the mouth and observed through a 22×22 mm coverslip (VWR International, West Chester, Pa.). Mice were immediately taken to the confocal microscope for imaging and were kept under anesthesia using 1-3% isofluorane gas mixed with oxygen. For upright confocal microscopy, mice were placed in a mouse/neonatal rat stereotactic holder (Stoelting, Co. Wood Dale, Ill.), calvarium was exposed as described above and tissue was kept moist using 1×PBS (Gibco).

Microscopy

Images were acquired by Leica LAS AF 1.8.2 software with either an inverted Leica SP5 confocal system using a Leica DMI6000CS microscope or an upright Leica SP5 2 confocal system using a Leica DM 6000 CFS microscope. Using the inverted microscope, images were acquired using a 10× Leica Plan Apochromat objective with 0.40 numerical aperture for quantitation and a 20× Leica Plan Apochromat objective with 0.70 numerical aperture. Using the upright microscope, images were acquired using an HCX APO L20× objective with a 1.0 numerical aperture for still images and subsequent movies. Imaging of calvarium ranged from 60-100 microns. CFP (excitation 458 nm, emission 463 to 500 nm), GFP (excitation 488 nm, emission 493 to 556 nm) and DsRed2 (excitation 561 nm, emission 566 to 650 nm) were excited with an Argon/2 (458, 477, 488, 496, 514 nm) and Diode pumped solid-state (561 nm) laser respectively. The power used for dsRed visualization was 8-12% of the appropriate laser. Images were continuously captured in 1024×1024 or 1024×512 format with line averaging of 4 (approximately 10 or 5 seconds per scan, respectively) for up to 8 hours. Multicolor imaging for CFP and GFP were captured sequentially.

Methylcellulose Colony Formation Assay

LT-HSCs (KLSCD150+CD48−) were isolated by FACS from bone marrow. Cells were plated in methylcellulose medium (Methocult GF M3434 from StemCell Technologies). Colonies were counted 7 days after plating.

In Vivo Transplantation Assay

500 LT-HSCs isolated from bone marrow of mice expressing CD45.2 were transplanted into lethally irradiated (9.5 Gy) CD45.1 recipient mice with $3\times10^5$ Sca1-depleted CD45.1 bone marrow cells. Peripheral blood of recipient mice was collected at 4 weeks after transplantation.

Chemotaxis Assay

Directed cell migration towards SDF1 was analyzed in vitro. Cells were kept in X-VIVO media (Lonza) and 600 ul X-VIVO media supplemented with 50 ng/ml of SDF1 was added to the lower chamber of the transwell (Costar, pore size 5 µm, 3421). 75,000 cells were loaded into the upper chamber and allowed to migrate for 18 hours at 37° C. in a humidified $CO_2$ incubator. After incubation, migrated cells were collected from the lower chamber and counted.

Ex Vivo Fetal Liver Preparation and Microscopy

Mouse embryonic fetal livers were dissected at stage E15.5 from timed mating females. Fetal livers were incubated on ice with fluorescently conjugated antibodies for VE-Cadherin and B220 (eBiosciences). Fetal livers were plated for imaging in 1.5% low melting agarose (Sigma) with X-VIVO media (Lonza) and 10% FBS. Cultures were maintained at 37° C. and 5% $CO_2$ using a Heating Insert P Lab-Tek 51 with an Incubator PM S1 (Zeiss). Images were acquired using an Axio Observer Z1 microscope with the LSM 700 scanning module (Zeiss).

In Vivo Probe Administration

Angiosense 680 and Osteosense 680 in vivo imaging probes (VisEn, Bedford, Mass.) were administered at a concentration of 2 nM in 150 µl per mouse, and imaged within 30 minutes (Angiosense) or at least 24 hours (Osteosense) after administration. Both products were excited using a HeNe 633 laser and emission was collected from 650 to 725 nm. Antibodies conjugated to AlexaFluor 647 for VE-cadherin (eBiosciences) and F4/80 (eBiosciences) were administered at a concentration of 10 ug diluted in 100 ul, 15 minutes prior to imaging. All products were excited using a HeNe 633 laser and emission was collected from 650 to 725 nm.

Quantitative Analysis

Images were analyzed using Volocity Software (Improvision, a PerkinElmer Company, Coventry, England). Red and green channel noise was optimized using the fine filter, and image intensity gamma was used to reduce background within the green channel. For GFP quantitation, 10×z-stacks (30 z-planes for 120µm) were analyzed. Briefly, objects were filtered by intensity and size and the sum of the isovolume ($\mu m^3$) measurements were compared between mice. Image enhancement and quantitation parameters were identical between paired animals for each experiment. Movies were made using Volocity software and exported to view as AVI movies at 15 frames per second and compressed using Microsoft Video 1 compression.

High Throughput Imaging Analysis

All image processing and object tracking was performed in MATLAB (R2010b). First, the movies were corrected for lateral (xy) drift by examining the cross-correlation between the first frame and every subsequent frame. Images labeled with cells were median filtered with a window size of 5 pixels, and then thresholded with a manual cutoff. Each candidate cell object was identified and the centroid calculated in each frame. Cells were tracked through time using particle-tracking software (physics.georgetown.edu/matlab/) and only tracks longer than 10 frames (~100 seconds) were considered valid. The cells moved occasionally in three dimensions, briefly disappearing from the image for certain time points. In such cases, the position data for that time point was estimated by linear interpolation between the values obtained from the preceding and following images. As a final check, the quantified data was superimposed on the image stacks, and the resulting movies were then subjected to a manual review to ensure that no errors were made in tracking. To classify cell locations as either vascular or endosteal, cell positions were compared to hand annotated images of vascular and endosteal regions, as shown in FIG. 52. The minimum distance to a vascular and endosteal region was calculated for each position. To specify proximal and contact interactions, the distances to vascular and endosteal regions were compared across all datasets for all time points and distance cutoffs chosen appropriately. Interactions were classified as vascular or endosteal based on which region was closest, and contact and proximal interactions were decided with the previously described distance cutoffs. False interactions were suppressed in two ways: 1) contact and proximal distances were automatically adjusted by +/−1 micron for each cell 2) adjacent transient interactions (less than 200 seconds) were merged together. Finally, the track and interaction graph for each cell was verified by manual inspection. MATLAB code will be made available upon request.

Embodiment 10: In Vivo Tracking of Cancer Heterogeneity and Therapy Resistance in Hematologic Malignancy Intratumoral heterogeneity is a common feature of many myeloid leukemias and a significant reason for treatment failure and relapse. However, the cells responsible for residual disease and tumor propagation are not always known and cannot easily be identified. This question is addressed using a recently developed knock-in reporter mouse that reflects the expression of the stem cell gene Musashi 2 (Msi2). Using blast crisis chronic myelogenous leukemia (CML) as a model, it is shown that Msi2 reporter expression effectively marked the population that drives tumor growth in vitro and in vivo. Further, Msi2 reporter can be used broadly in hematologic malignancies, as it allowed identification of cancer stem cells in diverse leukemias such as NPM1-driven myeloproliferative disease and de novo AML. Msi2 reporter expression also identified leukemic cells that were drug-resistant and allowed spatial localization of residual disease in vivo. Importantly, Msi expression contributed functionally to drug resistance: ectopic Msi2 expression improved recovery after exposure to DNA damaging agents and its loss disabled DNA repair and sensitized cells to treatment. These data collectively suggest that Msi2 reporter mice may serve as a tool to identify leukemia-propagating cells, and may be useful in developing new strategies to target residual disease and relapse.

Over the past decade, it has become increasingly clear that many cancers are heterogeneous and contain a distinct population of tumor-propagating cells that can also be highly resistant to anticancer therapies (Bao et al., 2006; Diehn et al., 2009; Li et al., 2008; O'Hare et al., 2006; Oravecz-Wilson et al., 2009). Existence of such a therapy-resistant, residual population explains why many cancers re-emerge after treatment. This is the case for human acute myeloid leukemia, where functionally identified CD34$^+$ CD38$^-$ leukemia-initiating cells have been shown to be quiescent, express elevated levels of multidrug resistance genes and exhibit reduced in vitro sensitivity to daunorubicin, a chemotherapy drug commonly used in leukemia treatment (Bonnet and Dick, 1997; Costello et al., 2000; Lapidot et al., 1994). Similarly, in BCR-ABL1-driven CML, tyrosine kinase inhibitors have been shown to effectively inhibit BCR-ABL activity but fail to eliminate quiescent CML stem cells and thus, the disease inevitably transitions into an aggressive blast crisis phase that remains refractory to standard therapy (Barnes and Melo, 2006; Chu et al., 2005; Copland et al., 2006; Corbin et al., 2011; Holyoake et al., 1999; Jiang et al., 2007; Jorgensen et al., 2007; Jorgensen et al., 2006; Khorashad et al., 2008; Konig et al., 2008a; Konig et al., 2008b; Sorel et al., 2004).

Cancer stem cells (CSCs) or tumor-propagating cells have been identified and isolated through approaches that have predominantly implemented the use of individual surface markers or their combinations. Numerous CSC markers for distinct solid and liquid tumor types have been defined in this way; these include use of antibodies against the surface markers CD133, CD34, CD24 and CD44 (Al-Hajj et al., 2003; Bonnet and Dick, 1997; Jordan et al., 2006; Ricci-Vitiani et al., 2007; Todaro et al., 2014). While these approaches have been powerful in allowing prospective isolation of cells and assessment of their functionality in context of cancer initiation and propagation, they are limited in their ability to identify CSCs within the tumor in vivo or in enabling visualization and tracking of residual disease in real time. Thus, development of novel ways to identify CSCs independent of cell surface marker expression is critical to move toward image-based detection of cancer stem cells in vivo.

One strategy to address this need is by exploiting molecular signals that are specifically active and utilized by CSCs for continued propagation and resistance to drugs post-therapy. Tracking such signals would allow marking of not only the tumor-propagating cells but also enable detection and assessment of residual disease post-therapy. Over the past few years, several key molecular pathways and genes have been identified that are preferentially utilized by leukemia stem cells (LSCs) to promote their continual growth and survival, including β-catenin (Hu et al., 2009; Wang et al., 2010; Zhao et al., 2007), promyelocytic leukemia protein (PML) (Ito et al., 2008), Alox5 (Chen et al., 2009), Smoothened (Dierks et al., 2008; Zhao et al., 2009) and Msi2 (Ito et al., 2010). The identification of these regulators has been critically important in understanding the mechanisms that govern LSC activity and provided a growing list of novel targets that may prove clinically beneficial. As described herein, Msi2 was pursued as one such molecular signal that can enable visualization of CSCs in vivo.

Musashi2 (Msi2) is an RNA binding protein that plays a critical role in progression of CML to blast crisis (Ito et al., 2010). Msi2 is highly expressed in immature leukemic cells and is significantly downregulated as cells differentiate in both mouse models of blast crisis CML as well as primary patient samples. This suggested that Msi2 might preferentially mark CSCs and thus, a system that "reports" Msi2 expression may serve as a useful tool to probe tumor heterogeneity and identify or track cancer stem cells. To test this, an enhanced green fluorescence protein (eGFP)-knock-in reporter mouse strain was used which was recently developed in which GFP expression effectively marked leukemia-propagating cells not only in blast crisis CML but also more generally in a diverse array of hematologic malignancies. Importantly, it is shown herein that Msi2 does not simply serve as an identifier of therapy-resistant leukemic cells but plays a key functional role in conferring this resistance by protecting cells from treatment-induced DNA damage.

Results

Functional Heterogeneity Defined by Msi2 Expression Levels in Blast Crisis CML

Msi2 enhanced green fluorescence protein (eGFP)-knock-in reporter mouse was developed by placing an eGFP expression cassette in frame with the Msi2 translation initiator ATG codon (Fox et al., 2016; Koechlein et al., 2016). In the blood system, the fact that the most dominant reporter expression was among immature hematopoietic cells (Koechlein et al., 2016), raised the possibility that Msi2 may also preferentially mark leukemia stem cells (LSCs), and that the Msi2 reporter (hereafter referred to as REporter for Musashi2, or REM2) may provide a platform to probe intratumor heterogeneity. To address this, blast crisis CML was modeled by transducing KLS cells isolated from REM2 mice with BCR-ABL1 and NUP98-HOXA9 and transplanting them into recipient mice. On average ~77% of leukemia cells isolated from the spleen of terminally ill mice were GFP-positive (FIGS. 38A and 38B). Further, while almost all of the GFP-negative cells (~91%) were positive for mature lineage markers (Lin$^+$), ~85% of GFP-positive cells were negative for mature lineage markers (Lin$^-$) (FIGS. 38C and 38D), suggesting that GFP marks the immature cell population within blast crisis CML.

To define the cellular basis of the tumor heterogeneity observed with GFP levels, functional differences between GFP$^+$ and GFP$^-$ leukemia cells was analyzed. In assays in vitro, GFP$^+$ cells formed 14.5-fold more colonies than GFP$^-$ cells (FIG. 38E), consistent with the finding that all LSC activity resides in the immature Lin$^-$ compartment of BCR-ABL1/NUP98-HOXA9-driven blast crisis CML (Neering et al., 2007). However, here the REM2 model was used to further fractionate the Lin$^-$ compartment into a GFP$^+$ and GFP$^-$ population (FIG. 38F). Interestingly, Lin$^-$ GFP$^+$ cell formed ~5-6-fold more colonies than Lin$^-$ GFP$^-$ cells in both primary and secondary plating assays (FIG. 38G). These data suggest functional heterogeneity exists even within the immature Lin$^-$ fraction of blast crisis CML, and that Msi2 reporter expression marks the more tumorigenic cells. To define whether GFP$^+$ leukemic cells are enriched for functional LSC activity in vivo, GFP$^+$ or GFP$^-$ cells from established blast crisis CML were transplanted and leukemia development monitored. Whereas none of the mice transplanted with GFP$^-$ cells developed leukemia, 100% of mice transplanted with GFP$^+$ cells succumbed to blast crisis CML and died within 23 days (FIGS. 38H and 38I), suggesting that the majority of LSC activity in vivo resides within the Msi2-expressing GFP$^+$ fraction of the leukemia. Collectively, these data demonstrate that in a mouse model of blast crisis CML, GFP marks LSCs in vivo, and thus, that Msi2 reporter mice can be used to assess tumor heterogeneity and identify the blast crisis CML stem cells in vivo.

Msi2 Marks Cancer Stem Cells in Diverse Hematologic Malignancies

The finding that the Msi2 reporter effectively identifies the LSC population in blast crisis CML suggested that Msi2 may mark CSCs in other hematological malignancies as well. It was first investigated in a mouse model of chronic phase CML. To generate chronic phase CML, KLS cells isolated from REM2 mice were infected with BCR-ABL1 and subsequently transplanted into recipient mice. Interestingly, only ~8% of the leukemia cells isolated from the spleen of terminally-ill mice were GFP$^+$ (FIGS. 39A and 39B). To test whether Msi2 effectively marks functional CSCs in CML, the ability of GFP$^+$ and GFP$^-$ cells to form colonies in vitro was tested, and found that only GFP$^+$ cells have colony-forming ability (FIG. 39C). Further, it was tested if Msi2 marked CSCs in mouse models of de novo AML as well using an AML-ETO9a/NRAS$^{G12V}$-driven model of AML. Interestingly, only a minor fraction (~12%) of leukemic spleen cells from morbid leukemic mice were GFP$^+$ (FIGS. 39D and 39E). Furthermore, GFP$^+$ leukemic cells formed on average ~8-fold more colonies than GFP$^-$ leukemic cells, indicating that GFP also marks the cancer stem cell population in AML-ETO9a/NRAS$^{G12V}$-driven AML (FIG. 39F).

Figure 43A:
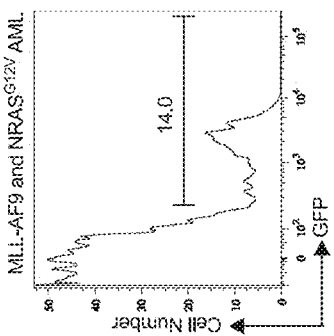
Figure 43B:
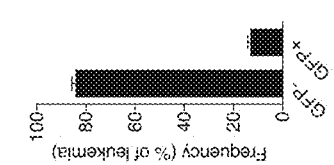
Figure 43C:
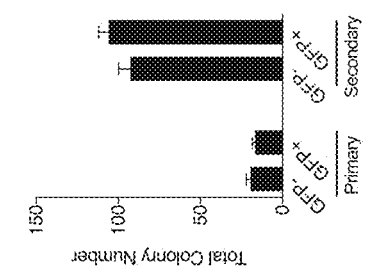
Figure 43D:
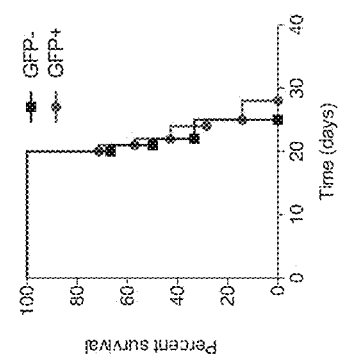
Figure 43E:
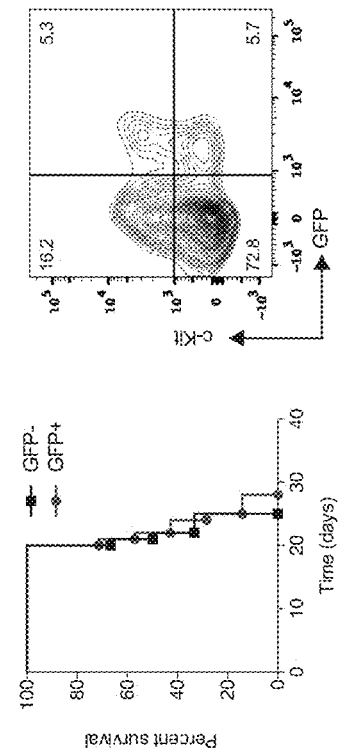

It was also tested whether Msi2 marks CSCs in a mouse model of mixed-lineage leukemia (MLL)-rearranged AML. To this end, KLS cells isolated from REM2 mice were co-infected with MLL-AF9 and NRAS$^{G12V}$ and subsequently transplanted into recipient mice. However, although GFP marks a rare population of leukemic cells (FIGS. 43A and 43B), GFP$^-$ and GFP$^+$ cells formed similar numbers of colonies in vitro (FIG. 43C), and were equally leukemogenic in vivo (FIG. 43D). These data suggest that GFP$^+$ cells are not functionally distinct from GFP$^-$ cells in MLL-AF9 AML, and are consistent with the fact that GFP does not enrich for c-Kit$^+$ leukemia cells (FIG. 43E) previously shown to contain LSCs. Previous studies have shown that nearly all cells in MLL-AF9-derived AML express the mature myeloid marker Mac-1 (Somervaille and Cleary, 2006); this suggests that Msi2 may not mark CSCs in leukemias originating from differentiated hematopoietic progenitors.

While the CSCs population for both CML and AML-ETO9a-driven AML has previously been defined largely based on cell surface marker expression (Hu et al., 2006), the current data demonstrates that the Msi2 reporter provides an alternative way to identify CSCs in these malignancies that is not reliant on surface marker expression. This may prove useful where the markers of CSCs is not known or may change as the disease progresses. To determine if the Msi2 reporter could be used in this context, it was tested whether Msi2 marks disease-propagating cells in a mouse model of myeloproliferative disease (MPD), where the identity of the cells responsible for driving disease remains unknown. To generate MPD, KLS cells from REM2 mice were infected with the nucleophosmin (NPM1) exon 12 mutations (NPM1c), which led to the development of MPD in mice based on histopathological analysis. Interestingly, in these MPD mice, only a minor fraction (~20%) of NPM1c+ spleen cells were GFP$^+$ (FIGS. 39G and 39H), and that only these cells formed colonies in vitro (FIG. 39I), suggesting that GFP also marks the disease-propagating population in MPD. Collectively, these data demonstrate that the Msi2 reporter could serve as strategy to study cancers in which the phenotypic identity of the CSC population is unknown and where marker-based approaches are not reliable or feasible.

Therapy-Resistant Population Defined by Msi2 Reporter

Figure 40A:
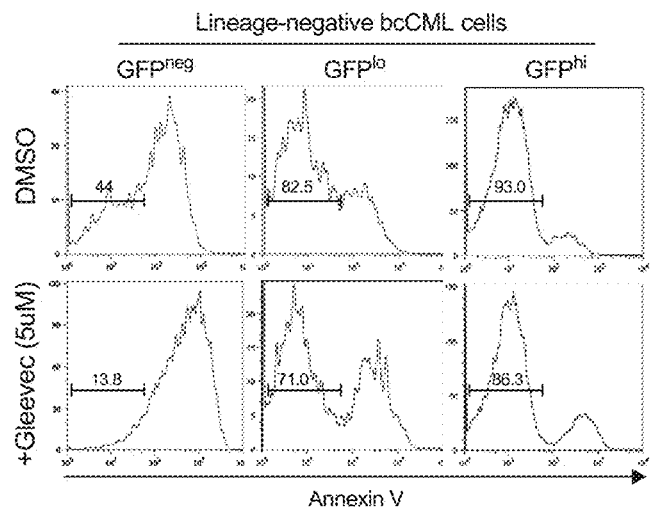
Figure 40B:
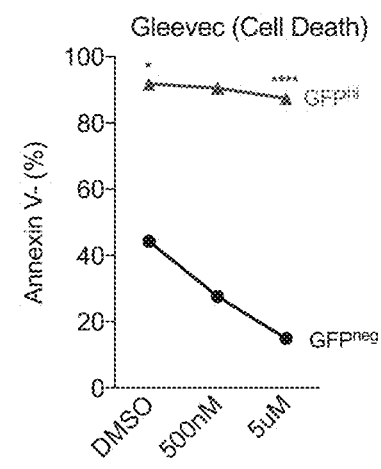
Figure 40C:
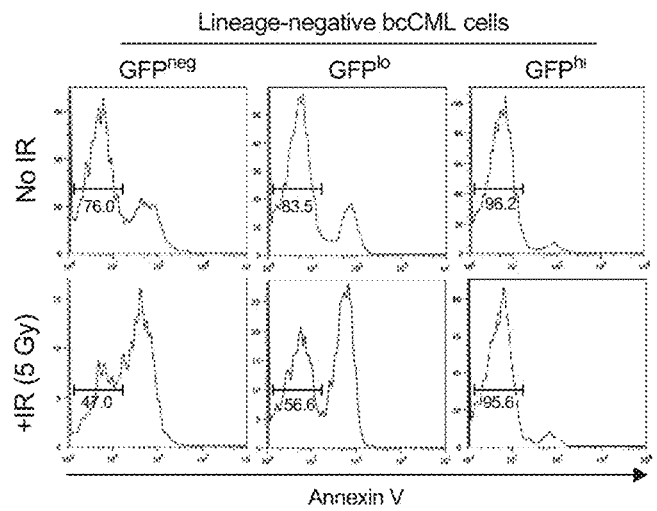
Figure 40D:
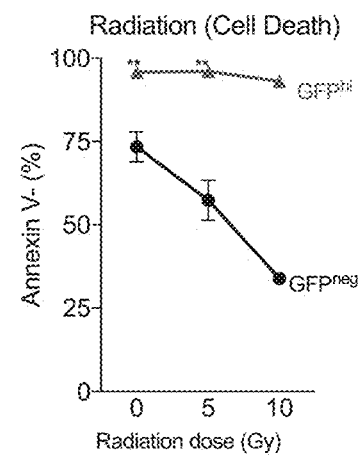

It has previously been shown that CSCs are resistant to conventional anticancer therapies and thus, residual CSCs that persist after treatment can drive disease relapse. To determine whether Msi2-expression can mark such a therapy-resistant population, we first tested the resistance of Msi2-expressing leukemia cells to the BCR-ABL tyrosine kinase inhibitor, imatinib mesylate (also known as Gleevec). Although imatinib effectively induces a complete hematologic response in almost all chronic phase CML, imatinib is much less effective in treating blast crisis CML (Kantarjian et al., 2002; Shah et al., 2002). To test whether Msi2-expressing cells within blast crisis CML mark the imatinib-resistant population, blast crisis CML cells were treated with imatinib in vitro and cell death was analyzed by Annexin V staining post-treatment. To account for any differences in cell survival between GFP$^+$ and GFP$^-$ cells that is solely due to differences in differentiation status, we specifically analyzed cell survival of GFP$^+$ and GFP$^-$ leukemia cells within the lineage-negative (Lin$^-$) fraction. Interestingly, it was found that only a small fraction (~14%) of Lin$^-$ GFP$^-$ cells were viable following imatinib exposure (FIGS. 40A and 40B); however, more than 86% of Lin$^-$ GFP$^+$ cells remained viable following drug treatment (FIGS. 40A and 40B), suggesting that GFP$^+$ cells are highly resistant to imatinib. Importantly, while Lin$^-$ GFP$^+$ cells displayed a 2-fold increase in cell viability compared to Lin$^-$ GFP$^-$ cells even in the absence of treatment, differences in cell survival increased by another 3-fold following imatinib treatment, indicating that Lin$^-$ GFP$^+$ cells are more resistant to imatinib (FIG. 40B). Not only did Msi2-expression mark imatinib-resistant cells within blast crisis CML, it also marked cells resistant to radiation. Radiation exposure led to effective elimination of 53% of Lin⁻ GFP⁻ cells but only 5% of the Lin⁻ GFP⁺ cells (FIG. 40C). In addition, while GFP⁻ cells showed increasing sensitivity to increasing doses of radiation (0 to 10 Gy) (FIG. 40D), GFP⁺ cells remained highly resistant to radiation, and were 93% viable even at the highest radiation dose used (10 Gy, FIG. 40D). Collectively, these data demonstrate that Msi2-expressing leukemia cells are insensitive to therapy-induced cell death, and the reporter could be used to effectively locate therapy-resistant cells.

Msi2 Reporter Identifies Sites that have an Enhanced Ability to Protect Therapy-Resistant Cells The findings that Msi2 effectively marks therapy-resistant leukemic cells suggest that the Msi2 reporter may provide a unique way to track residual cells in vivo and thus, effectively map zones that preferentially harbor therapy-resistant residual disease. To test this, REM2 mice were crossed with mice expressing dsRed under the control of a ubiquitous promoter (Vintersten et al., 2004). This allowed identification and tracking of both Msi2-expressing leukemic cells (GFP⁺ dsRed⁺) as well as Msi2-negative leukemia cells (GFP⁻ dsRed⁺) in vivo. To generate blast crisis CML, KLS isolated from REM2/dsRed mice were co-infected with BCR-ABL1 and NUP98-HOXA9 and subsequently transplanted into NOD-scid IL2Rg$^{null}$ (NSG) recipient mice (FIG. 41A). To determine the spatial localization of Msi2-expressing cells, a comprehensive flow cytometry-based analysis of terminally ill leukemic mice was performed and found that in five of the six anatomic sites analyzed (calvarium, femur, tibia, spleen and pelvis), ~66% of the leukemia cells were GFP⁺; for the sternum, this number was somewhat lower, with ~39% of the leukemia cells GFP⁺ (FIG. 41B). These data suggest that Msi2-expressing cell do not preferentially localize to one particular area of the body. Surprisingly however, it was found that following 4 days of imatinib treatment, residual Msi2-expressing cells were preferentially localized in the spleen compared to the other sites we analyzed. Whereas on average only ~37% of the GFP⁺ leukemic cell population remained in the calvarium, femur, tibia, sternum or pelvis following imatinib treatment, ~60% of the GFP⁺ leukemic cell population remained in the spleen following treatment (FIG. 41C). These data suggest that in blast crisis CML, the spleen preferentially harbors therapy-resistant residual cells and that targeting the spleen with more aggressive localized therapy could prove clinically beneficial and prevent relapse. Importantly, the fact that we could use the Msi2 reporter to identify and track therapy-resistant cells provides a proof of principle that reporters/probes that allow visualization of key molecular signals like Msi2 may be important tools to develop to assess efficiency of anticancer therapies targeting cancer stem cells.

Msi2 Enhances DNA Damage Response in Normal and Malignant Stem Cells

To determine whether Msi2 may actually functionally confer therapy resistance, genome wide expression analysis to define programs downstream of Msi2 was used. Gene ontology analysis of the differentially expressed gene sets in WT and Msi2-deficient stem cells and leukemia cells identified eleven biological processes affected in both normal stem cells and leukemia cells, of which DNA-related stress responses were among the most significantly affected (FIG. 44). This, together with the fact that both radiation and imatinib can either directly or indirectly lead to DNA damage (Czechowska et al., 2005; Suzuki et al., 2003), suggested that Msi2 may be needed for effective genome repair. Gain and loss of function approaches were both used to test this. To determine if gain of Msi2 can improve DNA repair a doxycycline-driven transgenic model was used (Kharas et al., 2010). Following doxycycline treatment, mice were irradiated and KLS cell function evaluated in semi-solid methylcellulose media. While radiation reduced colony forming capacity by ~17-fold, ectopic expression of MSI2 rescued this colony-forming defect to a significant degree (FIG. 42A, FIG. 45). To determine if Msi2 loss impairs this process and sensitizes cells to DNA damage, wild type and Msi2 gene-trap mutant mice (Msi2$^{Gt/Gt}$) were irradiated and KLS cells analyzed for expression of 53BP1, a marker for DNA double strand breaks (Panier and Boulton, 2014). At early time points both wild type and Msi2 mutant cells showed similar numbers of 53BP1-foci in the nucleus (~18 foci/nuclei; FIGS. 42B and 42C). However, while DNA foci had largely resolved in most wild type cells at 24 hours (FIGS. 42B and 42D), only 12.5% of Msi2–/– cells had resolved foci, and the remaining cells had more remaining foci per cell than wild-type cells (FIGS. 42B and 42D). Collectively, these data show that Msi2 gain can improve recovery after DNA damage, while loss of Msi2 leads to a defect and/or delay in DNA damage repair in normal stem cells, indicating a key role for Msi2 in these cells.

To determine if Msi2 also plays a role in DNA damage repair in leukemia, it was tested whether the repair process is impaired in Msi2-deficient blast crisis CML cells following radiation. Specifically, established blast crisis CML cells were irradiated at 3 Gy to induce DNA damage and subsequently immunostained for 53BP1. Two hours following irradiation, both wild type and Msi2 mutant Lin– leukemia cells showed similar numbers of 53BP1-foci in the nucleus (FIGS. 42E and 42F). However, by 24 hours, ~58% of the wild type leukemia cells showed no foci and, importantly, of the cells that still had foci, only ~4% had more than 6 foci remaining. On average, wild type leukemia cells presented with only ~1 foci/nuclei (FIGS. 42E and 42G). Thus, the majority of damage sites are effectively repaired within the first 24 hours post-irradiation. In contrast, in the absence of Msi2, only 11.8% of cells showed no foci. Of the cells with unresolved foci, ~31% had more than 6 foci remaining, and, on average, Msi2-deficient leukemia cells had ~5 foci/nuclei (FIGS. 42E and 42G). These data suggest that in the absence of Msi2, DNA damage repair is either impaired or significantly delayed in leukemia. Collectively, both the gain-of-function and loss-of-function experiments suggest that Msi2 plays a critical role in protecting both normal and malignant stem cells from DNA damage. Importantly, these data underscore the fact that Msi2 not only marks resistant cells but that it is functionally important in conferring this resistance.

Discussion

In this study, a recently developed mouse that reports expression of the stem cell-related gene Msi2 was used to understand and visualize heterogeneity in myeloid malignancies. Msi2 marks a population of cells with leukemia-initiating cell activity and therapy resistance in vivo. Importantly, Msi2 not only marks residual disease but also mediates effective DNA damage repair following radiation, an activity crucial for therapy resistance. Msi2's ability to mark therapy-resistant cells and protect cells from DNA damage may extend to other hematopoietic malignancies other than myeloid malignancies. In support of this, a recent study on T-cell acute lymphoblastic leukemia (T-ALL) found whereas 100% of patients with low MSI2 expression achieved complete remission (CR) after the 2$^{nd}$ round of chemotherapy, ~33% of patients with high MSI2 expression failed to achieve CR, suggesting MSI2 overexpression is associated with chemoresistance in human T-ALL (Lu et al., 2015).

The results have several broad clinical and translational implications. First, it was demonstrated that Msi2-expressing cells drive leukemic growth in multiple leukemias, and thereby provide a rationale for targeting this population to promote tumor regression and prevent residual disease in hematologic malignancies. Second, the findings that Msi2 is not simply a marker, but that its function is essential for DNA damage responses strongly suggests that inhibiting Msi2 activity may sensitize leukemia-initiating cells to conventional DNA damage-inducing chemotherapeutic agents such as doxorubicin and daunorubicin.

Past studies have predominately used cell surface markers to identify and isolate tumor cells with cancer stem cell-like properties. For example, CD133 (Prominin-1) has been shown to be a marker for radioresistant brain cancer stem cells (Bao et al., 2006). However, like many current cancer stem cell markers, whether CD133 can be used to track residual disease in vivo remains unknown. In recent years, the ability to identify and track tumor-propagating cells in solid cancers has been greatly improved by the use of reporter mice. Using a Nestin-GFP transgene in a mouse model of glioblastoma multiforme, Parada and colleagues showed that rare Nestin-expressing tumor cells exhibit many cancer stem cell-like characteristics and are resistant to temozolomide (TMZ)-induced cell death, which allows them to persist following treatment and drive tumor regrowth (Chen et al., 2012). However, while it has been shown that Nestin functionally contributes to tumorigenesis (Tschaharganeh et al., 2014), the mechanism by which it influences tumor growth as well as whether it can broadly mark cancer stem cells is not known. More recently, Blanpain and colleagues developed a SOX2-GFP knock-in mouse and showed that Sox2 marks tumor-propagating cells in skin squamous-cell carcinoma (SCC) (Boumandi et al., 2014). Interesting, Msi2, along with several other stem cell-related genes, is significantly downregulated following Sox2 deletion and is directly bound by SOX2 in primary SCC. These data suggest that Msi2 may also play an important role in SCC and that REM2 mice may be useful for identifying and tracking tumor-propagating cells in this disease as well. Msi expression could also have important implications in other solid cancers as well. For example, mammalian cells have two paralogous Musashi genes: Msi1 and Msi2; while normal hematopoietic and leukemia cells almost exclusively express Msi2, Msi1 is expressed in a wide range of tissue stem cells, including mammary, intestinal and neural stem cells as well as their cancer counterparts. Interestingly, tumor-initiating cells from glioblastoma and breast cancers have been shown to be enriched after radiation treatment (Bao et al., 2006; Diehn et al., 2009). Thus, it is tempting to speculate that Msi1 may define therapy-resistant cancer stem cells in these solid cancers as well as in other solid cancer types. In support of this, we recently used the described Msi reporter system to demonstrate that Msi marks therapy-resistant tumor-propagating cells in pancreatic cancer (Nature).

The ability to identify therapy-resistant tumor-propagating cells could also provide valuable opportunities for improving current approaches to therapy. For example, in a situation where leukemia is being treated by targeted therapy or in some cases radiation for allogeneic stem cell transplantation, the ability to track therapy-resistant cells could allow residual cell-enriched areas to be identified and targeted with higher localized doses to reduce the chance of disease relapse while minimizing collateral damage in normal tissues. Because we find that Msi-expressing cells are the most robust, drug resistant cells with the greatest capacity to drive disease in different aggressive malignancies, tracking these cells may therefore be of particular use for this type of image-based spatial analysis, which could be coupled with new methods of targeting to improve patient outcomes.

Collectively, by using the Msi2 reporter mouse we were able to identify and track the leukemia-propagating cell population in blast crisis CML independent of cell surface marker expression. Remarkably, use of the REM2 mouse allowed us to identify leukemia-propagating cells for a broad range of hematopoietic malignancies, including diseases where the cancer stem cell population had not been previously defined. In this regard, the strength of the Msi2 reporter may ultimately be in its use as an initial strategy to isolate and characterize putative cancer stem cell-like populations in diseases where the tumor-propagating population has not been phenotypically defined. Importantly, since Msi2+ leukemia-propagating cells are marked by GFP in REM2 mice, easily trackable high-throughput screens can now be performed to identify drugs that modulate the frequency and/or absolute number of GFP$^+$ tumor-propagating cells. In this regard, drugs that affect GFP levels or frequency of GFP$^+$ cells within a tumor may define a new class of drugs that can effectively eliminate tumor-propagating cells and thus alone or in combination with other standard therapies may drive tumor regression, and most importantly, eradicate residual disease.

Methods

Mice

The following mice were used: B6-CD45.1 (Strain: B6.SJL-Ptprc$^a$Pepc$^b$/BoyJ); NSG mice (Strain: NOD.Cg-Prkdc$^{scid}$Il2rg$^{tm1Wjl}$/SzJ); Actin-dsRed mice (also referred as Actb-DsRed.T3 mice, Strain: Tg(CAG-DsRed*MST) 1Nagy/J); MSI2 inducible mice (also known as Col1-TetO-MSI2; Strain: B6.Cg-Gt(ROSA)26Sor$^{tm1(rTA*M2)Jae}$ Col1a1$^{tm6(tetO-MSI2)/Jae}$/J) have been described previously (Kharas et al., 2010); Msi2 gene-trap mutant mice (Strain: B6;CB-Msi2$^{Gt(pU-21T)2Imeg}$ were made and established by gene-trap mutagenesis (CARD, Kumamoto University). Msi2$^{eGFP}$ reporter mouse strain (referred to as REporter for Musashi, or REM2) was generated via conventional gene targeting strategy by knocking-in an enhanced green fluorescence (eGFP) gene in-frame at the murine Msi2 gene locus (Genoway, Lyon, France). All mice were 8-16 weeks of age. Mice were bred and maintained in the animal care facilities at the University of California, San Diego. All animal experiments were performed according to protocols approved by the University of California, San Diego Institutional Animal Care and Use Committee.

Generation and Analysis of Leukemic Mice

For BCR-ABL1/NUP98-HOXA9-driven blast crisis CML (bcCML), AML-ETO9a-driven AML and NPM1-driven MPD, bone marrow-derived KLS cells were isolated and sorted from REM2 mice. For chronic phase CML, bone marrow-derived KLS cells were isolated and sorted from either REM2 mice or Msi2$^{GFP}$/Acb-DsRed mice. All sorted cells were cultured overnight in X-Vivo 15 media (Lonza) supplemented with 50 μM 2-mercaptoethanol, 10% (vol/vol) fetal bovine serum, SCF (100 ng/ml, R&D Systems) and TPO (20 ng/ml, R&D Systems). Cells were retrovirally infected with MSCV-BCR-ABL-IRES-YFP and MSCV-NUP98-HOXA9-IRES-NGFR to generate bcCML; MSCV-BCR-ABL-IRES-NGFR to generate chronic phase CML; MSCV-AML-ETO9a-IRES-huCD2 and MSCV-NRas$^{G12V}$-

IRES-YFP to generate AML-ETO9a-driven AML; MSCV-NPM1c-IRES-huCD2 and MSCV-FLT3-/TD-IRES-NGFR to generate NPM1-driven MPD. Subsequently, cells were harvested 48 hours after infection. For bcCML primary transplants, BCR-ABL+/NUP98HOXA9+ cells were transplanted retro-orbitally into cohorts of sub-lethally (6 Gy) irradiated CD45.1 mice. For bcCML secondary transplants, BCR-ABL+/NUP98-HOXA9+ spleen cells recovered from terminally ill primary recipients were sorted and either 5,000 GFP+ or GFP− leukemia cells were transplanted into sub-lethally (6 Gy) irradiated secondary recipients. For chronic phase CML transplants, 20,000-30,000 BCR-ABL+ cells were transplanted retro-orbitally into cohorts of NSG mice. For AML-ETO9a-driven AML transplants, 100,000 unsorted cells were transplanted retro-orbitally into cohorts of lethally (9.5 Gy) irradiated CD45.1 mice. For NPM1-driven MPD transplants, 250,000 unsorted cells were transplanted retro-orbitally into cohorts of lethally (9.5 Gy) irradiated CD45.1 mice. Cell isolation, culture, infection and primary and secondary transplantation assays for MLL-driven leukemia were performed as previously described (Kwon et al., 2015). Disease mice were analyzed as previously described (Zimdahl et al., 2014).

In Vivo Identification of Therapy-Resistant Cells

To determine sites that harbor therapy-resistant cells, bone marrow-derived KLS cells were isolated and sorted from Msi2$^{GFP}$/Acb-DsRed mice and cultured in X-Vivo 15 media (Lonza) supplemented with 50 µM 2-mercaptoethanol, 10% (vol/vol) fetal bovine serum, SCF (100 ng/ml, R&D Systems) and TPO (20 ng/ml, R&D Systems). Cells were retrovirally infected with MSCV-BCR-ABL-IRES-NGFR and MSCV-NUP98-HOXA9-huCD2 to generate bcCML. Subsequently, cells were harvested 48 hours after initial infection and re-sorted for GFP+ dsRed+ BCR-ABL+/NUP98-HOXA9+ and then transplanted retro-orbitally into cohorts of NSG mice. Fifteen days post-transplantation (D15), recipient mice were treated daily with Gleevec (150 mg/kg) or H$_2$O (control) via oral gavage for five consecutive days (D15 to D19) and analyzed by flow cytometry on D20.

In Vitro Radiation and Gleevec Treatment

Bulk blast crisis CML cells recovered from the spleen of terminally-ill recipient mice that were initially transplanted with BCR-ABL+/NUP98-HOXA9+ KLS cells isolated from REM2 mice were either irradiated (0, 5, or 10 Gy) in PBS with glucose and cultured in X-Vivo 15 media (Lonza) supplemented with 50 µM 2-mercaptoethanol, 10% (vol/vol) fetal bovine serum, SCF (100 ng/ml, R&D Systems) and TPO (20 ng/ml, R&D Systems) for 7 hours or treated with imatinib (0.5 or 5 µM) or control DMSO for 7 hours in X-Vivo 15 media (Lonza) supplemented with 50 µM 2-mercaptoethanol, 10% (vol/vol) fetal bovine serum, SCF (100 ng/ml, R&D Systems) and TPO (20 ng/ml, R&D Systems). Cells were then washed and stained with antibodies against lineage markers. Apoptosis assays were performed by staining cells with Annexin-V (BD Pharmingen).

In Vitro Methylcellulose Colony Formation Assays

For methylcellulose assays performed with blast crisis CML (bcCML) cells, BCR-ABL/NUP98-HOXA9-driven leukemia was generated using KLS cells isolated from REM2 mice. Primary bcCML cells were fractionated based on GFP expression (GFP+ or GFP−) and 250 cells from each fraction were plated in methylcellulose media: Iscove's modified medium-based methylcellulose medium (Methocult GM M3434, StemCell Technologies). For methylcellulose assays performed with lineage-negative bcCML cells, lineage-negative primary bcCML cells were fractionated based on GFP expression (GFP+ and GFP−) and 500 cells from each fraction were plated. For serial plating, 500 cells derived from primary colonies were re-plated in fresh methylcellulose media. For radiation resistance assays, MSI2 inducible mice were whole body irradiated (3 Gy) and administered 2 mg/mL doxycycline for three days in the drinking water. For primary colony forming assays, 500 KLS cells isolated from MSI2 inducible mice were plated in methylcellulose media. For secondary plating, 5,000 cells derived from primary colonies were re-plated. Colony-forming capacity was defined as total colony area following secondary plating and determined by multiplying the number of colonies to individual colony size. For methylcellulose assays performed with chronic phase CML cells, either 500 BCR-ABL+ GFP+ or GFP− spleen cells isolated from CML mice were plated in methylcellulose media. For methylcellulose assays performed with AML-ETO9a-driven leukemia, either 500 AML-ETO9a+/NRas+ GFP+ or GFP− spleen cells isolated from leukemic mice were plated in methylcellulose media. All NPM1-driven MPD experiments were done with NPM1c+ FLT3-ITD− MPD cells derived from the spleen of mice transplanted with unsorted KLS cells infected with NPM1c and FLT3-ITD. FLT3-ITD expression could not be detected by flow cytometry or by genomic PCR (data not shown) in NPM1c+ spleen cells recovered from these mice. Thus, for methylcellulose assays performed with NPM1-driven MPD cells, either 2,000 NPM1c+ GFP+ or GFP− spleen cells isolated from MPD mice were plated in methylcellulose media. For methylcellulose assays performed with MLL-AF9/NRas AML cells, either 200 MLL-AF9+/NRas+ GFP+ or GFP− spleen cells isolated from leukemic mice were plated in methylcellulose media. For serial plating, 2,000 cells derived from primary colonies were re-plated. ImageJ software was used to determine colony size.

Cell Isolation and FACS Analysis

Cells were suspended in Hanks' balanced salt solution (HBSS) (Gibco, Life Technologies) containing 5% (vol/vol) fetal bovine serum and 2 mM EDTA and prepared for FACS analysis and sorting as previously described (Domen et al., 2000). The following antibodies were used to define lineage positive cells: 145-2C11 (CD3ε), GK1.5 (CD4), 53-6.7 (CD8), RB6-8C5 (Ly-6G/Gr1), M1/70 (CD11b/Mac-1), TER119 (Ly-76/TER119), 6B2 (CD45R/B220), and MB19-1 (CD19). Red blood cells were lysed using RBC Lysis Buffer (eBioscience) before staining for lineage markers. The following additional antibodies were used to define HSC populations: 2B8 (CD117/c-kit), D7 (Ly-6A/E/Sca-1), TC15-12F12.2 (CD150), and A2F10 (CD135/Flt3). All antibodies were purchased from BD Pharmingen, eBioscience or BioLegend. Analysis and cell sorting were carried out on BD LSRFortessa, FACSCanto and FACSAria II and III machines (all from Becton Dickinson) and data were analyzed with FlowJo software (Tree Star Inc.).

Immunofluorescence Staining

Cells were either allowed to settle briefly on poly-L-lysine coated chamber slides (VWR) at 37° C. or cytospun, fixed with 4% paraformaldehyde (USB Corporation), permeabilized with 1× Dako wash buffer (Dako) and blocked with 10-20% normal goat serum (Invitrogen) or donkey serum (Abcam) in 1× Dako wash buffer. Primary antibody incubation was overnight at 4° C. The following primary antibodies were used: rabbit anti-Msi2 1:200 (Abcam), chicken anti-alpha-GFP 1:200 (Abcam) and rabbit anti-53BP1 1:1000 (Abcam). Alexafluor-conjugated secondary antibody incubation was performed for 1 hr at room temperature. DAPI (4-6-diamindino-2-phenylindole; Molecular Probes)

was used to detect DNA. Images were obtained with a Confocal Leica TCS SP5 II (Leica Microsystems).

Retroviral Constructs and Production

MIG-BCR-ABL was provided by Warren Pear and Ann Marie Pendergast and was cloned into the MSCV-IRES-YFP (or MSCV-IRES-NGFR) retroviral vector. MSCV-NUP98-HOXA9-IRES-YFP was provided by Gary Gilliland and was sub-cloned into the MSCV-IRES-NGFR vector (or MSCV-IRES-huCD2) retroviral vector. MSCV-MLL-AF9-IRES-GFP was provided by Scott Armstrong and was sub-cloned into the MSCV-IRES-NGFR retroviral vector. MSCV-AML-ETO9a-IRES-GFP was provided by Scott Lowe and was sub-cloned into the MSCV-IRES-huCD2 retroviral vector. NRAS$^{G12V}$ cDNA was a gift from Christopher Counter and was cloned into MSCV-IRES-YFP retroviral vector. The pEGFPc1-NPM1c+ construct was previously described (Falini et al., 2005) and was provided by Valentina Pettirossi. NPM1c+ (mutation A; most frequent mutation in cytoplasmic NPM exon 12) was sub-cloned into MSCV-IRES-huCD2. MSCV-FLT3-ITD-IRES-GFP construct was provided by Gary Gilliland and was sub-cloned into MSCV-IRES-RFP. Virus was produced in 293T cells transfected using the FuGENE®6 or X-tremeGENE HP (Roche) with viral constructs along with VSV-G and gag-pol. Viral supernatants were collected for three to six days followed by ultracentrifugal concentration at 50,000×g for 3 h.

Genome-Wide Expression Analysis

Gene expression analysis of Msi2-deficient blast crisis CML cells was described previously (Kwon et al., 2015). For HSC cohorts, bone marrow-derived HSCs (KLS CD150$^+$ CD48$^-$) were FACS-sorted from Msi2 mutant (Msi2$^{Gt/Gt}$) and wild-type (WT) mice. Total cellular RNAs were purified using an RNAqueous-Micro Total RNA Isolation Kit (Ambion). Total RNAs were amplified, labeled and hybridized on Affymetrix GeneChip Mouse Genome 430 2.0 Arrays, and raw hybridization data were collected (Asuragen Inc., Asuragen, Tex.). Expression level data were normalized as previously described (Sasik et al., 2004). Probes whose expression level exceeds a threshold value (found by inspection from the distribution plots of log 2 expression levels) in at least one sample were considered detected. Detected probes were sorted as previously described (Zimdahl et al., 2014). The probe list was translated into Entrez gene ID's and parsed so that where several different probes represent the same gene, only the highest-ranking probe was kept for further analysis. The sorted list of genes was subjected to a non-parametric variant of the Gene Set Enrichment Analysis (GSEA) (Subramanian et al., 2005), in which the p-value of a gene set was defined as previously described (Zimdahl et al., 2014). A Bonferroni adjustment of gene set p-values for the number of gene sets tested was performed. Gene sets with adjusted p-values <0.05 were reported. The GEO accession number for the microarray data associated with this paper is GEO: X.

Statistical Analysis

Statistical analyses were carried out using R language version 3.2.0 (r-project.org/) and GraphPad Prism software version 6.0f-h (GraphPad software Inc.). Data are mean±SEM. Chi-square test was used to determine deviation from Mendelian ratios. Two-tailed unpaired Student's t-tests with Welch's correction when appropriate were used to determine statistical significance (*p<0.05, p<0.01, *p<0.001, ****p<0.0001).

Embodiment 11: A Signaling Pathway that when Inhibited in HSCs Improved Stem Cell Function In Vitro A signaling pathway that when inhibited in HSCs improved stem cell function in vitro was recently identified. The data further suggest that inhibition of this pathway promotes expansion of the hematopoietic compartment in vivo. To visualize the impact of inhibiting this pathway on the stem cell compartment of irradiated mice in vivo after injury, a live bone marrow imaging system in conjunction with the Musashi2 knock-in reporter mouse line was utilized (reporter for Musashi2, REM2) (Fox et al. 2016). The Msi2GFPbright population can be used to visualize hematopoietic stem/progenitor cells in vivo (Fox et al. 2015; Koechlein et al. 2016). Msi2+/GFP mice were pretreated with inhibitor before a 6 Gy sublethal irradiation and imaged one week after radiation (Panel A). There was a clear enrichment of Msi2GFPbright immature hematopoietic cells (Panel B). Quantification revealed a 2.7 fold increase in Msi2GFPbright cells within the bone marrow (Panel C).

Embodiment 12: Msi2 Deletion Leads to Reduced Tumor Burden in a p53/Ras Induced Model of Lung Adenocarcinoma As shown in FIG. 53, Msi reporter expression in a Kras/p53 driven mouse model of lung cancer indicates that lung cancer cells express high levels of Msi. Thus this reporter could be used in lung cancer models and in human lung cancer cells to screen for drugs that eliminate Msi expressing lung cancer stem cells. FIG. 54 shows the Msi2 reporter expression in normal lung and lung cancer. Msi reporter expression in Kras/p53 driven mouse model of lung cancer indicates that lung cancer cells express high levels of Msi. Thus this reporter could be used in lung cancer models and in human lung cancer cells to screen for drugs that eliminate Msi expressing lung cancer stem cells. Elevated Msi expression may also be used to detect lung cancer.

Embodiment 13. Msi Reporter can be Used in Human Cells

As show in FIGS. 56-57, the reporter activity has been seen in human cells. Cells were infected with lentivirus vectors containing the Msi reporter and analyzed by FACS after 48 hours-gating on RFP+ (containing the vector) and GFP+ promoter activity. RFP+ cells were live imaged for promoter activity. Miapaca2 and FG cells, which have different levels of Msi expression were anlayzed to assess a difference in GFP+ reporter. FACS was used to analyze GFP+ activity in infected cells and plated cells were live imaged for promoter activity (quantified for Miapaca 2 and FG). Lower levels were observed in FG2 cells which express less Msi. As such, in the embodiments herein, stem cell expansion and regenerative medical uses of the reporter described herein could be used for multiple types of stem cells. Without being limiting the stem cells which can be utilized in the stem cell and regenerative medical uses described herein include hematopoietic stem cells, pancreatic beta cells and neural stem cells, for example.

Additional Embodiments

In some embodiments, a genetically engineered cell comprising a nucleic acid encoding a detectable polypeptide operably linked to the Msi1 promoter is provided. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a genetically engineered cell comprising a nucleic acid encoding a detectable polypeptide operably linked to the Msi2 promoter is provided. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a genetically engineered cell comprising a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a genetically engineered organism comprising the genetically engineered cell of any one of the alternatives herein is provided. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for determining the location of cancerous cells in an organism is provided, wherein the method comprises determining the location of the detectable polypeptide in a genetically engineered organism described herein. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some alternatives the location of the detectable polypeptide is determined using in vivo imaging. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for identifying cancer therapy resistant cancer cells is provided wherein the method comprises administering a cancer therapeutic agent to a genetically engineered organism of using a therapeutic regimen sufficient to kill cells which are not resistant to said cancer therapeutic agent; and detecting the location of genetically engineered cells producing the detectable polypeptide in said genetically engineered organism following the completion of said therapeutic regimen. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for identifying a candidate therapeutic agent which targets cancer therapy resistant cancer cells is provided. The method comprises contacting a genetically engineered cell which is cancer therapy resistant or a genetically engineered organism comprising genetically engineered cells which are cancer therapy resistant with a candidate therapeutic agent; and determining whether said candidate therapeutic agent is able to kill or inhibit the replication of said cancer therapy resistant genetically engineered cell or cancer therapy resistant genetically engineered cells in said genetically engineered organism. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, said cancer therapy resistant genetically engineered cell comprises a genetically engineered cell comprising a nucleic acid encoding a detectable polypeptide operably linked to the Msi2 promoter or said genetically engineered organism comprising cancer therapy resistant genetically engineered cells comprising a nucleic acid encoding a detectable polypeptide operably linked to the Msi2 promoter. In some embodiments, said cancer therapy resistant genetically engineered cells are resistant to radiation or Gleevec therapy or said genetically engineered organism comprises cancer therapy resistant genetically engineered cells which are resistant to radiation or Gleevec therapy. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for monitoring eradication of cancer therapy resistant cancer cells is provided. The method comprises contacting a genetically engineered organism comprising genetically engineered cells which are cancer therapy resistant with a candidate therapeutic agent; and monitoring the rate of proliferation of said cancer therapy resistant genetically engineered cells in said genetically engineered organism over a period of time. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell.

In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for identifying a candidate therapeutic agent is provided. The method comprises contacting a genetically engineered cell or a genetically engineered organism with a candidate therapeutic agent; and determining whether said candidate therapeutic agent is able to kill or inhibit the replication of said genetically engineered cell or genetically engineered cells in said genetically engineered organism. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for identifying a candidate therapeutic agent is provided, wherein the method comprises contacting a genetically engineered cell or a genetically engineered organism with a candidate therapeutic agent; and determining whether said candidate therapeutic agent is able reduce the level of expression or activity of Msi1 or Msi2 in said genetically engineered cell. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, method for identifying a molecular probe indicative of cancer is provided, the method comprising identifying nucleic acids or polypeptides which have differential levels or activity in in cancerous cells generated from any of the genetically engineered cells or generated from genetically engineered cells in a genetically engineered organism; and identifying a molecular probe which specifically recognizes said nucleic acids or polypeptides. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, said molecular probe comprises a nucleic acid which specifically binds to said nucleic acids which have differential levels or activity in said cancerous cells or an antibody or portion thereof which specifically recognizes said polypeptides which have differential levels or activity in said cancerous cells. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for detecting cancer is provided the method comprising contacting a sample obtained from a subject with a molecular probe which specifically binds to a nucleic acid or polypeptide which has differential levels or activity in in cancerous cells generated from any of the genetically engineered cells or generated from genetically engineered cells in a genetically engineered organism. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for monitoring cancer comprising monitoring the growth or location of said genetically engineered cells in a genetically engineered organism is provided. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-

HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for tracking circulating cancer cells comprising tracking the location of said genetically engineered cells in a genetically engineered organism is provided. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for identifying a candidate therapeutic agent which increases the proliferation of stem cells is provided, the method comprising: contacting a genetically engineered cell wherein said cell is a stem cell or a genetically engineered organism wherein said genetically engineered cells are stem cells with a candidate therapeutic agent; and determining whether said candidate therapeutic agent is able to increase the proliferation of said genetically engineered stem cell or said genetically engineered stem cells in said genetically engineered organism. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide has been increased. In some embodiments, the level or activity of the BCR-ABL polypeptide has been increased. In some embodiments, the level or activity of the Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

In some embodiments, a method for ameliorating cancer comprising reducing the level or activity of a nucleic acid encoding the Msi1 polypeptide or the Msi2 polypeptide or reducing the level or activity of Msi1 polypeptide or the Msi2 polypeptide is provided.

In some embodiments, a method of reducing the level or activity of a nucleic acid encoding the Msi1 polypeptide or the Msi2 polypeptide or reducing the level or activity of Msi1 polypeptide or the Msi2 polypeptide comprising contacting a cell with a nucleic acid which is complementary to at least a portion of a nucleic acid encoding the Msi1 polypeptide or the Msi2 polypeptide is provided.

A Genetically Engineered Cell

As described herein, a genetically engineered cell is provided. A genetically engineered organism can comprise a genetically engineered cell. These genetically engineered organism can be used in the identification of cancer therapy resistant cancer cells, identification of a candidate therapeutic agent which targets cancer therapy resistant cancer cells, monitoring eradication of cancer therapy resistant cancer cells, identifying a candidate therapeutic agent, for identifying a molecular probe indicative of cancer, detecting cancer, tracking circulating cancer cells, and identifying a candidate therapeutic agent. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, said one or more oncogenic polypeptides are associated with colon, lung, liver, breast, renal, prostate, ovarian, skin (including melanoma), bone, and brain cancer, adenocarcinoma, pancreatic cancer or leukemia. In some embodiments, the level or activity of a Kras polypeptide, BCR-ABL polypeptide, and/or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell is a precursor T cell. In some embodiments, the precursor T cell is hematopoietic stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide, BCR-ABL polypeptide or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with colon, lung, liver, breast, renal, prostate, ovarian, skin (including melanoma), bone, and brain cancer, adenocarcinoma, pancreatic cancer or leukemia. In some embodiments, the level or activity of the Kras polypeptide, BCR-ABL polypeptide or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

A Genetically Engineered Organism

In some embodiments, a genetically engineered organism comprising the genetically engineered cell is provided. The genetically engineered organism can comprise a genetically engineered cell. In some embodiments, the genetically engineered cell comprises a nucleic acid encoding a detectable polypeptide operably linked to the Msi1 promoter. In some embodiments, said nucleic acid encoding said detectable polypeptide is inserted into an exon of the Msi1 promoter such that said detectable polypeptide is expressed in a form which allows to be detected. In some embodiments, the level or activity of one or more oncogenic polypeptides has been increased. In some embodiments, said one or more oncogenic polypeptides are associated with colon, lung, liver, breast, renal, prostate, ovarian, skin (including melanoma), bone, and brain cancer, adenocarcinoma, pancreatic cancer or leukemia. In some embodiments, the level or activity of a Kras polypeptide, BCR-ABL polypeptide, and/or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the genetically engineered cell is a precursor T cell. In some embodiments, the precursor T cell is hematopoietic stem cell. In some embodiments, the genetically engineered cell comprises a nucleic acid encoding a detectable polypeptide operably linked to the Msi2 promoter. In some embodiments, said nucleic acid encoding said detectable polypeptide is inserted into an exon of the Msi2 promoter such that said detectable polypeptide is expressed in a form which allows to be detected. In some embodiments, the level or activity of one or more oncogenic polypeptides has been increased. In some embodiments, said one or more oncogenic polypeptides are associated with adenocarcinoma, pancreatic cancer or leukemia. In some embodiments, the level or activity of the Kras polypeptide, BCR-ABL polypeptide or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, the detectable polypeptide comprises a fluorescent polypeptide. In some embodiments, said cell is capable of forming a tumor. In some embodiments, said cell is a tumor stem cell. In some embodiments, the genetically engineered cell comprises a first nucleic acid encoding a first detectable polypeptide operably linked to the Msi1 promoter and a second nucleic acid encoding a second detectable polypeptide operably linked to the Msi2 promoter. In some embodiments, said first nucleic acid encoding said first detectable polypeptide is inserted into an exon of the Msi1 promoter such that said first detectable polypeptide is expressed in a form which allows to be detected and said second nucleic acid encoding said second detectable polypeptide is inserted into an exon of the Msi2 promoter such that said second detectable polypeptide is expressed in a form which allows to be detected. In some embodiments, the level or activity of one or more oncogenic polypeptides has been increased. In some embodiments, said one or more oncogenic polypeptides are associated with colon, lung, liver, breast, renal, prostate, ovarian, skin (including melanoma), bone, and brain cancer, adenocarcinoma, pancreatic cancer or leukemia. In some embodiments, the level or activity of the Kras polypeptide, BCR-ABL polypeptide or Nup98-HoxA9 transactivator polypeptide has been increased. In some embodiments, said cell comprises the KRASG12D allele. In some embodiments, the Kras oncogene is under the control of the Ptf1a promoter. In some embodiments, said cell comprises a genetic modification which reduces the level or activity of or inactivates one or more tumor suppressor proteins. In some embodiments, said one or more tumor suppressor protein is selected from the group consisting of p53, p16/INK4A, and SMAD4. In some embodiments, said tumor suppressor is encoded by a nucleic acid which can be conditionally deleted. In some embodiments, at least one of the first detectable polypeptide and the second detectable polypeptide comprises a fluorescent polypeptide. In some embodiments, said fluorescent polypeptide comprises eYFP or eGFP. In some embodiments, said cell is capable of forming a tumor. In some embodiments, said cell is a tumor stem cell. In some embodiments, the cell is a CD4+ expressing cell. In some embodiments, the cell is a CD8+ expressing cell. In some embodiments, the cell is derived from thymocytes or T-cells that are derived from engineered precursors. In some embodiments, the T cell is a precursor T cell. In some embodiments, the precursor T cell is a hematopoietic stem cell.

Methods

In some embodiments, a method for determining the location of cancerous cells in an organism is provided wherein the method comprises determining the location of the detectable polypeptide in a genetically engineered organism as described above. In some embodiments, the location of the detectable polypeptide is determined using in vivo imaging.

In some embodiments, a method for identifying cancer therapy resistant cancer cells is provided, comprising: administering a cancer therapeutic agent to a genetically engineered organism described herein, using a therapeutic regimen sufficient to kill cells which are not resistant to said cancer therapeutic agent; and detecting the location of genetically engineered cells producing the detectable polypeptide in said genetically engineered organism following the completion of said therapeutic regimen.

In some embodiments, a method for identifying a candidate therapeutic agent which targets cancer therapy resistant cancer cells is provided, comprising: contacting a genetically engineered cell of any of the embodiments herein, which is cancer therapy resistant or a genetically engineered organism of any of the embodiments described herein, comprising genetically engineered cells which are cancer therapy resistant with a candidate therapeutic agent; and determining whether said candidate therapeutic agent is able to kill or inhibit the replication of said cancer therapy resistant genetically engineered cell or cancer therapy resistant genetically engineered cells in said genetically engineered organism. In some embodiments, said cancer therapy resistant genetically engineered cell comprises a genetically engineered cell comprising a nucleic acid encoding a detectable polypeptide operably linked to the Msi2 promoter or said genetically engineered organism comprising cancer therapy resistant genetically engineered cells comprising a nucleic acid encoding a detectable polypeptide operably linked to the Msi2 promoter. In some embodiments, said cancer therapy resistant genetically engineered cells are resistant to radiation or Gleevec therapy or said genetically engineered organism comprises cancer therapy resistant genetically engineered cells which are resistant to radiation or Gleevec therapy.

In some embodiments, a method for monitoring eradication of cancer therapy resistant cancer cells is provided comprising: contacting a genetically engineered organism comprising genetically engineered cells of any one of the embodiments described herein, which are cancer therapy resistant with a candidate therapeutic agent; and monitoring the rate of proliferation of said cancer therapy resistant genetically engineered cells in said genetically engineered organism over a period of time.

In some embodiments, a method for identifying a candidate therapeutic agent is provided, comprising: contacting a genetically engineered cell of any one of the embodiments described herein or a genetically engineered organism of any one of the embodiments described herein with a candidate therapeutic agent; and determining whether said candidate therapeutic agent is able to kill or inhibit the replication of said genetically engineered cell or genetically engineered cells in said genetically engineered organism.

In some embodiments a method for identifying a candidate therapeutic agent is provided, comprising: contacting a genetically engineered cell of any one of the embodiments described herein or a genetically engineered organism of any one of the embodiments described herein with a candidate therapeutic agent; and determining whether said candidate therapeutic agent is able reduce the level of expression or activity of Msi1 or Msi2 in said genetically engineered cell.

In some embodiments, a method for identifying a molecular probe indicative of cancer is provided, comprising: identifying nucleic acids or polypeptides which have differential levels or activity in in cancerous cells generated from any of the genetically engineered cells of any one of the embodiments described herein or generated from genetically engineered cells in a genetically engineered organism of any one of the embodiments described herein, and identifying a molecular probe which specifically recognizes said nucleic acids or polypeptides. In some embodiments, said molecular probe comprises a nucleic acid which specifically binds to said nucleic acids which have differential levels or activity in said cancerous cells or an antibody or portion thereof which specifically recognizes said polypeptides which have differential levels or activity in said cancerous cells.

In some embodiments, a method for detecting cancer comprising contacting a sample obtained from a subject with a molecular probe which specifically binds to a nucleic acid or polypeptide which has differential levels or activity in in cancerous cells generated from any of the genetically engineered cells of any one of the embodiments described herein or generated from genetically engineered cells in a genetically engineered organism of any one of the embodiments described herein.

In some embodiments, a method for monitoring cancer comprising monitoring the growth or location of said genetically engineered cells in a genetically engineered organism o of any one of the embodiments described herein is provided.

In some embodiments, a method for tracking circulating cancer cells comprising tracking the location of said genetically engineered cells in a genetically engineered organism of any one of the embodiments described herein is provided.

In some embodiments, a method for identifying a candidate therapeutic agent which increases the proliferation of stem cells is provided, comprising: contacting a genetically engineered cell of any one of the embodiments described herein wherein said cell is a stem cell or a genetically engineered organism of any one of the embodiments described herein wherein said genetically engineered cells are stem cells with a candidate therapeutic agent; and determining whether said candidate therapeutic agent is able to increase the proliferation of said genetically engineered stem cell or said genetically engineered stem cells in said genetically engineered organism.

In some embodiments, a method for ameliorating cancer comprising reducing the level or activity of a nucleic acid encoding the Msi1 polypeptide or the Msi2 polypeptide or reducing the level or activity of Msi1 polypeptide or the Msi2 polypeptide is provided.

In some embodiments, a method of reducing the level or activity of a nucleic acid encoding the Msi1 polypeptide or the Msi2 polypeptide or reducing the level or activity of Msi1 polypeptide or the Msi2 polypeptide comprising contacting a cell with a nucleic acid which is complementary to at least a portion of a nucleic acid encoding the Msi1 polypeptide or the Msi2 polypeptide is provided.

The disclosures of all references cited herein are incorporated herein by reference in their entireties, including the references listed below:

REFERENCES AND NOTES

Almoguera, C. et al. Most human carcinomas of the exocrine pancreas contain mutant c-K-ras genes. Cell 53, 549-554 (1988).

Bardeesy, N. et al. Both p16Ink4a and the p19Arf-p53 pathway constrainprogression of pancreatic adenocarcinomain the mouse. PNAS April, vol. no. 103, 5947-5952 (2006).

Benjamini, Y. & Hochberg, Y. Controlling the false discovery rate: a practical and powerful approach to multiple testing. Journal of the Royal Statistical Society. Series B (Methodological) 289-300 (1995).

Carroll, J. B. et al. Potent and Selective Antisense Oligonucleotides Targeting Single-Nucleotide Polymorphisms in the Huntington Disease Gene/Allele-Specific Silencing of Mutant Huntingtin. Molecular Therapy 19, 2178-2185 (2009).

de Andrés-Aguayo, L. et al. Musashi 2 is a regulator of the HSC compartment identified by a retroviral insertion screen and knockout mice. Blood 118, 554-564 (2011).

Delitto, D., Vertes-George, E., Hughes, S. J., Behrns, K. E. & Trevino, J. G. c-Met signaling in the development of tumorigenesis and chemoresistance: potential applications in pancreatic cancer. World J. Gastroenterol. 20, 8458-8470 (2014).

Fan, L.-F. et al. Expression of putative stem cell genes Musashi-1 and β1-integrin in human colorectal adenomas and adenocarcinomas. Int J Colorectal Dis 25, 17-23 (2009).

Hahn, S. A. et al. DPC4, a candidate tumor suppressor gene at human chromosome 18q21.1. Science 271, 350-353 (1996).

Hermann, P. C. et al. Distinct Populations of Cancer Stem Cells Determine Tumor Growth and Metastatic Activity in Human Pancreatic Cancer. Cell Stem Cell 1, 313-323 (2007).

Hingorani, S. R. et al. Preinvasive and invasive ductal pancreatic cancer and its early detection in the mouse. Cancer Cell 4, 437-450 (2003).

Hope, K. J. et al. An RNAi screen identifies Msi2 and Prox1 as having opposite roles in the regulation of hematopoietic stem cell activity. Cell Stem Cell 7, 101-113 (2010).

Hung, G. et al. Characterization of Target mRNA Reduction Through In SituRNA Hybridization in Multiple Organ Systems Following Systemic Antisense Treatment in Animals. Nucleic Acid Therapeutics 23, 369-378 (2013).

Ito, T. et al. Regulation of myeloid leukaemia by the cell-fate determinant Musashi. Nature 466, 765-768 (2010).

Jackson, E. L. et al. Analysis of lung tumor initiation and progression using conditional expression of oncogenic K-ras. Genes & Development 15, 3243-3248 (2001).

Jemal, A. et al. Global cancer statistics. CA: A Cancer Journal for Clinicians 61, 69-90 (2011).

Jones, S. et al. Core signaling pathways in human pancreatic cancers revealed by global genomic analyses. Science 321, 1801-1806 (2008).

Kadowaki, Y. et al. Reg protein is overexpressed in gastric cancer cells, where it activates a signal transduction pathway that converges on ERK1/2 to stimulate growth. FEBS Letters 530, 59-64 (2002).

Kaneko, Y. et al. Musashi1: an evolutionally conserved marker for CNS progenitor cells including neural stem cells. Dev. Neurosci. 22, 139-153 (2000).

Kawaguchi, Y. et al. The role of the transcriptional regulator Ptf1a in converting intestinal to pancreatic progenitors. Nat Genet 32, 128-134 (2002).

Kharas, M. G. et al. Musashi-2 regulates normal hematopoiesis and promotes aggressive myeloid leukemia. Nat Med 16, 903-908 (2010).

Kim, M. P. et al. ALDH Activity Selectively Defines an Enhanced Tumor-Initiating Cell Population Relative to CD133 Expression in Human Pancreatic Adenocarcinoma. PLoS ONE 6, e20636 (2011).

Kwon, H. Y. et al. Tetraspanin 3 Is Required for the Development and Propagation of Acute Myelogenous Leukemia. Stem Cell 17, 152-164 (2015).

Lee, R. G., Crosby, J., Baker, B. F., Graham, M. J. & Crooke, R. M. Antisense technology: an emerging platform for cardiovascular disease therapeutics. J Cardiovasc Transl Res 6, 969-980 (2013).

Li, C. et al. c-Met is a marker of pancreatic cancer stem cells and therapeutic target. Gastroenterology 141, 2218-2227.e5 (2011).

Li, N., Li, Q., Tian, X.-Q., Qian, H.-Y. & Yang, Y.-J. Mipomersen is a Promising Therapy in the Management of Hypercholesterolemia: A Meta-Analysis of Randomized Controlled Trials. Am J Cardiovasc Drugs 14, 367-376 (2014).

MacNicol, A. M., Wilczynska, A. & MacNicol, M. C. Function and regulation of the mammalian Musashi mRNA translational regulator. Biochem. Soc. Trans 36, 528 (2008).

Marcato, P., Dean, C. A., Giacomantonio, C. A. & Lee, P. W. K. Aldehyde dehydrogenase: Its role as a cancer stem cell marker comes down to the specific isoform. cc 10, 1378-1384 (2011).

Marino, S., Vooijs, M., van Der Gulden, H., Jonkers, J. & Berns, A. Induction of medulloblastomas in p53-null mutant mice by somatic inactivation of Rb in the external granular layer cells of the cerebellum. Genes & Development 14, 994-1004 (2000).

Nakamura, M., Okano, H., Blendy, J. A. & Montell, C. Musashi, a neural RNA-binding protein required for Drosophila adult external sensory organ development. Neuron 13, 67-81 (1994).

Nikpour, P., Mowla, S. J., Forouzandeh-Moghaddam, M. & Ziaee, S. A. The stem cell self-renewal gene, Musashi 1, is highly expressed in tumor and non-tumor samples of human bladder. Indian J Cancer 50, 214-218 (2013).

Okano, H., Imai, T. & Okabe, M. Musashi: a translational regulator of cell fate. J. Cell. Sci. 115, 1355-1359 (2002).

Okano, H. et al. Function of RNA-binding protein Musashi-1 in stem cells. Experimental Cell Research 306, 349-356 (2005).

Paulson, A. S., Tran Cao, H. S., Tempero, M. A. & Lowy, A. M. Therapeutic advances in pancreatic cancer. Gastroenterology 144, 1316-1326 (2013).

Prakash, T. P. et al. Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models . . . . medicinal chemistry (2010).

Raal, F. J. et al. Mipomersen, an apolipoprotein B synthesis inhibitor, for lowering of LDL cholesterol concentrations in patients with homozygous familial hypercholesterolaemia: a randomised, double-blind, placebo-controlled trial. The Lancet 375, 998-1006 (2010).

Rasheed, Z. A. & Matsui, W. Biological and clinical relevance of stem cells in pancreatic adenocarcinoma. Journal of Gastroenterology and Hepatology 27, 15-18 (2012).

Redston, M. S. et al. p53 mutations in pancreatic carcinoma and evidence of common involvement of homocopolymer tracts in DNA microdeletions. Cancer Res. 54, 3025-3033 (1994).

Reya, T., Morrison, S. J., Clarke, M. F. & Weissman, I. L. Stem cells, cancer, and cancer stem cells. Nature 414 (6859):105-11 (2001).

Rhim, A. D. et al. EMT and dissemination precede pancreatic tumor formation. Cell 148, 349-361 (2012).

Rigo, F. et al. Pharmacology of a central nervous system delivered 2'-O-methoxyethyl-modified survival of motor neuron splicing oligonucleotide in mice and nonhuman primates. Journal of Pharmacology and Experimental Therapeutics 350, 46-55 (2014).

Rovira, M. et al. Isolation and characterization of centroacinar/terminal ductal progenitor cells in adult mouse pancreas. Proceedings of the National Academy of Sciences 107, 75-80 (2010).

Saad, F. et al. Randomized phase II trial of Custirsen (OGX-011) in combination with docetaxel or mitoxantrone as second-line therapy in patients with metastatic castrate-resistant prostate cancer progressing after first-line docetaxel: CUOG trial P-06c. Clin. Cancer Res. 17, 5765-5773 (2011).

Sakakibara, S.-I. et al. RNA-binding protein Musashi family: roles for CNS stem cells and a subpopulation of ependymal cells revealed by targeted disruption and antisense ablation. Proc. Natl. Acad. Sci. U.S.A. 99, 15194-15199 (2002).

Samuel, V. T. et al. Targeting foxo1 in mice using antisense oligonucleotide improves hepatic and peripheral insulin action. Diabetes 55, 2042-2050 (2006).

Sasik, R., Woelk, C. H. & Corbeil, J. Microarray truths and consequences. J. Mol. Endocrinol. 33, 1-9 (2004).

Sayer, R. A. et al. High insulin-like growth factor-2 (IGF-2) gene expression is an independent predictor of poor survival for patients with advanced stage serous epithelial ovarian cancer. Gynecologic Oncology 96, 355-361 (2005).

Schutte, M. et al. Abrogation of the Rb/p16 tumor-suppressive pathway in virtually all pancreatic carcinomas. Cancer Res. 57, 3126-3130 (1997).

Seth, P. P. et al. Short Antisense Oligonucleotides with Novel 2'-4' Conformationaly Restricted Nucleoside Analogues Show Improved Potency without Increased Toxicity in Animals. J. Med. Chem. 52, 10-13 (2009).

Shu, H.-J. et al. Expression of the Musashi1 gene encoding the RNA-binding protein in human hepatoma cell lines. Biochem. Biophys. Res. Commun. 293, 150-154 (2002).

Sutherland, J. M., McLaughlin, E. A., Hime, G. R. & Siddall, N. A. The Musashi family of RNA binding proteins: master regulators of multiple stem cell populations. Adv. Exp. Med. Biol. 786, 233-245 (2013).

Team, R. C. R: A language and environment for statistical computing. R Foundation for Statistical Computing, Vienna, Austria (2012).

Tusher, V. G., Tibshirani, R. & Chu, G. Significance analysis of microarrays applied to the ionizing radiation response. Proc. Natl. Acad. Sci. U.S.A. 98, 5116-5121 (2001).

Wang, J. C. Y. & Dick, J. E. Cancer stem cells: lessons from leukemia. Trends in Cell Biology 15, 494-501 (2005).

Wang, T. et al. Sequential expression of putative stem cell markers in gastric carcinogenesis. British Journal of Cancer 105, 658-665 (2011).

Wang, X.-Y. et al. Musashi1 regulates breast tumor cell proliferation and is a prognostic indicator of poor survival. Mol Cancer 9, 221 (2010).

Wang, X. et al. Overexpression of HMGA2 promotes metastasis and impacts survival of colorectal cancers. Clin. Cancer Res. 17, 2570-2580 (2011).

Wu, J., Irizarry with contributions from James MacDonald, R. & Gentry, J. gcrma: Background Adjustment Using Sequence Informatin. R package version 2.37.0.

Yachida, S. & Iacobuzio-Donahue, C. A. The pathology and genetics of metastatic pancreatic cancer. Arch. Pathol. Lab. Med. 133, 413-422 (2009).

What is claimed is:

1. An isolated, genetically engineered cell comprising a nucleic acid encoding a detectable polypeptide inserted into an exon of an endogenous Msi1 or Msi2 gene such that said detectable polypeptide is expressed in a form which allows it to be detected.

2. The genetically engineered cell of claim 1, wherein said cell further comprises one or more transgenes encoding one or more oncogenic polypeptides integrated into the genome, whereby said oncogenic polypeptides encoded by said transgenes are expressed.

3. The genetically engineered cell of claim 2, wherein said one or more oncogenic polypeptides are associated with adenocarcinoma, pancreatic cancer or leukemia.

4. The genetically engineered cell of claim 2, wherein said one or more oncogenic polypeptides is selected from the group consisting of Kras polypeptide, BCR-ABL polypeptide, and/or Nup98-HoxA9 transactivator polypeptide.

5. The genetically engineered cell of claim 1, wherein said cell further comprises a KRASG12D allele.

6. The genetically engineered cell of claim 4, wherein the oncogenic polypeptide is Kras polypeptide, and wherein the transgene encoding the Kras polypeptide is under the control of a Ptf1a promoter.

7. The genetically engineered cell of claim 1, wherein said cell further comprises a genetic modification which reduces the level or activity of or inactivates one or more tumor suppressor proteins.

8. The genetically engineered cell of claim 7, wherein said one or more tumor suppressor protein is selected from the group consisting of p53, p16/INK4A, and SMAD4.

9. The genetically engineered cell of claim 7, wherein said tumor suppressor is encoded by a nucleic acid which can be conditionally deleted.

10. The genetically engineered cell of claim 1, wherein the detectable polypeptide comprises a fluorescent polypeptide.

11. The genetically engineered cell of claim 10, wherein said fluorescent polypeptide comprises eYFP or eGFP.

12. The genetically engineered cell of claim 1, wherein said cell is capable of forming a tumor.

13. The genetically engineered cell of claim 1, wherein said cell is a tumor stem cell.

14. The genetically engineered cell of claim 1, wherein the genetically engineered cell is a precursor T cell.

15. The genetically engineered cell of claim 14, wherein the precursor T cell is hematopoietic stem cell.

* * * * *

SEQUENCE LISTING

<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: MSI1 shRNA target sequence

<400> SEQUENCE: 1
cccagatagc cttagagact at                                        22

<210> SEQ ID NO 2
<211> LENGTH: 22
<212> TYPE: DNA
<213> ORGANISM: Artificial Sequence
<220> FEATURE:
<223> OTHER INFORMATION: MSI2 shRNA target sequence

<400> SEQUENCE: 2
cccagatagc cttagagact at                                        22

<210> SEQ ID NO 3
<211> LENGTH: 22
<212> TYPE: DNA
<213> ORGANISM: Artificial Sequence
<220> FEATURE:
<223> OTHER INFORMATION: Control scrambled sequence

<400> SEQUENCE: 3
ctgtgccaga gtccttcgat ag                                        22

<210> SEQ ID NO 4
<211> LENGTH: 29
<212> TYPE: RNA
<213> ORGANISM: Homo sapiens

<400> SEQUENCE: 4
accgcgcugu ggguagugug ugaccgugg                                 29

<210> SEQ ID NO 5
<211> LENGTH: 30
<212> TYPE: RNA
<213> ORGANISM: Homo sapiens

<400> SEQUENCE: 5
uguacuguau agugaacaua guuggcauau                                30

<210> SEQ ID NO 6
<211> LENGTH: 30
<212> TYPE: RNA
<213> ORGANISM: Homo sapiens

<400> SEQUENCE: 6
guuucaaacu uuauuagucu auuuuuaauu                                30

<210> SEQ ID NO 7
<211> LENGTH: 29
<212> TYPE: RNA
<213> ORGANISM: Homo sapiens

<400> SEQUENCE: 7
cugcugagcu ggauaguuuu cucugcagc                                 29

```
<210> SEQ ID NO 8
<211> LENGTH: 29
<212> TYPE: RNA
<213> ORGANISM: Homo sapiens

<400> SEQUENCE: 8
aacucagaag agauaguaau gcucaggac                                29

<210> SEQ ID NO 9
<211> LENGTH: 31
<212> TYPE: RNA
<213> ORGANISM: Homo sapiens

<400> SEQUENCE: 9
ugucauucac ccauuaggua aacauucccu u                             31

<210> SEQ ID NO 10
<211> LENGTH: 29
<212> TYPE: RNA
<213> ORGANISM: Homo sapiens

<400> SEQUENCE: 10
guugccaggg cuguagugca gugguguga                                29

<210> SEQ ID NO 11
<211> LENGTH: 31
<212> TYPE: RNA
<213> ORGANISM: Homo sapiens

<400> SEQUENCE: 11
gcuugcuacu guauagugca ugguguag g                               31

<210> SEQ ID NO 12
<211> LENGTH: 31
<212> TYPE: RNA
<213> ORGANISM: Homo sapiens

<400> SEQUENCE: 12
ucacagcccc agguuuagug aaaaacugcu g                             31

<210> SEQ ID NO 13
<211> LENGTH: 29
<212> TYPE: RNA
<213> ORGANISM: Homo sapiens

<400> SEQUENCE: 13
cuuaaccuac uaauaguuug uugaucuga                                29

<210> SEQ ID NO 14
<211> LENGTH: 30
<212> TYPE: RNA
<213> ORGANISM: Homo sapiens

<400> SEQUENCE: 14
uguguuuuua agauuaguug aauauaagaa                               30

<210> SEQ ID NO 15
<211> LENGTH: 29
<212> TYPE: RNA
<213> ORGANISM: Homo sapiens

<400> SEQUENCE: 15
cugggccagg agguaguuuc ucaugacgg                                29
```

```
<210> SEQ ID NO 16
<211> LENGTH: 22
<212> TYPE: DNA
<213> ORGANISM: Artificial Sequence
<220> FEATURE:
<223> OTHER INFORMATION: MSI2 shRNA target sequence

<400> SEQUENCE: 16
atgagttaga ttccaagacg at                                            22

<210> SEQ ID NO 17
<211> LENGTH: 22
<212> TYPE: DNA
<213> ORGANISM: Artificial Sequence
<220> FEATURE:
<223> OTHER INFORMATION: Control scrambled sequence

<400> SEQUENCE: 17
aggattccaa ttcagcggga gc                                            22

<210> SEQ ID NO 18
<211> LENGTH: 16
<212> TYPE: DNA
<213> ORGANISM: Artificial Sequence
<220> FEATURE:
<223> OTHER INFORMATION: ASO-1

<400> SEQUENCE: 18
atatgataca ggacgg                                                   16

<210> SEQ ID NO 19
<211> LENGTH: 16
<212> TYPE: DNA
<213> ORGANISM: Artificial Sequence
<220> FEATURE:
<223> OTHER INFORMATION: ASO-2

<400> SEQUENCE: 19
ttacatatga tacagg                                                   16

<210> SEQ ID NO 20
<211> LENGTH: 16
<212> TYPE: DNA
<213> ORGANISM: Artificial Sequence
<220> FEATURE:
<223> OTHER INFORMATION: Gen 2.5 scrambled

<400> SEQUENCE: 20
ggctactacg ccgtca                                                   16
```